United States Patent
Lu et al.

(10) Patent No.: US 11,505,618 B2
(45) Date of Patent: *Nov. 22, 2022

(54) ANTIBODIES AND METHODS FOR MAKING AND USING THE SAME

(71) Applicants: AskGene Pharma Inc., Camarillo, CA (US); Jiangsu AoSaiKang Pharmaceutical Co., Ltd., Nanjing (CN)

(72) Inventors: Yuefeng Lu, Newbury Park, CA (US); Kurt Shanebeck, Camarillo, CA (US); Lu Li, Camarillo, CA (US); Lei Liu, Thousand Oaks, CA (US); Shiwen Zhang, Camarillo, CA (US); Lan Yang, Camarillo, CA (US); Jian-Feng Lu, Oak Park, CA (US)

(73) Assignees: AskGene Pharma Inc., Camarillo, CA (US); Jiangsu AoSaiKang Pharmaceutical Co., Ltd., Nanjing (CN)

( * ) Notice: Subject to any disclaimer, the term of this patent is extended or adjusted under 35 U.S.C. 154(b) by 256 days.

This patent is subject to a terminal disclaimer.

(21) Appl. No.: 16/516,223

(22) Filed: Jul. 18, 2019

(65) Prior Publication Data
US 2020/0040101 A1    Feb. 6, 2020

Related U.S. Application Data

(60) Provisional application No. 62/792,798, filed on Jan. 15, 2019, provisional application No. 62/700,174, filed on Jul. 18, 2018.

(51) Int. Cl.
| | |
|---|---|
| *C07K 16/30* | (2006.01) |
| *A61P 35/00* | (2006.01) |
| *A61K 47/68* | (2017.01) |
| *C07K 14/765* | (2006.01) |
| *C07K 14/55* | (2006.01) |
| *C07K 14/54* | (2006.01) |
| *C07K 16/28* | (2006.01) |
| *A61K 31/282* | (2006.01) |
| *A61K 31/337* | (2006.01) |
| *A61K 39/395* | (2006.01) |
| *A61K 39/00* | (2006.01) |

(52) U.S. Cl.
CPC ........ *C07K 16/3046* (2013.01); *A61K 31/282* (2013.01); *A61K 31/337* (2013.01); *A61K 39/39558* (2013.01); *A61K 47/6863* (2017.08); *A61P 35/00* (2018.01); *C07K 14/5443* (2013.01); *C07K 14/55* (2013.01); *C07K 14/765* (2013.01); *C07K 16/2809* (2013.01); *A61K 2039/505* (2013.01); *C07K 2317/24* (2013.01); *C07K 2317/31* (2013.01); *C07K 2317/33* (2013.01); *C07K 2317/565* (2013.01); *C07K 2317/732* (2013.01); *C07K 2317/734* (2013.01); *C07K 2317/76* (2013.01); *C07K 2317/92* (2013.01); *C07K 2319/30* (2013.01); *C07K 2319/31* (2013.01)

(58) Field of Classification Search
CPC ............ C07K 16/3046; C07K 14/5443; A61K 47/6863; A61K 31/282
See application file for complete search history.

(56) References Cited

U.S. PATENT DOCUMENTS

2021/0260163 A1* 8/2021 Yu .......................... C07K 14/52

OTHER PUBLICATIONS

Almagro & Fransson, Humanization of antibodies, Frontiers in Bioscience 2008; 13: 1619-33 (Year: 2008).*
Rudikoff et al., Single amino acid substitution altering antigen-binding specificity, PNAS, USA, 1982, 79: 1979-1983 (Year: 1982).*
Riemer et al., Matching of trastuzumab (Herceptin®) epitope mimics onto the surface of Her-2/neu—a new method of epitope definition, Mol Immunol, 2005 42(9): 1121-1124 (Year: 2005).*
Mini-antibodies discovered in sharks and camels could lead to drugs for cancer and other diseases | Science | AAAS (sciencemag.org) (Year: 2018).*
Bannas et al. Nanobodies and Nanobody-Based Human HeavyChain Antibodies as Antitumor Therapeutics, Frontiers in Immunology, vol. 8, article 1603 (Year: 2017).*
Holliger et al., Engineered antibody fragments and the rise of single domains, Nature Biotechnology, 23, 9, 1126-1136 (Year: 2005).*

* cited by examiner

*Primary Examiner* — Peter J Reddig
*Assistant Examiner* — Cheng Lu
(74) *Attorney, Agent, or Firm* — Entralta; James F. Fleming; Peter D. Weinstein

(57) ABSTRACT

Described and provided herein are novel antibodies for Claudin 18.2. Also described and provided are pharmaceutical compositions of the antibodies and methods of use for the treatment of cancer.

16 Claims, 17 Drawing Sheets
Specification includes a Sequence Listing.

| Load | KD (M) | kon(1/Ms) | kdis(1/s) | RMax | Full X^2 | Full R^2 |
|---|---|---|---|---|---|---|
| 5H1L3 | 2.49E-08 | 2.55E+03 | 6.35E-05 | 1.2132 | 3.0995 | 0.9951 |
| 6H1L2 | 4.03E-08 | 2.94E+03 | 1.19E-04 | 1.6376 | 7.9492 | 0.9931 |
| 26H3L3 | 2.52E-08 | 1.77E+03 | 4.46E-05 | 1.1683 | 2.2476 | 0.9887 |
| 30H10L2 | 3.08E-08 | 2.41E+03 | 7.42E-05 | 1.405 | 3.2817 | 0.9956 |
| 31H12L1 | 1.52E-07 | 1.17E+03 | 1.78E-04 | 1.0688 | 1.715 | 0.9696 |
| 33H3L1 | 1.64E-08 | 2.43E+03 | 4.00E-05 | 1.339 | 2.3685 | 0.995 |
| 42H1L11 | 3.02E-08 | 1.59E+03 | 4.78E-05 | 1.3831 | 1.2273 | 0.997 |
| 46H2L5 | 1.25E-08 | 2.32E+03 | 2.90E-05 | 1.2807 | 1.3601 | 0.9975 |
| 48H1L6 | 5.31E-08 | 1.21E+03 | 6.41E-05 | 1.1931 | 2.0349 | 0.9817 |
| 272 H1L5 | 1.31E-08 | 1.96E+03 | 2.57E-05 | 1.2669 | 1.1167 | 0.9971 |
| 312 H3L6 | 1.08E-08 | 2.11E+03 | 2.28E-05 | 1.1679 | 1.1946 | 0.9974 |
| reference | 8.69E-08 | 1.60E+03 | 1.39E-04 | 1.0563 | 2.266 | 0.9877 |

| 10 ug/ml | | | | | | | | | | |
|---|---|---|---|---|---|---|---|---|---|---|
| | 5H1L3 | 6H1L2 | 26H3L3 | 42H1L11 | 46H2L5 | 48H1L6 | 215H5L3 | 272H1L5 | 32H1L1 | 100F |
| mouse-18.2 | 2130.4 | 1534.5 | 2530.2 | 1121.9 | 3491.1 | 370.2 | 427.6 | 3862.3 | 2802.7 | 38.3 |
| Human 18.2 | 479.7 | 425.1 | 488.3 | 391.5 | 553.1 | 492.2 | 443.4 | 621.8 | 738.1 | 67.1 |
| mouse-18.1 | 21.1 | 22.2 | 20.3 | 17.6 | 18.9 | 17.6 | 17.4 | 18.2 | 20.0 | 39.4 |
| Human 18.1 | 21.9 | 21.1 | 21.7 | 18.6 | 19.4 | 18.6 | 18.6 | 18.7 | 20.9 | 99.9 |
| HEK293 | 15.9 | 13.8 | 14.3 | 14.2 | 14.2 | 15.0 | 13.9 | 14.3 | 15.1 | 24.9 |

FIG 5A
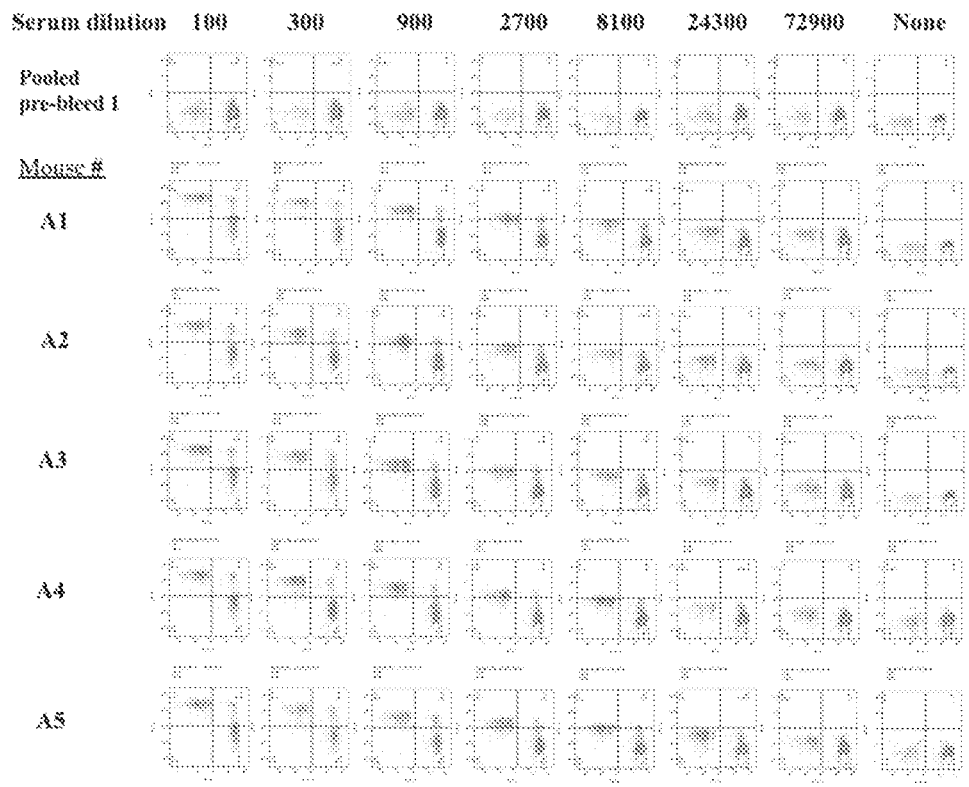
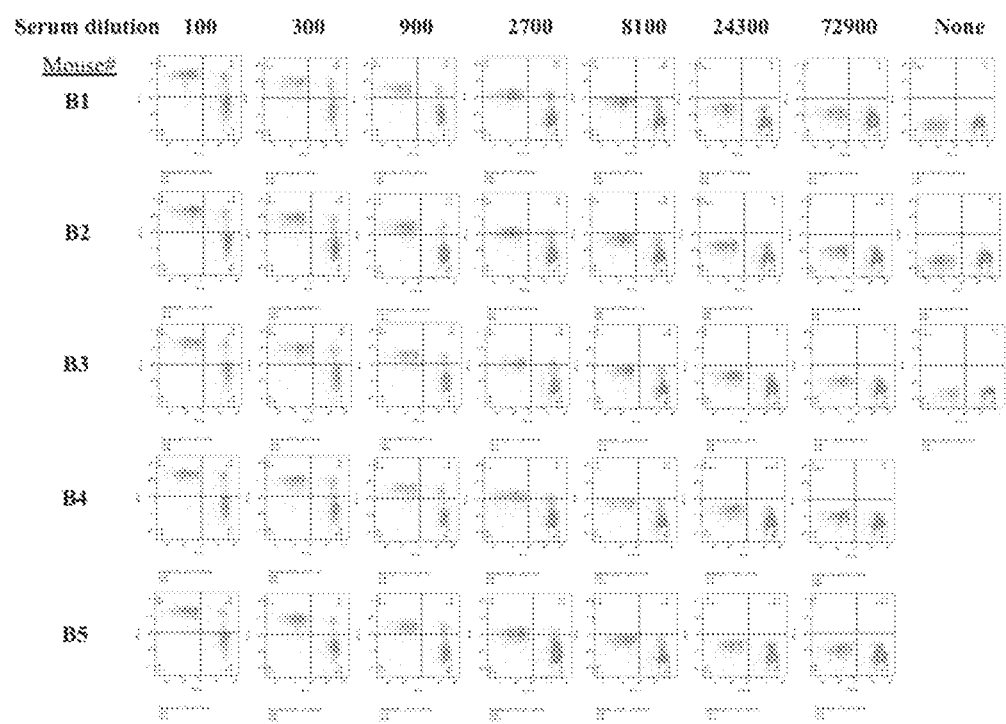

FIG 8
Figure 8A
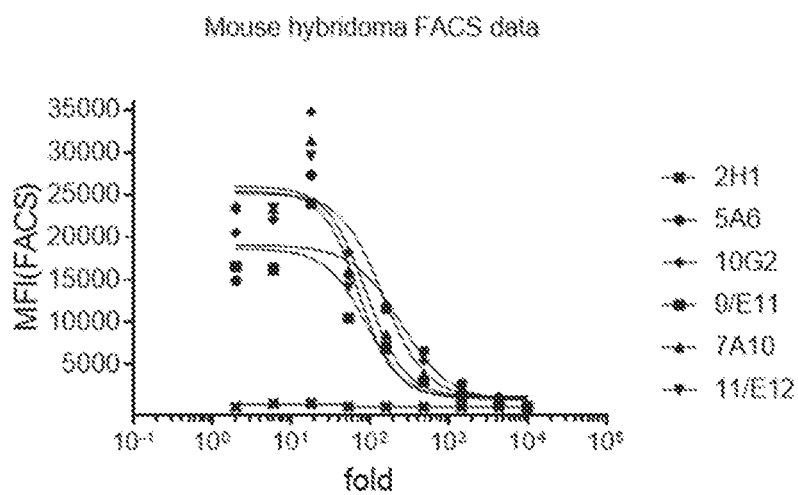
Figure 8B
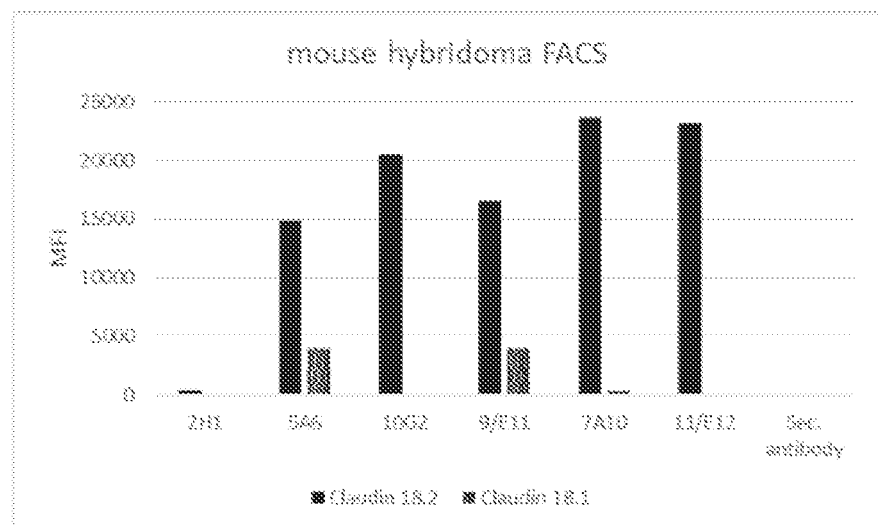
Figure 8C
|  | 2H1 | 5A6 | 10G2 | 9/E11 | 7A10 | 11/E12 | Sec. antibody |
|---|---|---|---|---|---|---|---|
| Claudin 18.2 | 425 | 14876 | 20534 | 16588 | 23630 | 23181 | 53 |
| Claudin 18.1 | 16 | 3925 | 95 | 3983 | 337 | 30 | 18 |

FIG 9
Figure 9A
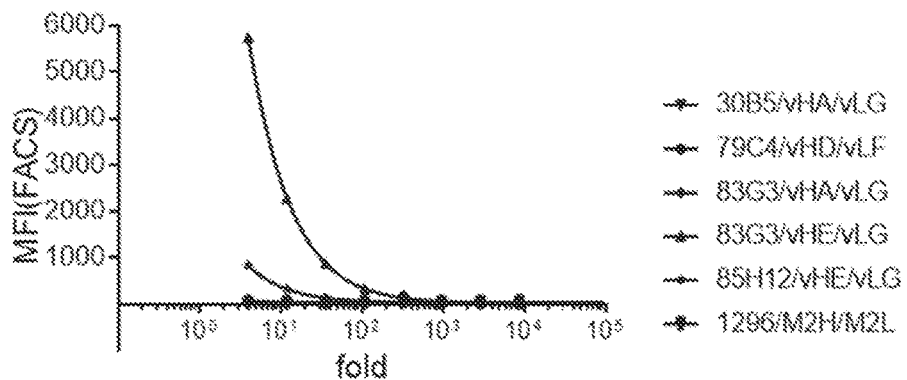
Figure 9B
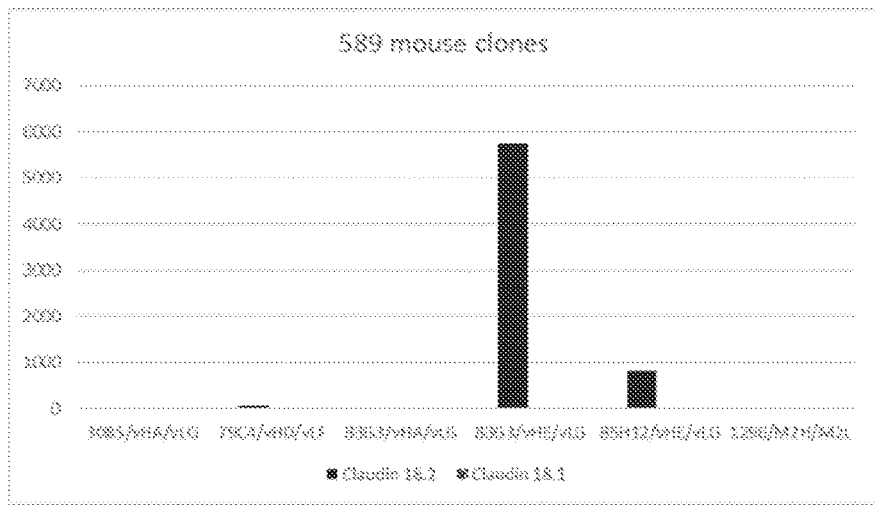
Figure 9C
|           | 30B5/ vHA/vLG | 79C4/ vHD/vLF | 83G3/ vHA/vLG | 83G3/ vHE/vLG | 85H12 vHE/vLG | A PDL1 antibody (negative control) |
|-----------|---------------|---------------|---------------|---------------|---------------|-------------------------------------|
| CLDN18.2  | 21.63         | 72.47         | 22.38         | 544.87        | 829.32        | 21.73                               |
| CLDN18.1  | 20.88         | 22.49         | 21.85         | 21.75         | 36.91         | 30.71                               |

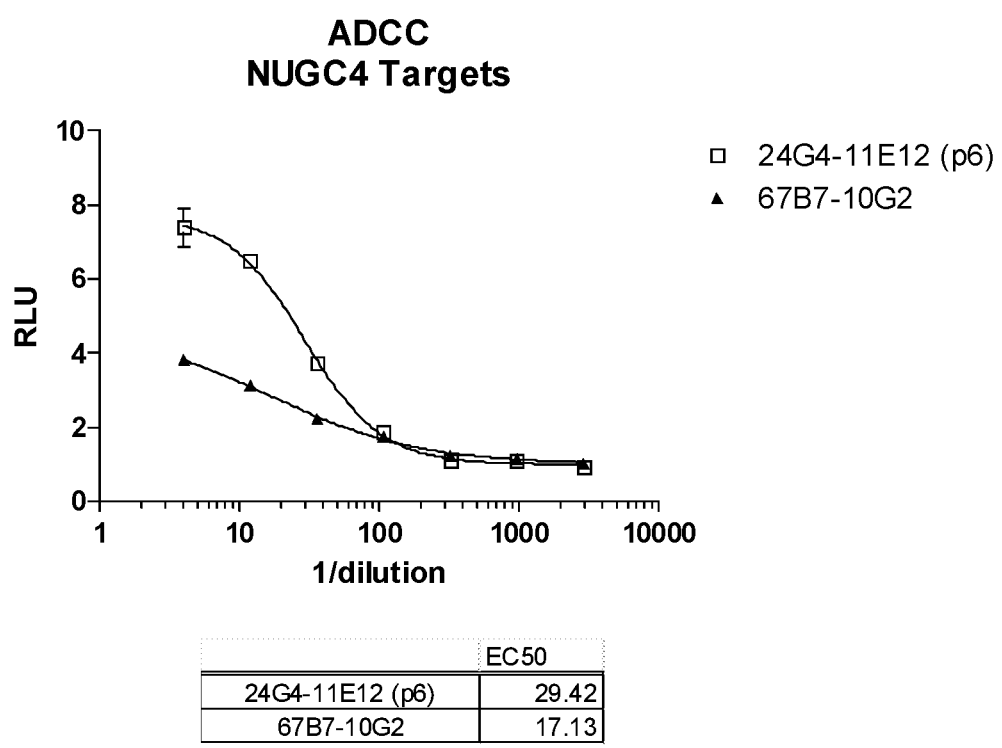

FIG 11
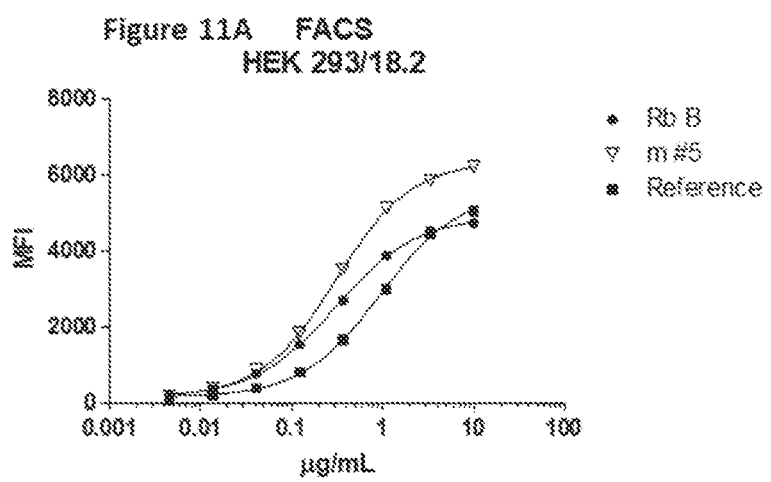
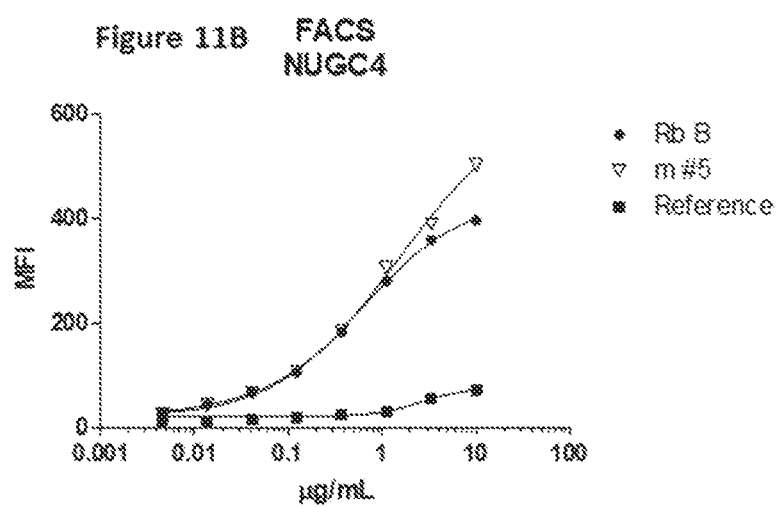

FIG 12
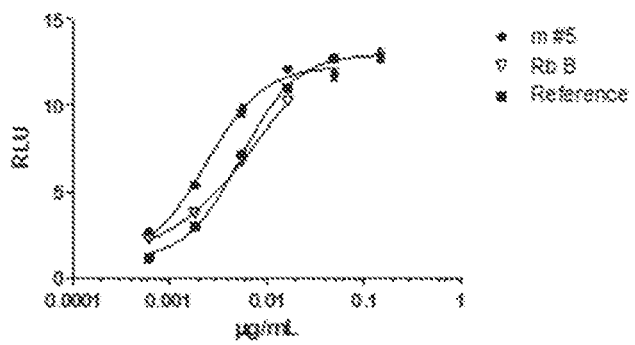
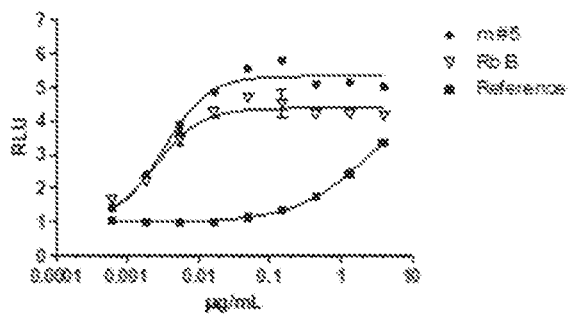
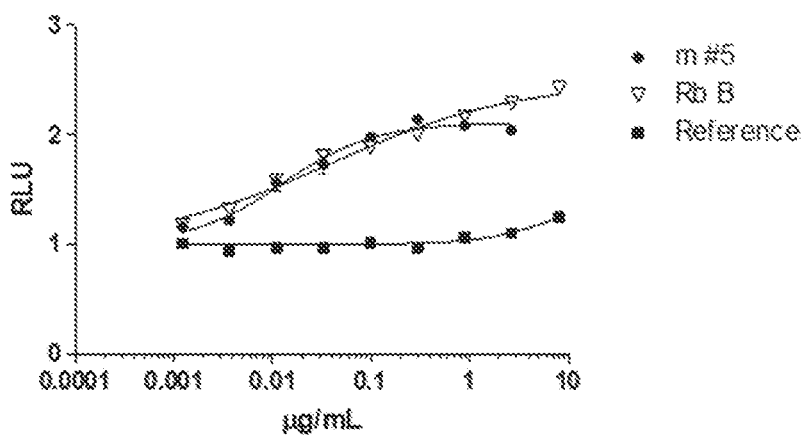

FIG 13
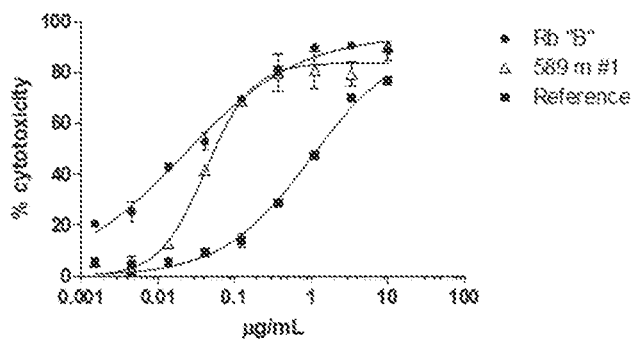
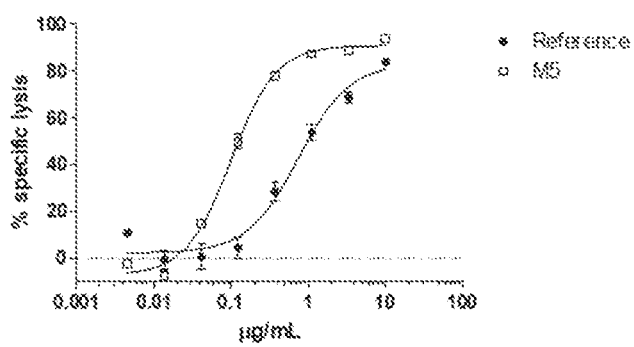
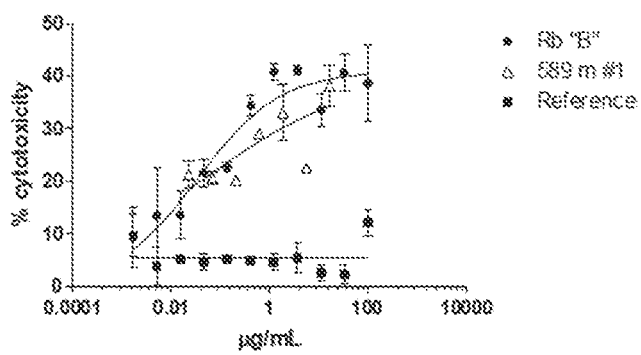

FIG 14
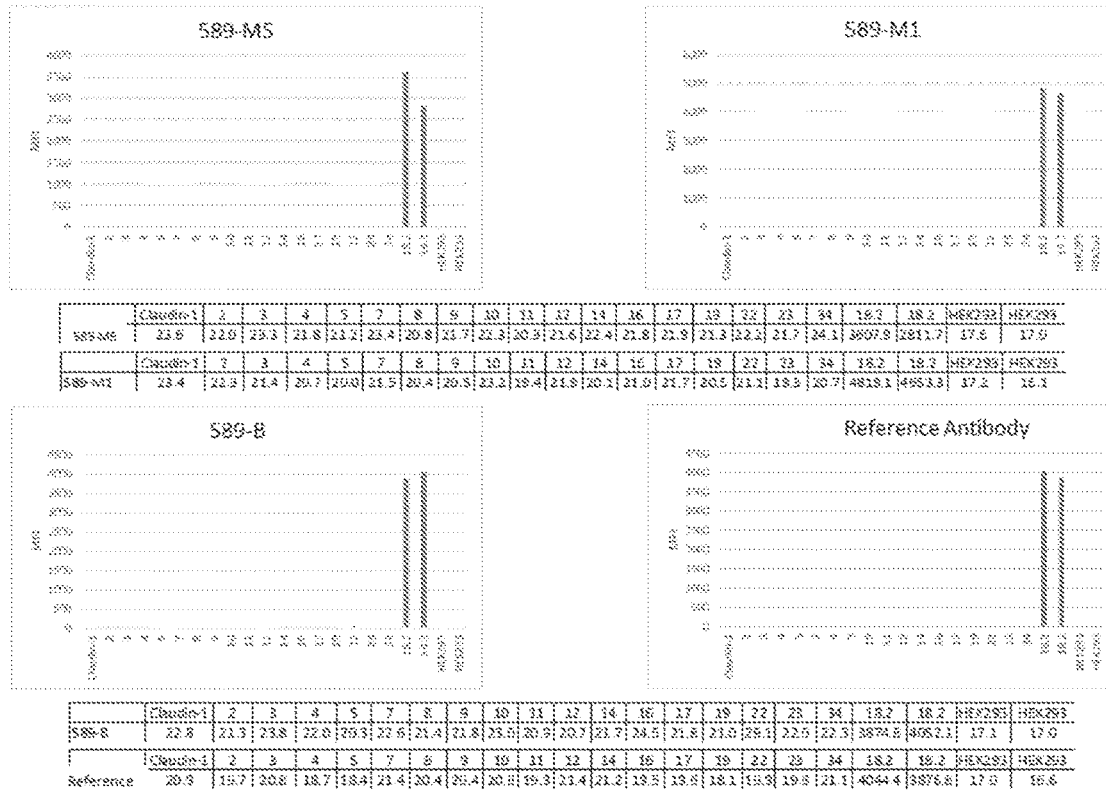
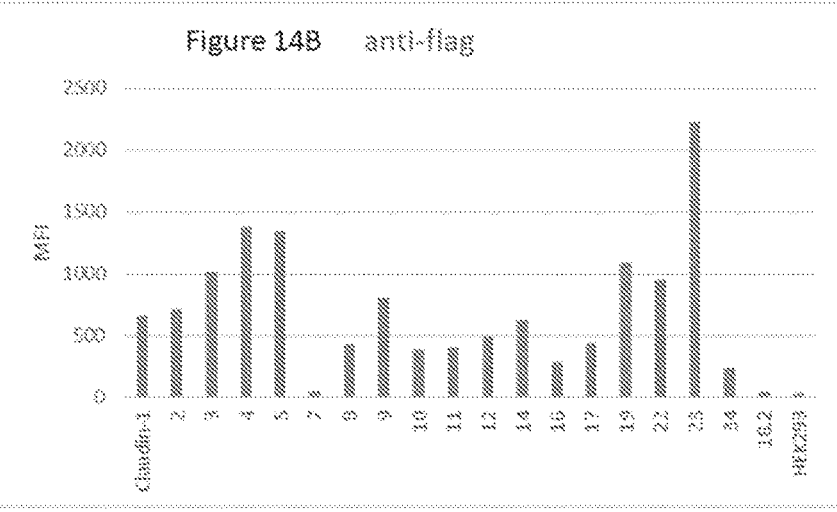

ND USING THE SAME

SEQUENCE LISTING

```
<160> NUMBER OF SEQ ID NOS: 269

<210> SEQ ID NO 1
<211> LENGTH: 127
<212> TYPE: PRT
<213> ORGANISM: Artificial Sequence
<220> FEATURE:
<223> OTHER INFORMATION: Heavy chain variable domain Protein Sequence

<400> SEQUENCE: 1

Cys Gln Ser Leu Glu Glu Ser Gly Gly Gly Leu Val Lys Pro Gly Gly
1               5                   10                  15

Thr Leu Thr Leu Thr Cys Lys Ala Ser Gly Ile Asp Phe Ser Ser Tyr
            20                  25                  30

Tyr Tyr Met Cys Trp Val Arg Gln Ala Pro Gly Lys Gly Leu Glu Trp
        35                  40                  45

Ile Ala Cys Ile Phe Asn Gly Asp Ala Ser Thr Tyr Tyr Ala Ser Trp
    50                  55                  60

Ala His Gly Arg Phe Thr Ile Ser Lys Thr Ser Ser Thr Thr Val Thr
65                  70                  75                  80

Leu Gln Met Thr Gly Leu Thr Ala Ala Asp Thr Ala Thr Tyr Phe Cys
                85                  90                  95

Ala Arg Ser Asp Tyr Ser Val Ala Phe Ala Ala Phe Leu Tyr Pro Thr
            100                 105                 110

Tyr Phe Thr Leu Trp Gly Pro Gly Thr Leu Val Thr Val Ser Ser
        115                 120                 125

<210> SEQ ID NO 2
<211> LENGTH: 121
<212> TYPE: PRT
<213> ORGANISM: Artificial Sequence
<220> FEATURE:
<223> OTHER INFORMATION: Heavy chain variable domain Protein Sequence

<400> SEQUENCE: 2

Cys Gln Ser Leu Glu Glu Ser Gly Gly Asp Leu Val Lys Pro Gly Ala
1               5                   10                  15

Ser Leu Thr Leu Thr Cys Thr Ala Ser Gly Phe Asp Leu Ser Ser Phe
            20                  25                  30

Val Tyr Ile Cys Trp Val Arg Gln Ala Pro Gly Lys Gly Leu Glu Trp
        35                  40                  45

Ile Gly Cys Ile Ala Ile Asn Gly Gly Val Thr Tyr Tyr Ala Ser Trp
    50                  55                  60
```

```
Ala Lys Gly Arg Phe Thr Ile Ser Lys Thr Ser Thr Thr Val Thr
 65                  70                  75                  80

Leu Gln Met Thr Ser Leu Thr Gly Ala Asp Thr Ala Thr Tyr Phe Cys
                 85                  90                  95

Ala Arg Asp Asp Thr Ser Ser Asn Ser Tyr Tyr Asn Asp Leu Trp Gly
            100                 105                 110

Pro Gly Thr Leu Val Thr Val Ser Ser
            115                 120
```

<210> SEQ ID NO 3
<211> LENGTH: 119
<212> TYPE: PRT
<213> ORGANISM: Artificial Sequence
<220> FEATURE:
<223> OTHER INFORMATION: Heavy chain variable domain Protein Sequence

<400> SEQUENCE: 3

```
Cys Gln Ser Leu Glu Glu Ser Gly Gly Gly Leu Val Gln Pro Gly Ala
  1               5                  10                  15

Ser Leu Thr Leu Thr Cys Lys Ala Ser Gly Phe Ser Phe Ser Ser Ser
                 20                  25                  30

Tyr Trp Ile Cys Trp Val Arg Gln Ala Pro Gly Lys Gly Leu Glu Trp
             35                  40                  45

Ile Ala Cys Ile Tyr Thr Thr Thr Ser Asn Ile Gly Tyr Ala Ser Trp
 50                  55                  60

Ala Lys Gly Arg Phe Thr Ile Ser Lys Thr Ser Ser Thr Thr Val Thr
 65                  70                  75                  80

Leu Gln Met Thr Ser Leu Thr Ala Ala Asp Thr Ala Thr Tyr Phe Cys
                 85                  90                  95

Ala Arg Glu Asp Tyr Asp Tyr Tyr Ser Phe His Pro Trp Gly Pro Gly
            100                 105                 110

Thr Leu Val Thr Val Ser Ser
            115
```

<210> SEQ ID NO 4
<211> LENGTH: 119
<212> TYPE: PRT
<213> ORGANISM: Artificial Sequence
<220> FEATURE:
<223> OTHER INFORMATION: Heavy chain variable domain Protein Sequence

<400> SEQUENCE: 4

```
Cys Gln Ser Leu Glu Glu Ser Gly Gly Gly Leu Val Gln Pro Glu Gly
  1               5                  10                  15

Ser Leu Thr Leu Thr Cys Thr Ala Ser Gly Phe Ser Phe Ser Ser Ser
                 20                  25                  30

Tyr Trp Ile Cys Trp Val Arg Gln Ala Pro Gly Lys Gly Leu Glu Trp
             35                  40                  45

Ile Ala Cys Val Tyr Thr Thr Thr Gly Asn Ile Gly Tyr Ala Ser Trp
 50                  55                  60

Ala Lys Gly Arg Phe Thr Ile Ser Val Pro Ser Ser Thr Thr Val Thr
 65                  70                  75                  80

Leu Gln Leu Thr Ser Leu Thr Ala Ala Asp Thr Ala Thr Tyr Phe Cys
                 85                  90                  95

Ala Arg Glu Gly Ser Asp Ile Tyr Ala Phe His Pro Trp Gly Pro Gly
            100                 105                 110

Thr Leu Val Thr Val Ser Ser
            115
```

```
<210> SEQ ID NO 5
<211> LENGTH: 121
<212> TYPE: PRT
<213> ORGANISM: Artificial Sequence
<220> FEATURE:
<223> OTHER INFORMATION: Heavy chain variable domain Protein Sequence

<400> SEQUENCE: 5

Gln Ser Leu Glu Glu Ser Gly Gly Asp Leu Val Lys Pro Gly Ala Ser
 1               5                  10                  15

Leu Thr Leu Thr Cys Lys Ala Ser Gly Phe Ser Phe Ser Ser Gly Tyr
            20                  25                  30

Tyr Ile Ser Trp Ile Arg Gln Ala Pro Gly Lys Gly Leu Glu Trp Ile
        35                  40                  45

Ala Cys Ile Tyr Ala Gly Gly Ser Gly Thr Thr Tyr Tyr Ala Thr Trp
    50                  55                  60

Ala Lys Gly Arg Phe Thr Val Ser Glu Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Asp Tyr Ile Gly Thr Arg Thr Tyr Tyr Phe Asp Phe Trp Gly
            100                 105                 110

Pro Gly Thr Leu Val Thr Val Ser Thr
        115                 120

<210> SEQ ID NO 6
<211> LENGTH: 122
<212> TYPE: PRT
<213> ORGANISM: Artificial Sequence
<220> FEATURE:
<223> OTHER INFORMATION: Heavy chain variable domain Protein Sequence

<400> SEQUENCE: 6

Gln Glu Gln Leu Val Glu Ser Gly Gly Gly Leu Val Gln Pro Glu Gly
 1               5                  10                  15

Ser Leu Thr Leu Thr Cys Thr Ala Ser Gly Phe Ser Phe Ser Gly Asn
            20                  25                  30

Tyr Tyr Met Trp Trp Val Arg Gln Ala Pro Gly Lys Gly Leu Glu Trp
        35                  40                  45

Ile Ala Cys Ile His Ile Asp Ser Gly Arg Pro Trp Tyr Ala Ser Trp
    50                  55                  60

Ala Lys Gly Arg Phe Thr Ile Ser Lys Thr Ser Ser Thr Thr Val Thr
65                  70                  75                  80

Leu Gln Met Thr Ser Leu Thr Val Ala Asp Thr Ala Thr Tyr Phe Cys
                85                  90                  95

Ala Arg Gly Val Ser Ser Val Tyr Trp Arg Thr Tyr Phe Asn Leu Trp
            100                 105                 110

Gly Pro Gly Thr Leu Val Thr Val Ser Ser
        115                 120

<210> SEQ ID NO 7
<211> LENGTH: 118
<212> TYPE: PRT
<213> ORGANISM: Artificial Sequence
<220> FEATURE:
<223> OTHER INFORMATION: Heavy chain variable domain Protein Sequence

<400> SEQUENCE: 7
```

```
Gln Gln Gln Leu Val Glu Ser Gly Gly Gly Leu Val Lys Pro Gly
1               5                   10                  15

Thr Leu Thr Leu Thr Cys Thr Val Ser Gly Phe Tyr Phe Asn Arg Gly
            20                  25                  30

Tyr Trp Ile Cys Trp Val Arg Gln Ala Pro Gly Lys Gly Leu Glu Trp
            35                  40                  45

Ile Gly Cys Ile Asp Thr Gly Ser Gly Val Pro Tyr Tyr Ala Asn Trp
    50                  55                  60

Ala Lys Gly Arg Phe Thr Ile Ser Lys Thr Ser Thr Ala Val Thr
65              70                  75                  80

Leu Gln Met Thr Ser Leu Thr Ala Ala Asp Thr Ala Thr Tyr Phe Cys
                85                  90                  95

Ala Arg Asn Ser Asp Ser Ile Tyr Phe Asn Leu Trp Gly Pro Gly Thr
                100                 105                 110

Leu Val Thr Val Ser Ser
            115
```

<210> SEQ ID NO 8
<211> LENGTH: 124
<212> TYPE: PRT
<213> ORGANISM: Artificial Sequence
<220> FEATURE:
<223> OTHER INFORMATION: Heavy chain variable domain Protein Sequence

<400> SEQUENCE: 8

```
Gln Glu Gln Leu Val Glu Ser Gly Gly Gly Leu Val Lys Pro Gly Gly
1               5                   10                  15

Thr Leu Thr Leu Thr Cys Thr Ala Ser Gly Phe Ser Phe Ser Ser Gly
            20                  25                  30

Phe Tyr Ile Ser Trp Val Arg Gln Ala Pro Gly Lys Gly Pro Glu Leu
            35                  40                  45

Ile Ser His Ile Tyr Thr Thr Ser Thr Thr Trp Tyr Ala Ser Trp
    50                  55                  60

Ala Lys Gly Arg Phe Thr Ile Ser Lys Thr Ser Ser Thr Val Thr
65              70                  75                  80

Leu Gln Met Thr Ser Leu Thr Ala Ala Asp Thr Ala Thr Tyr Phe Cys
                85                  90                  95

Ala Arg Ala Gly Tyr Val Asp Tyr Gly Tyr Ala Pro Tyr Asp Met Asp
                100                 105                 110

Leu Trp Gly Pro Gly Thr Leu Val Thr Val Ser Ser
            115                 120
```

<210> SEQ ID NO 9
<211> LENGTH: 120
<212> TYPE: PRT
<213> ORGANISM: Artificial Sequence
<220> FEATURE:
<223> OTHER INFORMATION: Heavy chain variable domain Protein Sequence

<400> SEQUENCE: 9

```
Gln Ser Leu Glu Glu Ser Gly Gly Gly Leu Val Gln Pro Glu Gly Ser
1               5                   10                  15

Leu Thr Leu Thr Cys Lys Ala Ser Gly Phe Ser Phe Ser Tyr Asn Val
            20                  25                  30

Tyr Met Cys Trp Val Arg Gln Ala Pro Gly Lys Gly Leu Glu Trp Ile
            35                  40                  45

Gly Cys Ile Tyr Ala Val Ser Ser Asn Thr Ile Tyr Tyr Ala Asn Trp
    50                  55                  60
```

```
Ala Lys Gly Arg Phe Thr Ile Ser Lys Thr Ser Ser Thr Val Thr
 65                  70                  75                  80

Leu Gln Leu Pro Ser Leu Thr Ala Ala Asp Thr Ala Thr Tyr Phe Cys
                 85                  90                  95

Ala Thr Arg Asp Ala Asn Ala Gly Tyr Ser Phe Asn Leu Trp Gly Pro
            100                 105                 110

Gly Thr Leu Val Thr Val Ser Ser
        115                 120

<210> SEQ ID NO 10
<211> LENGTH: 124
<212> TYPE: PRT
<213> ORGANISM: Artificial Sequence
<220> FEATURE:
<223> OTHER INFORMATION: Heavy chain variable domain Protein Sequence

<400> SEQUENCE: 10

Gln Ser Leu Glu Glu Ser Gly Gly Asp Leu Val Gln Pro Gly Gly Ser
 1               5                  10                  15

Leu Thr Leu Thr Cys Lys Ala Ser Gly Phe Ser Phe Ser Ser Gly Tyr
             20                  25                  30

Tyr Met Cys Trp Val Arg Gln Ala Pro Gly Lys Gly Leu Gly Leu Ile
         35                  40                  45

Ala Cys Ile Asp Ala Gly Gly Arg Gly Asp Thr Val Tyr Ala Ser Trp
     50                  55                  60

Ala Lys Gly Arg Phe Thr Ile Ser Lys Thr Ser Ser Thr Thr Val Thr
 65                  70                  75                  80

Leu Gln Leu Asn Ser Leu Thr Ala Ala Asp Thr Ala Ile Tyr Phe Cys
                 85                  90                  95

Ala Arg Arg Gly Tyr Ser Ser Ile Ser Ser Asn Phe Gly Ala Phe Asn
            100                 105                 110

Pro Trp Gly Pro Gly Thr Leu Val Thr Val Ser Ser
        115                 120

<210> SEQ ID NO 11
<211> LENGTH: 122
<212> TYPE: PRT
<213> ORGANISM: Artificial Sequence
<220> FEATURE:
<223> OTHER INFORMATION: Heavy chain variable domain Protein Sequence

<400> SEQUENCE: 11

Gln Glu Leu Lys Glu Ser Gly Gly Arg Leu Val Thr Pro Gly Gly Ser
 1               5                  10                  15

Leu Thr Leu Thr Cys Thr Ala Ser Gly Phe Ser Phe Asn Ser Asn Tyr
             20                  25                  30

Tyr Met Cys Trp Val Arg Gln Ala Pro Gly Lys Gly Leu Glu Trp Ile
         35                  40                  45

Ala Cys Ile Tyr Gly Gly Thr Thr Val Asn Thr Tyr Tyr Ala Thr Trp
     50                  55                  60

Ala Lys Gly Arg Phe Ala Ile Ser Lys Thr Ser Ser Thr Thr Val Thr
 65                  70                  75                  80

Leu Gln Met Thr Ser Leu Thr Ala Ala Asp Thr Ala Thr Tyr Phe Cys
                 85                  90                  95

Ala Arg Glu Asp Leu Thr Ala Tyr Ser Ser Tyr Val Ile Thr Leu Trp
            100                 105                 110

Gly Pro Gly Thr Leu Val Thr Val Ser Ser
        115                 120
```

-continued

<210> SEQ ID NO 12
<211> LENGTH: 118
<212> TYPE: PRT
<213> ORGANISM: Artificial Sequence
<220> FEATURE:
<223> OTHER INFORMATION: Heavy chain variable domain Protein Sequence

<400> SEQUENCE: 12

Gln Glu Gln Leu Glu Glu Ser Gly Gly Asp Leu Val Lys Pro Glu Gly
1               5                   10                  15

Ser Leu Thr Leu Thr Cys Thr Val Ser Gly Phe Ser Phe Asn Arg Gly
            20                  25                  30

Tyr Trp Ile Cys Trp Val Arg Gln Ala Pro Gly Lys Gly Leu Glu Trp
        35                  40                  45

Ile Gly Cys Val Asp Thr Gly Ser Gly Ser Ser Tyr Tyr Ala Asn Trp
    50                  55                  60

Ala Lys Gly Arg Phe Thr Ile Ser Lys Thr Ser Ser Thr Ala Val Thr
65                  70                  75                  80

Leu Gln Met Thr Ser Leu Thr Ala Ala Asp Thr Ala Thr Tyr Phe Cys
                85                  90                  95

Ala Arg Asn Ser Asp Ser Ile Tyr Phe Asn Leu Trp Gly Pro Gly Thr
            100                 105                 110

Leu Val Thr Val Ser Ser
        115

<210> SEQ ID NO 13
<211> LENGTH: 121
<212> TYPE: PRT
<213> ORGANISM: Artificial Sequence
<220> FEATURE:
<223> OTHER INFORMATION: Heavy chain variable domain Protein Sequence

<400> SEQUENCE: 13

Cys Gln Ser Leu Glu Glu Ser Gly Gly Ala Leu Val Lys Pro Gly Ala
1               5                   10                  15

Ser Leu Thr Leu Thr Cys Thr Ala Ser Gly Phe Ser Phe Thr Ser Arg
            20                  25                  30

Asp Tyr Ile Cys Trp Val Arg Gln Ala Pro Gly Lys Gly Leu Glu Trp
        35                  40                  45

Thr Gly Cys Ile Ala Ile Asp Gly Gly Val Ile Tyr Tyr Ala Thr Trp
    50                  55                  60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Asp Asp Ile Gly Ser Asn Ser Tyr Tyr Asn Asp Leu Trp Gly
            100                 105                 110

Pro Gly Thr Leu Val Thr Val Ser Ser
        115                 120

<210> SEQ ID NO 14
<211> LENGTH: 119
<212> TYPE: PRT
<213> ORGANISM: Artificial Sequence
<220> FEATURE:
<223> OTHER INFORMATION: Heavy chain variable domain Protein Sequence

<400> SEQUENCE: 14

```
Gln Glu Gln Leu Glu Glu Ser Gly Gly Gly Leu Val Lys Pro Gly Ala
1               5                   10                  15

Ser Leu Thr Leu Thr Cys Thr Ala Ser Gly Phe Ser Phe Ser Asn Asn
            20                  25                  30

Tyr Tyr Ile Ser Trp Val Arg Gln Ala Pro Gly Lys Gly Leu Glu Trp
            35                  40                  45

Ile Ala Cys Ile Tyr Thr Gly Tyr Ser Trp Thr Tyr Tyr Ala Ser Trp
50                  55                  60

Ala Lys Gly Arg Phe Thr Ile Ser Lys Thr Ser Ser Thr Thr Val Thr
65                  70                  75                  80

Leu Gln Met Thr Ser Leu Thr Val Ala Asp Thr Ala Thr Tyr Phe Cys
                85                  90                  95

Ala Arg Ala Asp Ser Gly Tyr Ser Gly Phe Asn Leu Trp Gly Pro Gly
                100                 105                 110

Thr Leu Val Thr Val Ser Ser
        115
```

<210> SEQ ID NO 15
<211> LENGTH: 119
<212> TYPE: PRT
<213> ORGANISM: Artificial Sequence
<220> FEATURE:
<223> OTHER INFORMATION: Heavy chain variable domain Protein Sequence

<400> SEQUENCE: 15

```
Cys Gln Ser Leu Glu Glu Ser Gly Gly Gly Leu Val Gln Pro Gly Ala
1               5                   10                  15

Ser Leu Thr Leu Thr Cys Thr Ala Ser Gly Phe Ser Phe Ser Ser Ser
            20                  25                  30

Tyr Trp Ile Cys Trp Val Arg Gln Ala Pro Gly Lys Gly Leu Glu Trp
            35                  40                  45

Ile Ala Cys Ile Tyr Thr Thr Thr Asn Asn Ile Gly Tyr Ala Asn Trp
50                  55                  60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Glu Asp Tyr Asp Tyr Tyr Ser Phe His Pro Trp Gly Pro Gly
                100                 105                 110

Thr Leu Val Thr Val Ser Ser
        115
```

<210> SEQ ID NO 16
<211> LENGTH: 120
<212> TYPE: PRT
<213> ORGANISM: Artificial Sequence
<220> FEATURE:
<223> OTHER INFORMATION: Heavy chain variable domain Protein Sequence

<400> SEQUENCE: 16

```
Gln Gln Gln Leu Glu Glu Ser Gly Gly Gly Leu Val Lys Pro Gly Gly
1               5                   10                  15

Thr Leu Thr Leu Thr Cys Thr Ala Ser Gly Phe Thr Phe Ser Ser Tyr
            20                  25                  30

Trp Ile Ser Trp Val Arg Gln Ala Pro Gly Lys Gly Leu Glu Trp Ile
            35                  40                  45

Ala Tyr Ile Phe Thr Ser Ser Ile Thr Phe Thr Ala Tyr Ala Ser Trp
```

```
                50                  55                  60
Ala Lys Gly Arg Phe Thr Val Ser Lys Thr Ser Ser Thr Val Thr
 65                  70                  75                  80

Leu Gln Leu Thr Ser Leu Thr Ala Ala Asp Thr Ala Thr Tyr Phe Cys
                 85                  90                  95

Ala Arg Asp Leu Ser Ser Thr Ser Tyr Tyr Phe Asn Leu Trp Gly Pro
                100                 105                 110

Gly Thr Leu Val Thr Val Ser Ser
            115                 120

<210> SEQ ID NO 17
<211> LENGTH: 122
<212> TYPE: PRT
<213> ORGANISM: Artificial Sequence
<220> FEATURE:
<223> OTHER INFORMATION: Heavy chain variable domain Protein Sequence

<400> SEQUENCE: 17

Gln Glu Gln Leu Val Glu Ser Gly Gly Gly Leu Val Gln Pro Glu Gly
 1               5                  10                  15

Ser Leu Thr Leu Thr Cys Thr Ala Ser Gly Phe Ser Phe Ser Gly Asn
                20                  25                  30

Tyr His Met Trp Val Arg Gln Ala Pro Gly Lys Gly Leu Glu Trp
             35                  40                  45

Ile Ala Cys Ile His Thr Asp Ser Gly Arg Thr Trp Tyr Ala Ser Trp
         50                  55                  60

Ala Lys Gly Arg Phe Thr Ile Ser Lys Thr Ser Ser Thr Thr Val Thr
 65                  70                  75                  80

Leu Gln Met Thr Ser Leu Thr Val Ala Asp Thr Ala Thr Tyr Phe Cys
                 85                  90                  95

Ala Arg Gly Val Ser Ser Val Tyr Trp Arg Thr Tyr Phe Asn Leu Trp
                100                 105                 110

Gly Pro Gly Thr Leu Val Thr Val Ser Ser
            115                 120

<210> SEQ ID NO 18
<211> LENGTH: 128
<212> TYPE: PRT
<213> ORGANISM: Artificial Sequence
<220> FEATURE:
<223> OTHER INFORMATION: Heavy chain variable domain Protein Sequence

<400> SEQUENCE: 18

Gln Glu Gln Leu Glu Glu Ser Gly Gly Gly Asp Leu Val Lys Pro Glu Gly
 1               5                  10                  15

Ser Leu Thr Leu Thr Cys Thr Val Ser Gly Phe Ser Phe Ser Asn Asn
                20                  25                  30

Tyr Trp Ile Cys Trp Val Arg Gln Ala Pro Gly Lys Gly Leu Glu Trp
             35                  40                  45

Ile Ala Cys Ile Tyr Leu Gly Ser Ser Gly Tyr Thr Tyr Phe Ala Ser
         50                  55                  60

Trp Ala Arg Gly Arg Phe Thr Ile Ser Lys Pro Ser Ser Thr Thr Val
 65                  70                  75                  80

Thr Leu Gln Met Thr Ser Leu Thr Ala Ala Asp Thr Ala Thr Tyr Phe
                 85                  90                  95

Cys Ala Arg Ser Tyr Tyr Thr Tyr Gly Tyr Ala Gly Tyr Ile Tyr Pro
                100                 105                 110
```

```
Thr Tyr Phe Asn Leu Trp Gly Pro Gly Thr Leu Val Thr Val Ser Ser
            115                 120                 125

<210> SEQ ID NO 19
<211> LENGTH: 124
<212> TYPE: PRT
<213> ORGANISM: Artificial Sequence
<220> FEATURE:
<223> OTHER INFORMATION: Heavy chain variable domain Protein Sequence

<400> SEQUENCE: 19

Gln Glu Gln Leu Val Glu Ser Gly Gly Gly Leu Val Lys Pro Gly Gly
1               5                   10                  15

Thr Leu Thr Leu Thr Cys Thr Ala Ser Gly Phe Ser Phe Ser Ser Gly
            20                  25                  30

Phe Tyr Ile Ser Trp Val Arg Gln Ala Pro Gly Lys Gly Pro Glu Leu
            35                  40                  45

Ile Ser His Ile Tyr Thr Thr Ser Thr Thr Trp Tyr Ala Ser Trp
        50                  55                  60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Ala Gly Tyr Val Asp Tyr Gly Tyr Ala Pro Tyr Asp Met Asp
            100                 105                 110

Leu Trp Gly Pro Gly Thr Leu Val Thr Val Ser Ser
            115                 120

<210> SEQ ID NO 20
<211> LENGTH: 120
<212> TYPE: PRT
<213> ORGANISM: Artificial Sequence
<220> FEATURE:
<223> OTHER INFORMATION: Heavy chain variable domain Protein Sequence

<400> SEQUENCE: 20

Glu Gln Leu Val Glu Ser Gly Gly Gly Leu Val Gln Pro Glu Gly Ser
1               5                   10                  15

Leu Thr Leu Thr Cys Thr Ala Ser Gly Phe Ser Phe Ser Ser Tyr Tyr
            20                  25                  30

Met Cys Trp Val Arg Gln Ala Pro Gly Lys Gly Leu Glu Trp Ile Gly
            35                  40                  45

Cys Ile His Thr Asp Ser Gly Arg Thr Trp Tyr Ala Ser Trp Ala Lys
        50                  55                  60

Gly Arg Phe Thr Ile Ser Lys Thr Ser Ser Thr Thr Val Thr Leu Gln
65                  70                  75                  80

Met Thr Ser Leu Thr Val Ala Asp Thr Ala Thr Tyr Phe Cys Ala Arg
                85                  90                  95

Gly Ile Ser Ser Val Tyr Trp Arg Thr Tyr Phe Asn Leu Trp Gly Pro
            100                 105                 110

Gly Thr Leu Val Thr Val Ser Ser
            115                 120

<210> SEQ ID NO 21
<211> LENGTH: 118
<212> TYPE: PRT
<213> ORGANISM: Artificial Sequence
<220> FEATURE:
<223> OTHER INFORMATION: Heavy chain variable domain Protein Sequence
```

-continued

```
<400> SEQUENCE: 21

Gln Gln Gln Leu Glu Glu Ser Gly Gly Gly Leu Val Lys Pro Gly Gly
1               5                   10                  15

Thr Leu Thr Leu Thr Cys Thr Val Ser Gly Phe Ser Phe Asn Ala Gly
            20                  25                  30

Tyr Trp Ile Cys Trp Val Arg Gln Ala Pro Gly Lys Gly Leu Glu Trp
        35                  40                  45

Ile Gly Cys Ile Asp Thr Gly Ser Gly Val Ser Tyr Tyr Ala Ser Trp
    50                  55                  60

Ala Lys Gly Arg Phe Thr Ile Ser Lys Thr Ser Ser Thr Ala Val Thr
65                  70                  75                  80

Leu Gln Met Thr Gly Leu Thr Val Ala Asp Thr Ala Thr Tyr Phe Cys
                85                  90                  95

Ala Arg Asn Thr Asp Ser Ile Tyr Phe Asn Leu Trp Gly Pro Gly Thr
            100                 105                 110

Leu Val Thr Val Ser Ser
        115

<210> SEQ ID NO 22
<211> LENGTH: 124
<212> TYPE: PRT
<213> ORGANISM: Artificial Sequence
<220> FEATURE:
<223> OTHER INFORMATION: Heavy chain variable domain Protein Sequence

<400> SEQUENCE: 22

Gln Ser Leu Glu Glu Ser Gly Gly Asp Leu Val Gln Pro Glu Gly Ser
1               5                   10                  15

Leu Thr Leu Thr Cys Lys Ala Ser Gly Phe Ser Phe Ser Ser Gly Tyr
            20                  25                  30

Tyr Met Cys Trp Val Arg Gln Ala Pro Gly Lys Gly Leu Gly Leu Ile
        35                  40                  45

Ala Cys Ile Asp Ala Gly Gly Arg Gly Asp Thr Val Tyr Ala Ser Trp
    50                  55                  60

Ala Lys Gly Arg Phe Thr Ile Ser Lys Thr Ser Ser Thr Thr Val Thr
65                  70                  75                  80

Leu Gln Leu Asn Ser Leu Thr Ala Ala Asp Thr Ala Ile Tyr Phe Cys
                85                  90                  95

Ala Arg Arg Gly Tyr Ser Ser Ile Ser Ser Asn Phe Gly Ala Phe Asn
            100                 105                 110

Pro Trp Gly Pro Gly Thr Leu Val Thr Val Ser Ser
        115                 120

<210> SEQ ID NO 23
<211> LENGTH: 121
<212> TYPE: PRT
<213> ORGANISM: Artificial Sequence
<220> FEATURE:
<223> OTHER INFORMATION: Heavy chain variable domain Protein Sequence

<400> SEQUENCE: 23

Gln Gln Gln Leu Glu Glu Ser Gly Gly Gly Leu Val Lys Pro Glu Gly
1               5                   10                  15

Ser Leu Thr Leu Thr Cys Lys Ala Ser Gly Phe Asp Phe Thr Ser Tyr
            20                  25                  30

Tyr Tyr Met Cys Trp Val Arg Gln Ala Pro Gly Lys Gly Leu Glu Leu
        35                  40                  45
```

```
Ile Ala Tyr Ile Glu Ser Ser Gly Arg Ile Trp Tyr Ala Ser Trp
     50                  55                  60
Ala Lys Gly Arg Phe Thr Ile Ser Lys Thr Ser Thr Thr Val Thr
 65                  70                  75                  80
Leu Gln Met Thr Ser Leu Thr Gly Ala Asp Thr Ala Ser Tyr Phe Cys
                 85                  90                  95
Ala Arg Asp Ile Ser Ser Gly Tyr His Gly Phe Lys Trp Trp Gly
                100                 105                 110
Pro Gly Thr Leu Val Thr Val Ser Ser
            115                 120

<210> SEQ ID NO 24
<211> LENGTH: 112
<212> TYPE: PRT
<213> ORGANISM: Artificial Sequence
<220> FEATURE:
<223> OTHER INFORMATION: Light chain variable domain Protein Sequence

<400> SEQUENCE: 24

Asp Ile Val Met Thr Gln Thr Pro Val Ser Val Ser Glu Pro Val Gly
 1               5                  10                  15
Gly Ile Val Thr Ile Lys Cys Gln Ala Ser Gln Ser Ile Gly Ser Asn
                 20                  25                  30
Leu Ala Trp Tyr Gln Gln Lys Pro Gly Gln Pro Pro Lys Leu Leu Ile
             35                  40                  45
Tyr Leu Ala Ser Thr Leu Ala Ser Gly Val Pro Ser Arg Phe Lys Gly
     50                  55                  60
Ser Gly Ser Gly Thr Glu Phe Thr Leu Thr Ile Ser Asp Leu Glu Cys
 65                  70                  75                  80
Ala Asp Ala Ala Thr Tyr Tyr Cys Gln Gly Tyr Tyr Trp Ser Ser Ser
                 85                  90                  95
Arg Ser Tyr Gly Ser Ala Phe Gly Gly Gly Thr Glu Val Val Val Val
                100                 105                 110

<210> SEQ ID NO 25
<211> LENGTH: 110
<212> TYPE: PRT
<213> ORGANISM: Artificial Sequence
<220> FEATURE:
<223> OTHER INFORMATION: Light chain variable domain Protein Sequence

<400> SEQUENCE: 25

Ala Tyr Asp Met Thr Gln Thr Pro Ala Ser Val Ser Glu Pro Val Gly
 1               5                  10                  15
Gly Ala Val Thr Ile Lys Cys Gln Ala Ser Gln Ser Ile Gly Ser Asn
                 20                  25                  30
Leu Ala Trp Tyr Gln Gln Lys Pro Gly Gln Pro Pro Lys Leu Leu Ile
             35                  40                  45
Tyr Gly Ala Ser Thr Leu Ala Ser Gly Val Ser Ser Arg Phe Lys Gly
     50                  55                  60
Ser Gly Ser Gly Thr Gln Phe Thr Leu Thr Ile Ser Gly Val Glu Cys
 65                  70                  75                  80
Ala Asp Ala Ala Thr Tyr Tyr Cys Gln Gln Gly Tyr Thr Tyr Ser His
                 85                  90                  95
Ala Asp Asn Ala Phe Gly Gly Gly Thr Glu Val Val Val Val
                100                 105                 110

<210> SEQ ID NO 26
```

```
<211> LENGTH: 110
<212> TYPE: PRT
<213> ORGANISM: Artificial Sequence
<220> FEATURE:
<223> OTHER INFORMATION: Light chain variable domain Protein Sequence

<400> SEQUENCE: 26

Ala Tyr Asp Met Thr Gln Thr Pro Ser Ser Val Ser Ala Ala Val Gly
1               5                   10                  15

Gly Thr Val Thr Ile Lys Cys Gln Ala Ser Gln Ser Ile Gly Thr Tyr
            20                  25                  30

Leu Ala Trp Tyr Gln Gln Lys Pro Gly Gln Pro Pro Lys Arg Leu Ile
        35                  40                  45

Tyr Lys Ala Ser Ser Leu Pro Ser Gly Val Ser Ser Arg Phe Lys Gly
50                  55                  60

Gly Gly Ser Gly Thr Glu Phe Thr Leu Thr Ile Ser Gly Val Glu Cys
65                  70                  75                  80

Ala Asp Ala Ala Thr Tyr Tyr Cys Gln Gln Ala Tyr Thr His Thr Tyr
                85                  90                  95

Leu Asp Asn Gly Phe Gly Gly Gly Thr Glu Val Val Val Val
            100                 105                 110

<210> SEQ ID NO 27
<211> LENGTH: 110
<212> TYPE: PRT
<213> ORGANISM: Artificial Sequence
<220> FEATURE:
<223> OTHER INFORMATION: Light chain variable domain Protein Sequence

<400> SEQUENCE: 27

Ala Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Ser Ser Tyr
            20                  25                  30

Leu Ser Trp Tyr Gln Gln Lys Pro Gly Gln Pro Pro Lys Leu Leu Ile
        35                  40                  45

Tyr Lys Ala Ser Thr Leu Ala Ser Gly Val Ser Ser Arg Phe Lys Gly
50                  55                  60

Ser Gly Ser Gly Thr Glu Phe Thr Leu Thr Ile Ser Gly Val Glu Cys
65                  70                  75                  80

Ala Asp Ala Ala Thr Tyr Tyr Cys Gln Gln Ala Tyr Thr His Thr Asn
                85                  90                  95

Leu Asp Asn Gly Phe Gly Gly Gly Thr Glu Val Val Val Val
            100                 105                 110

<210> SEQ ID NO 28
<211> LENGTH: 113
<212> TYPE: PRT
<213> ORGANISM: Artificial Sequence
<220> FEATURE:
<223> OTHER INFORMATION: Light chain variable domain Protein Sequence

<400> SEQUENCE: 28

Ala Gln Val Leu Thr Gln Thr Pro Ser Ser Val Ser Ala Ala Val Gly
1               5                   10                  15

Gly Thr Val Thr Ile Asn Cys Gln Ala Ser Gln Ser Val Tyr Lys Asn
            20                  25                  30

Asn Tyr Leu Ser Trp Tyr Gln Gln Lys Pro Gly Gln Pro Pro Lys Leu
        35                  40                  45
```

```
Leu Ile Tyr Glu Ala Ser Lys Leu Ala Ser Gly Val Pro Ser Arg Phe
 50                  55                  60
Ser Gly Ser Gly Ser Gly Thr Gln Phe Thr Leu Thr Ile Ser Gly Val
 65                  70                  75                  80
Gln Cys Asp Asp Ala Ala Thr Tyr Tyr Cys Ala Gly Glu Phe Thr Cys
                 85                  90                  95
Ile Ser Ala Asp Cys Phe Ala Phe Gly Gly Gly Thr Glu Val Val Val
                100                 105                 110
Val
```

<210> SEQ ID NO 29
<211> LENGTH: 110
<212> TYPE: PRT
<213> ORGANISM: Artificial Sequence
<220> FEATURE:
<223> OTHER INFORMATION: Light chain variable domain Protein Sequence

<400> SEQUENCE: 29

```
Asp Val Val Leu Thr Gln Thr Pro Ser Ser Ala Ser Glu Pro Val Gly
 1                5                  10                  15
Gly Thr Val Thr Ile Lys Cys Gln Ala Ser Gln Thr Ile Gly Ser Asn
                 20                  25                  30
Leu Ala Trp Tyr Gln Gln Lys Pro Gly Gln Pro Pro Lys Leu Leu Ile
             35                  40                  45
Tyr Gly Ala Ser Asn Leu Pro Ser Gly Val Pro Ser Arg Phe Ser Gly
 50                  55                  60
Ser Ala Ser Gly Thr Glu Phe Thr Leu Thr Ile Ser Gly Val Gln Cys
 65                  70                  75                  80
Asp Asp Ala Ala Thr Tyr Tyr Cys Gln Ser Ala Tyr Trp Leu Asp Ser
                 85                  90                  95
Gly Asp Asn Gly Phe Gly Gly Gly Thr Glu Val Val Val Val
                100                 105                 110
```

<210> SEQ ID NO 30
<211> LENGTH: 110
<212> TYPE: PRT
<213> ORGANISM: Artificial Sequence
<220> FEATURE:
<223> OTHER INFORMATION: Light chain variable domain Protein Sequence

<400> SEQUENCE: 30

```
Asp Ile Val Met Thr Gln Thr Pro Ala Ser Val Ser Glu Pro Val Gly
 1                5                  10                  15
Gly Thr Val Thr Ile Lys Cys Gln Ala Ser Gln Ser Ile Gly Gly Tyr
                 20                  25                  30
Leu Ser Trp Tyr Gln Gln Lys Pro Gly Gln Pro Pro Lys Leu Leu Ile
             35                  40                  45
Tyr Lys Ala Ser Thr Leu Ala Ser Gly Val Pro Ser Arg Phe Lys Gly
 50                  55                  60
Ser Gly Ser Gly Thr Asp Phe Thr Leu Thr Ile Ser Asp Leu Glu Cys
 65                  70                  75                  80
Ala Asp Ala Ala Thr Tyr Tyr Cys Gln Asn Tyr Ala Gly Val Ser Ile
                 85                  90                  95
Tyr Gly Ala Val Phe Gly Gly Gly Thr Lys Val Val Val Val
                100                 105                 110
```

<210> SEQ ID NO 31
<211> LENGTH: 110

```
<212> TYPE: PRT
<213> ORGANISM: Artificial Sequence
<220> FEATURE:
<223> OTHER INFORMATION: Light chain variable domain Protein Sequence

<400> SEQUENCE: 31

Ala Leu Val Met Thr Gln Thr Pro Ser Ser Val Ser Ala Ala Val Gly
1               5                   10                  15

Gly Thr Val Thr Ile Lys Cys Gln Ala Ser Gln Ser Ile Ser Gly Tyr
            20                  25                  30

Leu Ala Trp Tyr Gln Gln Lys Pro Gly Gln Pro Pro Lys Leu Leu Ile
        35                  40                  45

Tyr Arg Ala Ser Thr Leu Ala Ser Gly Val Ser Ser Arg Phe Lys Gly
50                  55                  60

Ser Gly Ser Gly Thr Glu Tyr Thr Leu Thr Ile Ser Gly Val Glu Cys
65                  70                  75                  80

Ala Asp Ala Ala Thr Tyr Tyr Cys Gln Gln Gly Tyr Ser Met Tyr Tyr
                85                  90                  95

Ile Glu Thr Ser Phe Gly Gly Gly Thr Lys Val Val Val Val
            100                 105                 110

<210> SEQ ID NO 32
<211> LENGTH: 109
<212> TYPE: PRT
<213> ORGANISM: Artificial Sequence
<220> FEATURE:
<223> OTHER INFORMATION: Light chain variable domain Protein Sequence

<400> SEQUENCE: 32

Gly Tyr Asp Met Thr Gln Thr Pro Ala Ser Val Ser Ala Ala Val Gly
1               5                   10                  15

Gly Thr Ile Thr Ile Lys Cys Gln Ala Ser Gln Ser Ile Ser Asn Trp
            20                  25                  30

Leu Ala Trp Tyr Gln Gln Lys Pro Gly Gln Pro Pro Lys Leu Leu Ile
        35                  40                  45

Tyr Ser Ala Ser Thr Leu Ala Ser Gly Val Pro Ser Arg Phe Lys Gly
50                  55                  60

Ser Gly Ser Gly Thr Gln Phe Thr Leu Thr Ile Ser Asp Met Gln Cys
65                  70                  75                  80

Asp Asp Ala Ala Thr Tyr Tyr Cys Glu Gly Gly Tyr Ser Ser Gly Asp
                85                  90                  95

Arg Asn Val Phe Gly Gly Gly Thr Lys Val Val Val Val
            100                 105

<210> SEQ ID NO 33
<211> LENGTH: 110
<212> TYPE: PRT
<213> ORGANISM: Artificial Sequence
<220> FEATURE:
<223> OTHER INFORMATION: Light chain variable domain Protein Sequence

<400> SEQUENCE: 33

Ala Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Ser Ser Tyr
            20                  25                  30

Leu Ala Trp Tyr Gln Gln Lys Pro Gly Gln Pro Pro Lys Gln Leu Ile
        35                  40                  45

Tyr Gly Ala Ser Thr Leu Ala Ser Gly Val Ser Ser Arg Phe Lys Gly
```

```
                        50                  55                  60
Ser Gly Ser Gly Thr Gln Phe Thr Leu Thr Ile Ser Gly Val Glu Cys
 65                  70                  75                  80

Ala Asp Ser Ala Thr Tyr Tyr Cys Gln Gln Gly Tyr Thr Ser Ile Tyr
                    85                  90                  95

Val Asp Asn Ala Phe Gly Gly Gly Thr Lys Val Val Val Val
                100                 105                 110

<210> SEQ ID NO 34
<211> LENGTH: 110
<212> TYPE: PRT
<213> ORGANISM: Artificial Sequence
<220> FEATURE:
<223> OTHER INFORMATION: Light chain variable domain Protein Sequence

<400> SEQUENCE: 34

Ala Tyr Asp Met Thr Gln Thr Pro Ala Ser Val Ser Glu Pro Val Gly
  1               5                  10                  15

Gly Thr Val Thr Ile Lys Cys Gln Ala Ser Glu Thr Ile Tyr Arg Asn
                 20                  25                  30

Leu Ala Trp Tyr Gln Gln Lys Pro Gly Gln Pro Pro Lys Leu Leu Ile
                35                  40                  45

Tyr Ala Ala Ser Thr Leu Ala Ser Gly Val Pro Ser Arg Phe Lys Gly
 50                  55                  60

Ser Gly Ser Gly Thr Gln Phe Thr Leu Thr Ile Ser Asp Leu Glu Cys
 65                  70                  75                  80

Ala Asp Ala Ala Thr Tyr Tyr Cys Gln Gln Ala Tyr Thr Arg Val Asn
                    85                  90                  95

Ile Asp Asn Ala Phe Gly Gly Gly Thr Lys Val Val Val Val
                100                 105                 110

<210> SEQ ID NO 35
<211> LENGTH: 110
<212> TYPE: PRT
<213> ORGANISM: Artificial Sequence
<220> FEATURE:
<223> OTHER INFORMATION: Light chain variable domain Protein Sequence

<400> SEQUENCE: 35

Asp Ile Val Met Thr Gln Thr Pro Val Ser Val Ser Glu Pro Val Gly
  1               5                  10                  15

Gly Thr Val Thr Ile Lys Cys Gln Ala Ser Gln Ser Ile Ser Ser Tyr
                 20                  25                  30

Leu Ser Trp Tyr Gln Gln Lys Pro Gly Gln Pro Pro Lys Leu Leu Ile
                35                  40                  45

Tyr Arg Ala Ser Thr Leu Ala Ser Gly Val Pro Ser Arg Phe Lys Gly
 50                  55                  60

Ser Gly Ser Gly Thr Glu Tyr Thr Leu Thr Ile Ser Asp Leu Glu Cys
 65                  70                  75                  80

Ala Asp Ala Ala Ala Tyr Tyr Cys Gln Asn Tyr Ala Gly Val Ser Leu
                    85                  90                  95

Tyr Gly Ala Val Phe Gly Gly Gly Thr Glu Val Val Val Val
                100                 105                 110

<210> SEQ ID NO 36
<211> LENGTH: 110
<212> TYPE: PRT
<213> ORGANISM: Artificial Sequence
<220> FEATURE:
```

<223> OTHER INFORMATION: Light chain variable domain Protein Sequence

<400> SEQUENCE: 36

```
Ala Tyr Asp Met Thr Gln Thr Pro Ala Ser Val Ser Ala Ala Val Gly
1               5                   10                  15

Gly Thr Val Thr Ile Asn Cys Gln Ala Ser Gln Asn Ile Tyr Ser Asn
            20                  25                  30

Leu Ala Trp Tyr Gln Gln Lys Pro Gly Gln Arg Pro Lys Leu Leu Ile
        35                  40                  45

Tyr Arg Ala Ser Thr Leu Ala Ser Gly Val Pro Ser Arg Phe Arg Gly
    50                  55                  60

Ser Gly Ser Gly Thr Gln Phe Thr Leu Thr Ile Ser Asp Leu Glu Cys
65                  70                  75                  80

Ala Asp Ala Ala Thr Tyr Tyr Cys Gln Gln Gly Tyr Thr Tyr Ile His
                85                  90                  95

Ala Asp Asn Ala Phe Gly Gly Gly Thr Glu Val Val Val Val
            100                 105                 110
```

<210> SEQ ID NO 37
<211> LENGTH: 111
<212> TYPE: PRT
<213> ORGANISM: Artificial Sequence
<220> FEATURE:
<223> OTHER INFORMATION: Light chain variable domain Protein Sequence

<400> SEQUENCE: 37

```
Asp Val Val Met Thr Gln Thr Pro Ala Ser Val Ser Glu Pro Val Gly
1               5                   10                  15

Gly Thr Val Thr Ile Lys Cys Gln Ala Ser Gln Ser Ile Asp Ser Arg
            20                  25                  30

Leu Ala Trp Tyr Gln Gln Lys Pro Gly Gln Pro Pro Lys Leu Leu Ile
        35                  40                  45

Tyr Gly Ala Ser Thr Leu Ala Ser Gly Val Pro Ser Arg Phe Lys Gly
    50                  55                  60

Ser Gly Ser Gly Thr Glu Tyr Thr Leu Thr Ile Ser Gly Val Gln Cys
65                  70                  75                  80

Ala Asp Ala Ala Thr Tyr Tyr Cys Gln Cys Ser Val Thr Ile Ser Thr
                85                  90                  95

Gly Val Gly Gly Ala Phe Gly Gly Thr Lys Val Val Val Val
            100                 105                 110
```

<210> SEQ ID NO 38
<211> LENGTH: 110
<212> TYPE: PRT
<213> ORGANISM: Artificial Sequence
<220> FEATURE:
<223> OTHER INFORMATION: Light chain variable domain Protein Sequence

<400> SEQUENCE: 38

```
Ala Tyr Asp Met Thr Gln Thr Pro Ala Ser Val Ser Ala Ala Val Gly
1               5                   10                  15

Gly Thr Val Thr Ile Lys Cys Gln Ala Ser Gln Ser Ile Gly Thr Tyr
            20                  25                  30

Leu Ala Trp Tyr Gln Gln Lys Pro Gly Gln Pro Pro Lys Arg Leu Leu
        35                  40                  45

Tyr Lys Ala Ser Ser Leu Ala Ser Gly Val Ser Ser Arg Phe Lys Gly
    50                  55                  60

Gly Gly Ser Gly Thr Glu Phe Ser Leu Thr Ile Ser Gly Val Glu Cys
```

```
                65                  70                  75                  80
Ala Asp Ala Ala Thr Tyr Tyr Cys Gln Gln Ala Tyr Thr His Thr Tyr
                        85                  90                  95

Leu Asp Asn Gly Phe Gly Gly Gly Thr Lys Val Val Val Val
                100                 105                 110

<210> SEQ ID NO 39
<211> LENGTH: 110
<212> TYPE: PRT
<213> ORGANISM: Artificial Sequence
<220> FEATURE:
<223> OTHER INFORMATION: Light chain variable domain Protein Sequence

<400> SEQUENCE: 39

Ala Tyr Asp Val Thr Gln Thr Pro Ala Ser Val Glu Val Ala Val Gly
1               5                   10                  15

Gly Thr Val Thr Ile Lys Cys Gln Ala Ser Glu Thr Val Ser Tyr Arg
                20                  25                  30

Leu Ala Trp Tyr Gln Gln Lys Pro Gly Gln Pro Pro Lys Leu Leu Ile
            35                  40                  45

Tyr Asp Ala Ser Thr Leu Ala Ser Gly Val Pro Ser Arg Phe Ser Gly
    50                  55                  60

Ser Gly Ser Glu Thr Glu Phe Thr Leu Thr Ile Ser Gly Val Glu Cys
65                  70                  75                  80

Ala Asp Ala Ala Ile Tyr Tyr Cys Gln Gln Gly Tyr Thr Arg Asn Asn
                85                  90                  95

Ile Asp Asn Thr Phe Gly Gly Gly Thr Lys Val Val Val Val
                100                 105                 110

<210> SEQ ID NO 40
<211> LENGTH: 110
<212> TYPE: PRT
<213> ORGANISM: Artificial Sequence
<220> FEATURE:
<223> OTHER INFORMATION: Light chain variable domain Protein Sequence

<400> SEQUENCE: 40

Asp Val Val Leu Thr Gln Thr Pro Ser Ser Ala Ser Glu Pro Val Gly
1               5                   10                  15

Gly Thr Val Thr Ile Lys Cys Gln Ala Ser Gln Thr Ile Gly Ser Asn
                20                  25                  30

Leu Ala Trp Tyr His Gln Lys Pro Gly Gln Pro Pro Lys Leu Leu Ile
            35                  40                  45

Tyr Gly Ala Ser Asn Leu Ala Ser Gly Val Pro Ser Arg Phe Ser Gly
    50                  55                  60

Ser Ala Ser Gly Thr Gln Phe Thr Leu Thr Ile Ser Gly Val Gln Cys
65                  70                  75                  80

Asp Asp Ala Ala Thr Tyr Tyr Cys Gln Ser Ala Tyr Trp Leu Asp Ser
                85                  90                  95

Gly Asp Asn Gly Phe Gly Gly Gly Thr Lys Val Val Val Val
                100                 105                 110

<210> SEQ ID NO 41
<211> LENGTH: 113
<212> TYPE: PRT
<213> ORGANISM: Artificial Sequence
<220> FEATURE:
<223> OTHER INFORMATION: Light chain variable domain Protein Sequence

<400> SEQUENCE: 41
```

Asn Ile Val Met Thr Gln Thr Pro Ser Pro Val Ser Ala Ala Val Gly
1               5                   10                  15

Gly Thr Val Thr Ile Lys Cys Gln Ala Ser Gln Ser Ile Ser Ser Tyr
                20                  25                  30

Leu Ala Trp Tyr Gln Gln Lys Pro Gly Gln Pro Pro Lys Leu Leu Ile
            35                  40                  45

Tyr Lys Ala Ser Thr Leu Ala Ser Gly Val Ser Ser Arg Leu Lys Gly
50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Thr Tyr Asp Tyr Ser Ser Ser
                85                  90                  95

Asn Ser Tyr Gly Ser Asn Ala Phe Gly Gly Gly Thr Lys Val Val Val
            100                 105                 110

Val

<210> SEQ ID NO 42
<211> LENGTH: 110
<212> TYPE: PRT
<213> ORGANISM: Artificial Sequence
<220> FEATURE:
<223> OTHER INFORMATION: Light chain variable domain Protein Sequence

<400> SEQUENCE: 42

Ala Leu Val Met Thr Gln Thr Pro Ser Ser Val Ser Ala Ala Val Gly
1               5                   10                  15

Gly Thr Val Thr Ile Lys Cys Gln Ala Ser Gln Ser Ile Ser Gly Tyr
                20                  25                  30

Leu Ala Trp Tyr Gln Gln Lys Pro Gly Gln Pro Pro Lys Leu Leu Ile
            35                  40                  45

Tyr Arg Ala Ser Thr Leu Ala Ser Gly Val Ser Ser Arg Phe Lys Gly
50                  55                  60

Ser Gly Ser Gly Thr Glu Tyr Thr Leu Thr Ile Ser Gly Val Glu Cys
65                  70                  75                  80

Ala Asp Ala Ala Thr Tyr Tyr Cys Gln Gln Gly Tyr Ser Met Tyr Tyr
                85                  90                  95

Ile Glu Thr Ser Phe Gly Gly Gly Thr Glu Val Val Val Val
            100                 105                 110

<210> SEQ ID NO 43
<211> LENGTH: 110
<212> TYPE: PRT
<213> ORGANISM: Artificial Sequence
<220> FEATURE:
<223> OTHER INFORMATION: Light chain variable domain Protein Sequence

<400> SEQUENCE: 43

Asp Val Val Met Thr Gln Thr Pro Ser Ser Val Ser Glu Pro Val Gly
1               5                   10                  15

Gly Thr Val Thr Ile Arg Cys Gln Ala Ser Gln Ser Ile Gly Ser Asn
                20                  25                  30

Leu Ala Trp Tyr Gln Gln Lys Pro Gly Gln Pro Pro Lys Leu Leu Ile
            35                  40                  45

Tyr Gly Ala Ser Asn Leu Ala Ser Gly Val Pro Ser Arg Phe Ser Gly
50                  55                  60

Ser Ala Ser Gly Thr Gln Phe Thr Leu Thr Ile Ser Gly Val Gln Cys
65                  70                  75                  80

```
Asp Asp Ala Ala Thr Tyr Tyr Cys Gln Ser Ala Tyr Trp Leu Asp Ser
                85                  90                  95

Gly Asp Asn Gly Phe Gly Gly Gly Thr Glu Val Val Val Val
            100                 105                 110

<210> SEQ ID NO 44
<211> LENGTH: 110
<212> TYPE: PRT
<213> ORGANISM: Artificial Sequence
<220> FEATURE:
<223> OTHER INFORMATION: Light chain variable domain Protein Sequence

<400> SEQUENCE: 44

Asp Ile Val Met Thr Gln Thr Pro Ala Ser Val Glu Ala Ala Val Gly
1               5                   10                  15

Gly Thr Val Thr Ile Lys Cys Gln Ala Ser Gln Thr Ile Tyr Ser Tyr
                20                  25                  30

Leu Ser Trp Tyr Gln Gln Lys Pro Gly Gln Pro Pro Lys Leu Leu Ile
                35                  40                  45

Tyr Lys Ala Ser Thr Leu Ala Ser Gly Val Ser Ser Arg Phe Lys Gly
            50                  55                  60

Ser Gly Ser Gly Thr Glu Phe Thr Leu Thr Ile Ser Asp Leu Glu Cys
65                  70                  75                  80

Ala Asp Ala Ala Tyr Tyr Cys Gln Thr Tyr Ala Gly Val Ser Ile
                85                  90                  95

Tyr Gly Ala Ala Phe Gly Gly Gly Thr Lys Val Val Val Val
            100                 105                 110

<210> SEQ ID NO 45
<211> LENGTH: 110
<212> TYPE: PRT
<213> ORGANISM: Artificial Sequence
<220> FEATURE:
<223> OTHER INFORMATION: Light chain variable domain Protein Sequence

<400> SEQUENCE: 45

Ala Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Ser Ser Tyr
                20                  25                  30

Leu Ala Trp Tyr Gln Gln Lys Pro Gly Gln Pro Pro Lys Gln Leu Ile
                35                  40                  45

Tyr Gly Ala Ser Thr Leu Ala Ser Gly Val Ser Ser Arg Phe Lys Gly
            50                  55                  60

Ser Gly Ser Gly Thr Gln Phe Thr Leu Thr Ile Ser Gly Val Glu Cys
65                  70                  75                  80

Ala Asp Ser Ala Thr Tyr Tyr Cys Gln Gln Gly Tyr Thr Ser Ile Tyr
                85                  90                  95

Val Asp Asn Ala Phe Gly Gly Gly Thr Lys Val Val Val Val
            100                 105                 110

<210> SEQ ID NO 46
<211> LENGTH: 110
<212> TYPE: PRT
<213> ORGANISM: Artificial Sequence
<220> FEATURE:
<223> OTHER INFORMATION: Light chain variable domain Protein Sequence

<400> SEQUENCE: 46
```

```
Ala Ile Lys Met Thr Gln Thr Pro Ala Ser Val Glu Ala Val Gly
1               5                   10                  15

Gly Thr Val Thr Ile Lys Cys Gln Ala Ser Gln Ser Ile Ser Asn Tyr
            20                  25                  30

Leu Ala Trp Tyr Gln Gln Lys Pro Gly Gln Pro Pro Lys Leu Leu Ile
            35                  40                  45

Tyr Arg Ala Ser Thr Leu Glu Ser Gly Val Pro Ser Arg Phe Lys Gly
50                  55                  60

Ser Gly Ser Gly Thr Asp Phe Thr Leu Thr Ile Ser Asp Leu Glu Cys
65                  70                  75                  80

Ala Asp Ala Ala Thr Tyr Tyr Cys Gln Gln Val Tyr Ser Ile Thr Asn
                85                  90                  95

Ile Asp Asn Ala Phe Gly Gly Gly Thr Glu Val Val Val Val
            100                 105                 110

<210> SEQ ID NO 47
<211> LENGTH: 9
<212> TYPE: PRT
<213> ORGANISM: Artificial Sequence
<220> FEATURE:
<223> OTHER INFORMATION: Clone 49E05

<400> SEQUENCE: 47

Gly Ile Asp Phe Ser Ser Tyr Tyr Tyr
1               5

<210> SEQ ID NO 48
<211> LENGTH: 8
<212> TYPE: PRT
<213> ORGANISM: Artificial Sequence
<220> FEATURE:
<223> OTHER INFORMATION: Clone 49E05

<400> SEQUENCE: 48

Ile Phe Asn Gly Asp Ala Ser Thr
1               5

<210> SEQ ID NO 49
<211> LENGTH: 19
<212> TYPE: PRT
<213> ORGANISM: Artificial Sequence
<220> FEATURE:
<223> OTHER INFORMATION: Clone 49E05

<400> SEQUENCE: 49

Arg Ser Asp Tyr Ser Val Ala Phe Ala Ala Phe Leu Tyr Pro Thr Tyr
1               5                   10                  15

Phe Thr Leu

<210> SEQ ID NO 50
<211> LENGTH: 6
<212> TYPE: PRT
<213> ORGANISM: Artificial Sequence
<220> FEATURE:
<223> OTHER INFORMATION: Clone 49E05

<400> SEQUENCE: 50

Gln Ser Ile Gly Ser Asn
1               5

<210> SEQ ID NO 51
<211> LENGTH: 3
<212> TYPE: PRT
```

```
<213> ORGANISM: Artificial Sequence
<220> FEATURE:
<223> OTHER INFORMATION: Clone 49E05

<400> SEQUENCE: 51

Leu Ala Ser
1

<210> SEQ ID NO 52
<211> LENGTH: 14
<212> TYPE: PRT
<213> ORGANISM: Artificial Sequence
<220> FEATURE:
<223> OTHER INFORMATION: Clone 49E12

<400> SEQUENCE: 52

Gln Gly Tyr Tyr Trp Ser Ser Ser Arg Ser Tyr Gly Ser Ala
1               5                   10

<210> SEQ ID NO 53
<211> LENGTH: 9
<212> TYPE: PRT
<213> ORGANISM: Artificial Sequence
<220> FEATURE:
<223> OTHER INFORMATION: Clone 49E12

<400> SEQUENCE: 53

Gly Phe Asp Leu Ser Ser Phe Val Tyr
1               5

<210> SEQ ID NO 54
<211> LENGTH: 7
<212> TYPE: PRT
<213> ORGANISM: Artificial Sequence
<220> FEATURE:
<223> OTHER INFORMATION: Clone 49E12

<400> SEQUENCE: 54

Ile Ala Ile Asn Gly Gly Val
1               5

<210> SEQ ID NO 55
<211> LENGTH: 14
<212> TYPE: PRT
<213> ORGANISM: Artificial Sequence
<220> FEATURE:
<223> OTHER INFORMATION: Clone 49E12

<400> SEQUENCE: 55

Ala Arg Asp Asp Thr Ser Ser Asn Ser Tyr Tyr Asn Asp Leu
1               5                   10

<210> SEQ ID NO 56
<211> LENGTH: 6
<212> TYPE: PRT
<213> ORGANISM: Artificial Sequence
<220> FEATURE:
<223> OTHER INFORMATION: Clone 49E12

<400> SEQUENCE: 56

Gln Ser Ile Gly Ser Asn
1               5

<210> SEQ ID NO 57
<211> LENGTH: 3
<212> TYPE: PRT
<213> ORGANISM: Artificial Sequence
```

```
<220> FEATURE:
<223> OTHER INFORMATION: Clone 49E12

<400> SEQUENCE: 57

Gly Ala Ser
1

<210> SEQ ID NO 58
<211> LENGTH: 12
<212> TYPE: PRT
<213> ORGANISM: Artificial Sequence
<220> FEATURE:
<223> OTHER INFORMATION: Clone 49E12

<400> SEQUENCE: 58

Gln Gln Gly Tyr Thr Tyr Ser His Ala Asp Asn Ala
1               5                   10

<210> SEQ ID NO 59
<211> LENGTH: 9
<212> TYPE: PRT
<213> ORGANISM: Artificial Sequence
<220> FEATURE:
<223> OTHER INFORMATION: Clone 50H08

<400> SEQUENCE: 59

Gly Phe Ser Phe Ser Ser Ser Tyr Trp
1               5

<210> SEQ ID NO 60
<211> LENGTH: 7
<212> TYPE: PRT
<213> ORGANISM: Artificial Sequence
<220> FEATURE:
<223> OTHER INFORMATION: Clone 50H08

<400> SEQUENCE: 60

Ile Tyr Thr Thr Thr Ser Asn
1               5

<210> SEQ ID NO 61
<211> LENGTH: 12
<212> TYPE: PRT
<213> ORGANISM: Artificial Sequence
<220> FEATURE:
<223> OTHER INFORMATION: Clone 50H08

<400> SEQUENCE: 61

Ala Arg Glu Asp Tyr Asp Tyr Tyr Ser Phe His Pro
1               5                   10

<210> SEQ ID NO 62
<211> LENGTH: 6
<212> TYPE: PRT
<213> ORGANISM: Artificial Sequence
<220> FEATURE:
<223> OTHER INFORMATION: Clone 50H08

<400> SEQUENCE: 62

Gln Ser Ile Gly Thr Tyr
1               5

<210> SEQ ID NO 63
<211> LENGTH: 3
<212> TYPE: PRT
<213> ORGANISM: Artificial Sequence
<220> FEATURE:
```

<223> OTHER INFORMATION: Clone 50H08

<400> SEQUENCE: 63

Lys Ala Ser
1

<210> SEQ ID NO 64
<211> LENGTH: 12
<212> TYPE: PRT
<213> ORGANISM: Artificial Sequence
<220> FEATURE:
<223> OTHER INFORMATION: Clone 50H08

<400> SEQUENCE: 64

Gln Gln Ala Tyr Thr His Thr Tyr Leu Asp Asn Gly
1               5                   10

<210> SEQ ID NO 65
<211> LENGTH: 9
<212> TYPE: PRT
<213> ORGANISM: Artificial Sequence
<220> FEATURE:
<223> OTHER INFORMATION: Clone 52E07

<400> SEQUENCE: 65

Gly Phe Ser Phe Ser Ser Ser Tyr Trp
1               5

<210> SEQ ID NO 66
<211> LENGTH: 7
<212> TYPE: PRT
<213> ORGANISM: Artificial Sequence
<220> FEATURE:
<223> OTHER INFORMATION: Clone 52E07

<400> SEQUENCE: 66

Val Tyr Thr Thr Thr Gly Asn
1               5

<210> SEQ ID NO 67
<211> LENGTH: 12
<212> TYPE: PRT
<213> ORGANISM: Artificial Sequence
<220> FEATURE:
<223> OTHER INFORMATION: Clone 52E07

<400> SEQUENCE: 67

Ala Arg Glu Gly Ser Asp Ile Tyr Ala Phe His Pro
1               5                   10

<210> SEQ ID NO 68
<211> LENGTH: 6
<212> TYPE: PRT
<213> ORGANISM: Artificial Sequence
<220> FEATURE:
<223> OTHER INFORMATION: Clone 52E07

<400> SEQUENCE: 68

Gln Ser Ile Ser Ser Tyr
1               5

<210> SEQ ID NO 69
<211> LENGTH: 3
<212> TYPE: PRT
<213> ORGANISM: Artificial Sequence
<220> FEATURE:
<223> OTHER INFORMATION: Clone 52E07

```
<400> SEQUENCE: 69

Lys Ala Ser
1

<210> SEQ ID NO 70
<211> LENGTH: 12
<212> TYPE: PRT
<213> ORGANISM: Artificial Sequence
<220> FEATURE:
<223> OTHER INFORMATION: Clone 52E07

<400> SEQUENCE: 70

Gln Gln Ala Tyr Thr His Thr Asn Leu Asp Asn Gly
1               5                   10

<210> SEQ ID NO 71
<211> LENGTH: 9
<212> TYPE: PRT
<213> ORGANISM: Artificial Sequence
<220> FEATURE:
<223> OTHER INFORMATION: Clone 52G02

<400> SEQUENCE: 71

Gly Phe Ser Phe Ser Ser Gly Tyr Tyr
1               5

<210> SEQ ID NO 72
<211> LENGTH: 9
<212> TYPE: PRT
<213> ORGANISM: Artificial Sequence
<220> FEATURE:
<223> OTHER INFORMATION: Clone 52G02

<400> SEQUENCE: 72

Ile Tyr Ala Gly Gly Ser Gly Thr Thr
1               5

<210> SEQ ID NO 73
<211> LENGTH: 14
<212> TYPE: PRT
<213> ORGANISM: Artificial Sequence
<220> FEATURE:
<223> OTHER INFORMATION: Clone 52G02

<400> SEQUENCE: 73

Ala Arg Asp Tyr Ile Gly Thr Arg Thr Tyr Tyr Phe Asp Phe
1               5                   10

<210> SEQ ID NO 74
<211> LENGTH: 8
<212> TYPE: PRT
<213> ORGANISM: Artificial Sequence
<220> FEATURE:
<223> OTHER INFORMATION: Clone 52G02

<400> SEQUENCE: 74

Gln Ser Val Tyr Lys Asn Asn Tyr
1               5

<210> SEQ ID NO 75
<211> LENGTH: 3
<212> TYPE: PRT
<213> ORGANISM: Artificial Sequence
<220> FEATURE:
<223> OTHER INFORMATION: Clone 52G02
```

```
<400> SEQUENCE: 75

Glu Ala Ser
1

<210> SEQ ID NO 76
<211> LENGTH: 13
<212> TYPE: PRT
<213> ORGANISM: Artificial Sequence
<220> FEATURE:
<223> OTHER INFORMATION: Clone 52G02

<400> SEQUENCE: 76

Ala Gly Glu Phe Thr Cys Ile Ser Ala Asp Cys Phe Ala
1               5                   10

<210> SEQ ID NO 77
<211> LENGTH: 9
<212> TYPE: PRT
<213> ORGANISM: Artificial Sequence
<220> FEATURE:
<223> OTHER INFORMATION: Clone 54B08

<400> SEQUENCE: 77

Gly Phe Ser Phe Ser Gly Asn Tyr Tyr
1               5

<210> SEQ ID NO 78
<211> LENGTH: 8
<212> TYPE: PRT
<213> ORGANISM: Artificial Sequence
<220> FEATURE:
<223> OTHER INFORMATION: Clone 54B08

<400> SEQUENCE: 78

Ile His Ile Asp Ser Gly Arg Pro
1               5

<210> SEQ ID NO 79
<211> LENGTH: 14
<212> TYPE: PRT
<213> ORGANISM: Artificial Sequence
<220> FEATURE:
<223> OTHER INFORMATION: Clone 54B08

<400> SEQUENCE: 79

Arg Gly Val Ser Ser Val Tyr Trp Arg Thr Tyr Phe Asn Leu
1               5                   10

<210> SEQ ID NO 80
<211> LENGTH: 6
<212> TYPE: PRT
<213> ORGANISM: Artificial Sequence
<220> FEATURE:
<223> OTHER INFORMATION: Clone 54B08

<400> SEQUENCE: 80

Gln Thr Ile Gly Ser Asn
1               5

<210> SEQ ID NO 81
<211> LENGTH: 3
<212> TYPE: PRT
<213> ORGANISM: Artificial Sequence
<220> FEATURE:
<223> OTHER INFORMATION: Clone 54B08

<400> SEQUENCE: 81
```

```
Gly Ala Ser
1

<210> SEQ ID NO 82
<211> LENGTH: 12
<212> TYPE: PRT
<213> ORGANISM: Artificial Sequence
<220> FEATURE:
<223> OTHER INFORMATION: Clone 54B08

<400> SEQUENCE: 82

Gln Ser Ala Tyr Trp Leu Asp Ser Gly Asp Asn Gly
1               5                   10

<210> SEQ ID NO 83
<211> LENGTH: 9
<212> TYPE: PRT
<213> ORGANISM: Artificial Sequence
<220> FEATURE:
<223> OTHER INFORMATION: Clone 54C02

<400> SEQUENCE: 83

Gly Phe Tyr Phe Asn Arg Gly Tyr Trp
1               5

<210> SEQ ID NO 84
<211> LENGTH: 7
<212> TYPE: PRT
<213> ORGANISM: Artificial Sequence
<220> FEATURE:
<223> OTHER INFORMATION: Clone 54C02

<400> SEQUENCE: 84

Ile Asp Thr Gly Ser Gly Val
1               5

<210> SEQ ID NO 85
<211> LENGTH: 11
<212> TYPE: PRT
<213> ORGANISM: Artificial Sequence
<220> FEATURE:
<223> OTHER INFORMATION: Clone 54C02

<400> SEQUENCE: 85

Ala Arg Asn Ser Asp Ser Ile Tyr Phe Asn Leu
1               5                   10

<210> SEQ ID NO 86
<211> LENGTH: 6
<212> TYPE: PRT
<213> ORGANISM: Artificial Sequence
<220> FEATURE:
<223> OTHER INFORMATION: Clone 54C02

<400> SEQUENCE: 86

Gln Ser Ile Gly Gly Tyr
1               5

<210> SEQ ID NO 87
<211> LENGTH: 3
<212> TYPE: PRT
<213> ORGANISM: Artificial Sequence
<220> FEATURE:
<223> OTHER INFORMATION: Clone 54C02

<400> SEQUENCE: 87
```

Lys Ala Ser
1

<210> SEQ ID NO 88
<211> LENGTH: 12
<212> TYPE: PRT
<213> ORGANISM: Artificial Sequence
<220> FEATURE:
<223> OTHER INFORMATION: Clone 54C02

<400> SEQUENCE: 88

Gln Asn Tyr Ala Gly Val Ser Ile Tyr Gly Ala Val
1               5                   10

<210> SEQ ID NO 89
<211> LENGTH: 9
<212> TYPE: PRT
<213> ORGANISM: Artificial Sequence
<220> FEATURE:
<223> OTHER INFORMATION: Clone 59A08

<400> SEQUENCE: 89

Gly Phe Ser Phe Ser Ser Gly Phe Tyr
1               5

<210> SEQ ID NO 90
<211> LENGTH: 8
<212> TYPE: PRT
<213> ORGANISM: Artificial Sequence
<220> FEATURE:
<223> OTHER INFORMATION: Clone 59A08

<400> SEQUENCE: 90

Ile Tyr Thr Thr Ser Thr Thr Thr
1               5

<210> SEQ ID NO 91
<211> LENGTH: 16
<212> TYPE: PRT
<213> ORGANISM: Artificial Sequence
<220> FEATURE:
<223> OTHER INFORMATION: Clone 59A08

<400> SEQUENCE: 91

Arg Ala Gly Tyr Val Asp Tyr Gly Tyr Ala Pro Tyr Asp Met Asp Leu
1               5                   10                  15

<210> SEQ ID NO 92
<211> LENGTH: 6
<212> TYPE: PRT
<213> ORGANISM: Artificial Sequence
<220> FEATURE:
<223> OTHER INFORMATION: Clone 59A08

<400> SEQUENCE: 92

Gln Ser Ile Ser Gly Tyr
1               5

<210> SEQ ID NO 93
<211> LENGTH: 3
<212> TYPE: PRT
<213> ORGANISM: Artificial Sequence
<220> FEATURE:
<223> OTHER INFORMATION: Clone 59A08

<400> SEQUENCE: 93

Arg Ala Ser

```
<210> SEQ ID NO 94
<211> LENGTH: 12
<212> TYPE: PRT
<213> ORGANISM: Artificial Sequence
<220> FEATURE:
<223> OTHER INFORMATION: Clone 59A08

<400> SEQUENCE: 94

Gln Gln Gly Tyr Ser Met Tyr Tyr Ile Glu Thr Ser
1               5                   10

<210> SEQ ID NO 95
<211> LENGTH: 9
<212> TYPE: PRT
<213> ORGANISM: Artificial Sequence
<220> FEATURE:
<223> OTHER INFORMATION: Clone 59E07

<400> SEQUENCE: 95

Gly Phe Ser Phe Ser Tyr Asn Val Tyr
1               5

<210> SEQ ID NO 96
<211> LENGTH: 9
<212> TYPE: PRT
<213> ORGANISM: Artificial Sequence
<220> FEATURE:
<223> OTHER INFORMATION: Clone 59E07

<400> SEQUENCE: 96

Ile Tyr Ala Val Ser Ser Asn Thr Ile
1               5

<210> SEQ ID NO 97
<211> LENGTH: 13
<212> TYPE: PRT
<213> ORGANISM: Artificial Sequence
<220> FEATURE:
<223> OTHER INFORMATION: Clone 59E07

<400> SEQUENCE: 97

Ala Thr Arg Asp Ala Asn Ala Gly Tyr Ser Phe Asn Leu
1               5                   10

<210> SEQ ID NO 98
<211> LENGTH: 6
<212> TYPE: PRT
<213> ORGANISM: Artificial Sequence
<220> FEATURE:
<223> OTHER INFORMATION: Clone 59E07

<400> SEQUENCE: 98

Gln Ser Ile Ser Asn Trp
1               5

<210> SEQ ID NO 99
<211> LENGTH: 3
<212> TYPE: PRT
<213> ORGANISM: Artificial Sequence
<220> FEATURE:
<223> OTHER INFORMATION: Clone 59E07

<400> SEQUENCE: 99

Ser Ala Ser
1
```

<210> SEQ ID NO 100
<211> LENGTH: 11
<212> TYPE: PRT
<213> ORGANISM: Artificial Sequence
<220> FEATURE:
<223> OTHER INFORMATION: Clone 59E07

<400> SEQUENCE: 100

Glu Gly Gly Tyr Ser Ser Gly Asp Arg Asn Val
1               5                   10

<210> SEQ ID NO 101
<211> LENGTH: 9
<212> TYPE: PRT
<213> ORGANISM: Artificial Sequence
<220> FEATURE:
<223> OTHER INFORMATION: Clone 59F10

<400> SEQUENCE: 101

Gly Phe Ser Phe Ser Ser Gly Tyr Tyr
1               5

<210> SEQ ID NO 102
<211> LENGTH: 9
<212> TYPE: PRT
<213> ORGANISM: Artificial Sequence
<220> FEATURE:
<223> OTHER INFORMATION: Clone 59F10

<400> SEQUENCE: 102

Ile Asp Ala Gly Gly Arg Gly Asp Thr
1               5

<210> SEQ ID NO 103
<211> LENGTH: 17
<212> TYPE: PRT
<213> ORGANISM: Artificial Sequence
<220> FEATURE:
<223> OTHER INFORMATION: Clone 59F10

<400> SEQUENCE: 103

Ala Arg Arg Gly Tyr Ser Ser Ile Ser Ser Asn Phe Gly Ala Phe Asn
1               5                   10                  15

Pro

<210> SEQ ID NO 104
<211> LENGTH: 6
<212> TYPE: PRT
<213> ORGANISM: Artificial Sequence
<220> FEATURE:
<223> OTHER INFORMATION: Clone 59F10

<400> SEQUENCE: 104

Gln Ser Ile Ser Ser Tyr
1               5

<210> SEQ ID NO 105
<211> LENGTH: 3
<212> TYPE: PRT
<213> ORGANISM: Artificial Sequence
<220> FEATURE:
<223> OTHER INFORMATION: Clone 59F10

<400> SEQUENCE: 105

Gly Ala Ser

```
<210> SEQ ID NO 106
<211> LENGTH: 12
<212> TYPE: PRT
<213> ORGANISM: Artificial Sequence
<220> FEATURE:
<223> OTHER INFORMATION: Clone 59F10

<400> SEQUENCE: 106

Gln Gln Gly Tyr Thr Ser Ile Tyr Val Asp Asn Ala
1               5                   10

<210> SEQ ID NO 107
<211> LENGTH: 9
<212> TYPE: PRT
<213> ORGANISM: Artificial Sequence
<220> FEATURE:
<223> OTHER INFORMATION: Clone 59G03

<400> SEQUENCE: 107

Gly Phe Ser Phe Asn Ser Asn Tyr Tyr
1               5

<210> SEQ ID NO 108
<211> LENGTH: 9
<212> TYPE: PRT
<213> ORGANISM: Artificial Sequence
<220> FEATURE:
<223> OTHER INFORMATION: Clone 59G03

<400> SEQUENCE: 108

Ile Tyr Gly Gly Thr Thr Val Asn Thr
1               5

<210> SEQ ID NO 109
<211> LENGTH: 15
<212> TYPE: PRT
<213> ORGANISM: Artificial Sequence
<220> FEATURE:
<223> OTHER INFORMATION: Clone 59G03

<400> SEQUENCE: 109

Ala Arg Glu Asp Leu Thr Ala Tyr Ser Ser Tyr Val Ile Thr Leu
1               5                   10                  15

<210> SEQ ID NO 110
<211> LENGTH: 6
<212> TYPE: PRT
<213> ORGANISM: Artificial Sequence
<220> FEATURE:
<223> OTHER INFORMATION: Clone 59G03

<400> SEQUENCE: 110

Glu Thr Ile Tyr Arg Asn
1               5

<210> SEQ ID NO 111
<211> LENGTH: 3
<212> TYPE: PRT
<213> ORGANISM: Artificial Sequence
<220> FEATURE:
<223> OTHER INFORMATION: Clone 59G03

<400> SEQUENCE: 111

Ala Ala Ser
1
```

<210> SEQ ID NO 112
<211> LENGTH: 12
<212> TYPE: PRT
<213> ORGANISM: Artificial Sequence
<220> FEATURE:
<223> OTHER INFORMATION: Clone 59G03

<400> SEQUENCE: 112

Gln Gln Ala Tyr Thr Arg Val Asn Ile Asp Asn Ala
1               5                   10

<210> SEQ ID NO 113
<211> LENGTH: 9
<212> TYPE: PRT
<213> ORGANISM: Artificial Sequence
<220> FEATURE:
<223> OTHER INFORMATION: Clone 77B06

<400> SEQUENCE: 113

Gly Phe Ser Phe Asn Arg Gly Tyr Trp
1               5

<210> SEQ ID NO 114
<211> LENGTH: 7
<212> TYPE: PRT
<213> ORGANISM: Artificial Sequence
<220> FEATURE:
<223> OTHER INFORMATION: Clone 77B06

<400> SEQUENCE: 114

Val Asp Thr Gly Ser Gly Ser
1               5

<210> SEQ ID NO 115
<211> LENGTH: 11
<212> TYPE: PRT
<213> ORGANISM: Artificial Sequence
<220> FEATURE:
<223> OTHER INFORMATION: Clone 77B06

<400> SEQUENCE: 115

Ala Arg Asn Ser Asp Ser Ile Tyr Phe Asn Leu
1               5                   10

<210> SEQ ID NO 116
<211> LENGTH: 6
<212> TYPE: PRT
<213> ORGANISM: Artificial Sequence
<220> FEATURE:
<223> OTHER INFORMATION: Clone 77B06

<400> SEQUENCE: 116

Gln Ser Ile Ser Ser Tyr
1               5

<210> SEQ ID NO 117
<211> LENGTH: 3
<212> TYPE: PRT
<213> ORGANISM: Artificial Sequence
<220> FEATURE:
<223> OTHER INFORMATION: Clone 77B06

<400> SEQUENCE: 117

Arg Ala Ser
1

<210> SEQ ID NO 118
<211> LENGTH: 12
<212> TYPE: PRT
<213> ORGANISM: Artificial Sequence
<220> FEATURE:
<223> OTHER INFORMATION: Clone 77B06

<400> SEQUENCE: 118

Gln Asn Tyr Ala Gly Val Ser Leu Tyr Gly Ala Val
1               5                   10

<210> SEQ ID NO 119
<211> LENGTH: 9
<212> TYPE: PRT
<213> ORGANISM: Artificial Sequence
<220> FEATURE:
<223> OTHER INFORMATION: Clone 80D08

<400> SEQUENCE: 119

Gly Phe Ser Phe Thr Ser Arg Asp Tyr
1               5

<210> SEQ ID NO 120
<211> LENGTH: 7
<212> TYPE: PRT
<213> ORGANISM: Artificial Sequence
<220> FEATURE:
<223> OTHER INFORMATION: Clone 80D08

<400> SEQUENCE: 120

Ile Ala Ile Asp Gly Gly Val
1               5

<210> SEQ ID NO 121
<211> LENGTH: 14
<212> TYPE: PRT
<213> ORGANISM: Artificial Sequence
<220> FEATURE:
<223> OTHER INFORMATION: Clone 80D08

<400> SEQUENCE: 121

Ala Arg Asp Asp Ile Gly Ser Asn Ser Tyr Tyr Asn Asp Leu
1               5                   10

<210> SEQ ID NO 122
<211> LENGTH: 6
<212> TYPE: PRT
<213> ORGANISM: Artificial Sequence
<220> FEATURE:
<223> OTHER INFORMATION: Clone 80D08

<400> SEQUENCE: 122

Gln Asn Ile Tyr Ser Asn
1               5

<210> SEQ ID NO 123
<211> LENGTH: 3
<212> TYPE: PRT
<213> ORGANISM: Artificial Sequence
<220> FEATURE:
<223> OTHER INFORMATION: Clone 80D08

<400> SEQUENCE: 123

Arg Ala Ser
1

```
<210> SEQ ID NO 124
<211> LENGTH: 12
<212> TYPE: PRT
<213> ORGANISM: Artificial Sequence
<220> FEATURE:
<223> OTHER INFORMATION: Clone 80D08

<400> SEQUENCE: 124

Gln Gln Gly Tyr Thr Tyr Ile His Ala Asp Asn Ala
1               5                   10

<210> SEQ ID NO 125
<211> LENGTH: 9
<212> TYPE: PRT
<213> ORGANISM: Artificial Sequence
<220> FEATURE:
<223> OTHER INFORMATION: Clone 80G08

<400> SEQUENCE: 125

Gly Phe Ser Phe Ser Asn Asn Tyr Tyr
1               5

<210> SEQ ID NO 126
<211> LENGTH: 7
<212> TYPE: PRT
<213> ORGANISM: Artificial Sequence
<220> FEATURE:
<223> OTHER INFORMATION: Clone 80G08

<400> SEQUENCE: 126

Ile Tyr Thr Gly Tyr Ser Trp
1               5

<210> SEQ ID NO 127
<211> LENGTH: 12
<212> TYPE: PRT
<213> ORGANISM: Artificial Sequence
<220> FEATURE:
<223> OTHER INFORMATION: Clone 80G08

<400> SEQUENCE: 127

Ala Arg Ala Asp Ser Gly Tyr Ser Gly Phe Asn Leu
1               5                   10

<210> SEQ ID NO 128
<211> LENGTH: 6
<212> TYPE: PRT
<213> ORGANISM: Artificial Sequence
<220> FEATURE:
<223> OTHER INFORMATION: Clone 80G08

<400> SEQUENCE: 128

Gln Ser Ile Asp Ser Arg
1               5

<210> SEQ ID NO 129
<211> LENGTH: 3
<212> TYPE: PRT
<213> ORGANISM: Artificial Sequence
<220> FEATURE:
<223> OTHER INFORMATION: Clone 80G08

<400> SEQUENCE: 129

Gly Ala Ser
1

<210> SEQ ID NO 130
```

```
<211> LENGTH: 13
<212> TYPE: PRT
<213> ORGANISM: Artificial Sequence
<220> FEATURE:
<223> OTHER INFORMATION: Clone 80G08

<400> SEQUENCE: 130

Gln Cys Ser Val Thr Ile Ser Thr Gly Val Gly Gly Ala
1               5                   10

<210> SEQ ID NO 131
<211> LENGTH: 9
<212> TYPE: PRT
<213> ORGANISM: Artificial Sequence
<220> FEATURE:
<223> OTHER INFORMATION: Clone 81E11

<400> SEQUENCE: 131

Gly Phe Ser Phe Ser Ser Ser Tyr Trp
1               5

<210> SEQ ID NO 132
<211> LENGTH: 7
<212> TYPE: PRT
<213> ORGANISM: Artificial Sequence
<220> FEATURE:
<223> OTHER INFORMATION: Clone 81E11

<400> SEQUENCE: 132

Ile Tyr Thr Thr Thr Asn Asn
1               5

<210> SEQ ID NO 133
<211> LENGTH: 12
<212> TYPE: PRT
<213> ORGANISM: Artificial Sequence
<220> FEATURE:
<223> OTHER INFORMATION: Clone 81E11

<400> SEQUENCE: 133

Ala Arg Glu Asp Tyr Asp Tyr Tyr Ser Phe His Pro
1               5                   10

<210> SEQ ID NO 134
<211> LENGTH: 6
<212> TYPE: PRT
<213> ORGANISM: Artificial Sequence
<220> FEATURE:
<223> OTHER INFORMATION: Clone 81E11

<400> SEQUENCE: 134

Gln Ser Ile Gly Thr Tyr
1               5

<210> SEQ ID NO 135
<211> LENGTH: 3
<212> TYPE: PRT
<213> ORGANISM: Artificial Sequence
<220> FEATURE:
<223> OTHER INFORMATION: Clone 81E11

<400> SEQUENCE: 135

Lys Ala Ser
1

<210> SEQ ID NO 136
<211> LENGTH: 12
```

```
<212> TYPE: PRT
<213> ORGANISM: Artificial Sequence
<220> FEATURE:
<223> OTHER INFORMATION: Clone 81E11

<400> SEQUENCE: 136

Gln Gln Ala Tyr Thr His Thr Tyr Leu Asp Asn Gly
1               5                   10

<210> SEQ ID NO 137
<211> LENGTH: 8
<212> TYPE: PRT
<213> ORGANISM: Artificial Sequence
<220> FEATURE:
<223> OTHER INFORMATION: Clone 82C08

<400> SEQUENCE: 137

Gly Phe Thr Phe Ser Ser Tyr Trp
1               5

<210> SEQ ID NO 138
<211> LENGTH: 8
<212> TYPE: PRT
<213> ORGANISM: Artificial Sequence
<220> FEATURE:
<223> OTHER INFORMATION: Clone 82C08

<400> SEQUENCE: 138

Ile Phe Thr Ser Ser Ile Thr Phe
1               5

<210> SEQ ID NO 139
<211> LENGTH: 13
<212> TYPE: PRT
<213> ORGANISM: Artificial Sequence
<220> FEATURE:
<223> OTHER INFORMATION: Clone 82C08

<400> SEQUENCE: 139

Ala Arg Asp Leu Ser Ser Thr Ser Tyr Tyr Phe Asn Leu
1               5                   10

<210> SEQ ID NO 140
<211> LENGTH: 6
<212> TYPE: PRT
<213> ORGANISM: Artificial Sequence
<220> FEATURE:
<223> OTHER INFORMATION: Clone 82C08

<400> SEQUENCE: 140

Glu Thr Val Ser Tyr Arg
1               5

<210> SEQ ID NO 141
<211> LENGTH: 3
<212> TYPE: PRT
<213> ORGANISM: Artificial Sequence
<220> FEATURE:
<223> OTHER INFORMATION: Clone 82C08

<400> SEQUENCE: 141

Asp Ala Ser
1

<210> SEQ ID NO 142
<211> LENGTH: 12
<212> TYPE: PRT
```

```
<213> ORGANISM: Artificial Sequence
<220> FEATURE:
<223> OTHER INFORMATION: Clone 82C08

<400> SEQUENCE: 142

Gln Gln Gly Tyr Thr Arg Asn Asn Ile Asp Asn Thr
1               5                   10

<210> SEQ ID NO 143
<211> LENGTH: 9
<212> TYPE: PRT
<213> ORGANISM: Artificial Sequence
<220> FEATURE:
<223> OTHER INFORMATION: Clone 82F02

<400> SEQUENCE: 143

Gly Phe Ser Phe Ser Gly Asn Tyr His
1               5

<210> SEQ ID NO 144
<211> LENGTH: 8
<212> TYPE: PRT
<213> ORGANISM: Artificial Sequence
<220> FEATURE:
<223> OTHER INFORMATION: Clone 82F02

<400> SEQUENCE: 144

Ile His Thr Asp Ser Gly Arg Thr
1               5

<210> SEQ ID NO 145
<211> LENGTH: 14
<212> TYPE: PRT
<213> ORGANISM: Artificial Sequence
<220> FEATURE:
<223> OTHER INFORMATION: Clone 82F02

<400> SEQUENCE: 145

Arg Gly Val Ser Ser Val Tyr Trp Arg Thr Tyr Phe Asn Leu
1               5                   10

<210> SEQ ID NO 146
<211> LENGTH: 6
<212> TYPE: PRT
<213> ORGANISM: Artificial Sequence
<220> FEATURE:
<223> OTHER INFORMATION: Clone 82F02

<400> SEQUENCE: 146

Gln Thr Ile Gly Ser Asn
1               5

<210> SEQ ID NO 147
<211> LENGTH: 3
<212> TYPE: PRT
<213> ORGANISM: Artificial Sequence
<220> FEATURE:
<223> OTHER INFORMATION: Clone 82F02

<400> SEQUENCE: 147

Gly Ala Ser
1

<210> SEQ ID NO 148
<211> LENGTH: 12
<212> TYPE: PRT
<213> ORGANISM: Artificial Sequence
```

```
<220> FEATURE:
<223> OTHER INFORMATION: Clone 82F02

<400> SEQUENCE: 148

Gln Ser Ala Tyr Trp Leu Asp Ser Gly Asp Asn Gly
1               5                   10

<210> SEQ ID NO 149
<211> LENGTH: 9
<212> TYPE: PRT
<213> ORGANISM: Artificial Sequence
<220> FEATURE:
<223> OTHER INFORMATION: Clone 99A09

<400> SEQUENCE: 149

Gly Phe Ser Phe Ser Asn Asn Tyr Trp
1               5

<210> SEQ ID NO 150
<211> LENGTH: 9
<212> TYPE: PRT
<213> ORGANISM: Artificial Sequence
<220> FEATURE:
<223> OTHER INFORMATION: Clone 99A09

<400> SEQUENCE: 150

Ile Tyr Leu Gly Ser Ser Gly Tyr Thr
1               5

<210> SEQ ID NO 151
<211> LENGTH: 20
<212> TYPE: PRT
<213> ORGANISM: Artificial Sequence
<220> FEATURE:
<223> OTHER INFORMATION: Clone 99A09

<400> SEQUENCE: 151

Ala Arg Ser Tyr Tyr Thr Tyr Gly Tyr Ala Gly Tyr Ile Tyr Pro Thr
1               5                   10                  15

Tyr Phe Asn Leu
            20

<210> SEQ ID NO 152
<211> LENGTH: 6
<212> TYPE: PRT
<213> ORGANISM: Artificial Sequence
<220> FEATURE:
<223> OTHER INFORMATION: Clone 99A09

<400> SEQUENCE: 152

Gln Ser Ile Ser Ser Tyr
1               5

<210> SEQ ID NO 153
<211> LENGTH: 3
<212> TYPE: PRT
<213> ORGANISM: Artificial Sequence
<220> FEATURE:
<223> OTHER INFORMATION: Clone 99A09

<400> SEQUENCE: 153

Lys Ala Ser
1

<210> SEQ ID NO 154
<211> LENGTH: 15
```

```
<212> TYPE: PRT
<213> ORGANISM: Artificial Sequence
<220> FEATURE:
<223> OTHER INFORMATION: Clone 99A09

<400> SEQUENCE: 154

Gln Thr Tyr Asp Tyr Ser Ser Ser Asn Ser Tyr Gly Ser Asn Ala
1               5                   10                  15

<210> SEQ ID NO 155
<211> LENGTH: 9
<212> TYPE: PRT
<213> ORGANISM: Artificial Sequence
<220> FEATURE:
<223> OTHER INFORMATION: Clone SD215

<400> SEQUENCE: 155

Gly Phe Ser Phe Ser Ser Gly Phe Tyr
1               5

<210> SEQ ID NO 156
<211> LENGTH: 8
<212> TYPE: PRT
<213> ORGANISM: Artificial Sequence
<220> FEATURE:
<223> OTHER INFORMATION: Clone SD215

<400> SEQUENCE: 156

Ile Tyr Thr Thr Ser Thr Thr Thr
1               5

<210> SEQ ID NO 157
<211> LENGTH: 16
<212> TYPE: PRT
<213> ORGANISM: Artificial Sequence
<220> FEATURE:
<223> OTHER INFORMATION: Clone SD215

<400> SEQUENCE: 157

Arg Ala Gly Tyr Val Asp Tyr Gly Tyr Ala Pro Tyr Asp Met Asp Leu
1               5                   10                  15

<210> SEQ ID NO 158
<211> LENGTH: 6
<212> TYPE: PRT
<213> ORGANISM: Artificial Sequence
<220> FEATURE:
<223> OTHER INFORMATION: Clone SD215

<400> SEQUENCE: 158

Gln Ser Ile Ser Gly Tyr
1               5

<210> SEQ ID NO 159
<211> LENGTH: 3
<212> TYPE: PRT
<213> ORGANISM: Artificial Sequence
<220> FEATURE:
<223> OTHER INFORMATION: Clone SD215

<400> SEQUENCE: 159

Arg Ala Ser
1

<210> SEQ ID NO 160
<211> LENGTH: 12
<212> TYPE: PRT
```

```
<213> ORGANISM: Artificial Sequence
<220> FEATURE:
<223> OTHER INFORMATION: Clone SD215

<400> SEQUENCE: 160

Gln Gln Gly Tyr Ser Met Tyr Tyr Ile Glu Thr Ser
1               5                   10

<210> SEQ ID NO 161
<211> LENGTH: 8
<212> TYPE: PRT
<213> ORGANISM: Artificial Sequence
<220> FEATURE:
<223> OTHER INFORMATION: Clone SD232

<400> SEQUENCE: 161

Gly Phe Ser Phe Ser Ser Tyr Tyr
1               5

<210> SEQ ID NO 162
<211> LENGTH: 7
<212> TYPE: PRT
<213> ORGANISM: Artificial Sequence
<220> FEATURE:
<223> OTHER INFORMATION: Clone SD232

<400> SEQUENCE: 162

Ile His Thr Asp Ser Gly Arg
1               5

<210> SEQ ID NO 163
<211> LENGTH: 15
<212> TYPE: PRT
<213> ORGANISM: Artificial Sequence
<220> FEATURE:
<223> OTHER INFORMATION: Clone SD232

<400> SEQUENCE: 163

Ala Arg Gly Ile Ser Ser Val Tyr Trp Arg Thr Tyr Phe Asn Leu
1               5                   10                  15

<210> SEQ ID NO 164
<211> LENGTH: 6
<212> TYPE: PRT
<213> ORGANISM: Artificial Sequence
<220> FEATURE:
<223> OTHER INFORMATION: Clone SD232

<400> SEQUENCE: 164

Gln Ser Ile Gly Ser Asn
1               5

<210> SEQ ID NO 165
<211> LENGTH: 3
<212> TYPE: PRT
<213> ORGANISM: Artificial Sequence
<220> FEATURE:
<223> OTHER INFORMATION: Clone SD232

<400> SEQUENCE: 165

Gly Ala Ser
1

<210> SEQ ID NO 166
<211> LENGTH: 12
<212> TYPE: PRT
<213> ORGANISM: Artificial Sequence
```

```
<220> FEATURE:
<223> OTHER INFORMATION: Clone SD232

<400> SEQUENCE: 166

Gln Ser Ala Tyr Trp Leu Asp Ser Gly Asp Asn Gly
1               5                   10

<210> SEQ ID NO 167
<211> LENGTH: 9
<212> TYPE: PRT
<213> ORGANISM: Artificial Sequence
<220> FEATURE:
<223> OTHER INFORMATION: Clone SD272

<400> SEQUENCE: 167

Gly Phe Ser Phe Asn Ala Gly Tyr Trp
1               5

<210> SEQ ID NO 168
<211> LENGTH: 8
<212> TYPE: PRT
<213> ORGANISM: Artificial Sequence
<220> FEATURE:
<223> OTHER INFORMATION: Clone SD272

<400> SEQUENCE: 168

Ile Asp Thr Gly Ser Gly Val Ser
1               5

<210> SEQ ID NO 169
<211> LENGTH: 10
<212> TYPE: PRT
<213> ORGANISM: Artificial Sequence
<220> FEATURE:
<223> OTHER INFORMATION: Clone SD272

<400> SEQUENCE: 169

Arg Asn Thr Asp Ser Ile Tyr Phe Asn Leu
1               5                   10

<210> SEQ ID NO 170
<211> LENGTH: 6
<212> TYPE: PRT
<213> ORGANISM: Artificial Sequence
<220> FEATURE:
<223> OTHER INFORMATION: Clone SD272

<400> SEQUENCE: 170

Gln Thr Ile Tyr Ser Tyr
1               5

<210> SEQ ID NO 171
<211> LENGTH: 3
<212> TYPE: PRT
<213> ORGANISM: Artificial Sequence
<220> FEATURE:
<223> OTHER INFORMATION: Clone SD272

<400> SEQUENCE: 171

Lys Ala Ser
1

<210> SEQ ID NO 172
<211> LENGTH: 12
<212> TYPE: PRT
<213> ORGANISM: Artificial Sequence
<220> FEATURE:
```

<223> OTHER INFORMATION: Clone SD272

<400> SEQUENCE: 172

Gln Thr Tyr Ala Gly Val Ser Ile Tyr Gly Ala Ala
1               5                   10

<210> SEQ ID NO 173
<211> LENGTH: 9
<212> TYPE: PRT
<213> ORGANISM: Artificial Sequence
<220> FEATURE:
<223> OTHER INFORMATION: Clone SD312

<400> SEQUENCE: 173

Gly Phe Ser Phe Ser Ser Gly Tyr Tyr
1               5

<210> SEQ ID NO 174
<211> LENGTH: 9
<212> TYPE: PRT
<213> ORGANISM: Artificial Sequence
<220> FEATURE:
<223> OTHER INFORMATION: Clone SD312

<400> SEQUENCE: 174

Ile Asp Ala Gly Gly Arg Gly Asp Thr
1               5

<210> SEQ ID NO 175
<211> LENGTH: 17
<212> TYPE: PRT
<213> ORGANISM: Artificial Sequence
<220> FEATURE:
<223> OTHER INFORMATION: Clone SD312

<400> SEQUENCE: 175

Ala Arg Arg Gly Tyr Ser Ser Ile Ser Ser Asn Phe Gly Ala Phe Asn
1               5                   10                  15

Pro

<210> SEQ ID NO 176
<211> LENGTH: 6
<212> TYPE: PRT
<213> ORGANISM: Artificial Sequence
<220> FEATURE:
<223> OTHER INFORMATION: Clone SD312

<400> SEQUENCE: 176

Gln Ser Ile Ser Ser Tyr
1               5

<210> SEQ ID NO 177
<211> LENGTH: 3
<212> TYPE: PRT
<213> ORGANISM: Artificial Sequence
<220> FEATURE:
<223> OTHER INFORMATION: Clone SD312

<400> SEQUENCE: 177

Gly Ala Ser
1

<210> SEQ ID NO 178
<211> LENGTH: 12
<212> TYPE: PRT
<213> ORGANISM: Artificial Sequence

```
<220> FEATURE:
<223> OTHER INFORMATION: Clone SD312

<400> SEQUENCE: 178

Gln Gln Gly Tyr Thr Ser Ile Tyr Val Asp Asn Ala
1               5                   10

<210> SEQ ID NO 179
<211> LENGTH: 9
<212> TYPE: PRT
<213> ORGANISM: Artificial Sequence
<220> FEATURE:
<223> OTHER INFORMATION: Clone SD331

<400> SEQUENCE: 179

Gly Phe Asp Phe Thr Ser Tyr Tyr Tyr
1               5

<210> SEQ ID NO 180
<211> LENGTH: 8
<212> TYPE: PRT
<213> ORGANISM: Artificial Sequence
<220> FEATURE:
<223> OTHER INFORMATION: Clone SD331

<400> SEQUENCE: 180

Ile Glu Ser Ser Ser Gly Arg Ile
1               5

<210> SEQ ID NO 181
<211> LENGTH: 13
<212> TYPE: PRT
<213> ORGANISM: Artificial Sequence
<220> FEATURE:
<223> OTHER INFORMATION: Clone SD331

<400> SEQUENCE: 181

Arg Asp Ile Ser Ser Ser Gly Tyr His Gly Phe Lys Trp
1               5                   10

<210> SEQ ID NO 182
<211> LENGTH: 6
<212> TYPE: PRT
<213> ORGANISM: Artificial Sequence
<220> FEATURE:
<223> OTHER INFORMATION: Clone SD331

<400> SEQUENCE: 182

Gln Ser Ile Ser Asn Tyr
1               5

<210> SEQ ID NO 183
<211> LENGTH: 3
<212> TYPE: PRT
<213> ORGANISM: Artificial Sequence
<220> FEATURE:
<223> OTHER INFORMATION: Clone SD331

<400> SEQUENCE: 183

Arg Ala Ser
1

<210> SEQ ID NO 184
<211> LENGTH: 12
<212> TYPE: PRT
<213> ORGANISM: Artificial Sequence
<220> FEATURE:
```

-continued

<223> OTHER INFORMATION: Clone SD331

<400> SEQUENCE: 184

Gln Gln Val Tyr Ser Ile Thr Asn Ile Asp Asn Ala
1               5                   10

<210> SEQ ID NO 185

<400> SEQUENCE: 185

000

<210> SEQ ID NO 186
<211> LENGTH: 467
<212> TYPE: PRT
<213> ORGANISM: Artificial Sequence
<220> FEATURE:
<223> OTHER INFORMATION: Heavy Chain Humanized Variant

<400> SEQUENCE: 186

Met Gly Trp Thr Leu Val Phe Leu Phe Leu Ser Val Thr Ala Gly
1               5                   10                  15

Val His Ser Gln Gln Gln Leu Val Glu Ser Gly Gly Leu Val Lys
                20                  25                  30

Pro Gly Gly Thr Leu Thr Leu Thr Cys Thr Val Ser Gly Phe Tyr Phe
            35                  40                  45

Asn Arg Gly Tyr Trp Ile Cys Trp Val Arg Gln Ala Pro Gly Lys Gly
        50                  55                  60

Leu Glu Trp Ile Gly Cys Ile Asp Thr Gly Ser Gly Val Pro Tyr Tyr
65                  70                  75                  80

Ala Asn Trp Ala Lys Gly Arg Phe Thr Ile Ser Lys Thr Ser Ser Thr
                85                  90                  95

Ala Val Thr Leu Gln Met Thr Ser Leu Thr Ala Ala Asp Thr Ala Thr
            100                 105                 110

Tyr Phe Cys Ala Arg Asn Ser Asp Ser Ile Tyr Phe Asn Leu Trp Gly
        115                 120                 125

Pro Gly Thr Leu Val Thr Val Ser Ser Ala Ser Thr Lys Gly Pro Ser
130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val

```
                290                 295                 300
His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
                340                 345                 350

Glu Lys Thr Ile Ser Lys Ala Lys Gly Gln Pro Arg Glu Pro Gln Val
            355                 360                 365

Tyr Thr Leu Pro Pro Ser Arg Asp Glu Leu Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
            450                 455                 460

Pro Gly Lys
465

<210> SEQ ID NO 187
<211> LENGTH: 468
<212> TYPE: PRT
<213> ORGANISM: Artificial Sequence
<220> FEATURE:
<223> OTHER INFORMATION: Heavy Chain Humanized Variant

<400> SEQUENCE: 187

Met Gly Trp Thr Leu Val Phe Leu Phe Leu Leu Ser Val Thr Ala Gly
1               5                   10                  15

Val His Ser Glu Val Gln Leu Val Glu Ser Gly Gly Gly Leu Val Lys
                20                  25                  30

Pro Gly Gly Ser Leu Arg Leu Ser Cys Thr Ala Ser Gly Phe Tyr Phe
            35                  40                  45

Asn Arg Gly Tyr Trp Ile Cys Trp Leu Arg Gln Ala Pro Gly Lys Gly
        50                  55                  60

Leu Glu Trp Val Ala Cys Ile Asp Thr Gly Ser Gly Val Pro Tyr Tyr
65                  70                  75                  80

Ala Asn Trp Ala Lys Gly Arg Phe Thr Val Ser Arg Asp Asn Ala Lys
                85                  90                  95

Asn Ser Leu Phe Leu Gln Met Asn Ser Leu Arg Ala Glu Asp Thr Ala
                100                 105                 110

Val Tyr Tyr Cys Ala Arg Asn Ser Asp Ser Ile Tyr Phe Asn Leu Trp
            115                 120                 125

Gly Pro Gly Thr Leu Val Thr Val Ser Ser Ala Ser Thr Lys Gly Pro
130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
```

```
                180             185             190
Ala Val Leu Gln Ser Ser Gly Leu Tyr Ser Leu Ser Val Val Thr
            195                 200                 205
Val Pro Ser Ser Leu Gly Thr Gln Thr Tyr Ile Cys Asn Val Asn
        210                 215                 220
His Lys Pro Ser Asn Thr Lys Val Asp Lys Val Glu Pro Lys Ser
225                 230                 235                 240
Cys Asp Lys Thr His Thr Cys Pro Pro Cys Pro Ala Pro Glu Leu Leu
                245                 250                 255
Gly Gly Pro Ser Val Phe Leu Phe Pro Pro Lys Pro Lys Asp Thr Leu
            260                 265                 270
Met Ile Ser Arg Thr Pro Glu Val Thr Cys Val Val Val Asp Val Ser
        275                 280                 285
His Glu Asp Pro Glu Val Lys Phe Asn Trp Tyr Val Asp Gly Val Glu
    290                 295                 300
Val His Asn Ala Lys Thr Lys Pro Arg Glu Glu Gln Tyr Asn Ser Thr
305                 310                 315                 320
Tyr Arg Val Val Ser Val Leu Thr Val Leu His Gln Asp Trp Leu Asn
                325                 330                 335
Gly Lys Glu Tyr Lys Cys Lys Val Ser Asn Lys Ala Leu Pro Ala Pro
            340                 345                 350
Ile Glu Lys Thr Ile Ser Lys Ala Lys Gly Gln Pro Arg Glu Pro Gln
        355                 360                 365
Val Tyr Thr Leu Pro Pro Ser Arg Asp Glu Leu Thr Lys Asn Gln Val
    370                 375                 380
Ser Leu Thr Cys Leu Val Lys Gly Phe Tyr Pro Ser Asp Ile Ala Val
385                 390                 395                 400
Glu Trp Glu Ser Asn Gly Gln Pro Glu Asn Asn Tyr Lys Thr Thr Pro
                405                 410                 415
Pro Val Leu Asp Ser Asp Gly Ser Phe Phe Leu Tyr Ser Lys Leu Thr
            420                 425                 430
Val Asp Lys Ser Arg Trp Gln Gln Gly Asn Val Phe Ser Cys Ser Val
        435                 440                 445
Met His Glu Ala Leu His Asn His Tyr Thr Gln Lys Ser Leu Ser Leu
    450                 455                 460
Ser Pro Gly Lys
465

<210> SEQ ID NO 188
<211> LENGTH: 468
<212> TYPE: PRT
<213> ORGANISM: Artificial Sequence
<220> FEATURE:
<223> OTHER INFORMATION: Heavy Chain Humanized Variant

<400> SEQUENCE: 188

Met Gly Trp Thr Leu Val Phe Leu Phe Leu Leu Ser Val Thr Ala Gly
1               5                   10                  15
Val His Ser Gln Val Gln Leu Val Glu Ser Gly Gly Gly Val Val Gln
            20                  25                  30
Pro Gly Arg Ser Leu Arg Leu Pro Cys Ala Ala Ser Gly Phe Tyr Phe
        35                  40                  45
Asn Arg Gly Tyr Trp Ile Cys Trp Val Arg Gln Ala Pro Gly Lys Gly
    50                  55                  60
Leu Glu Trp Val Ala Cys Ile Asp Thr Gly Ser Gly Val Pro Tyr Tyr
```

```
                65                  70                  75                  80
Ala Asn Trp Ala Lys Gly Arg Phe Thr Ile Ser Arg Asp Thr Ser Lys
                    85                  90                  95

Asn Thr Leu Tyr Leu Gln Met Asp Ser Leu Arg Ala Glu Asp Thr Ala
                100                 105                 110

Val Tyr Tyr Cys Ala Arg Asn Ser Asp Ser Ile Tyr Phe Asn Leu Trp
                115                 120                 125

Gly Arg Gly Thr Leu Val Thr Val Ser Ser Ala Ser Thr Lys Gly Pro
            130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
                180                 185                 190

Ala Val Leu Gln Ser Ser Gly Leu Tyr Ser Leu Ser Ser Val Val Thr
                195                 200                 205

Val Pro Ser Ser Ser Leu Gly Thr Gln Thr Tyr Ile Cys Asn Val Asn
            210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
                260                 265                 270

Met Ile Ser Arg Thr Pro Glu Val Thr Cys Val Val Val Asp Val Ser
            275                 280                 285

His Glu Asp Pro Glu Val Lys Phe Asn Trp Tyr Val Asp Gly Val Glu
            290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
                340                 345                 350

Ile Glu Lys Thr Ile Ser Lys Ala Lys Gly Gln Pro Arg Glu Pro Gln
                355                 360                 365

Val Tyr Thr Leu Pro Pro Ser Arg Asp Glu Leu Thr Lys Asn Gln Val
            370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
                420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
            450                 455                 460

Ser Pro Gly Lys
465

<210> SEQ ID NO 189
```

<211> LENGTH: 468
<212> TYPE: PRT
<213> ORGANISM: Artificial Sequence
<220> FEATURE:
<223> OTHER INFORMATION: Heavy Chain Humanized Variant

<400> SEQUENCE: 189

```
Met Gly Trp Thr Leu Val Phe Leu Phe Leu Ser Val Thr Ala Gly
1               5                   10                  15

Val His Ser Glu Val Gln Leu Val Glu Ser Gly Gly Asp Leu Ala Gln
            20                  25                  30

Pro Gly Gly Ser Leu Arg Leu Ser Cys Ala Val Ser Gly Phe Tyr Phe
        35                  40                  45

Asn Arg Gly Tyr Trp Ile Cys Trp Val Arg Gln Ala Pro Gly Lys Gly
    50                  55                  60

Leu Glu Trp Val Ser Cys Ile Asp Thr Gly Ser Gly Val Pro Tyr Tyr
65                  70                  75                  80

Ala Asn Trp Ala Lys Gly Arg Phe Thr Ile Ser Arg Asp Asn Ser Lys
                85                  90                  95

Asn Thr Val Tyr Leu Gln Met Thr Ser Leu Arg Ala Glu Asp Thr Ala
            100                 105                 110

Leu Tyr Phe Cys Ala Arg Asn Ser Asp Ser Ile Tyr Phe Asn Leu Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380
```

```
Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465

<210> SEQ ID NO 190
<211> LENGTH: 468
<212> TYPE: PRT
<213> ORGANISM: Artificial Sequence
<220> FEATURE:
<223> OTHER INFORMATION: Heavy Chain Humanized Variant

<400> SEQUENCE: 190

Met Gly Trp Thr Leu Val Phe Leu Phe Leu Leu Ser Val Thr Ala Gly
1               5                   10                  15

Val His Ser Gln Val Gln Leu Val Glu Ser Gly Gly Gly Leu Val Lys
            20                  25                  30

Pro Gly Gly Ser Leu Arg Leu Ser Cys Ala Ala Ser Gly Phe Tyr Phe
        35                  40                  45

Asn Arg Gly Tyr Trp Ile Cys Trp Ile Arg Gln Ala Pro Gly Lys Gly
    50                  55                  60

Leu Glu Trp Val Ser Cys Ile Asp Thr Gly Ser Gly Val Pro Tyr Tyr
65                  70                  75                  80

Ala Asn Trp Ala Lys Gly Arg Phe Thr Ile Ser Arg Asp Asn Ala Lys
                85                  90                  95

Asn Ser Leu Tyr Leu Gln Met Asn Ser Leu Arg Thr Glu Asp Thr Ala
            100                 105                 110

Val Tyr Phe Cys Ala Arg Asn Ser Asp Ser Ile Tyr Phe Asn Leu Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270
```

```
Met Ile Ser Arg Thr Pro Glu Val Thr Cys Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465

<210> SEQ ID NO 191
<211> LENGTH: 468
<212> TYPE: PRT
<213> ORGANISM: Artificial Sequence
<220> FEATURE:
<223> OTHER INFORMATION: Heavy Chain Humanized Variant

<400> SEQUENCE: 191

Met Gly Trp Thr Leu Val Phe Leu Phe Leu Leu Ser Val Thr Ala Gly
1               5                   10                  15

Val His Ser Glu Val Gln Leu Val Glu Ser Gly Gly Gly Leu Val Lys
            20                  25                  30

Pro Gly Gly Ser Leu Arg Leu Ser Cys Ala Val Ser Gly Phe Tyr Phe
        35                  40                  45

Asn Arg Gly Tyr Trp Ile Cys Trp Val Arg Gln Ala Pro Gly Lys Gly
    50                  55                  60

Leu Glu Trp Ile Gly Cys Ile Asp Thr Gly Ser Gly Val Pro Tyr Tyr
65                  70                  75                  80

Ala Asn Trp Ala Lys Gly Arg Phe Thr Ile Ser Arg His Thr Ser Lys
                85                  90                  95

Thr Thr Leu Thr Leu Gln Met Asn Ser Leu Arg Ala Glu Asp Thr Ala
            100                 105                 110

Ser Tyr Phe Cys Ala Arg Asn Ser Asp Ser Ile Tyr Phe Asn Leu Trp
        115                 120                 125

Gly Pro Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160
```

```
Ala Ala Leu Gly Cys Leu Val Lys Asp Tyr Phe Pro Glu Pro Val Thr
            165                 170                 175

Val Ser Trp Asn Ser Gly Ala Leu Thr Ser Gly Val His Thr Phe Pro
        180                 185                 190

Ala Val Leu Gln Ser Ser Gly Leu Tyr Ser Leu Ser Ser Val Val Thr
        195                 200                 205

Val Pro Ser Ser Leu Gly Thr Gln Thr Tyr Ile Cys Asn Val Asn
210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
            245                 250                 255

Gly Gly Pro Ser Val Phe Leu Phe Pro Pro Lys Pro Lys Asp Thr Leu
        260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
            325                 330                 335

Gly Lys Glu Tyr Lys Cys Lys Val Ser Asn Lys Ala Leu Pro Ala Pro
        340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
        370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
            405                 410                 415

Pro Val Leu Asp Ser Asp Gly Ser Phe Phe Leu Tyr Ser Lys Leu Thr
        420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
450                 455                 460

Ser Pro Gly Lys
465

<210> SEQ ID NO 192
<211> LENGTH: 237
<212> TYPE: PRT
<213> ORGANISM: Artificial Sequence
<220> FEATURE:
<223> OTHER INFORMATION: Heavy Chain Humanized Variant

<400> SEQUENCE: 192

Met Val Ser Ser Ala Gln Phe Leu Gly Leu Leu Leu Leu Cys Phe Gln
1               5                   10                  15

Gly Thr Arg Cys Asp Ile Val Met Thr Gln Thr Pro Ala Ser Val Ser
            20                  25                  30

Glu Pro Val Gly Gly Thr Val Thr Ile Lys Cys Gln Ala Ser Gln Ser
        35                  40                  45
```

```
Ile Gly Gly Tyr Leu Ser Trp Tyr Gln Gln Lys Pro Gly Gln Pro Pro
        50                  55                  60

Lys Leu Leu Ile Tyr Lys Ala Ser Thr Leu Ala Ser Gly Val Pro Ser
 65                  70                  75                  80

Arg Phe Lys Gly Ser Gly Ser Gly Thr Asp Phe Thr Leu Thr Ile Ser
                 85                  90                  95

Asp Leu Glu Cys Ala Asp Ala Ala Thr Tyr Tyr Cys Gln Asn Tyr Ala
                100                 105                 110

Gly Val Ser Ile Tyr Gly Ala Val Phe Gly Gly Thr Lys Val Val
                115                 120                 125

Val Val Arg Thr Val Ala Ala Pro Ser Val Phe Ile Phe Pro Pro Ser
        130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
                180                 185                 190

Asp Ser Thr Tyr Ser Leu Ser Ser Thr Leu Thr Leu Ser Lys Ala Asp
                195                 200                 205

Tyr Glu Lys His Lys Val Tyr Ala Cys Glu Val Thr His Gln Gly Leu
        210                 215                 220

Ser Ser Pro Val Thr Lys Ser Phe Asn Arg Gly Glu Cys
225                 230                 235

<210> SEQ ID NO 193
<211> LENGTH: 237
<212> TYPE: PRT
<213> ORGANISM: Artificial Sequence
<220> FEATURE:
<223> OTHER INFORMATION: Heavy Chain Humanized Variant

<400> SEQUENCE: 193

Met Val Ser Ser Ala Gln Phe Leu Gly Leu Leu Leu Cys Phe Gln
 1               5                  10                  15

Gly Thr Arg Cys Asp Ile Val Met Thr Gln Ser Pro Ser Ser Leu Ser
                 20                  25                  30

Ala Ser Val Gly Asp Arg Val Thr Ile Thr Cys Gln Ala Ser Gln Ser
        35                  40                  45

Ile Gly Gly Tyr Leu Ser Trp Tyr Gln Gln Lys Pro Gly Lys Ala Pro
        50                  55                  60

Lys Leu Leu Ile Tyr Lys Ala Ser Thr Leu Ala Ser Gly Val Pro Ser
 65                  70                  75                  80

Arg Phe Ser Gly Ser Gly Ser Gly Thr Asp Phe Thr Leu Thr Ile Ser
                 85                  90                  95

Ser Leu Gln Pro Glu Asp Phe Ala Thr Tyr Tyr Cys Gln Asn Tyr Ala
                100                 105                 110

Gly Val Ser Ile Tyr Gly Ala Val Phe Gly Gly Thr Lys Val Val
                115                 120                 125

Ile Lys Arg Thr Val Ala Ala Pro Ser Val Phe Ile Phe Pro Pro Ser
        130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175
```

```
Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
            195                 200                 205

Tyr Glu Lys His Lys Val Tyr Ala Cys Glu Val Thr His Gln Gly Leu
        210                 215                 220

Ser Ser Pro Val Thr Lys Ser Phe Asn Arg Gly Glu Cys
225                 230                 235
```

<210> SEQ ID NO 194
<211> LENGTH: 237
<212> TYPE: PRT
<213> ORGANISM: Artificial Sequence
<220> FEATURE:
<223> OTHER INFORMATION: Heavy Chain Humanized Variant

<400> SEQUENCE: 194

```
Met Val Ser Ser Ala Gln Phe Leu Gly Leu Leu Leu Leu Cys Phe Gln
1               5                   10                  15

Gly Thr Arg Cys Asp Ile Val Leu Thr Gln Ser Pro Ser Ser Leu Ser
            20                  25                  30

Ala Ser Val Gly Asp Arg Ile Thr Ile Thr Cys Gln Ala Ser Gln Ser
        35                  40                  45

Ile Gly Gly Tyr Leu Ser Trp Tyr Gln Gln Lys Pro Gly Thr Pro Pro
    50                  55                  60

Lys Leu Leu Ile Tyr Lys Ala Ser Thr Leu Ala Ser Gly Val Pro Ser
65                  70                  75                  80

Arg Phe Ser Gly Ser Gly Ser Gly Thr Asp Phe Thr Leu Thr Ile Ser
                85                  90                  95

Arg Leu Gln Pro Glu Asp Val Ala Thr Tyr Tyr Cys Gln Asn Tyr Ala
            100                 105                 110

Gly Val Ser Ile Tyr Gly Ala Val Phe Gly Gly Gly Thr Lys Leu Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
            195                 200                 205

Tyr Glu Lys His Lys Val Tyr Ala Cys Glu Val Thr His Gln Gly Leu
        210                 215                 220

Ser Ser Pro Val Thr Lys Ser Phe Asn Arg Gly Glu Cys
225                 230                 235
```

<210> SEQ ID NO 195
<211> LENGTH: 237
<212> TYPE: PRT
<213> ORGANISM: Artificial Sequence
<220> FEATURE:
<223> OTHER INFORMATION: Heavy Chain Humanized Variant

<400> SEQUENCE: 195

Met Val Ser Ser Ala Gln Phe Leu Gly Leu Leu Leu Leu Cys Phe Gln

```
1               5                   10                  15
Gly Thr Arg Cys Asp Ile Gln Met Thr Gln Ser Pro Ser Ser Leu Ser
                20                  25                  30

Ala Ser Val Gly Asp Arg Ile Thr Ile Thr Cys Gln Ala Ser Gln Ser
                35                  40                  45

Ile Gly Gly Tyr Leu Ser Trp Tyr Gln Gln Lys Pro Gly Arg Val Pro
        50                  55                  60

Lys Leu Leu Ile Tyr Lys Ala Ser Thr Leu Ala Ser Gly Val Pro Ser
65                  70                  75                  80

Arg Phe Ser Gly Ser Gly Ser Gly Thr Glu Phe Thr Leu Thr Ile Ser
                85                  90                  95

Ser Leu Gln Ala Glu Asp Val Ala Thr Tyr Tyr Cys Gln Asn Tyr Ala
                100                 105                 110

Gly Val Ser Ile Tyr Gly Ala Val Phe Gly Gly Gly Thr Lys Val Glu
                115                 120                 125

Ile Lys Arg Thr Val Ala Ala Pro Ser Val Phe Ile Phe Pro Pro Ser
        130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
                180                 185                 190

Asp Ser Thr Tyr Ser Leu Ser Ser Thr Leu Thr Leu Ser Lys Ala Asp
                195                 200                 205

Tyr Glu Lys His Lys Val Tyr Ala Cys Glu Val Thr His Gln Gly Leu
        210                 215                 220

Ser Ser Pro Val Thr Lys Ser Phe Asn Arg Gly Glu Cys
225                 230                 235

<210> SEQ ID NO 196
<211> LENGTH: 237
<212> TYPE: PRT
<213> ORGANISM: Artificial Sequence
<220> FEATURE:
<223> OTHER INFORMATION: Heavy Chain Humanized Variant

<400> SEQUENCE: 196

Met Val Ser Ser Ala Gln Phe Leu Gly Leu Leu Leu Leu Cys Phe Gln
1               5                   10                  15

Gly Thr Arg Cys Asp Ile Gln Met Thr Gln Ser Pro Ser Ser Leu Ser
                20                  25                  30

Ala Ser Val Gly Asp Arg Val Thr Ile Ser Cys Gln Ala Ser Gln Ser
                35                  40                  45

Ile Gly Gly Tyr Leu Ser Trp Tyr Gln Gln Lys Pro Gly Gln Ala Pro
        50                  55                  60

Lys Leu Leu Ile Tyr Lys Ala Ser Thr Leu Ala Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Val Ala Thr Tyr Tyr Cys Gln Asn Tyr Ala
                100                 105                 110

Gly Val Ser Ile Tyr Gly Ala Val Phe Gly Gln Gly Thr Lys Val Glu
                115                 120                 125

Ile Lys Arg Thr Val Ala Ala Pro Ser Val Phe Ile Phe Pro Pro Ser
```

```
            130                 135                 140
Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
                195                 200                 205

Tyr Glu Lys His Lys Val Tyr Ala Cys Glu Val Thr His Gln Gly Leu
            210                 215                 220

Ser Ser Pro Val Thr Lys Ser Phe Asn Arg Gly Glu Cys
225                 230                 235

<210> SEQ ID NO 197
<211> LENGTH: 237
<212> TYPE: PRT
<213> ORGANISM: Artificial Sequence
<220> FEATURE:
<223> OTHER INFORMATION: Heavy Chain Humanized Variant

<400> SEQUENCE: 197

Met Val Ser Ser Ala Gln Phe Leu Gly Leu Leu Leu Cys Phe Gln
1               5                   10                  15

Gly Thr Arg Cys Asp Ile Gln Met Thr Gln Ser Pro Ser Ser Val Ser
                20                  25                  30

Ala Ser Val Gly Asp Arg Val Thr Ile Thr Cys Gln Ala Ser Gln Ser
            35                  40                  45

Ile Gly Gly Tyr Leu Ser Trp Tyr Gln Gln Lys Pro Gly Gln Pro Pro
        50                  55                  60

Lys Leu Leu Ile Tyr Lys Ala Ser Thr Leu Ala Ser Gly Val Pro Ser
65                  70                  75                  80

Arg Phe Lys Gly Ser Gly Ser Gly Thr Asp Phe Thr Leu Thr Ile Ser
                85                  90                  95

Ser Leu Asp Ser Glu Asp Ala Ala Thr Tyr Tyr Cys Gln Asn Tyr Ala
            100                 105                 110

Gly Val Ser Ile Tyr Gly Ala Val Phe Gly Gly Gly Thr Lys Val Val
        115                 120                 125

Val Lys Arg Thr Val Ala Ala Pro Ser Val Phe Ile Phe Pro Pro Ser
130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
                195                 200                 205

Tyr Glu Lys His Lys Val Tyr Ala Cys Glu Val Thr His Gln Gly Leu
            210                 215                 220

Ser Ser Pro Val Thr Lys Ser Phe Asn Arg Gly Glu Cys
225                 230                 235

<210> SEQ ID NO 198
<211> LENGTH: 11
<212> TYPE: PRT
```

<213> ORGANISM: Artificial Sequence
<220> FEATURE:
<223> OTHER INFORMATION: Heavy Chain Humanized Variant

<400> SEQUENCE: 198

Ala Arg Asn Ser Asp Ser Ile Tyr Phe Asn Ile
1               5                   10

<210> SEQ ID NO 199
<211> LENGTH: 468
<212> TYPE: PRT
<213> ORGANISM: Artificial Sequence
<220> FEATURE:
<223> OTHER INFORMATION: Heavy Chain Humanized Variant

<400> SEQUENCE: 199

Met Gly Trp Thr Leu Val Phe Leu Phe Leu Ser Val Thr Ala Gly
1               5                   10                  15

Val His Ser Gln Val Gln Leu Val Glu Ser Gly Gly Gly Leu Val Lys
                20                  25                  30

Pro Gly Gly Ser Leu Arg Leu Ser Cys Ala Ala Ser Gly Phe Tyr Phe
            35                  40                  45

Asn Arg Gly Tyr Trp Ile Cys Trp Ile Arg Gln Ala Pro Gly Lys Gly
50                  55                  60

Leu Glu Trp Val Ser Cys Ile Asp Thr Gly Ser Gly Val Pro Tyr Tyr
65                  70                  75                  80

Ala Asn Trp Ala Lys Gly Arg Phe Thr Ile Ser Arg Asp Asn Ala Lys
                85                  90                  95

Asn Ser Leu Tyr Leu Gln Met Asn Ser Leu Arg Thr Glu Asp Thr Ala
            100                 105                 110

Val Tyr Phe Cys Ala Arg Asn Ser Asp Ser Ile Tyr Phe Asn Ile Trp
        115                 120                 125

Gly Gln Gly Thr Leu Val Thr Val Ser Ser Ala Ser Thr Lys Gly Pro
130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
            325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
            355                 360                 365

Val Tyr Thr Leu Pro Pro Ser Arg Asp Glu Leu Thr Lys Asn Gln Val
370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
            405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
            450                 455                 460

Ser Pro Gly Lys
465

<210> SEQ ID NO 200
<211> LENGTH: 468
<212> TYPE: PRT
<213> ORGANISM: Artificial Sequence
<220> FEATURE:
<223> OTHER INFORMATION: Heavy Chain Humanized Variant

<400> SEQUENCE: 200

Met Gly Trp Thr Leu Val Phe Leu Phe Leu Leu Ser Val Thr Ala Gly
1               5                   10                  15

Val His Ser Gln Val Gln Leu Val Glu Ser Gly Gly Gly Leu Val Lys
            20                  25                  30

Pro Gly Gly Ser Leu Arg Leu Ser Cys Ala Ala Ser Gly Phe Tyr Phe
        35                  40                  45

Asn Arg Gly Tyr Trp Ile Ser Trp Ile Arg Gln Ala Pro Gly Lys Gly
    50                  55                  60

Leu Glu Trp Val Ser Ser Ile Asp Thr Gly Ser Gly Val Pro Tyr Tyr
65                  70                  75                  80

Ala Asn Trp Ala Lys Gly Arg Phe Thr Ile Ser Arg Asp Asn Ala Lys
                85                  90                  95

Asn Ser Leu Tyr Leu Gln Met Asn Ser Leu Arg Thr Glu Asp Thr Ala
            100                 105                 110

Val Tyr Phe Cys Ala Arg Asn Ser Asp Ser Ile Tyr Phe Asn Leu Trp
        115                 120                 125

Gly Gln Gly Thr Leu Val Thr Val Ser Ser Ala Ser Thr Lys Gly Pro
130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

```
Val Pro Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465

<210> SEQ ID NO 201
<211> LENGTH: 468
<212> TYPE: PRT
<213> ORGANISM: Artificial Sequence
<220> FEATURE:
<223> OTHER INFORMATION: Heavy Chain Humanized Variant

<400> SEQUENCE: 201

Met Gly Trp Thr Leu Val Phe Leu Phe Leu Leu Ser Val Thr Ala Gly
1               5                   10                  15

Val His Ser Gln Val Gln Leu Val Glu Ser Gly Gly Gly Leu Val Lys
            20                  25                  30

Pro Gly Gly Ser Leu Arg Leu Ser Cys Ala Ala Ser Gly Phe Tyr Phe
        35                  40                  45

Asn Arg Gly Tyr Trp Ile Ser Trp Ile Arg Gln Ala Pro Gly Lys Gly
    50                  55                  60

Leu Glu Trp Val Ser Ser Ile Asp Thr Gly Ser Gly Val Pro Tyr Tyr
65                  70                  75                  80

Ala Asn Trp Ala Lys Gly Arg Phe Thr Ile Ser Arg Asp Asn Ala Lys
                85                  90                  95
```

Asn Ser Leu Tyr Leu Gln Met Asn Ser Leu Arg Thr Glu Asp Thr Ala
            100                 105                 110

Val Tyr Phe Cys Ala Arg Asn Ser Asp Ser Ile Tyr Phe Asn Ile Trp
115                 120                 125

Gly Gln Gly Thr Leu Val Thr Val Ser Ser Ala Ser Thr Lys Gly Pro
            130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
            165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
            195                 200                 205

Val Pro Ser Ser Ser Leu Gly Thr Gln Thr Tyr Ile Cys Asn Val Asn
210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
            245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
            275                 280                 285

His Glu Asp Pro Glu Val Lys Phe Asn Trp Tyr Val Asp Gly Val Glu
            290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
            325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
            355                 360                 365

Val Tyr Thr Leu Pro Pro Ser Arg Asp Glu Leu Thr Lys Asn Gln Val
            370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
            405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
            450                 455                 460

Ser Pro Gly Lys
465

<210> SEQ ID NO 202
<211> LENGTH: 468
<212> TYPE: PRT
<213> ORGANISM: Artificial Sequence
<220> FEATURE:
<223> OTHER INFORMATION: Heavy Chain Humanized Variant

<400> SEQUENCE: 202

```
Met Gly Trp Thr Leu Val Phe Leu Phe Leu Leu Ser Val Thr Ala Gly
1               5                   10                  15

Val His Ser Glu Val Gln Leu Val Glu Ser Gly Gly Gly Leu Val Lys
            20                  25                  30

Pro Gly Gly Ser Leu Arg Leu Ser Cys Ala Val Ser Gly Phe Tyr Phe
        35                  40                  45

Asn Arg Gly Tyr Trp Ile Cys Trp Val Arg Gln Ala Pro Gly Lys Gly
    50                  55                  60

Leu Glu Trp Ile Gly Cys Ile Asp Thr Gly Ser Gly Val Pro Tyr Tyr
65                  70                  75                  80

Ala Asn Trp Ala Lys Gly Arg Phe Thr Ile Ser Arg His Thr Ser Lys
                85                  90                  95

Thr Thr Leu Thr Leu Gln Met Asn Ser Leu Arg Ala Glu Asp Thr Ala
            100                 105                 110

Ser Tyr Phe Cys Ala Arg Asn Ser Asp Ser Ile Tyr Phe Asn Ile Trp
        115                 120                 125

Gly Pro Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
```

```
                    405                 410                 415
Pro Val Leu Asp Ser Asp Gly Ser Phe Phe Leu Tyr Ser Lys Leu Thr
                420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
    450                 455                 460

Ser Pro Gly Lys
465

<210> SEQ ID NO 203
<211> LENGTH: 468
<212> TYPE: PRT
<213> ORGANISM: Artificial Sequence
<220> FEATURE:
<223> OTHER INFORMATION: Heavy Chain Humanized Variant

<400> SEQUENCE: 203

Met Gly Trp Thr Leu Val Phe Leu Phe Leu Leu Ser Val Thr Ala Gly
1               5                   10                  15

Val His Ser Glu Val Gln Leu Val Glu Ser Gly Gly Gly Leu Val Lys
            20                  25                  30

Pro Gly Gly Ser Leu Arg Leu Ser Cys Ala Val Ser Gly Phe Tyr Phe
        35                  40                  45

Asn Arg Gly Tyr Trp Ile Ser Trp Val Arg Gln Ala Pro Gly Lys Gly
    50                  55                  60

Leu Glu Trp Ile Gly Ser Ile Asp Thr Gly Ser Gly Val Pro Tyr Tyr
65                  70                  75                  80

Ala Asn Trp Ala Lys Gly Arg Phe Thr Ile Ser Arg His Thr Ser Lys
                85                  90                  95

Thr Thr Leu Thr Leu Gln Met Asn Ser Leu Arg Ala Glu Asp Thr Ala
            100                 105                 110

Ser Tyr Phe Cys Ala Arg Asn Ser Asp Ser Ile Tyr Phe Asn Leu Trp
        115                 120                 125

Gly Pro Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
```

```
              290                 295                 300
Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
                340                 345                 350

Ile Glu Lys Thr Ile Ser Lys Ala Lys Gly Gln Pro Arg Glu Pro Gln
            355                 360                 365

Val Tyr Thr Leu Pro Pro Ser Arg Asp Glu Leu Thr Lys Asn Gln Val
        370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
                420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
        450                 455                 460

Ser Pro Gly Lys
465

<210> SEQ ID NO 204
<211> LENGTH: 468
<212> TYPE: PRT
<213> ORGANISM: Artificial Sequence
<220> FEATURE:
<223> OTHER INFORMATION: Heavy Chain Humanized Variant

<400> SEQUENCE: 204

Met Gly Trp Thr Leu Val Phe Leu Phe Leu Leu Ser Val Thr Ala Gly
1               5                   10                  15

Val His Ser Glu Val Gln Leu Val Glu Ser Gly Gly Gly Leu Val Lys
            20                  25                  30

Pro Gly Gly Ser Leu Arg Leu Ser Cys Ala Val Ser Gly Phe Tyr Phe
        35                  40                  45

Asn Arg Gly Tyr Trp Ile Ser Trp Val Arg Gln Ala Pro Gly Lys Gly
    50                  55                  60

Leu Glu Trp Ile Gly Ser Ile Asp Thr Gly Ser Gly Val Pro Tyr Tyr
65                  70                  75                  80

Ala Asn Trp Ala Lys Gly Arg Phe Thr Ile Ser Arg His Thr Ser Lys
                85                  90                  95

Thr Thr Leu Thr Leu Gln Met Asn Ser Leu Arg Ala Glu Asp Thr Ala
            100                 105                 110

Ser Tyr Phe Cys Ala Arg Asn Ser Asp Ser Ile Tyr Phe Asn Ile Trp
        115                 120                 125

Gly Pro Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
```

```
            180                 185                 190
Ala Val Leu Gln Ser Ser Gly Leu Tyr Ser Leu Ser Val Val Thr
            195                 200                 205

Val Pro Ser Ser Ser Leu Gly Thr Gln Thr Tyr Ile Cys Asn Val Asn
            210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
            275                 280                 285

His Glu Asp Pro Glu Val Lys Phe Asn Trp Tyr Val Asp Gly Val Glu
            290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
            355                 360                 365

Val Tyr Thr Leu Pro Pro Ser Arg Asp Glu Leu Thr Lys Asn Gln Val
            370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
450                 455                 460

Ser Pro Gly Lys
465

<210> SEQ ID NO 205
<211> LENGTH: 237
<212> TYPE: PRT
<213> ORGANISM: Artificial Sequence
<220> FEATURE:
<223> OTHER INFORMATION: Heavy Chain Humanized Variant

<400> SEQUENCE: 205

Met Val Ser Ser Ala Gln Phe Leu Gly Leu Leu Leu Leu Cys Phe Gln
1               5                   10                  15

Gly Thr Arg Cys Asp Ile Val Met Thr Gln Ser Pro Ser Ser Leu Ser
            20                  25                  30

Ala Ser Val Gly Asp Arg Val Thr Ile Thr Cys Gln Ala Ser Gln Ser
        35                  40                  45

Ile Gly Gly Tyr Ile Ser Trp Tyr Gln Gln Lys Pro Gly Lys Ala Pro
    50                  55                  60

Lys Leu Leu Ile Tyr Lys Ala Ser Thr Leu Ala Ser Gly Val Pro Ser
```

```
                65                  70                  75                  80
Arg Phe Ser Gly Ser Gly Ser Gly Thr Asp Phe Thr Leu Thr Ile Ser
                    85                  90                  95

Ser Leu Gln Pro Glu Asp Phe Ala Thr Tyr Tyr Cys Gln Asn Tyr Ala
                    100                 105                 110

Gly Val Ser Ile Tyr Gly Ala Val Phe Gly Gly Thr Lys Val Val
            115                 120                 125

Ile Lys Arg Thr Val Ala Ala Pro Ser Val Phe Ile Phe Pro Pro Ser
        130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235

<210> SEQ ID NO 206
<211> LENGTH: 237
<212> TYPE: PRT
<213> ORGANISM: Artificial Sequence
<220> FEATURE:
<223> OTHER INFORMATION: Heavy Chain Humanized Variant

<400> SEQUENCE: 206

Met Val Ser Ser Ala Gln Phe Leu Gly Leu Leu Leu Cys Phe Gln
1               5                   10                  15

Gly Thr Arg Cys Asp Ile Gln Met Thr Gln Ser Pro Ser Ser Val Ser
            20                  25                  30

Ala Ser Val Gly Asp Arg Val Thr Ile Thr Cys Gln Ala Ser Gln Ser
        35                  40                  45

Ile Gly Gly Tyr Ile Ser Trp Tyr Gln Gln Lys Pro Gly Gln Pro Pro
    50                  55                  60

Lys Leu Leu Ile Tyr Lys Ala Ser Thr Leu Ala Ser Gly Val Pro Ser
65                  70                  75                  80

Arg Phe Lys Gly Ser Gly Ser Gly Thr Asp Phe Thr Leu Thr Ile Ser
                    85                  90                  95

Ser Leu Asp Ser Glu Asp Ala Ala Thr Tyr Tyr Cys Gln Asn Tyr Ala
                    100                 105                 110

Gly Val Ser Ile Tyr Gly Ala Val Phe Gly Gly Thr Lys Val Val
            115                 120                 125

Val Lys Arg Thr Val Ala Ala Pro Ser Val Phe Ile Phe Pro Pro Ser
        130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
```

```
                195                 200                 205
Tyr Glu Lys His Lys Val Tyr Ala Cys Glu Val Thr His Gln Gly Leu
        210                 215                 220

Ser Ser Pro Val Thr Lys Ser Phe Asn Arg Gly Glu Cys
225                 230                 235

<210> SEQ ID NO 207
<211> LENGTH: 10
<212> TYPE: PRT
<213> ORGANISM: Artificial Sequence
<220> FEATURE:
<223> OTHER INFORMATION: Clone 79C4

<400> SEQUENCE: 207

Gly Phe Thr Phe Ser Asn Tyr Trp Met Asn
1               5                   10

<210> SEQ ID NO 208
<211> LENGTH: 19
<212> TYPE: PRT
<213> ORGANISM: Artificial Sequence
<220> FEATURE:
<223> OTHER INFORMATION: Clone 79C4

<400> SEQUENCE: 208

Glu Ile Arg Leu Lys Ser Lys Asn Tyr Ala Thr His Tyr Ala Glu Ser
1               5                   10                  15

Val Lys Gly

<210> SEQ ID NO 209
<211> LENGTH: 10
<212> TYPE: PRT
<213> ORGANISM: Artificial Sequence
<220> FEATURE:
<223> OTHER INFORMATION: Clone 79C4

<400> SEQUENCE: 209

Gly His Tyr Gly Thr Asn Tyr Gly Asp Tyr
1               5                   10

<210> SEQ ID NO 210
<211> LENGTH: 11
<212> TYPE: PRT
<213> ORGANISM: Artificial Sequence
<220> FEATURE:
<223> OTHER INFORMATION: Clone 79C4

<400> SEQUENCE: 210

Arg Ala Ser Gln Glu Ile Ser Gly Tyr Leu Ser
1               5                   10

<210> SEQ ID NO 211
<211> LENGTH: 7
<212> TYPE: PRT
<213> ORGANISM: Artificial Sequence
<220> FEATURE:
<223> OTHER INFORMATION: Clone 79C4

<400> SEQUENCE: 211

Ala Ala Ser Thr Leu Asp Ser
1               5

<210> SEQ ID NO 212
<211> LENGTH: 9
<212> TYPE: PRT
```

```
<213> ORGANISM: Artificial Sequence
<220> FEATURE:
<223> OTHER INFORMATION: Clone 79C4

<400> SEQUENCE: 212

Leu Gln Tyr Asp Ser Ser Pro Trp Thr
1               5

<210> SEQ ID NO 213
<211> LENGTH: 10
<212> TYPE: PRT
<213> ORGANISM: Artificial Sequence
<220> FEATURE:
<223> OTHER INFORMATION: Clone 11E12

<400> SEQUENCE: 213

Gly Tyr Thr Phe Thr Ser Tyr Val Ile Asn
1               5                   10

<210> SEQ ID NO 214
<211> LENGTH: 17
<212> TYPE: PRT
<213> ORGANISM: Artificial Sequence
<220> FEATURE:
<223> OTHER INFORMATION: Clone 11E12

<400> SEQUENCE: 214

Glu Ile His Pro Arg Gly Gly Asn Thr Tyr Tyr Ser Glu Lys Phe Arg
1               5                   10                  15

Gly

<210> SEQ ID NO 215
<211> LENGTH: 9
<212> TYPE: PRT
<213> ORGANISM: Artificial Sequence
<220> FEATURE:
<223> OTHER INFORMATION: Clone 11E12

<400> SEQUENCE: 215

Leu Arg Arg Gly Asn Ala Met Asp Tyr
1               5

<210> SEQ ID NO 216
<211> LENGTH: 17
<212> TYPE: PRT
<213> ORGANISM: Artificial Sequence
<220> FEATURE:
<223> OTHER INFORMATION: Clone 11E12

<400> SEQUENCE: 216

Lys Ser Ser Gln Ser Leu Leu Asn Ser Gly Asn Gln Arg Asn Tyr Leu
1               5                   10                  15

Thr

<210> SEQ ID NO 217
<211> LENGTH: 7
<212> TYPE: PRT
<213> ORGANISM: Artificial Sequence
<220> FEATURE:
<223> OTHER INFORMATION: Clone 11E12

<400> SEQUENCE: 217

Trp Ala Ser Thr Arg Glu Ser
1               5
```

```
<210> SEQ ID NO 218
<211> LENGTH: 9
<212> TYPE: PRT
<213> ORGANISM: Artificial Sequence
<220> FEATURE:
<223> OTHER INFORMATION: Clone 11E12

<400> SEQUENCE: 218

Gln Asn Ser Tyr Asn Tyr Pro Tyr Thr
1               5

<210> SEQ ID NO 219
<211> LENGTH: 10
<212> TYPE: PRT
<213> ORGANISM: Artificial Sequence
<220> FEATURE:
<223> OTHER INFORMATION: Clone 83G3

<400> SEQUENCE: 219

Gly Phe Thr Phe Thr Ser Tyr Trp Ile His
1               5                   10

<210> SEQ ID NO 220
<211> LENGTH: 17
<212> TYPE: PRT
<213> ORGANISM: Artificial Sequence
<220> FEATURE:
<223> OTHER INFORMATION: Clone 83G3

<400> SEQUENCE: 220

Tyr Ile Asp Pro Ser Asn Thr Tyr Thr Lys Phe Asn Gln Lys Phe Lys
1               5                   10                  15

Asp

<210> SEQ ID NO 221
<211> LENGTH: 6
<212> TYPE: PRT
<213> ORGANISM: Artificial Sequence
<220> FEATURE:
<223> OTHER INFORMATION: Clone 83G3

<400> SEQUENCE: 221

Gly Arg Gly Phe Ala Tyr
1               5

<210> SEQ ID NO 222
<211> LENGTH: 18
<212> TYPE: PRT
<213> ORGANISM: Artificial Sequence
<220> FEATURE:
<223> OTHER INFORMATION: Clone 83G3

<400> SEQUENCE: 222

Asp Lys Ser Ser Gln Ser Leu Phe Asn Ser Gly Asn Gln Lys His Tyr
1               5                   10                  15

Leu Thr

<210> SEQ ID NO 223
<211> LENGTH: 7
<212> TYPE: PRT
<213> ORGANISM: Artificial Sequence
<220> FEATURE:
<223> OTHER INFORMATION: Clone 83G3

<400> SEQUENCE: 223

Arg Ala Ser Thr Arg Glu Ser
```

```
1               5

<210> SEQ ID NO 224
<211> LENGTH: 9
<212> TYPE: PRT
<213> ORGANISM: Artificial Sequence
<220> FEATURE:
<223> OTHER INFORMATION: Clone 83G3

<400> SEQUENCE: 224

Gln Asn Asp Tyr Ser Phe Pro Leu Thr
1               5

<210> SEQ ID NO 225
<211> LENGTH: 10
<212> TYPE: PRT
<213> ORGANISM: Artificial Sequence
<220> FEATURE:
<223> OTHER INFORMATION: Clone 30B5

<400> SEQUENCE: 225

Gly Phe Thr Phe Ser Asn Tyr Trp Met Asn
1               5                   10

<210> SEQ ID NO 226
<211> LENGTH: 19
<212> TYPE: PRT
<213> ORGANISM: Artificial Sequence
<220> FEATURE:
<223> OTHER INFORMATION: Clone 30B5

<400> SEQUENCE: 226

Glu Ile Arg Leu Lys Ser Lys Asn Tyr Ala Thr His Tyr Ala Glu Ser
1               5                   10                  15

Val Lys Gly

<210> SEQ ID NO 227
<211> LENGTH: 10
<212> TYPE: PRT
<213> ORGANISM: Artificial Sequence
<220> FEATURE:
<223> OTHER INFORMATION: Clone 30B5

<400> SEQUENCE: 227

Gly His Tyr Gly Thr Asn Tyr Gly Asp Tyr
1               5                   10

<210> SEQ ID NO 228
<211> LENGTH: 17
<212> TYPE: PRT
<213> ORGANISM: Artificial Sequence
<220> FEATURE:
<223> OTHER INFORMATION: Clone 30B5

<400> SEQUENCE: 228

Lys Ser Ser Gln Ser Leu Phe Asn Ser Gly Asn Gln Lys His Tyr Leu
1               5                   10                  15

Thr

<210> SEQ ID NO 229
<211> LENGTH: 7
<212> TYPE: PRT
<213> ORGANISM: Artificial Sequence
<220> FEATURE:
<223> OTHER INFORMATION: Clone 30B5
```

```
<400> SEQUENCE: 229

Arg Ala Ser Thr Arg Glu Ser
1               5

<210> SEQ ID NO 230
<211> LENGTH: 9
<212> TYPE: PRT
<213> ORGANISM: Artificial Sequence
<220> FEATURE:
<223> OTHER INFORMATION: Clone 30B5

<400> SEQUENCE: 230

Gln Asn Asp Tyr Ser Phe Pro Leu Thr
1               5

<210> SEQ ID NO 231
<211> LENGTH: 10
<212> TYPE: PRT
<213> ORGANISM: Artificial Sequence
<220> FEATURE:
<223> OTHER INFORMATION: Clone 85H12

<400> SEQUENCE: 231

Gly Phe Thr Phe Ser Asn Tyr Trp Met Asn
1               5                   10

<210> SEQ ID NO 232
<211> LENGTH: 19
<212> TYPE: PRT
<213> ORGANISM: Artificial Sequence
<220> FEATURE:
<223> OTHER INFORMATION: Clone 85H12

<400> SEQUENCE: 232

Glu Ile Arg Leu Lys Ser Lys Asn Tyr Ala Thr His Tyr Ala Glu Ser
1               5                   10                  15

Val Lys Gly

<210> SEQ ID NO 233
<211> LENGTH: 10
<212> TYPE: PRT
<213> ORGANISM: Artificial Sequence
<220> FEATURE:
<223> OTHER INFORMATION: Clone 85H12

<400> SEQUENCE: 233

Gly His Tyr Gly Thr Asn Tyr Gly Asp Tyr
1               5                   10

<210> SEQ ID NO 234
<211> LENGTH: 17
<212> TYPE: PRT
<213> ORGANISM: Artificial Sequence
<220> FEATURE:
<223> OTHER INFORMATION: Clone 85H12

<400> SEQUENCE: 234

Lys Ser Ser Gln Ser Leu Phe Asn Ser Gly Asn Gln Lys His Tyr Leu
1               5                   10                  15

Thr

<210> SEQ ID NO 235
<211> LENGTH: 7
<212> TYPE: PRT
<213> ORGANISM: Artificial Sequence
```

<220> FEATURE:
<223> OTHER INFORMATION: Clone 85H12

<400> SEQUENCE: 235

Arg Ala Ser Thr Arg Glu Ser
1               5

<210> SEQ ID NO 236
<211> LENGTH: 9
<212> TYPE: PRT
<213> ORGANISM: Artificial Sequence
<220> FEATURE:
<223> OTHER INFORMATION: Clone 85H12

<400> SEQUENCE: 236

Gln Asn Asp Tyr Ser Phe Pro Leu Thr
1               5

<210> SEQ ID NO 237
<211> LENGTH: 121
<212> TYPE: PRT
<213> ORGANISM: Artificial Sequence
<220> FEATURE:
<223> OTHER INFORMATION: Heavy chain variable domain

<400> SEQUENCE: 237

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Lys Asn Tyr Ala Thr His Tyr Ala Glu
    50                  55                  60

Ser Val Lys Gly Arg Phe Thr Ile Ser Arg Asp Asp Ser Ile Gly Ser
65                  70                  75                  80

Val Tyr Leu Gln Met Asn Asn Leu Arg Ala Glu Asp Thr Gly Ile Tyr
                85                  90                  95

Tyr Cys Ala Arg Gly His Tyr Gly Thr Asn Tyr Gly Asp Tyr Trp Gly
            100                 105                 110

Gln Gly Thr Ser Val Thr Val Ser Ser
        115                 120

<210> SEQ ID NO 238
<211> LENGTH: 118
<212> TYPE: PRT
<213> ORGANISM: Artificial Sequence
<220> FEATURE:
<223> OTHER INFORMATION: Heavy chain variable domain

<400> SEQUENCE: 238

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Val Ile Asn Trp Val Lys Gln Leu Thr Gly Gln Gly Leu Glu Trp Ile
        35                  40                  45

Gly Glu Ile His Pro Arg Gly Gly Asn Thr Tyr Tyr Ser Glu Lys Phe
    50                  55                  60

Arg Gly Arg Ala Thr Leu Thr Ala Asp Lys Ser Ser Ser Thr Ala Tyr
65                  70                  75                  80

```
Met Glu Phe Arg Ser Leu Thr Ser Glu Asp Ser Ala Val Tyr Phe Cys
                85                  90                  95

Ala Ile Leu Arg Arg Gly Asn Ala Met Asp Tyr Trp Asp Gln Gly Thr
            100                 105                 110

Ala Val Thr Val Ser Ser
        115
```

<210> SEQ ID NO 239
<211> LENGTH: 115
<212> TYPE: PRT
<213> ORGANISM: Artificial Sequence
<220> FEATURE:
<223> OTHER INFORMATION: Heavy chain variable domain

<400> SEQUENCE: 239

```
Gln Val Gln Leu Gln Gln Ser Gly Ala Glu Leu Ala Lys Pro Gly Ala
1               5                   10                  15

Ser Val Lys Leu Ser Cys Lys Ala Ser Gly Phe Thr Phe Thr Ser Tyr
            20                  25                  30

Trp Ile His Trp Val Lys Gln Arg Pro Gly Gln Gly Leu Glu Trp Ile
        35                  40                  45

Gly Tyr Ile Asp Pro Ser Asn Thr Tyr Thr Lys Phe Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Asn Ser Leu Thr Phe Glu Asp Ser Ala Val Tyr Tyr Cys
                85                  90                  95

Ala Thr Gly Arg Gly Phe Ala Tyr Trp Gly Gln Gly Thr Leu Val Thr
            100                 105                 110

Val Ser Ser
        115
```

<210> SEQ ID NO 240
<211> LENGTH: 121
<212> TYPE: PRT
<213> ORGANISM: Artificial Sequence
<220> FEATURE:
<223> OTHER INFORMATION: Heavy chain variable domain

<400> SEQUENCE: 240

```
Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Lys Asn Tyr Ala Thr His Tyr Ala Glu
    50                  55                  60

Ser Val Lys Gly Arg Phe Thr Ile Ser Arg Asp Asp Ser Ile Gly Ser
65                  70                  75                  80

Val Tyr Leu Gln Met Asn Asn Leu Arg Ala Glu Asp Thr Gly Ile Tyr
                85                  90                  95

Tyr Cys Ala Arg Gly His Tyr Gly Thr Asn Tyr Gly Asp Tyr Trp Gly
            100                 105                 110

Gln Gly Thr Ser Val Thr Val Ser Ser
        115                 120
```

-continued

```
<210> SEQ ID NO 241
<211> LENGTH: 121
<212> TYPE: PRT
<213> ORGANISM: Artificial Sequence
<220> FEATURE:
<223> OTHER INFORMATION: Heavy chain variable domain

<400> SEQUENCE: 241

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Lys Asn Tyr Ala Thr His Tyr Ala Glu
    50                  55                  60

Ser Val Lys Gly Arg Phe Thr Ile Ser Arg Asp Asp Ser Ile Gly Ser
65                  70                  75                  80

Val Tyr Leu Gln Met Asn Asn Leu Arg Ala Glu Asp Thr Gly Ile Tyr
                85                  90                  95

Tyr Cys Ala Arg Gly His Tyr Gly Thr Asn Tyr Gly Asp Tyr Trp Gly
            100                 105                 110

Gln Gly Thr Ser Val Thr Val Ser Ser
        115                 120

<210> SEQ ID NO 242
<211> LENGTH: 107
<212> TYPE: PRT
<213> ORGANISM: Artificial Sequence
<220> FEATURE:
<223> OTHER INFORMATION: Light chain variable domain Protein Sequence

<400> SEQUENCE: 242

Asp Ile Gln Thr Thr Gln Ser Pro Ser Ser Leu Ser Ala Ser Leu Gly
1               5                   10                  15

Glu Arg Val Thr Leu Thr Cys Arg Ala Ser Gln Glu Ile Ser Gly Tyr
            20                  25                  30

Leu Ser Trp Leu Gln Gln Lys Pro Asp Gly Thr Ile Lys Arg Leu Ile
        35                  40                  45

Tyr Ala Ala Ser Thr Leu Asp Ser Gly Val Pro Lys Arg Phe Ser Gly
    50                  55                  60

Ser Arg Ser Gly Ser Asp Tyr Ser Leu Thr Ile Asn Ser Leu Glu Ser
65                  70                  75                  80

Glu Asp Phe Val Asp Tyr Tyr Cys Leu Gln Tyr Asp Ser Ser Pro Trp
                85                  90                  95

Thr Phe Gly Gly Gly Thr Lys Leu Glu Ile Lys
            100                 105

<210> SEQ ID NO 243
<211> LENGTH: 113
<212> TYPE: PRT
<213> ORGANISM: Artificial Sequence
<220> FEATURE:
<223> OTHER INFORMATION: Light chain variable domain Protein Sequence

<400> SEQUENCE: 243

Asp Ile Val Met Thr Gln Ser Pro Ser Ser Leu Pro Val Thr Ala Gly
1               5                   10                  15

Glu Met Val Thr Met Ser Cys Lys Ser Ser Gln Ser Leu Leu Asn Ser
            20                  25                  30
```

Gly Asn Gln Arg Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Gln Asn
                85                  90                  95

Ser Tyr Asn Tyr Pro Tyr Thr Phe Gly Gly Gly Thr Lys Leu Glu Arg
            100                 105                 110

Lys

<210> SEQ ID NO 244
<211> LENGTH: 113
<212> TYPE: PRT
<213> ORGANISM: Artificial Sequence
<220> FEATURE:
<223> OTHER INFORMATION: Light chain variable domain Protein Sequence

<400> SEQUENCE: 244

Asp Ile Val Met Thr Gln Ser Pro Ser Ser Leu Thr Val Thr Ala Gly
 1               5                  10                  15

Glu Lys Val Thr Val Ser Cys Lys Ser Ser Gln Ser Leu Phe Asn Ser
                20                  25                  30

Gly Asn Gln Lys His Tyr Leu Thr Trp Tyr Gln Gln Lys Pro Gly Gln
            35                  40                  45

Pro Pro Lys Leu Leu Ile Tyr Arg Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Arg Asn Val Gln Ala Glu Asp Leu Ala Val Tyr Tyr Cys Gln Asn
                85                  90                  95

Asp Tyr Ser Phe Pro Leu Thr Phe Gly Ala Gly Thr Lys Leu Glu Leu
            100                 105                 110

Lys

<210> SEQ ID NO 245
<211> LENGTH: 113
<212> TYPE: PRT
<213> ORGANISM: Artificial Sequence
<220> FEATURE:
<223> OTHER INFORMATION: Light chain variable domain Protein Sequence

<400> SEQUENCE: 245

Asp Ile Val Met Thr Gln Ser Pro Ser Ser Leu Thr Val Thr Ala Gly
 1               5                  10                  15

Glu Lys Val Thr Val Ser Cys Lys Ser Ser Gln Ser Leu Phe Asn Ser
                20                  25                  30

Gly Asn Gln Lys His Tyr Leu Thr Trp Tyr Gln Gln Lys Pro Gly Gln
            35                  40                  45

Pro Pro Lys Leu Leu Ile Tyr Arg Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Arg Asn Val Gln Ala Glu Asp Leu Ala Val Tyr Tyr Cys Gln Asn
                85                  90                  95

```
Asp Tyr Ser Phe Pro Leu Thr Phe Gly Ala Gly Thr Lys Leu Glu Leu
            100                 105                 110

Lys

<210> SEQ ID NO 246
<211> LENGTH: 113
<212> TYPE: PRT
<213> ORGANISM: Artificial Sequence
<220> FEATURE:
<223> OTHER INFORMATION: Light chain variable domain Protein Sequence

<400> SEQUENCE: 246

Asp Ile Val Met Thr Gln Ser Pro Ser Ser Leu Thr Val Thr Ala Gly
1               5                   10                  15

Glu Lys Val Thr Val Ser Cys Lys Ser Ser Gln Ser Leu Phe Asn Ser
            20                  25                  30

Gly Asn Gln Lys His Tyr Leu Thr Trp Tyr Gln Gln Lys Pro Gly Gln
        35                  40                  45

Pro Pro Lys Leu Leu Ile Tyr Arg Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Arg Asn Val Gln Ala Glu Asp Leu Ala Val Tyr Tyr Cys Gln Asn
                85                  90                  95

Asp Tyr Ser Phe Pro Leu Thr Phe Gly Ala Gly Thr Lys Leu Glu Leu
            100                 105                 110

Lys

<210> SEQ ID NO 247
<211> LENGTH: 9
<212> TYPE: PRT
<213> ORGANISM: Artificial Sequence
<220> FEATURE:
<223> OTHER INFORMATION: Clone 11E12

<400> SEQUENCE: 247

Ile Arg Arg Gly Asn Ala Met Asp Tyr
1               5

<210> SEQ ID NO 248
<211> LENGTH: 118
<212> TYPE: PRT
<213> ORGANISM: Artificial Sequence
<220> FEATURE:
<223> OTHER INFORMATION: Heavy chain variable domain

<400> SEQUENCE: 248

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Val Ile Asn Trp Val Lys Gln Lys Thr Gly Gln Gly Leu Glu Trp Ile
        35                  40                  45

Gly Glu Ile His Pro Arg Gly Gly Asn Thr Tyr Tyr Ser Glu Lys Phe
    50                  55                  60

Arg Gly Arg Ala Thr Leu Thr Ala Asp Lys Ser Ser Ser Thr Ala Tyr
65                  70                  75                  80

Met Glu Phe Arg Ser Leu Thr Ser Glu Asp Ser Ala Val Tyr Phe Cys
                85                  90                  95
```

Ala Arg Ile Arg Arg Gly Asn Ala Met Asp Tyr Trp Asp Gln Gly Thr
            100                 105                 110

Ala Val Thr Val Ser Ser
            115

<210> SEQ ID NO 249
<211> LENGTH: 448
<212> TYPE: PRT
<213> ORGANISM: Artificial Sequence
<220> FEATURE:
<223> OTHER INFORMATION: Heavy Chain Humanized Variant

<400> SEQUENCE: 249

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Ile Asn Trp Val Arg Gln Ala Thr Gly Gln Gly Leu Glu Trp Ile
            35                  40                  45

Gly Glu Ile His Pro Arg Gly Gly Asn Thr Tyr Tyr Ser Glu Lys Phe
        50                  55                  60

Arg Gly Arg Ala Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ile Arg Arg Gly Asn Ala Met Asp Tyr Trp Gly Gln Gly Thr
            100                 105                 110

Thr Leu Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

```
Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 250
<211> LENGTH: 448
<212> TYPE: PRT
<213> ORGANISM: Artificial Sequence
<220> FEATURE:
<223> OTHER INFORMATION: Heavy Chain Humanized Variant

<400> SEQUENCE: 250

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Ile Asn Trp Val Arg Gln Ala Thr Gly Gln Gly Leu Glu Trp Ile
        35                  40                  45

Gly Glu Ile His Pro Arg Gly Gly Asn Thr Tyr Tyr Ser Glu Lys Phe
    50                  55                  60

Arg Gly Arg Ala Thr Leu Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ile Arg Arg Gly Asn Ala Met Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255
```

```
Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 251
<211> LENGTH: 448
<212> TYPE: PRT
<213> ORGANISM: Artificial Sequence
<220> FEATURE:
<223> OTHER INFORMATION: Heavy Chain Humanized Variant

<400> SEQUENCE: 251

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Ile Asn Trp Val Arg Gln Ala Thr Gly Gln Gly Leu Glu Trp Ile
        35                  40                  45

Gly Glu Ile His Pro Arg Gly Gly Asn Thr Tyr Tyr Ser Glu Lys Phe
    50                  55                  60

Arg Gly Arg Ala Thr Leu Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Arg Arg Gly Asn Ala Met Asp Tyr Trp Gly Gln Gly Thr
            100                 105                 110

Thr Leu Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175
```

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 252
<211> LENGTH: 220
<212> TYPE: PRT
<213> ORGANISM: Artificial Sequence
<220> FEATURE:
<223> OTHER INFORMATION: Heavy Chain Humanized Variant

<400> SEQUENCE: 252

Asp Ile Val Met Thr Gln Ser Pro Ser Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Arg Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Ser Tyr Asn Tyr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 253
<211> LENGTH: 220
<212> TYPE: PRT
<213> ORGANISM: Artificial Sequence
<220> FEATURE:
<223> OTHER INFORMATION: Heavy Chain Humanized Variant

<400> SEQUENCE: 253

Asp Ile Val Met Thr Gln Ser Pro Ser Ser Leu Pro Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Arg Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Ser Tyr Asn Tyr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 254
<211> LENGTH: 118

```
<212> TYPE: PRT
<213> ORGANISM: Artificial Sequence
<220> FEATURE:
<223> OTHER INFORMATION: Humanized heavy chain and light chain variable
      domain Protein Sequences

<400> SEQUENCE: 254

Gln Val Gln Leu Val Gln Ser Gly Ala Glu Val Lys Lys Pro Gly Ala
1               5                  10                  15

Ser Val Lys Val Ser Cys Lys Ala Ser Gly Tyr Thr Phe Thr Ser Tyr
            20                  25                  30

Val Ile Asn Trp Val Arg Gln Ala Thr Gly Gln Gly Leu Glu Trp Ile
        35                  40                  45

Gly Glu Ile His Pro Arg Gly Gly Asn Thr Tyr Tyr Ser Glu Lys Phe
    50                  55                  60

Arg Gly Arg Val Thr Leu Thr Ala Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Ile Leu Arg Arg Gly Asn Ala Met Asp Tyr Trp Asp Gln Gly Thr
            100                 105                 110

Thr Val Thr Val Ser Ser
        115

<210> SEQ ID NO 255
<211> LENGTH: 118
<212> TYPE: PRT
<213> ORGANISM: Artificial Sequence
<220> FEATURE:
<223> OTHER INFORMATION: Humanized heavy chain and light chain variable
      domain Protein Sequences

<400> SEQUENCE: 255

Gln Val Gln Leu Val Gln Ser Gly Ala Glu Val Lys Lys Pro Gly Ala
1               5                  10                  15

Ser Val Lys Val Ser Cys Lys Ala Ser Gly Tyr Thr Phe Thr Ser Tyr
            20                  25                  30

Val Ile Asn Trp Val Lys Gln Lys Thr Gly Gln Gly Leu Glu Trp Ile
        35                  40                  45

Gly Glu Ile His Pro Arg Gly Gly Asn Thr Tyr Tyr Ser Glu Lys Phe
    50                  55                  60

Arg Gly Arg Ala Thr Leu Thr Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Ile Leu Arg Arg Gly Asn Ala Met Asp Tyr Trp Asp Gln Gly Thr
            100                 105                 110

Thr Val Thr Val Ser Ser
        115

<210> SEQ ID NO 256
<211> LENGTH: 118
<212> TYPE: PRT
<213> ORGANISM: Artificial Sequence
<220> FEATURE:
<223> OTHER INFORMATION: Humanized heavy chain and light chain variable
      domain Protein Sequences

<400> SEQUENCE: 256

Gln Val Gln Leu Val Gln Ser Gly Ala Glu Val Lys Lys Pro Gly Ala
```

```
                1               5                  10                 15
Ser Val Lys Leu Ser Cys Lys Ala Ser Gly Tyr Thr Phe Thr Ser Tyr
                20                 25                 30

Val Ile Asn Trp Val Lys Gln Lys Thr Gly Gln Gly Leu Glu Trp Ile
        35                 40                 45

Gly Glu Ile His Pro Arg Gly Gly Asn Thr Tyr Tyr Ser Glu Lys Phe
        50                 55                 60

Arg Gly Arg Ala Thr Leu Thr Ala Asp Lys Ser Ile Ser Thr Ala Tyr
65                 70                 75                 80

Met Glu Leu Ser Ser Leu Arg Ser Glu Asp Thr Ala Val Tyr Phe Cys
                85                 90                 95

Ala Ile Leu Arg Arg Gly Asn Ala Met Asp Tyr Trp Asp Gln Gly Thr
                100                105                110

Thr Val Thr Val Ser Ser
        115
```

<210> SEQ ID NO 257
<211> LENGTH: 118
<212> TYPE: PRT
<213> ORGANISM: Artificial Sequence
<220> FEATURE:
<223> OTHER INFORMATION: Humanized heavy chain and light chain variable
      domain Protein Sequences

<400> SEQUENCE: 257

```
Gln Val Gln Leu Val Gln Ser Gly Ala Glu Val Lys Lys Pro Gly Ala
1               5                  10                 15

Ser Val Lys Val Ser Cys Lys Ala Ser Gly Tyr Thr Phe Thr Ser Tyr
                20                 25                 30

Val Ile Asn Trp Val Arg Gln Ala Thr Gly Gln Gly Leu Glu Trp Ile
        35                 40                 45

Gly Glu Ile His Pro Arg Gly Gly Asn Thr Tyr Tyr Ser Glu Lys Phe
        50                 55                 60

Arg Gly Arg Val Thr Leu Thr Ala Asp Thr Ser Ile Ser Thr Ala Tyr
65                 70                 75                 80

Met Glu Leu Ser Ser Leu Arg Ser Glu Asp Thr Ala Val Tyr Tyr Cys
                85                 90                 95

Ala Arg Leu Arg Arg Gly Asn Ala Met Asp Tyr Trp Asp Gln Gly Thr
                100                105                110

Thr Val Thr Val Ser Ser
        115
```

<210> SEQ ID NO 258
<211> LENGTH: 118
<212> TYPE: PRT
<213> ORGANISM: Artificial Sequence
<220> FEATURE:
<223> OTHER INFORMATION: Humanized heavy chain and light chain variable
      domain Protein Sequences

<400> SEQUENCE: 258

```
Gln Val Gln Leu Val Gln Ser Gly Ala Glu Val Lys Lys Pro Gly Ala
1               5                  10                 15

Ser Val Lys Val Ser Cys Lys Ala Ser Gly Tyr Thr Phe Thr Ser Tyr
                20                 25                 30

Val Ile Asn Trp Val Lys Gln Lys Thr Gly Gln Gly Leu Glu Trp Ile
        35                 40                 45

Gly Glu Ile His Pro Arg Gly Gly Asn Thr Tyr Tyr Ser Glu Lys Phe
```

```
                    50                  55                  60
Arg Gly Arg Ala Thr Leu Thr Ala Asp Lys Ser Ile Ser Thr Ala Tyr
 65                  70                  75                  80

Met Glu Leu Ser Ser Leu Arg Ser Glu Asp Thr Ala Val Tyr Phe Cys
                    85                  90                  95

Ala Arg Leu Arg Arg Gly Asn Ala Met Asp Tyr Trp Asp Gln Gly Thr
                100                 105                 110

Thr Val Thr Val Ser Ser
            115

<210> SEQ ID NO 259
<211> LENGTH: 118
<212> TYPE: PRT
<213> ORGANISM: Artificial Sequence
<220> FEATURE:
<223> OTHER INFORMATION: Humanized heavy chain and light chain variable
      domain Protein Sequences

<400> SEQUENCE: 259

Gln Val Gln Leu Val Gln Ser Gly Ala Glu Val Lys Lys Pro Gly Ala
 1               5                  10                  15

Ser Val Lys Leu Ser Cys Lys Ala Ser Gly Tyr Thr Phe Thr Ser Tyr
                20                  25                  30

Val Ile Asn Trp Val Lys Gln Lys Thr Gly Gln Gly Leu Glu Trp Ile
             35                  40                  45

Gly Glu Ile His Pro Arg Gly Gly Asn Thr Tyr Tyr Ser Glu Lys Phe
     50                  55                  60

Arg Gly Arg Ala Thr Leu Thr Ala Asp Lys Ser Ile Ser Thr Ala Tyr
 65                  70                  75                  80

Met Glu Leu Ser Ser Leu Arg Ser Glu Asp Thr Ala Val Tyr Phe Cys
                85                  90                  95

Ala Arg Leu Arg Arg Gly Asn Ala Met Asp Tyr Trp Asp Gln Gly Thr
                100                 105                 110

Thr Val Thr Val Ser Ser
            115

<210> SEQ ID NO 260
<211> LENGTH: 113
<212> TYPE: PRT
<213> ORGANISM: Artificial Sequence
<220> FEATURE:
<223> OTHER INFORMATION: Humanized heavy chain and light chain variable
      domain Protein Sequences

<400> SEQUENCE: 260

Asp Ile Val Met Thr Gln Ser Pro Ser Ser Leu Ala Val Ser Leu Gly
 1               5                  10                  15

Glu Met Ala Thr Ile Asn Cys Lys Ser Ser Gln Ser Leu Leu Asn Ser
                20                  25                  30

Gly Asn Gln Arg Asn Tyr Leu Thr Trp Tyr Gln Gln Lys Pro Gly Gln
             35                  40                  45

Pro Pro Lys Leu Leu Ile Tyr Trp Ala Ser Thr Arg Glu Ser Gly Val
     50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Asn
                85                  90                  95

Ser Tyr Asn Tyr Pro Tyr Thr Phe Gly Gln Gly Thr Lys Leu Glu Arg
```

<210> SEQ ID NO 261
<211> LENGTH: 113
<212> TYPE: PRT
<213> ORGANISM: Artificial Sequence
<220> FEATURE:
<223> OTHER INFORMATION: Humanized heavy chain and light chain variable
      domain Protein Sequences

<400> SEQUENCE: 261

Asp Ile Val Met Thr Gln Ser Pro Ser Ser Leu Ala Val Ser Ala Gly
1               5                   10                  15

Glu Met Val Thr Met Asn Cys Lys Ser Ser Gln Ser Leu Leu Asn Ser
            20                  25                  30

Gly Asn Gln Arg Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Ser Tyr Asn Tyr Pro Tyr Thr Phe Gly Gln Gly Thr Lys Leu Glu Ile
            100                 105                 110

Lys

<210> SEQ ID NO 262
<211> LENGTH: 113
<212> TYPE: PRT
<213> ORGANISM: Artificial Sequence
<220> FEATURE:
<223> OTHER INFORMATION: Humanized heavy chain and light chain variable
      domain Protein Sequences

<400> SEQUENCE: 262

Asp Ile Val Met Thr Gln Ser Pro Ser Ser Leu Ala Val Ser Ala Gly
1               5                   10                  15

Glu Met Val Thr Met Asn Cys Lys Ser Ser Gln Ser Leu Leu Asn Ser
            20                  25                  30

Gly Asn Gln Arg Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Ser Tyr Asn Tyr Pro Tyr Thr Phe Gly Gln Gly Thr Lys Leu Glu Arg
            100                 105                 110

Lys

<210> SEQ ID NO 263
<211> LENGTH: 115
<212> TYPE: PRT
<213> ORGANISM: Artificial Sequence
<220> FEATURE:
<223> OTHER INFORMATION: 83G3 Humanized Sequences

<400> SEQUENCE: 263

```
Gln Val Gln Leu Val Gln Ser Gly Ala Glu Val Lys Lys Pro Gly Ala
1               5                   10                  15
Ser Val Lys Val Ser Cys Lys Ala Ser Gly Phe Thr Phe Thr Ser Tyr
            20                  25                  30
Trp Ile His Trp Val Arg Gln Arg Pro Gly Gln Gly Leu Glu Trp Ile
        35                  40                  45
Gly Tyr Ile Asp Pro Ser Asn Thr Tyr Thr Lys Phe Asn Gln Lys Phe
    50                  55                  60
Lys Asp Arg Val Thr Leu Thr Ala Asp Thr Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Thr Gly Arg Gly Phe Ala Tyr Trp Gly Gln Gly Thr Leu Val Thr
            100                 105                 110
Val Ser Ser
        115
```

<210> SEQ ID NO 264
<211> LENGTH: 115
<212> TYPE: PRT
<213> ORGANISM: Artificial Sequence
<220> FEATURE:
<223> OTHER INFORMATION: 83G3 Humanized Sequences

<400> SEQUENCE: 264

```
Gln Val Gln Leu Val Gln Ser Gly Ala Glu Val Lys Lys Pro Gly Ala
1               5                   10                  15
Ser Val Lys Leu Ser Cys Lys Ala Ser Gly Phe Thr Phe Thr Ser Tyr
            20                  25                  30
Trp Ile His Trp Val Arg Gln Arg Pro Gly Gln Gly Leu Glu Trp Ile
        35                  40                  45
Gly Tyr Ile Asp Pro Ser Asn Thr Tyr Thr Lys Phe Asn Gln Lys Phe
    50                  55                  60
Lys Asp Arg Ala Thr Leu Thr Ala Asp Thr Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Thr Gly Arg Gly Phe Ala Tyr Trp Gly Gln Gly Thr Leu Val Thr
            100                 105                 110
Val Ser Ser
        115
```

<210> SEQ ID NO 265
<211> LENGTH: 115
<212> TYPE: PRT
<213> ORGANISM: Artificial Sequence
<220> FEATURE:
<223> OTHER INFORMATION: 83G3 Humanized Sequences

<400> SEQUENCE: 265

```
Gln Val Gln Leu Gln Gln Ser Gly Ala Glu Val Lys Lys Pro Gly Ala
1               5                   10                  15
Ser Val Lys Leu Ser Cys Lys Ala Ser Gly Phe Thr Phe Thr Ser Tyr
            20                  25                  30
Trp Ile His Trp Val Arg Gln Arg Pro Gly Gln Gly Leu Glu Trp Ile
        35                  40                  45
```

```
Gly Tyr Ile Asp Pro Ser Asn Thr Tyr Thr Lys Phe Asn Gln Lys Phe
        50                  55                  60

Lys Asp Arg Ala Thr Leu Thr Ala Asp Thr Ser Ser Thr Ala Tyr
 65                  70                  75                  80

Met Glu Leu Ser Ser Leu Arg Ser Glu Asp Thr Ala Val Tyr Tyr Cys
                85                  90                  95

Ala Thr Gly Arg Gly Phe Ala Tyr Trp Gly Gln Gly Thr Leu Val Thr
                100                 105                 110

Val Ser Ser
        115

<210> SEQ ID NO 266
<211> LENGTH: 113
<212> TYPE: PRT
<213> ORGANISM: Artificial Sequence
<220> FEATURE:
<223> OTHER INFORMATION: 83G3 Humanized Sequences

<400> SEQUENCE: 266

Asp Ile Val Met Thr Gln Ser Pro Ser Ser Leu Ala Val Ser Leu Gly
 1               5                  10                  15

Glu Arg Ala Thr Ile Asn Cys Lys Ser Ser Gln Ser Leu Phe Asn Ser
                20                  25                  30

Gly Asn Gln Lys His Tyr Leu Thr Trp Tyr Gln Gln Lys Pro Gly Gln
                35                  40                  45

Pro Pro Lys Leu Leu Ile Tyr Arg Ala Ser Thr Arg Glu Ser Gly Val
        50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Asn
                85                  90                  95

Asp Tyr Ser Phe Pro Leu Thr Phe Gly Gln Gly Thr Lys Leu Glu Ile
                100                 105                 110

Lys

<210> SEQ ID NO 267
<211> LENGTH: 113
<212> TYPE: PRT
<213> ORGANISM: Artificial Sequence
<220> FEATURE:
<223> OTHER INFORMATION: 83G3 Humanized Sequences

<400> SEQUENCE: 267

Asp Ile Val Met Thr Gln Ser Pro Ser Ser Leu Ala Val Ser Leu Gly
 1               5                  10                  15

Glu Arg Ala Thr Val Asn Cys Lys Ser Ser Gln Ser Leu Phe Asn Ser
                20                  25                  30

Gly Asn Gln Lys His Tyr Leu Thr Trp Tyr Gln Gln Lys Pro Gly Gln
                35                  40                  45

Pro Pro Lys Leu Leu Ile Tyr Arg Ala Ser Thr Arg Glu Ser Gly Val
        50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Asn
                85                  90                  95

Asp Tyr Ser Phe Pro Leu Thr Phe Gly Gln Gly Thr Lys Leu Glu Ile
                100                 105                 110
```

Lys

<210> SEQ ID NO 268
<211> LENGTH: 113
<212> TYPE: PRT
<213> ORGANISM: Artificial Sequence
<220> FEATURE:
<223> OTHER INFORMATION: 83G3 Humanized Sequences

<400> SEQUENCE: 268

Asp Ile Val Met Thr Gln Ser Pro Ser Ser Leu Ala Val Ser Leu Gly
1               5                   10                  15

Glu Arg Ala Thr Val Asn Cys Lys Ser Ser Gln Ser Leu Phe Asn Ser
            20                  25                  30

Gly Asn Gln Lys His Tyr Leu Thr Trp Tyr Gln Gln Lys Pro Gly Gln
        35                  40                  45

Pro Pro Lys Leu Leu Ile Tyr Arg Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Arg Ser Leu Gln Ala Glu Asp Val Ala Val Tyr Tyr Cys Gln Asn
                85                  90                  95

Asp Tyr Ser Phe Pro Leu Thr Phe Gly Gln Gly Thr Lys Leu Glu Ile
            100                 105                 110

Lys

<210> SEQ ID NO 269
<211> LENGTH: 113
<212> TYPE: PRT
<213> ORGANISM: Artificial Sequence
<220> FEATURE:
<223> OTHER INFORMATION: 83G3 Humanized Sequences

<400> SEQUENCE: 269

Asp Ile Val Met Thr Gln Ser Pro Ser Ser Leu Ala Val Ser Leu Gly
1               5                   10                  15

Glu Arg Ala Thr Val Asn Cys Lys Ser Ser Gln Ser Leu Phe Asn Ser
            20                  25                  30

Gly Asn Gln Lys His Tyr Leu Thr Trp Tyr Gln Gln Lys Pro Gly Gln
        35                  40                  45

Pro Pro Lys Leu Leu Ile Tyr Arg Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Phe Pro Leu Thr Phe Gly Gln Gly Thr Lys Leu Glu Ile
            100                 105                 110

Lys

ANTIBODIES AND METHODS FOR MAKING AND USING THE SAME

CROSS REFERENCE TO RELATED APPLICATIONS

The present application is claims priority to U.S. provisional patent applications 62/700,174 filed on Jul. 18, 2018 and 62/792,798 filed on Jan. 15, 2019, and each is incorporated by reference herein in their entirety.

REFERENCE TO SEQUENCE LISTING

The entire content of the following electronic submission of the sequence listing via the USPTO EFS-WEB server, as authorized and set forth in MPEP § 1730 II.B.2(a)(C), is incorporated herein by reference in its entirety for all purposes. The sequence listing is identified on the electronically filed text file as follows: File Name: SEQLIST-AG3-015US; Date of Creation: Oct. 24, 2019; Size (bytes): 193 KB

BACKGROUND

The following includes information that may be useful in understanding the present inventions. It is not an admission that any of the information provided herein is prior art, or relevant, to the presently described or claimed inventions, or that any publication or document that is specifically or implicitly referenced is prior art.

It was recently shown that there were close to one million new cases of gastric cancer worldwide every year. The worldwide mortality rate for gastric cancer was over 700,000 in 2012. According to the American Cancer Society, in 2018, about 26,400 people were diagnosed with gastric cancer in the United States with about 10,800 expected fatalities. The incidence of gastric cancer as a percentage of the overall population is higher in Asia, with about 40% of all gastric cancer cases reported worldwide in 2012 or approximately 400,000 cases found to occur in China. 325,000 people died of gastric cancer in China in 2012. These demographic data make it clear that gastric cancer is a severe unmet medical condition with limited therapy options in which existing methods of treatment are not adequate and new therapeutic compounds and treatments are urgently needed.

To treat gastric cancer, a combination of 5-Fu and Cisplatin is often the first line treatment in many countries. However, the combination of Paclitaxel and Cisplatin is often used to treat gastric patients in China and was said to have better therapeutic efficacy.

Antibodies are a relatively new class of targeted therapeutic compounds that are now widely used for a variety of cancers. Antibody-based therapeutics have the potential for higher specificity and lower side effects compared to many traditional non-antibody type oncology therapeutics. Generally, potential targets for antibody-based therapeutics need to discriminate between normal and neoplastic cells. Not surprisingly, cell surface proteins are a potential area of development of antibody-based targets that might be exposed on tumor cells. Claudin 18.2 was recently found to be a target for antibody therapy for gastric and esophageal cancers (J Hematol Oncol. 2017 (1):105). It was also a target for developing antibody drugs for pancreatic cancer. Claudin 18.2 belongs to the claudin family of proteins, which has at least 24 closely related transmembrane proteins (for review, see Ouban A, Ahmed A A.: "Claudins in human cancer: a review", Histol Histopathol. 2010 January; 25(1):83-90).

Claudins are tight junction proteins which regulate paracellular ion flux. Certain claudin protein members are differentially expressed in malignancies. In the case of Claudin 18.2, it is a highly selective gastric lineage antigen expressed exclusively on short-lived differentiated gastric epithelial cells, which has only limited accessibility to antibody drugs (Sahin U et al: "Claudin18 splice variant 2 is a pan-cancer target suitable for therapeutic antibody development." Clin Cancer Res 2008, 14:7624-34; and Tureci O et al. "Claudin-18 gene structure, regulation, and expression is evolutionary conserved in mammal." Gene 2011, 481:83-92). Claudin18.2 is maintained during the course of malignant transformation and thus frequently displayed on the surface of human gastric cancer cells (Wöll et all: "Claudin 18.2 is a target for IMAB362 antibody in pancreatic neoplasms." Int. J. Cancer: 134, 731-739, 2014).

An antibody against Claudin 18.2 designated IMAB362 was recently disclosed in U.S. Pat. No. 8,168,427. In a Phase 2 study published in 2016, patients with advanced or recurrent gastric cancer and gastroesophageal junction carcinomas treated with IMAB362 added to standard chemotherapy demonstrated a 53% reduced risk for progression and a 49% reduced risk of death compared with patients who received only standard EOX (Epirubicin, Oxaliplatin and Capecitabine). However, the binding affinity of the particular antibody IMAb362 to the target Claudin 18.2 appeared to be relatively modest, and the dosages required appeared to be relatively high. In addition, the antibody in the clinical development was a chimeric molecule, which could potentially have immunogenicity risk after repeating doses.

New antibodies to Claudin 18.2 with higher efficacy, lower dosage/cost, and/or lower immunogenicity risk are needed.

SUMMARY

The inventions described and claimed herein have many attributes and embodiments including, but not limited to, those set forth or described or referenced in this Brief Summary. The inventions described and claimed herein are not limited to, or by, the features or embodiments identified in this Summary, which is included for purposes of illustration only and not restriction.

Described and provided herein are novel antibodies for Claudin 18.2. As will be described in further detail herein, antibodies according to the invention include but are not limited to the following characteristics: i) high relative binding affinity for Claudin 18.2, ii) human or humanized antibody, iii) enhanced antibody-drug conjugation capabilities, iv) enhanced combination use with immune-therapy, v) enhanced ADCC functionality, and vi) enhanced therapeutic efficacy.

In one aspect, the present invention provides an antibody which binds to human CLDN18.2 protein, the antibody selected from the group consisting of:

(1) an antibody comprising a heavy chain variable region comprising heavy chain CDR1 having the amino acid sequence as set forth in SEQ ID NO: 47, heavy chain CDR2 having the amino acid sequence as set forth in SEQ ID NO: 48, and heavy chain CDR3 having the amino acid sequence as set forth in SEQ ID NO: 49, and a light chain variable region comprising light chain CDR1 having the amino acid sequence as set forth in SEQ ID NO: 50, light chain CDR2 having the amino acid sequence as set forth in SEQ ID NO: 51, and light chain CDR3 having the amino acid sequence as set forth in SEQ ID NO: 52;

(2) an antibody comprising a heavy chain variable region comprising heavy chain CDR1 having the amino acid sequence as set forth in SEQ ID NO: 53, heavy chain CDR2 having the amino acid sequence as set forth in SEQ ID NO: 54, and heavy chain CDR3 having the amino acid sequence as set forth in SEQ ID NO: 55, and a light chain variable region comprising light chain CDR1 having the amino acid sequence as set forth in SEQ ID NO: 56, light chain CDR2 having the amino acid sequence as set forth in SEQ ID NO: 57, and light chain CDR3 having the amino acid sequence as set forth in SEQ ID NO: 58;

(3) an antibody comprising a heavy chain variable region comprising heavy chain CDR1 having the amino acid sequence as set forth in SEQ ID NO: 59, heavy chain CDR2 having the amino acid sequence as set forth in SEQ ID NO: 60, and heavy chain CDR3 having the amino acid sequence as set forth in SEQ ID NO: 61, and a light chain variable region comprising light chain CDR1 having the amino acid sequence as set forth in SEQ ID NO: 62, light chain CDR2 having the amino acid sequence as set forth in SEQ ID NO: 63, and light chain CDR3 having the amino acid sequence as set forth in SEQ ID NO: 64;

(4) an antibody comprising a heavy chain variable region comprising heavy chain CDR1 having the amino acid sequence as set forth in SEQ ID NO: 65, heavy chain CDR2 having the amino acid sequence as set forth in SEQ ID NO: 66, and heavy chain CDR3 having the amino acid sequence as set forth in SEQ ID NO: 67, and a light chain variable region comprising light chain CDR1 having the amino acid sequence as set forth in SEQ ID NO: 68, light chain CDR2 having the amino acid sequence as set forth in SEQ ID NO: 69, and light chain CDR3 having the amino acid sequence as set forth in SEQ ID NO: 70;

(5) an antibody comprising a heavy chain variable region comprising heavy chain CDR1 having the amino acid sequence as set forth in SEQ ID NO: 71, heavy chain CDR2 having the amino acid sequence as set forth in SEQ ID NO: 72, and heavy chain CDR3 having the amino acid sequence as set forth in SEQ ID NO: 73, and a light chain variable region comprising light chain CDR1 having the amino acid sequence as set forth in SEQ ID NO: 74, light chain CDR2 having the amino acid sequence as set forth in SEQ ID NO: 75, and light chain CDR3 having the amino acid sequence as set forth in SEQ ID NO: 76;

(6) an antibody comprising a heavy chain variable region comprising heavy chain CDR1 having the amino acid sequence as set forth in SEQ ID NO: 77, heavy chain CDR2 having the amino acid sequence as set forth in SEQ ID NO: 78, and heavy chain CDR3 having the amino acid sequence as set forth in SEQ ID NO: 79, and a light chain variable region comprising light chain CDR1 having the amino acid sequence as set forth in SEQ ID NO: 80, light chain CDR2 having the amino acid sequence as set forth in SEQ ID NO: 81, and light chain CDR3 having the amino acid sequence as set forth in SEQ ID NO: 82;

(7) an antibody comprising a heavy chain variable region comprising heavy chain CDR1 having the amino acid sequence as set forth in SEQ ID NO: 83, heavy chain CDR2 having the amino acid sequence as set forth in SEQ ID NO: 84, and heavy chain CDR3 having the amino acid sequence as set forth in SEQ ID NO: 85, and a light chain variable region comprising light chain CDR1 having the amino acid sequence as set forth in SEQ ID NO: 86, light chain CDR2 having the amino acid sequence as set forth in SEQ ID NO: 87, and light chain CDR3 having the amino acid sequence as set forth in SEQ ID NO: 88;

(8) an antibody comprising a heavy chain variable region comprising heavy chain CDR1 having the amino acid sequence as set forth in SEQ ID NO: 89, heavy chain CDR2 having the amino acid sequence as set forth in SEQ ID NO: 90, and heavy chain CDR3 having the amino acid sequence as set forth in SEQ ID NO: 91, and a light chain variable region comprising light chain CDR1 having the amino acid sequence as set forth in SEQ ID NO: 92, light chain CDR2 having the amino acid sequence as set forth in SEQ ID NO: 93, and light chain CDR3 having the amino acid sequence as set forth in SEQ ID NO: 94;

(9) an antibody comprising a heavy chain variable region comprising heavy chain CDR1 having the amino acid sequence as set forth in SEQ ID NO: 95, heavy chain CDR2 having the amino acid sequence as set forth in SEQ ID NO: 96, and heavy chain CDR3 having the amino acid sequence as set forth in SEQ ID NO: 97, and a light chain variable region comprising light chain CDR1 having the amino acid sequence as set forth in SEQ ID NO: 98, light chain CDR2 having the amino acid sequence as set forth in SEQ ID NO: 99, and light chain CDR3 having the amino acid sequence as set forth in SEQ ID NO: 100;

(10) an antibody comprising a heavy chain variable region comprising heavy chain CDR1 having the amino acid sequence as set forth in SEQ ID NO: 101, heavy chain CDR2 having the amino acid sequence as set forth in SEQ ID NO: 102, and heavy chain CDR3 having the amino acid sequence as set forth in SEQ ID NO: 103, and a light chain variable region comprising light chain CDR1 having the amino acid sequence as set forth in SEQ ID NO: 104, light chain CDR2 having the amino acid sequence as set forth in SEQ ID NO: 105, and light chain CDR3 having the amino acid sequence as set forth in SEQ ID NO: 106;

(11) an antibody comprising a heavy chain variable region comprising heavy chain CDR1 having the amino acid sequence as set forth in SEQ ID NO: 107, heavy chain CDR2 having the amino acid sequence as set forth in SEQ ID NO: 108, and heavy chain CDR3 having the amino acid sequence as set forth in SEQ ID NO: 109, and a light chain variable region comprising light chain CDR1 having the amino acid sequence as set forth in SEQ ID NO: 110, light chain CDR2 having the amino acid sequence as set forth in SEQ ID NO: 111, and light chain CDR3 having the amino acid sequence as set forth in SEQ ID NO: 112;

(12) an antibody comprising a heavy chain variable region comprising heavy chain CDR1 having the amino acid sequence as set forth in SEQ ID NO: 113, heavy chain CDR2 having the amino acid sequence as set forth in SEQ ID NO: 114, and heavy chain CDR3 having the amino acid sequence as set forth in SEQ ID NO: 115, and a light chain variable region comprising light chain CDR1 having the amino acid sequence as set forth in SEQ ID NO: 116, light chain CDR2 having the amino acid sequence as set forth in SEQ ID NO: 117, and light chain CDR3 having the amino acid sequence as set forth in SEQ ID NO: 118;

(13) an antibody comprising a heavy chain variable region comprising heavy chain CDR1 having the amino acid sequence as set forth in SEQ ID NO: 119, heavy chain CDR2 having the amino acid sequence as set forth in SEQ ID NO: 120, and heavy chain CDR3 having the amino acid sequence as set forth in SEQ ID NO: 121, and a light chain variable region comprising light chain CDR1 having the amino acid sequence as set forth in SEQ ID NO: 122, light chain CDR2 having the amino acid sequence as set forth in SEQ ID NO: 123, and light chain CDR3 having the amino acid sequence as set forth in SEQ ID NO: 124;

(14) an antibody comprising a heavy chain variable region comprising heavy chain CDR1 having the amino acid sequence as set forth in SEQ ID NO: 125, heavy chain CDR2 having the amino acid sequence as set forth in SEQ ID NO: 126, and heavy chain CDR3 having the amino acid sequence as set forth in SEQ ID NO: 127, and a light chain variable region comprising light chain CDR1 having the amino acid sequence as set forth in SEQ ID NO: 128, light chain CDR2 having the amino acid sequence as set forth in SEQ ID NO: 129, and light chain CDR3 having the amino acid sequence as set forth in SEQ ID NO: 130;

(15) an antibody comprising a heavy chain variable region comprising heavy chain CDR1 having the amino acid sequence as set forth in SEQ ID NO: 131, heavy chain CDR2 having the amino acid sequence as set forth in SEQ ID NO: 132, and heavy chain CDR3 having the amino acid sequence as set forth in SEQ ID NO: 133, and a light chain variable region comprising light chain CDR1 having the amino acid sequence as set forth in SEQ ID NO: 134, light chain CDR2 having the amino acid sequence as set forth in SEQ ID NO: 135, and light chain CDR3 having the amino acid sequence as set forth in SEQ ID NO: 136;

(16) an antibody comprising a heavy chain variable region comprising heavy chain CDR1 having the amino acid sequence as set forth in SEQ ID NO: 137, heavy chain CDR2 having the amino acid sequence as set forth in SEQ ID NO: 138, and heavy chain CDR3 having the amino acid sequence as set forth in SEQ ID NO: 139, and a light chain variable region comprising light chain CDR1 having the amino acid sequence as set forth in SEQ ID NO: 140, light chain CDR2 having the amino acid sequence as set forth in SEQ ID NO: 141, and light chain CDR3 having the amino acid sequence as set forth in SEQ ID NO: 142;

(17) an antibody comprising a heavy chain variable region comprising heavy chain CDR1 having the amino acid sequence as set forth in SEQ ID NO: 143, heavy chain CDR2 having the amino acid sequence as set forth in SEQ ID NO: 144, and heavy chain CDR3 having the amino acid sequence as set forth in SEQ ID NO: 145, and a light chain variable region comprising light chain CDR1 having the amino acid sequence as set forth in SEQ ID NO: 146, light chain CDR2 having the amino acid sequence as set forth in SEQ ID NO: 147, and light chain CDR3 having the amino acid sequence as set forth in SEQ ID NO: 148;

(18) an antibody comprising a heavy chain variable region comprising heavy chain CDR1 having the amino acid sequence as set forth in SEQ ID NO: 149, heavy chain CDR2 having the amino acid sequence as set forth in SEQ ID NO: 150, and heavy chain CDR3 having the amino acid sequence as set forth in SEQ ID NO: 151, and a light chain variable region comprising light chain CDR1 having the amino acid sequence as set forth in SEQ ID NO: 152, light chain CDR2 having the amino acid sequence as set forth in SEQ ID NO: 153, and light chain CDR3 having the amino acid sequence as set forth in SEQ ID NO: 154;

(19) an antibody comprising a heavy chain variable region comprising heavy chain CDR1 having the amino acid sequence as set forth in SEQ ID NO: 155, heavy chain CDR2 having the amino acid sequence as set forth in SEQ ID NO: 156, and heavy chain CDR3 having the amino acid sequence as set forth in SEQ ID NO: 157, and a light chain variable region comprising light chain CDR1 having the amino acid sequence as set forth in SEQ ID NO: 158, light chain CDR2 having the amino acid sequence as set forth in SEQ ID NO: 159, and light chain CDR3 having the amino acid sequence as set forth in SEQ ID NO: 160;

(20) an antibody comprising a heavy chain variable region comprising heavy chain CDR1 having the amino acid sequence as set forth in SEQ ID NO: 161, heavy chain CDR2 having the amino acid sequence as set forth in SEQ ID NO: 162, and heavy chain CDR3 having the amino acid sequence as set forth in SEQ ID NO: 163, and a light chain variable region comprising light chain CDR1 having the amino acid sequence as set forth in SEQ ID NO: 164, light chain CDR2 having the amino acid sequence as set forth in SEQ ID NO: 165, and light chain CDR3 having the amino acid sequence as set forth in SEQ ID NO: 166;

(21) an antibody comprising a heavy chain variable region comprising heavy chain CDR1 having the amino acid sequence as set forth in SEQ ID NO: 167, heavy chain CDR2 having the amino acid sequence as set forth in SEQ ID NO: 168, and heavy chain CDR3 having the amino acid sequence as set forth in SEQ ID NO: 169, and a light chain variable region comprising light chain CDR1 having the amino acid sequence as set forth in SEQ ID NO: 170, light chain CDR2 having the amino acid sequence as set forth in SEQ ID NO: 171, and light chain CDR3 having the amino acid sequence as set forth in SEQ ID NO: 172;

(22) an antibody comprising a heavy chain variable region comprising heavy chain CDR1 having the amino acid sequence as set forth in SEQ ID NO: 173, heavy chain CDR2 having the amino acid sequence as set forth in SEQ ID NO: 174, and heavy chain CDR3 having the amino acid sequence as set forth in SEQ ID NO: 175, and a light chain variable region comprising light chain CDR1 having the amino acid sequence as set forth in SEQ ID NO: 176, light chain CDR2 having the amino acid sequence as set forth in SEQ ID NO: 177, and light chain CDR3 having the amino acid sequence as set forth in SEQ ID NO: 178;

(23) an antibody comprising a heavy chain variable region comprising heavy chain CDR1 having the amino acid sequence as set forth in SEQ ID NO: 179, heavy chain CDR2 having the amino acid sequence as set forth in SEQ ID NO: 180, and heavy chain CDR3 having the amino acid sequence as set forth in SEQ ID NO: 181, and a light chain variable region comprising light chain CDR1 having the amino acid sequence as set forth in SEQ ID NO: 182, light chain CDR2 having the amino acid sequence as set forth in SEQ ID NO: 183, and light chain CDR3 having the amino acid sequence as set forth in SEQ ID NO: 184;

(24) an antibody comprising a heavy chain variable region comprising heavy chain CDR1 containing the amino acid sequence as set forth in SEQ ID NO: 207, heavy chain CDR2 containing the amino acid sequence as set forth in SEQ ID NO: 208, and heavy chain CDR3 containing the amino acid sequence as set forth in SEQ ID NO: 209, and a light chain variable region comprising light chain CDR1 containing the amino acid sequence as set forth in SEQ ID NO: 210, light chain CDR2 containing the amino acid sequence as set forth in SEQ ID NO: 211, and light chain CDR3 containing the amino acid sequence as set forth in SEQ ID NO: 212.

(25) an antibody comprising a heavy chain variable region comprising heavy chain CDR1 containing the amino acid sequence as set forth in SEQ ID NO: 213, heavy chain CDR2 containing the amino acid sequence as set forth in SEQ ID NO: 214, and heavy chain CDR3 containing the amino acid sequence as set forth in SEQ ID NO: 215, and a light chain variable region comprising light chain CDR1 containing the amino acid sequence as set forth in SEQ ID NO: 216, light chain CDR2 containing the amino acid sequence as set forth in SEQ ID NO: 217, and light chain CDR3 containing the amino acid sequence as set forth in SEQ ID NO: 218.

(26) an antibody comprising a heavy chain variable region comprising heavy chain CDR1 containing the amino acid sequence as set forth in SEQ ID NO: 213, heavy chain CDR2 containing the amino acid sequence as set forth in SEQ ID NO: 214, and heavy chain CDR3 containing the amino acid sequence as set forth in SEQ ID NO: 247, and a light chain variable region comprising light chain CDR1 containing the amino acid sequence as set forth in SEQ ID NO: 216, light chain CDR2 containing the amino acid sequence as set forth in SEQ ID NO: 217, and light chain CDR3 containing the amino acid sequence as set forth in SEQ ID NO: 218.

(27) an antibody comprising a heavy chain variable region comprising heavy chain CDR1 containing the amino acid sequence as set forth in SEQ ID NO: 219, heavy chain CDR2 containing the amino acid sequence as set forth in SEQ ID NO: 220, and heavy chain CDR3 containing the amino acid sequence as set forth in SEQ ID NO: 221, and a light chain variable region comprising light chain CDR1 containing the amino acid sequence as set forth in SEQ ID NO: 222, light chain CDR2 containing the amino acid sequence as set forth in SEQ ID NO: 223, and light chain CDR3 containing the amino acid sequence as set forth in SEQ ID NO: 224.

(28) an antibody comprising a heavy chain variable region comprising heavy chain CDR1 containing the amino acid sequence as set forth in SEQ ID NO: 225, heavy chain CDR2 containing the amino acid sequence as set forth in SEQ ID NO: 226, and heavy chain CDR3 containing the amino acid sequence as set forth in SEQ ID NO: 227, and a light chain variable region comprising light chain CDR1 containing the amino acid sequence as set forth in SEQ ID NO: 228, light chain CDR2 containing the amino acid sequence as set forth in SEQ ID NO: 229, and light chain CDR3 containing the amino acid sequence as set forth in SEQ ID NO: 230.

(29) an antibody comprising a heavy chain variable region comprising heavy chain CDR1 containing the amino acid sequence as set forth in SEQ ID NO: 231, heavy chain CDR2 containing the amino acid sequence as set forth in SEQ ID NO: 232, and heavy chain CDR3 containing the amino acid sequence as set forth in SEQ ID NO: 233, and a light chain variable region comprising light chain CDR1 containing the amino acid sequence as set forth in SEQ ID NO: 234, light chain CDR2 containing the amino acid sequence as set forth in SEQ ID NO: 235, and light chain CDR3 containing the amino acid sequence as set forth in SEQ ID NO: 236.

In one aspect, the present invention provides an antibody which binds to human CLDN18.2 protein, comprising a heavy chain variable domain selected from the group consisting of SEQ ID NO: 1, 2, 3, 4, 5, 6, 7, 8, 9, 10, 11, 12, 13, 14, 15, 16, 17, 18, 19, 20, 21, 22, 23, 237, 238, 239, 240, 241, and 248, and in another aspect the present invention provides an antibody which binds to human CLDN18.2 protein comprising a light chain variable domain selected from the group consisting of SEQ ID NO: 24, 25, 26, 27, 28, 29, 30 31, 32, 33, 34, 35, 36, 37, 38, 39, 40, 41, 42, 43, 44, 45, 46, 242, 243, 244, 245, and 246.

In one embodiment, the antibody is humanized. In another embodiment, the CDR domains of the antibody have one, two, three, four or five amino acids substituted, mutated, deleted or added.

In one embodiment, the antibody is humanized, which comprises a light chain with an amino acid sequence at least 95%, at least 99%, or 100% identical as the one selected from SEQ ID NO: 193-197, 205 and 206, and a heavy chain with an amino acid sequence at least 95%, at least 99%, or 100% identical as the one selected from SEQ ID NO: 187-191, 199-203, and 204.

In one embodiment, the antibody is humanized, which comprises a light chain with an amino acid sequence at least 95%, at least 99%, or 100% identical as the one selected from SEQ ID NO: 252 and 253, and a heavy chain with an amino acid sequence at least 95%, at least 99%, or 100% identical as the one selected from SEQ ID NO: 249, 250 and 251.

In one embodiment, the antibody is humanized, which comprises a heavy chain variable domain with an amino acid sequence at least 95%, at least 99%, or 100% identical as the one selected from SEQ ID NO: 254-258, and 259, and a light chain variable domain with an amino acid sequence at least 95%, at least 99%, or 100% identical as the one selected from SEQ ID NO: 260, 261 and 262.

In one embodiment, the antibody is humanized, which comprises a heavy chain variable domain with an amino acid sequence at least 95%, at least 99%, or 100% identical as the one selected from consisting of SEQ ID NO: 263, 264, and 265, and a light chain variable domain with an amino acid sequence at least 95%, at least 99%, or 100% identical as the one selected from the group consisting of SEQ ID NO: 266, 267, 268 and 269.

In one embodiment, the antibody is selected from a single-chain Fv antibody (scFv), a Fab antibody, a Fab' antibody, a (Fab')2 antibody, a domain antibody, a nanobody, a minibody, a maxibody, and a diabody.

In one aspect, the above said antibody is conjugated with one or more cytotoxic agent. In one embodiment, the heavy chain and/or light chain of said antibody is fused with a human albumin; and wherein said albumin domain is conjugated with one or more cytotoxic agent.

In one aspect, the antibody is fused with an immune-stimulant. In some embodiment, the heavy chain and/or light chain of said antibody is fused with one or more IL-2 polypeptides, one or more IL-2 analogs, one or more IL-15 polypeptides, or one or more IL-15 analogs. In some embodiment, said antibody further comprises one or more antagonists of IL-2 or IL-15. In some embodiment, the heavy chain and/or light chain of said antibody is fused with an antigen binding domain, and wherein said antigen binding domain binds human CD3. In some embodiment, the heavy chain and/or light chain of said antibody is fused with one or more antigen binding domains, and wherein said antigen binding domain binds human PD-L1, CD47 or signal-regulatory protein alpha (SIRPα).

In another aspect, the present invention provides a pharmaceutical composition comprising an antibody as described above.

In another aspect, the present invention provides a method of treating cancer, the method comprising the step of administering a pharmaceutical composition as described above to a subject in need thereof, wherein the cancer is selected from the group consisting of pancreas, stomach, esophagus, and liver cancer.

In another aspect, the present invention further provides a method of treating cancer, wherein the method comprising the step of administration of above said pharmaceutical composition to a patient in need thereof, and in combination of a chemotherapy regimen suitable for said cancer, wherein the cancer is selected from the group consisting of gastric, esophagus, pancreatic, and liver cancer.

In some embodiment, said chemotherapy regimen is selected from nucleoside analogs, platinum compounds, camptothecin analogs, taxanes, prodrugs thereof, salts thereof, and combinations thereof.

In some embodiment, said chemotherapy regimen consists of gemcitabine, 5-fluorouracil, oxaliplatin, irinotecan, paclitaxel, prodrugs thereof, salts thereof, and combinations thereof.

In some embodiment, said chemotherapy regimen consists of the combination of oxaliplatin and paclitaxel, or their prodrugs or salts.

BRIEF DESCRIPTION OF THE DRAWINGS

The accompanying drawings illustrate aspects of the present invention. In such drawings:

FIGS. 5A and 5B. Analysis of 20 Immunized Mice Serum Samples by FACS.

FIG. 8. FACS Analysis the Supernants from the Cultured Positive Hybridoma Subclones. FIG. 8A shows titration curves of the bindings of the supernants of the hybridomas to CLDN 18.2 expressed on HEK 293 cells. FIG. 8B shows the specificity of the bindings of the supernants to HEK 293 cells expressing CLDN 18.2 vs. 18.1. FIG. 8C shows the FACS intensity of the binding of the supernants to CLDN 18.2 vs CLDN 18.1 expressed on the HEK 293 cells.

FIG. 9. FACS Analysis of the Supernants of HEK 293 Cells Transiently Transfected with the Genes Cloned from Positive Subclones. FIG. 9A shows titration curves of the bindings of the supernants of the clones to CLDN 18.2 expressed on HEK 293 cells. FIG. 9B shows the specificity of the bindings of the supernants to HEK 293 cells expressing CLDN 18.2 vs. 18.1. FIG. 9C shows the FACS intensity of the binding of the supernants to CLDN 18.2 vs CLDN 18.1 expressed on the HEK 293 cells.

FIG. 10. ADCC Reporter Assay of the Chimeric Molecules.

FIG. 11. Binding of the Humanized Antibodies to CLDN18.2 Expressed on HEK 293 Cells (FIG. 11A) and NUGC4 Gastric Cancer Cells (FIG. 11B) as Analyzed by FACS FIG. 12. Results of ADCC Reporter Assay for the Humanized Antibodies M5 and B with Target Cells HEK 293 Expressing CLDN 18.2 (FIG. 12A), Gastric Cancer Cells NUGC4 (FIG. 12B) and Gastric Cancer Cells DAN-G (FIG. 12C).

FIG. 13. CDC Results of the Humanized Molecules B, M1 and M5. FIG. 13A Shows the Results with B and M1 versus Reference against Target HEK293 Cells Expressing CLDN 18.2; FIG. 13B Shows the Results with M5 versus Reference against Target HEK293 Cells Expressing CLDN 18.2; FIG. 13C Shows the Results with B and M1 versus Reference against Target NUGC4 Cells.

FIG. 14. Specificity Results of the humanized mouse and rabbit antibodies. FIG. 14A shows the FACS binding of the humanized antibodies M1, M5 and B to claudin family proteins; FIG. 14B shows the FACS binding of anti-FLAG antibody (Note that CLDN7 and CLDN18.2 molecules were not fused with FLAG).

Figure 1:
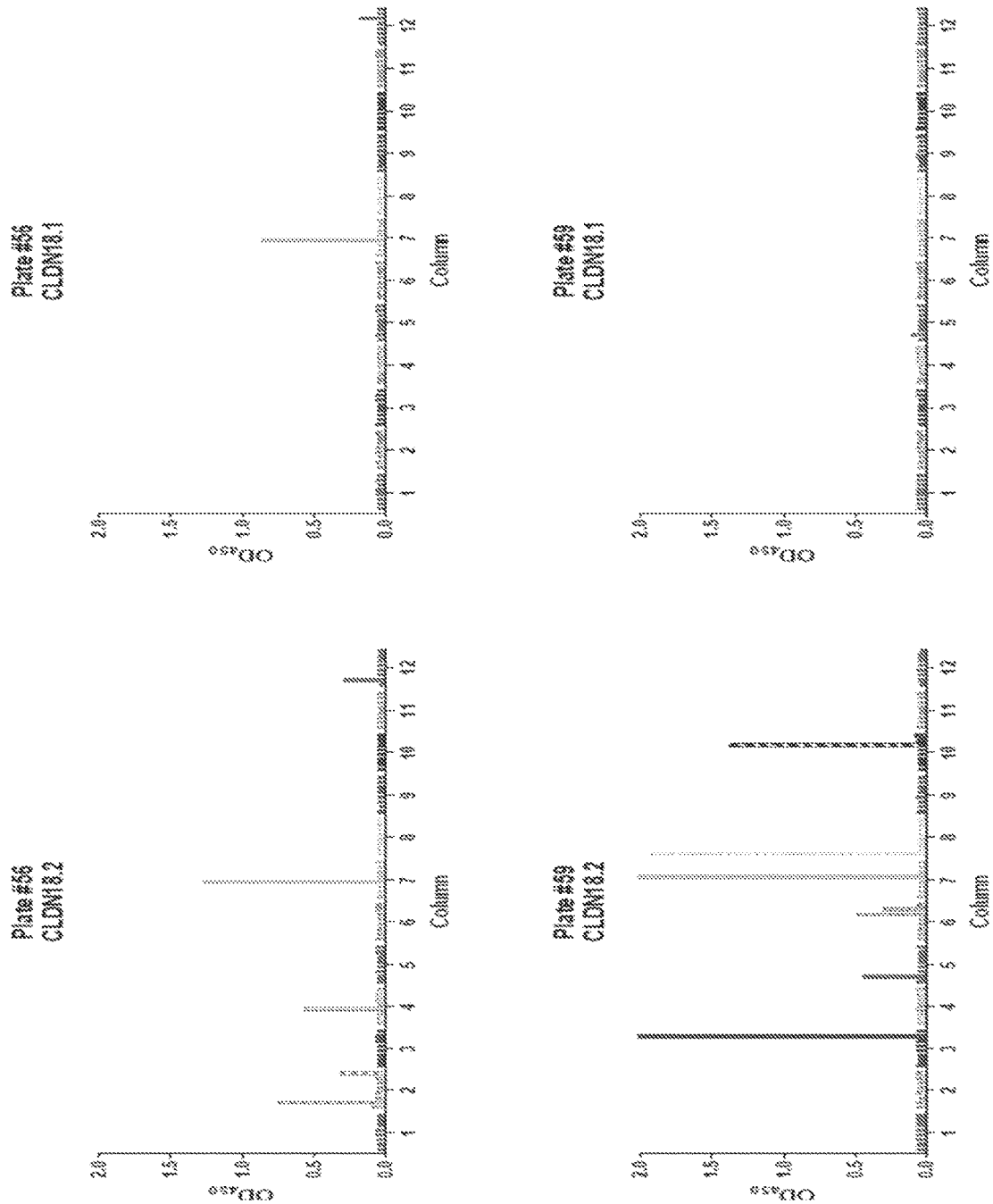
FIG. 1: ELISA-based screening of B cells. B cells selectively binding to CLDN 18.2 but not CLDN 18.1 were identified.

The above described drawing figures illustrate aspects of the invention in at least one of its exemplary embodiments, which are further defined in detail in the following description. Features, elements, and aspects of the invention that are referenced by the same numerals in different figures represent the same, equivalent, or similar features, elements, or aspects, in accordance with one or more embodiments

DETAILED DESCRIPTION

The present invention relates to compositions and methods for therapy of a subject afflicted with diseases such as cancer, which methods comprise administering to the subject a composition comprising a therapeutically effective amount of an anti-CLDN18.2 antibody or portion thereof that potentiates an endogenous immune response, either stimulating the activation of the endogenous response or inhibiting the suppression of the endogenous response. In one embodiment, an antibody is designated 49E05, 49E12, 50H08, 52E07, 52G02, 54B08, 54C02, 59A08, 59E07, 59F10, 59G03, 77B06, 80D08, 80G08, 81E11, 82C08, 82F02, 99A09, SD215, SD232, SD272, SD312, SD331, 79C4, 11E12, 83G3, 30B5, or 85H12. These antibodies have the respective CDRs listed in Tables 4-26, 29-32, and 33 below. In another embodiment, antibodies 49E05, 49E12, 50H08, 52E07, 52G02, 54B08, 54C02, 59A08, 59E07, 59F10, 59G03, 77B06, 80D08, 80G08, 81E11, 82C08, 82F02, 99A09, SD215, SD232, SD272, SD312, SD331, 79C4, 11E12, 83G3, 30B5, and 85H12 have the respective light and heavy chain variable regions as listed in Tables 2, 3, 34 and 35 below.

Hybridoma line 11E12 expressing an anti-CLDN18.2 antibody has been deposited with the American Type Culture Collection [ATCC; 10801 University Blvd., Manassas, Va. 20110-2209 (USA)] on Jun. 12, 2019, under Patent Deposit Number PTA-125950.

In certain other embodiments, the subject is selected as suitable for therapy in a method comprising measuring the surface expression of CLDN18.2 in a test tissue sample obtained from a patient with cancer, for example, determining the proportion of cells in the test tissue sample that express CLDN18.2 on the cell surface, and selecting the patient for therapy based on an assessment that CLDN18.2 is expressed on the surface of cells in the test tissue sample.

The claudin 18 (CLD18) molecule (Genbank accession number: splice variant 1 (CLD18A1): NP_057453, NM_016369, and splice variant 2 (CLD18A2): NM_001002026, NP 001002026) is an integral transmembrane protein with a molecular weight of approximately 27.9/27.7 KD. Claudins are integral membrane proteins located within the tight junctions of epithelia and endothelia.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Methods for obtaining (e.g., producing, isolating, purifying, synthesizing, and recombinantly manufacturing) polypeptides are well known to one of ordinary skill in the art.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refer to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The present composition encompasses amino acid substitutions in proteins and peptides, which do not generally alter the activity of the proteins or peptides (H. Neurath, R. L. Hill, The Proteins, Academic Press, New York, 1979). In one embodiment, these substitutions are "conservative" amino acid substitutions. The most commonly occurring substitutions are Ala/Ser, Val/Ile, Asp/Glu, Thr/Ser, Ala/Gly, Ala/Thr, Ser/Asn, Ala/Val, Ser/Gly, Ala/Pro, Lys/Arg, Asp/Asn, Leu/Ile, Leu/Val, Ala/Glu and Asp/Gly, in both directions.

As to "conservatively modified variants" of amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

Analogue as used herein denotes a peptide, polypeptide, or protein sequence which differs from a reference peptide, polypeptide, or protein sequence. Such differences may be the addition, deletion, or substitution of amino acids, phosphorylation, sulfation, acrylation, glycosylation, methylation, farnesylation, acetylation, amidation, and the like, the use of non-natural amino acid structures, or other such modifications as known in the art.

In one embodiment, an anti-CLDN18.2 antibody of the invention is designated as either 49E05, 49E12, 50H08, 52E07, 54B08, 54C02, 59A08, 59E07, 59F10, 59G03, 77B06, 80D08, 80G08, 81E11, 82C08, 82F02, 99A09, SD215, SD232, SD272, SD312, SD331, 79C4, 11E12, 83G3, 30B5, or 85H12 and each comprises a heavy chain CDR and a light chain CDR, wherein the heavy chain CDR comprises a sequence having at least 70%, at least 75%, at least 80%, at least 85%, at least 90%, at least 95%, at least 96%, at least 97%, at least 98%, at least 99% or 100% sequence identity to the respective CDRs listed in Tables 4-26 below, and wherein the light chain CDR comprises a sequence having at least 70%, at least 75%, at least 80%, at least 85%, at least 90%, at least 95%, at least 96%, at least 97%, at least 98%, at least 99% or 100% sequence identity to the respective CDRs listed in Tables 4-26 below.

In another embodiment, an anti-CLDN18.2 antibody of the invention designated as either 49E05, 49E12, 50H08, 52E07, 54B08, 54C02, 59A08, 59E07, 59F10, 59G03, 77B06, 80D08, 80G08, 81E11, 82C08, 82F02, 99A09, SD215, SD232, SD272, SD312, SD331, 79C4, 11E12, 83G3, 30B5, or 85H12 and each comprises a heavy chain variable region and a light chain variable region, wherein the heavy chain variable region comprises a sequence having at least 70%, at least 75%, at least 80%, at least 85%, at least 90%, at least 95%, at least 96%, at least 97%, at least 98%, at least 99% or 100% sequence identity to the respective heavy chain variable regions listed in Table 2 below, and wherein the light chain variable region comprises a sequence having at least 70%, at least 75%, at least 80%, at least 85%, at least 90%, at least 95%, at least 96%, at least 97%, at least 98%, at least 99% or 100% sequence identity to the respective light chain variable region selected from the ones listed in Table 3 below.

In a further embodiment an humanized anti-CLDN 18.2 antibody comprises a heavy chain and a light chain, wherein the heavy chain comprises a sequence having at least 95%, at least 96%, at least 97%, at least 98%, at least 99% or 100% sequence identity to the respective heavy chain variable region selected from SEQ ID NO: 187-191, 199-203, 204, 249, 250 and 251 listed in Table 27 below, and wherein the light chain comprises a sequence having at least 90%, at least 95%, at least 96%, at least 97%, at least 98%, at least 99% or 100% sequence identity to the respective light chain variable regions with SEQ ID NO: 193-197, 205, 206, 252 and 253 listed in Table 28 below.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region, thereby converting the F(ab)'2 dimer into an Fab' monomer. The Fab' monomer is essentially Fab with part of the hinge region (see Fundamental Immunology, Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

Accordingly, in either aspect of the invention, the term antibody also embraces minibodies, diabodies, triabodies and the like. Diabodies are small bivalent biospecific antibody fragments with high avidity and specificity. Their high signal to noise ratio is typically better due to a better specificity and fast blood clearance increasing their potential for diagnostic and therapeutic targeting of specific antigen (Sundaresan et al., J Nucl Med 44:1962-9 (2003). In addition, these antibodies are advantageous because they can be engineered if necessary as different types of antibody fragments ranging from a small single chain Fv to an intact IgG with varying isoforms (Wu & Senter, Nat. Biotechnol. 23:1137-1146 (2005)). In some embodiments, the antibody fragment is part of a diabody. In some embodiments, in either aspect, the invention provides high avidity antibodies for use according to the invention.

The CDR regions provided by the invention may be used to construct an anti-CLDN18.2 binding protein, including without limitation, an antibody, a scFv, a triabody, a diabody, a minibody, and the like. In a certain embodiment, an anti-CLDN18.2 protein of the invention will comprise at least one CDR region from Tables 4-26 listed below or a sequence having at least 70%, at least 75%, at least 80%, at least 85%, at least 90%, at least 95%, at least 96%, at least 97%, at least 98%, at least 99% or 100% sequence identity to the CDR regions listed in Tables 4-26. Anti-CLDN18.2 binding proteins may comprise, for example, a CDR-H1, a CDR-H2, a CDR-H3, a CDR-L1, a CDR-L2, a CDR-L3, or combinations thereof, from an antibody provided herein. In particular embodiments of the invention, an anti-CLDN18.2 binding protein may comprise all three CDR-H sequences of an antibody provided herein, all three CDR-L sequences of an antibody provided herein, or both. Anti-CLDN18.2 CDR sequences may be used on an antibody backbone, or fragment thereof, and likewise may include humanized antibodies, or antibodies containing humanized sequences. In some embodiments, the CDR regions may be defined using the Kabat definition, the Chothia definition, the AbM definition, the contact definition, or any other suitable CDR numbering system.

In some embodiments, the invention provides antibodies (e.g., diabodies, minibodies, triabodies) or fragments thereof having the CDRs of Tables 4-26 or a sequence having at least 70%, at least 75%, at least 80%, at least 85%, at least 90%, at least 95%, at least 96%, at least 97%, at least 98%, at least 99% or 100% sequence identity to the CDRs of Tables 4-26. In other embodiments, the diabodies possess the light and heavy chain of Tables 2 and 3 or a sequence having at least 70%, at least 75%, at least 80%, at least 85%, at least 90%, at least 95%, at least 96%, at least 97%, at least 98%, at least 99% or 100% sequence identity to the sequences of Tables 2 and 3.

Diabodies, first described by Hollinger et al., PNAS (USA) 90(14): 6444-6448 (1993), may be constructed using heavy and light chains disclosed herein, as well as by using individual CDR regions disclosed herein. Typically, diabody fragments comprise a heavy chain variable domain (VH) connected to a light chain variable domain (VL) by a linker which is too short to allow pairing between the two domains on the same chain. Accordingly, the VH and VL domains of one fragment are forced to pair with the complementary VH and VL domains of another fragment, thereby forming two antigen-binding sites. Triabodies can be similarly constructed with three antigen-binding sites. An Fv fragment contains a complete antigen-binding site which includes a VL domain and a VH domain held together by non-covalent interactions. Fv fragments embraced by the present invention also include constructs in which the VH and VL domains are crosslinked through glutaraldehyde, intermolecular disulfides, or other linkers. The variable domains of the heavy and light chains can be fused together to form a single chain variable fragment (scFv), which retains the original specificity of the parent immunoglobulin. Single chain Fv (scFv) dimers, first described by Gruber et al., J. Immunol. 152(12):5368-74 (1994), may be constructed using heavy and light chains disclosed herein, as well as by using individual CDR regions disclosed herein. Many techniques known in the art can be used to prepare the specific binding constructs of the present invention (see, U.S. Patent Application Publication No. 20070196274 and U.S. Patent Application Publication No. 20050163782, which are each herein incorporated by reference in their entireties for all purposes, particularly with respect to minibody and diabody design).

Bispecific antibodies can be generated by chemical cross-linking or by the hybrid hybridoma technology. Alternatively, bispecific antibody molecules can be produced by recombinant techniques. Dimerization can be promoted by reducing the length of the linker joining the VH and the VL domain from about 15 amino acids, routinely used to produce scFv fragments, to about 5 amino acids. These linkers favor intrachain assembly of the VH and VL domains. Any suitable short linker can be used. Thus, two fragments assemble into a dimeric molecule. Further reduction of the linker length to 0-2 amino acids can generate trimeric (triabodies) or tetrameric (tetrabodies) molecules.

For preparation of antibodies, e.g., recombinant, monoclonal, or polyclonal antibodies, many techniques known in the art can be used (see, e.g., Kohler & Milstein, Nature 256:495-497 (1975); Kozbor et al., Immunology Today 4:72 (1983); Cole et al., in Monoclonal Antibodies and Cancer Therapy, Alan R. Liss, Inc., pp. 77-96 (1985); Coligan, Current Protocols in Immunology (1991); Harlow & Lane, Antibodies, A Laboratory Manual (1988); and Goding, Monoclonal Antibodies: Principles and Practice (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, Immunology (3rd ed. 1997)). Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); and Lonberg & Huszar, Intern. Rev. Immunol. 13:65-93 (1995)). Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)). Antibodies can also be made bispecific, i.e., able to recognize two different antigens (see, e.g., WO 93/08829, Traunecker et al., EMBO J. 10:3655-3659 (1991); and Suresh et al., Methods in Enzymology 121:210 (1986)). Antibodies can also be heteroconjugates, e.g., two covalently joined antibodies, or immunotoxins (see, e.g., U.S. Pat. No. 4,676,980, WO 91/00360; and WO 92/200373).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., Nature 321:522-525 (1986); Riechmann et al., Nature 332: 323-327 (1988); Verhoeyen et al., Science 239:1534-1536 (1988) and Presta, Curr. Op. Struct. Biol. 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998) for a description of immunoassay formats and conditions that can be used to determine specific immunoreactivity).

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including Abs, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity, neurodegeneration or pathological inflammation, normal human cells or tissues.

An "immunoregulator" refers to a substance, an agent, a signaling pathway or a component thereof that regulates an immune response. "Regulating," "modifying" or "modulating" an immune response refers to any alteration in a cell of the immune system or in the activity of such cell. Such regulation includes stimulation or suppression of the immune system which may be manifested by an increase or decrease in the number of various cell types, an increase or decrease in the activity of these cells, or any other changes which can occur within the immune system. Both inhibitory and stimulatory immunoregulators have been identified, some of which may have enhanced function in the cancer, infectious disease or neurodegenerative microenvironment.

The term "immunotherapy" refers to the treatment of a subject afflicted with, or at risk of contracting or suffering a recurrence of, a disease by a method comprising inducing, enhancing, suppressing or otherwise modifying an immune response. "Treatment" or "therapy" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication, condition or biochemical indicia associated with a disease.

"Potentiating an endogenous immune response" means increasing the effectiveness or potency of an existing immune response in a subject. This increase in effectiveness and potency may be achieved, for example, by overcoming mechanisms that suppress the endogenous host immune response or by stimulating mechanisms that enhance the endogenous host immune response.

A "predetermined threshold value," relating to cell surface CLDN18.2 expression, refers to the proportion of cells in a test tissue sample comprising tumor cells and tumor-infiltrating inflammatory cells above which the sample is scored as being positive for cell surface CLDN18.2 expression. For cell surface expression, the predetermined threshold value for cells expressing CLDN18.2 on the cell surface ranges from at least about 0.01% to at least about 20% of the total number of cells. In preferred embodiments, the predetermined threshold value for cells expressing CLDN18.2 on the cell surface ranges from at least about 0.1% to at least about 10% of the total number of cells. More preferably, the predetermined threshold value is at least about 5%. Even more preferably, the predetermined threshold value is at least about 1%.

Construction of suitable vectors containing the desired sequences and control sequences employs standard ligation and restriction techniques, which are well understood in the art (see Maniatis et al., in Molecular Cloning: A Laboratory Manual, Cold Spring Harbor Laboratory, New York (1982)). Isolated plasmids, DNA sequences, or synthesized oligonucleotides are cleaved, tailored, and re-ligated in the form desired.

Nucleic acid is "operably linked" when it is placed into a functional relationship with another nucleic acid sequence. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection. Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to the full length of the reference sequence, usually about 25 to 100, or 50 to about 150, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

A preferred example of algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher et al., J. Biol. Chem. 273(52):35095-35101 (1998).

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

"Cancer" refers to human cancers and carcinomas, sarcomas, adenocarcinomas, etc., including but not limited to solid tumors, anal, kidney, breast, cardiac, cervical, ovarian, primary peritoneal, colorectal, lung, uterine, endometrial, esophageal, eye, fallopian tube, gall bladder, gastric, testicular, kidney, bladder, bile duct, bone, melanoma, karposi sarcoma, urinary tract, urethra, penis, vulva, vagina, cervical, parathyroid, penile, pituitary, colon, throat, thyroid, ovarian, prostate, mesothelioma, pancreas, rectal, stomach, brain, head and neck, small intestine, skin, uterine, testicular, esophagus, and liver cancer. Cancer can also include lymphomas and leukemias, including Burkitt lumphoma, Hodgkin lymphoma, non-Hodgkin lymphoma, cutaneious T-cell lymphoma, acute myeloid leukemia, acute lymphoblastic leukemia, hairy cell leukemia and acute myeloid leukemia. Lung cancer can include small cell lung cancer and non-small cell lung cancer.

In any of the embodiments above, one or more cancer therapies, e.g., chemotherapy, radiation therapy, immunotherapy, surgery, or hormone therapy can be co-administered further with the antibody of the invention.

In one embodiment, the chemotherapeutic reagent is an alkylating agent: nitrogen mustards, nitrosoureas, tetrazines, aziridines, cisplatins and derivatives, and non-classical alkylating agents. Nitrogen mustards include mechlorethamine, cyclophosphamide, melphalan, chlorambucil, ifosfamide and busulfan. Nitrosoureas include N-Nitroso-N-methylurea (MNU), carmustine (BCNU), lomustine (CCNU) and semustine (MeCCNU), fotemustine and streptozotocin. Tetrazines include dacarbazine, mitozolomide and temozolomide. Aziridines include thiotepa, mytomycin and diaziquone (AZQ). Cisplatin and derivatives include cisplatin, carboplatin and oxaliplatin. In one embodiment the chemotherapeutic reagent is an anti-metabolites: the anti-folates (e.g., methotrexate), fluoropyrimidines (e.g., fluorouracil and capecitabine), deoxynucleoside analogues and thiopurines. In another embodiment the chemoptheraputic reagent is an anti-microtubule agent such as *vinca* alkaloids (e.g., vincristine and vinblastine) and taxanes (e.g., paclitaxel and docetaxel). In another embodiment the chemotherapeutic reagent is a topoisomerase inhibitor or a cytotoxic antibiotic such as doxorubicin, mitoxantrone, bleomycin, actinomycin, and mitomycin.

The contacting of the patient with the antibody or antibody fragment, can be by administering the antibody to the patient intravenously, intraperitoneally, intramuscularly, intratumorally, or intradermally. In some embodiments the antibody is co-administered with a cancer therapy agent.

The term "refolding" as used herein refers to the process by which a protein structure assumes its functional shape or conformation. It is the physical process by which a polypeptide folds into its characteristic and functional three-dimensional structure from random coil. It takes place at a basic pH (typically pH 8.0-10.0, pH 8.5-10, or pH 8.5-9.6), a low temperature (typically 0.0° C. to 10.0° C. or 2.0° C. to 8.0° C.), preferably with the presence of a redox pair at suitable concentrations, and/or at the presence of oxygen, and/or at the presence of catalyst(s) such as copper ions at suitable concentration.

The term "recombinant" as used herein refers to a polypeptide produced through a biological host, selected from a mammalian expression system, an insect cell expression system, a yeast expression system, and a bacterial expression system.

The term "formulation" as used herein refers to the antibodies disclosed herein and excipients combined together which can be administered and has the ability to bind to the corresponding receptors and initiate a signal transduction pathway resulting in the desired activity. The formulation can optionally comprise other agents.

The present specification also provides a pharmaceutical composition for the administration to a subject. The pharmaceutical composition disclosed herein may further include a pharmaceutically acceptable carrier, excipient, or diluent. As used herein, the term "pharmaceutically acceptable" means that the composition is sufficient to achieve the therapeutic effects without deleterious side effects, and may be readily determined depending on the type of the diseases, the patient's age, body weight, health conditions, gender, and drug sensitivity, administration route, administration mode, administration frequency, duration of treatment, drugs used in combination or coincident with the composition disclosed herein, and other factors known in medicine.

The pharmaceutical composition including the antibody disclosed herein may further include a pharmaceutically acceptable carrier. For oral administration, the carrier may include, but is not limited to, a binder, a lubricant, a disintegrant, an excipient, a solubilizer, a dispersing agent, a stabilizer, a suspending agent, a colorant, and a flavorant. For injectable preparations, the carrier may include a buffering agent, a preserving agent, an analgesic, a solubilizer, an isotonic agent, and a stabilizer. For preparations for topical administration, the carrier may include a base, an excipient, a lubricant, and a preserving agent.

The disclosed compositions may be formulated into a variety of dosage forms in combination with the aforementioned pharmaceutically acceptable carriers. For example, for oral administration, the pharmaceutical composition may be formulated into tablets, troches, capsules, elixirs, suspensions, syrups or wafers. For injectable preparations, the pharmaceutical composition may be formulated into an ampule as a single dosage form or a multidose container. The pharmaceutical composition may also be formulated into solutions, suspensions, tablets, pills, capsules and long-acting preparations.

On the other hand, examples of the carrier, the excipient, and the diluent suitable for the pharmaceutical formulations include, without limitation, lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oils. In addition, the pharmaceutical formulations may further include fillers, anti-coagulating agents, lubricants, humectants, flavorants, and antiseptics.

Further, the pharmaceutical composition disclosed herein may have any formulation selected from the group consisting of tablets, pills, powders, granules, capsules, suspensions, liquids for internal use, emulsions, syrups, sterile aqueous solutions, non-aqueous solvents, lyophilized formulations and suppositories.

The composition may be formulated into a single dosage form suitable for the patient's body, and preferably is formulated into a preparation useful for peptide drugs according to the typical method in the pharmaceutical field so as to be administered by an oral or parenteral route such as through skin, intravenous, intramuscular, intra-arterial, intramedullary, intramedullary, intraventricular, pulmonary, transdermal, subcutaneous, intraperitoneal, intranasal, intracolonic, topical, sublingual, vaginal, or rectal administration, but is not limited thereto.

The composition may be used by blending with a variety of pharmaceutically acceptable carriers such as physiological saline or organic solvents. In order to increase the stability or absorptivity, carbohydrates such as glucose, sucrose or dextrans, antioxidants such as ascorbic acid or glutathione, chelating agents, low molecular weight proteins or other stabilizers may be used.

The administration dose and frequency of the pharmaceutical composition disclosed herein are determined by the type of active ingredient, together with various factors such as the disease to be treated, administration route, patient's age, gender, and body weight, and disease severity.

The total effective dose of the compositions disclosed herein may be administered to a patient in a single dose, or may be administered for a long period of time in multiple doses according to a fractionated treatment protocol. In the pharmaceutical composition disclosed herein, the content of active ingredient may vary depending on the disease severity. Preferably, the total daily dose of the peptide disclosed herein may be approximately 0.0001 jig to 500 mg per 1 kg of body weight of a patient. However, the effective dose of the peptide is determined considering various factors including patient's age, body weight, health conditions, gender, disease severity, diet, and secretion rate, in addition to administration route and treatment frequency of the pharmaceutical composition. In view of this, those skilled in the art may easily determine an effective dose suitable for the particular use of the pharmaceutical composition disclosed herein. The pharmaceutical composition disclosed herein is not particularly limited to the formulation, and administration route and mode, as long as it shows suitable effects.

Moreover, the pharmaceutical composition may be administered alone or in combination or coincident with other pharmaceutical formulations showing prophylactic or therapeutic efficacy.

In still another aspect, the present specification provides a method for preventing or treating of cancer, infectious diseases or neurodegenerative diseases comprising the step of administering to a subject the chimeric protein or the pharmaceutical composition including the same.

As used herein, the term "prevention" means all of the actions by which the occurrence of the disease is restrained or retarded.

As used herein, the term "treatment" means all of the actions by which the symptoms of the disease have been alleviated, improved or ameliorated. In the present specification, "treatment" means that the symptoms of cancer, neurodegeneration, or infectious disease are alleviated, improved or ameliorated by administration of the antibodies disclosed herein.

As used herein, the term "administration" means introduction of an amount of a predetermined substance into a patient by a certain suitable method. The composition disclosed herein may be administered via any of the common routes, as long as it is able to reach a desired tissue, for example, but is not limited to, intraperitoneal, intravenous, intramuscular, subcutaneous, intradermal, oral, topical, intranasal, intrapulmonary, or intrarectal administration. However, since peptides are digested upon oral administration, active ingredients of a composition for oral administration should be coated or formulated for protection against degradation in the stomach.

In the present specification, the term "subject" is those suspected of having or diagnosed with cancer, a neurodegenerative or an infectious disease. However, any subject to be treated with the pharmaceutical composition disclosed herein is included without limitation. The pharmaceutical composition including the anti-CLDN18.2 antibody disclosed herein is administered to a subject suspected of having cancer, a neurodegenerative or an infectious disease.

The therapeutic method of the present specification may include the step of administering the composition including the antibody at a pharmaceutically effective amount. The total daily dose should be determined through appropriate medical judgment by a physician, and administered once or several times. The specific therapeutically effective dose level for any particular patient may vary depending on various factors well known in the medical art, including the kind and degree of the response to be achieved, concrete compositions according to whether other agents are used therewith or not, the patient's age, body weight, health condition, gender, and diet, the time and route of administration, the secretion rate of the composition, the time period of therapy, other drugs used in combination or coincident with the composition disclosed herein, and like factors well known in the medical arts.

In still another aspect, the present specification provides a use of the therapeutic protein or the pharmaceutical composition including the same in the preparation of drugs for the prevention or treatment of cancer, a neurodegenerative or an infectious disease.

In one embodiment, the dose of the composition may be administered daily, semi-weekly, weekly, bi-weekly, or monthly. The period of treatment may be for a week, two weeks, a month, two months, four months, six months, eight months, a year, or longer. The initial dose may be larger than a sustaining dose. In one embodiment, the dose ranges from a weekly dose of at least 0.01 mg, at least 0.25 mg, at least 0.3 mg, at least 0.5 mg, at least 0.75 mg, at least 1 mg, at least 1.25 mg, at least 1.5 mg, at least 2 mg, at least 2.5 mg, at least 3 mg, at least 4 mg, at least 5 mg, at least 6 mg, at least 7 mg, at least 8 mg, at least 9 mg, at least 10 mg, at least 15 mg, at least 20 mg, at least 25 mg, at least 30 mg, at least 35 mg, at least 40 mg, at least 50 mg, at least 55 mg, at least 60 mg, at least 65 mg, or at least 70 mg. In one embodiment, a weekly dose may be at most 0.5 mg, at most 0.75 mg, at most 1 mg, at most 1.25 mg, at most 1.5 mg, at most 2 mg, at most 2.5 mg, at most 3 mg, at most 4 mg, at most 5 mg, at most 6 mg, at most 7 mg, at most 8 mg, at most 9 mg, at most 10 mg, at most 15 mg, at most 20 mg, at most 25 mg, at most 30 mg, at most 35 mg, at most 40 mg, at most 45 mg, at most 50 mg, at most 55 mg, at most 60 mg, at most 65 mg, or at most 70 mg. In a particular aspect, the weekly dose may range from 0.25 mg to 2.0 mg, from 0.5 mg to 1.75 mg. In an alternative aspect, the weekly dose may range from 10 mg to 70 mg.

In other aspects of this embodiment, an antibody herein reduces the severity of a cancer by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other aspects of this embodiment, an antibody herein reduces the severity of a cancer from, e.g., about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

An antibody disclosed herein may comprise a therapeutic compound in an amount sufficient to allow customary administration to a human or nonhuman mammal, including a human, a cat, a dog, a horse, a sheep, a cow, a goat, a pig or other animal.

Aspects of the present specification disclose, in part, treating a human or nonhuman mammalian individual suffering from a disease, including cancer. As used herein, the term "treating," refers to reducing or eliminating in a human or nonhuman, mammalian a clinical symptom of cancer; or delaying or preventing in a human or nonhuman, mammalian the onset of a clinical symptom of cancer. For example, the term "treating" can mean reducing a symptom of a condition characterized by cancer, including, but not limited to, reduction of the severity of the disease, by, e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90% at least 95%, or at least 100%. The actual symptoms associated with cancer are well known and can be determined by a person of ordinary skill in the art by taking into account factors, including, without limitation, the location of the disease, the cause of the disease, the severity of the disease, and/or the tissue or organ affected by the disease. Those of skill in the art will know the appropriate symptoms or indicators associated with a specific type of disease, and will know how to determine if an individual is a candidate for treatment as disclosed herein.

In aspects of this embodiment, a therapeutically effective amount of an antibody of the present invention herein reduces the severity of a cancer by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 100%. In other aspects of this embodiment, a therapeutically effective amount of an antibody of the present invention herein reduces the severity of a cancer by, e.g., at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90%, at most 95% or at most 100%. In yet other aspects of this embodiment, a therapeutically effective amount of an antibody of the present invention herein reduces the severity of a cancer by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%.

In yet other aspects of this embodiment, an antibody disclosed herein generally is in the range of about 0.001 mg/kg/day to about 100 mg/kg/day. In aspects of this embodiment, an effective amount of a therapeutic compound disclosed herein may be, e.g., at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day. In other aspects of this embodiment, an effective amount of an antibody disclosed herein may be in the range of, e.g., about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day. In yet other aspects of this embodiment, an effective amount of a therapeutic compound disclosed herein may be in the range of, e.g., about 0.01 mg/kg/day to about 10 mg/kg/day, about 0.01 mg/kg/day to about 15 mg/kg/day, about 0.01 mg/kg/day to about 20 mg/kg/day, about 0.01 mg/kg/day to about 25 mg/kg/day, about 0.01 mg/kg/day to about 30 mg/kg/day, about 0.01 mg/kg/day to about 35 mg/kg/day, about 0.01 mg/kg/day to about 40 mg/kg/day, about 0.01 mg/kg/day to about 45 mg/kg/day, about 0.01 mg/kg/day to about 50 mg/kg/day, about 0.01 mg/kg/day to about 75 mg/kg/day, or about 0.01 mg/kg/day to about 100 mg/kg/day. In still other aspects of this embodiment, an antibody disclosed herein may be in the range of, e.g., about 0.1 mg/kg/day to about 10 mg/kg/day, about 0.1 mg/kg/day to about 15 mg/kg/day, about 0.1 mg/kg/day to about 20 mg/kg/day, about 0.1 mg/kg/day to about 25 mg/kg/day, about 0.1 mg/kg/day to about 30 mg/kg/day, about 0.1 mg/kg/day to about 35 mg/kg/day, about 0.1 mg/kg/day to about 40 mg/kg/day, about 0.1 mg/kg/day to about 45 mg/kg/day, about 0.1 mg/kg/day to about 50 mg/kg/day, about 0.1 mg/kg/day to about 75 mg/kg/day, or about 0.1 mg/kg/day to about 100 mg/kg/day.

In other aspects of this embodiment, an effective amount of an antibody disclosed herein may be in the range of, e.g., about 1 mg/kg/day to about 10 mg/kg/day, about 1 mg/kg/day to about 15 mg/kg/day, about 1 mg/kg/day to about 20 mg/kg/day, about 1 mg/kg/day to about 25 mg/kg/day, about 1 mg/kg/day to about 30 mg/kg/day, about 1 mg/kg/day to about 35 mg/kg/day, about 1 mg/kg/day to about 40 mg/kg/day, about 1 mg/kg/day to about 45 mg/kg/day, about 1 mg/kg/day to about 50 mg/kg/day, about 1 mg/kg/day to about 75 mg/kg/day, or about 1 mg/kg/day to about 100 mg/kg/day. In yet other aspects of this embodiment, an effective amount of an antibody disclosed herein may be in the range of, e.g., about 5 mg/kg/day to about 10 mg/kg/day, about 5 mg/kg/day to about 15 mg/kg/day, about 5 mg/kg/day to about 20 mg/kg/day, about 5 mg/kg/day to about 25 mg/kg/day, about 5 mg/kg/day to about 30 mg/kg/day, about 5 mg/kg/day to about 35 mg/kg/day, about 5 mg/kg/day to about 40 mg/kg/day, about 5 mg/kg/day to about 45 mg/kg/day, about 5 mg/kg/day to about 50 mg/kg/day, about 5 mg/kg/day to about 75 mg/kg/day, or about 5 mg/kg/day to about 100 mg/kg/day.

In liquid and semi-solid formulations, a concentration of an antibody disclosed herein typically may be between about 50 mg/mL to about 1,000 mg/mL. In aspects of this embodiment, a therapeutically effective amount of an antibody disclosed herein may be from, e.g., about 50 mg/mL to about 100 mg/mL, about 50 mg/mL to about 200 mg/mL, about 50 mg/mL to about 300 mg/mL, about 50 mg/mL to about 400 mg/mL, about 50 mg/mL to about 500 mg/mL, about 50 mg/mL to about 600 mg/mL, about 50 mg/mL to about 700 mg/mL, about 50 mg/mL to about 800 mg/mL, about 50 mg/mL to about 900 mg/mL, about 50 mg/mL to about 1,000 mg/mL, about 100 mg/mL to about 200 mg/mL, about 100 mg/mL to about 300 mg/mL, about 100 mg/mL to about 400 mg/mL, about 100 mg/mL to about 500 mg/mL, about 100 mg/mL to about 600 mg/mL, about 100 mg/mL to about 700 mg/mL, about 100 mg/mL to about 800 mg/mL, about 100 mg/mL to about 900 mg/mL, about 100 mg/mL to about 1,000 mg/mL, about 200 mg/mL to about 300 mg/mL, about 200 mg/mL to about 400 mg/mL, about 200 mg/mL to about 500 mg/mL, about 200 mg/mL to about 600 mg/mL, about 200 mg/mL to about 700 mg/mL, about 200 mg/mL to about 800 mg/mL, about 200 mg/mL to about 900 mg/mL, about 200 mg/mL to about 1,000 mg/mL, about 300 mg/mL to about 400 mg/mL, about 300 mg/mL to about 500 mg/mL, about 300 mg/mL to about 600 mg/mL, about 300 mg/mL to about 700 mg/mL, about 300 mg/mL to about 800 mg/mL, about 300 mg/mL to about 900 mg/mL, about 300 mg/mL to about 1,000 mg/mL, about 400 mg/mL to about 500 mg/mL, about 400 mg/mL to about 600 mg/mL, about 400 mg/mL to about 700 mg/mL, about 400 mg/mL to about 800 mg/mL, about 400 mg/mL to about 900 mg/mL, about 400 mg/mL to about 1,000 mg/mL, about 500 mg/mL to about 600 mg/mL, about 500 mg/mL to about 700 mg/mL, about 500 mg/mL to about 800 mg/mL, about 500 mg/mL to about 900 mg/mL, about 500 mg/mL to about 1,000 mg/mL, about 600 mg/mL to about 700 mg/mL, about 600 mg/mL to about 800 mg/mL, about 600 mg/mL to about 900 mg/mL, or about 600 mg/mL to about 1,000 mg/mL.

Dosing can be single dosage or cumulative (serial dosing), and can be readily determined by one skilled in the art. For instance, treatment of a cancer may comprise a one-time administration of an effective dose of a therapeutic compound or a pharmaceutical composition disclosed herein. Alternatively, treatment of a cancer may comprise multiple administrations of an effective dose of a pharmaceutical composition carried out over a range of time periods, such as, e.g., once daily, twice daily, trice daily, once every few days, or once weekly. The timing of administration can vary from individual to individual, depending upon such factors as the severity of an individual's symptoms. For example, an effective dose of an antibody disclosed herein can be administered to an individual once daily for an indefinite period of time, or until the individual no longer requires therapy. A person of ordinary skill in the art will recognize that the condition of the individual can be monitored throughout the course of treatment and that the effective amount of an antibody disclosed herein that is administered can be adjusted accordingly.

In one embodiment, an antibody disclosed herein is capable of reducing the number of cancer cells or tumor size in an individual suffering from a cancer by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95% as compared to a patient not receiving the same treatment. In other aspects of this embodiment, an antibody is capable of reducing the number of cancer cells or tumor size in an individual suffering from a cancer by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70% as compared to a patient not receiving the same treatment.

In a further embodiment, an antibody and its derivatives have half-lives of 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 7 days, 1 week, 2 weeks, 3 weeks, 4 weeks, one month, two months, three months, four months or more.

In an embodiment, the period of administration of an antibody is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

In aspects of this embodiment, an antibody disclosed herein reduces or maintains a cancer cell population and/or tumor cell size in an individual by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 100%. In other aspects of this embodiment, an antibody disclosed herein reduces or maintains a disease or a cancer cell population and/or tumor cell size in an individual by, e.g., at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90%, at most 95% or at most 100%. In yet other aspects of this embodiment, an antibody disclosed herein reduces or maintains a cancer cell population and/or tumor cell size in an individual by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%.

Typically, any individual who is a candidate for treatment is a candidate with some form of cancer, whether the cancer is benign or malignant, a tumor, solid or otherwise, a cancer call not located in a tumor or some other form of cancer. Pre-operative evaluation typically includes routine history and physical examination in addition to thorough informed consent disclosing all relevant risks and benefits of the procedure.

EXAMPLES

The following non-limiting examples are provided for illustrative purposes only in order to facilitate a more complete understanding of representative embodiments now contemplated. These examples are intended to be a mere illustration only and not to constitute a limitation on the scope of the invention.

Thus, these examples should not be construed to limit any of the embodiments described in the present specification.

Generation of Rabbit Antibodies Against CLD18.2

Example 1. Expression and Purification of CLDN 18.1 and CLDN18.2

CLDN 18.2 and 18.1 were overexpressed in *E. coli* BL21 DE3 using Pet 28 vector (MilliporeSigma). Cell lysate in 25 mM Tris, 100 mM NaCl, pH7.5 was centrifuged under 2000×g for 20 min. The supernatant was further separated by ultracentrifugation 100,000×g for 1 hour to get membrane particles. 1% n-dodecyl-β-D-maltopyranoside (DDM) in lysate buffer was used to solubilize membrane at 4° C. overnight. Insolubilized membrane was removed by ultracentrifugation 100,000×g for 1 hour. Supernatant was loaded to HisPur Cobalt resin (Thermo Scientific) column in the presence of 15 mM imidazole. Washed the column with 0.1% DDM, 15 mM imidazole in PBS. The claudin protein was eluted using PBS with 0.05% DDM. 0.002% cholesteryl hemisuccinate tris salt (CHS), 200 mM imidazole. The purified proteins were stored at 2-8° C. for short term use or at −80° C. for longer term storage.

Example 2. Immunizations

New Zealand White rabbits were immunized with eukaryotic expression vectors, encoding human CLD18.2 or its fragments. The presence of antibodies directed against human CLD18.2 in sera of rabbit was monitored by FACS analysis. The immune fluorescence was determined using HEK293 cells transiently transfected with a nucleic acid encoding a construct comprising human CLD18.2. Rabbits with detectable immune responses were boosted by intraperitoneal injection of the purified CLDN18.2 protein and/or alternatively $1 \times 10^8$ HEK293 cells transiently transfected with a nucleic acid encoding human CLD18.2.

Example 3. B-Cell Cloning

Complete medium includes RPMI 1640 (Life Technologies, cat. #11875-119), 10% fetal bovine serum (Sciencell, cat. #0500), non-essential amino acids (Life Technologies, cat. #11140-050), sodium pyruvate (Life Technologies, cat. #11360-070), 2-mercaptoethanol (Life Technologies, cat. #21-985-023), and gentamicin (Life Technologies, cat. #15710-072). Rabbit thymocytes (Spring Valley Labs, Woodbine, Md.) at $2 \times 10^6$/mL were cultured with $2 \times 10^6$/mL rabbit splenocytes (Spring Valley Labs, Woodbine, Md.) in complete medium containing 10 ng/mL PMA (Sigma-Aldrich, cat. #P1585) and 0.5% PHA-m (ThermoFisher, cat. #10576-015) for 48 hours. Supernatant was 0.2 uM filtered and stored at −20° C.

A 60 mm petri dish was coated with 3 mL human CLDN18.2-his at 2 ug/mL in PBS and incubated overnight at 4° C. Coating solution was removed and 3 mL PBS/5% BSA was added to block at room temperature for 1-2 hours. The blocking solution was removed and the plate was washed 4 times with PBS. Single cell suspensions of splenic lymphocytes from immunized rabbit were added to the plate in 3 mL PBS/2.5% BSA, and incubated for 45 minutes at 4° C. The dish was then washed 5 times with PBS/BSA to remove non-adherent cells, and then the adherent cells were harvested into complete medium by scraping with a cell scraper.

Alternatively, splenic lymphocytes were panned using CLDN 18.1 and CLDN 18.2 proteins. The claudin proteins were biotinylated using EZ-Link™ NHS-PEG4 Biotinylation Kit from Thermo Asher Scientific. For the negative panning, single cell suspensions of splenic lymphocytes from immunized rabbit were resuspended in MACS buffer (PBS/0.5% BSA/2 mM EDTA) containing the biotinylated CLDN18.1 and incubated for 15 minutes at 4° C. Cells were washed 2× with MACS buffer and resuspended in MACS buffer+Miltenyi Biotec streptavidin microbeads. After a 15-minute incubation cells were washed and passed over a magnetic column (LS column, Miltenyi Biotec). Unbound cells were collected to be used in positive selection. Cells were resuspended in MACS buffer containing biotinylated CLDN18.2 and incubated for 15 minutes. Cells were washed 2× with MACS buffer, resuspended in MACS buffer+streptavidin microbeads and incubated for 15 minutes. Cells were washed once, then passed over a magnetic column (MS column, Miltenyi Biotec), Positively selected, bound cells were eluted and used for B cell cloning.

Figure 2:
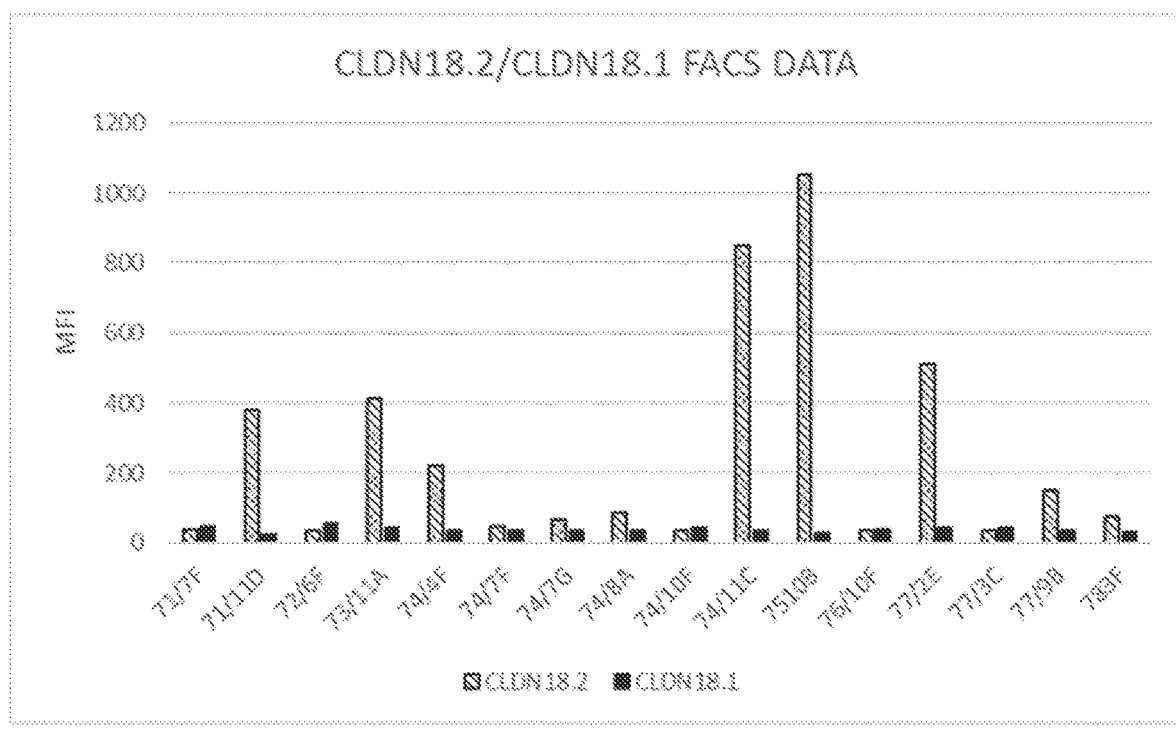
FIG. 2: FACS-based screening of B cell clones. Supernant from each clone was tested for their ability to bind to stable cell lines expressing CLDN18.2 (left) and CLDN18.1 (right) using FACS.

Cells were then plated into 96 well round-bottom plates at 10-50 cells/well in complete medium containing 2% rabbit spleen/thymus conditioned medium, human IL-2 (Prospec, cat. #cyt-095) at 5-10 ng/mL, Pansorbin (EMD Millipore, cat. #507858) at 1:20,000, and $5 \times 10^4$ mitomycin-c (Sigma-Aldrich, cat. #M4284) treated (50 ug/mL for 45 minutes) EL4-B5 cells/well. Plates were incubated for 7 days at 37° C. in CO2 incubator, supernatants were removed for ELISA and FACS analysis, and plates containing the cells were frozen at −80° C. for subsequent antibody v-region rescue. An example of the ELISA-based screening is given in FIG. 1. An example of the FACS-based screening is given in FIG. 2.

Example 4. Transient Transfection

Confirmation of successful v-region rescue was done by transfecting the heavy and light chains of the chimeric antibodies into HEK293 cells and testing the supernatant for recovery of CLDN18.2 binding activity. HEK293 cells were plated at $1.5 \times 10^5$ cells/well in 1 mL complete medium in a 24 well tissue culture plate, and cultured overnight. Transfection was performed using 500 ng heavy chain DNA and 500 ng light chain DNA with Lipofectamine 3000 (Life Technologies, cat. #L3000015) per manufacturer's instructions. Supernatants were harvested after 3-5 days and assayed for binding activity by ELISA.

Larger scale transfections to generate material for purification were performed with HEK293 cells cultured in 5% ultra-low IgG fetal bovine serum (Life technologies, cat. #16250-078) using Lipofectamine 3000 per manufacturer's instructions.

Example 5. CLDN18.2 Binding ELISA

B cell cloning supernatants were tested for binding to CLDN18.2 by ELISA. ELISA plates were coated with 100 uL antigen at 0.5 or 1 ug/mL in PBS (Life Technologies, cat. #14190-250) overnight at 4° C. or for 1 hour at 37° C. Both CLDN18.2 and 18.1 were expressed in *E. coli* and SF9 cells and partially purified using similar methods as described by Suzuki et al (Science 344, 304 (2014)). Plates were then blocked with PBS+10% goat serum for 1 hour. After washing with deionized water, samples were added in PBS/10% goat serum and incubated for 1 hour. Plates were washed, and 100 uL goat anti-rabbit IgG Fc-HRP (Jackson ImmunoResearch, cat. #111-035-046) was added at a 1:5000 dilution in PBS/10% goat serum for 1 hour. Plates were then washed with deionized water and 100 uL TMB substrate (Thermo Scientific, cat. #P1134021) was added to each well. Development was stopped with 100 uL 1N $H_2SO_4$, and OD450 was measured using a microplate spectrophotometer.

Purified chimeric and humanized antibodies were tested for binding to CLDN18.2 by ELISA. Protocols were the same as for testing B cell cloning supernatants.

Example 6. CLDN18.2 Binding as Tested by FACS

Stable HEK 293 cell lines expressing CLDN18.1 or CLDN 18.2 were cultured. The cells were detached with non-enzymatic cell dissociation solutions. Cells were counted and the cell density was adjusted to approximately 3 million cells/ml with FACS washing buffer, which comprised 3% FBS in PBS. 50 uL cells (150000 cells/well) were added into each well of a 96 well plate. Primary antibody or supernatant expressing the antibody of interest was added to the cells at prespecified concentration. The plate was incubated on ice for 1 hr. The plate was washed 3 times with the FACS washing buffer. Fluorescence conjugated secondary antibody was added to the cells (concentration depending on manufacture instruction). The plate was incubated on ice for 1 hr. The plate was washed again. PI staining solution was added at 0.1 ug/mL and the plate was incubated for 10 min on ice. The cell fluorescence was measured with Flow Cytometry instrument.

Example 7. Affinity Measurement

Figure 3:
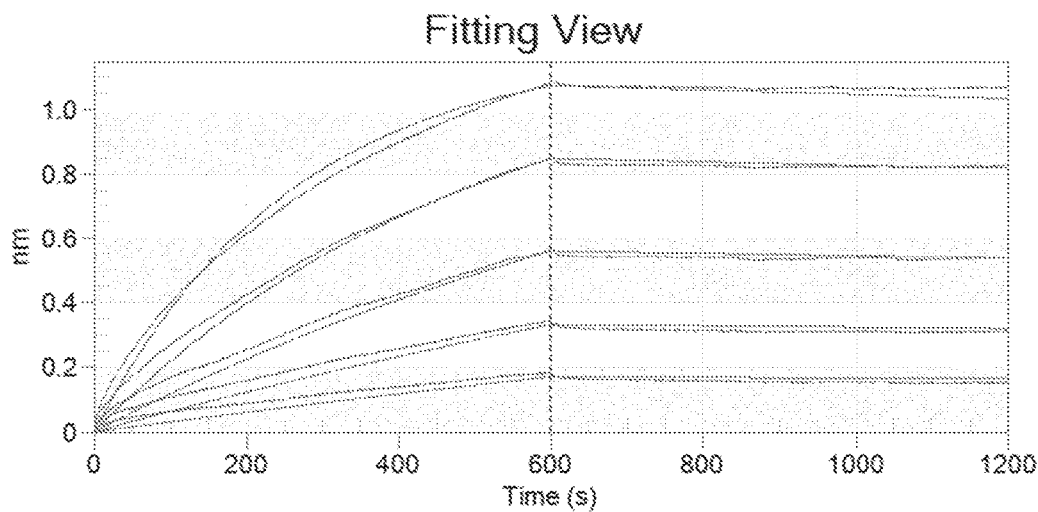
FIG. 3: Measurement of binding affinity between the antibodies and antigen CLDN 18.2. The binding kinetics for one particular clone (5) are shown at the top and a Table illustrating the binding kinetics of selected clones is presented at the bottom.

The affinity measurement was conducted with Octet RED 96 (ForteBio) instrument at 30° C. Briefly, anti-human IgG capture sensor (AHC from ForteBio cat #18-5060) was equilibrated with assay buffer (1× dilution of 10× Kinetics Buffer (ForteBio, Cat #18-5032). Test antibody samples were diluted to 2 microg/mL and allowed to bind to the sensors for 5 min. The sensors were then washed in assay buffer for 3 minutes, and CLDN18.2 ligand diluted at different concentrations were allowed to bind to the mAb coated on the sensors for 5 minutes. Afterwards, dissociation was followed for 10 minutes in the assay buffer. The sensors could be regenerated by washing in glycine buffer and assay buffer 3 times. The data were fitted with 1:1 binding model using the ForteBio software. An example of the affinity measurement is given in FIG. 3. Measurement of binding affinity between the antibodies and antigen CLDN 18.2. The example binding kinetics of Clone 5 is shown here. The parameters of the binding kinetics of the selected clones are shown in a table in FIG. 3.

Example 8. Antibody-Dependent Cellular Cytotoxicity (ADCC)

The ADCC Reporter assay was carried out following the protocol described below:
Material:
1. Culture medium—RPMI 1640, 10% fetal bovine serum, non-essential amino acids, sodium pyruvate, 50 uM beta-mercaptoethanol, penicillin/streptomycin;
2. Assay medium—Same as culture medium except use low IgG Fetal bovine serum
3. Effector Cell line—ADCC Bioassay effector cell line V variant (BPS Biosciences #60541)
4. Target cell line—HEK 293/18.2 (HEK 293 cells transfected with target antigen)
5. Target cell line—NUGC4 (gastric cancer cell line that expresses target antigen)
6. Pierce Firefly One-Step Glow assay kit #16196.
Assay Protocol:
1. Harvest target cell line. Plate 15,000 cells/well in 50 uL assay medium in white 96 well assay plates. Spin down effector cells and resuspend in assay medium. Culture overnight.
2. Prepare serial dilutions of test articles at 4× concentration in assay medium (typically dilution series starts at 16 ug/mL (4×), titer 3× dilutions 9 wells).
3. Transfer 25 uL of 4× sample to assay plate containing target cells. Incubate 15 minutes.
4. Harvest and count effector cells. Dispense 70,000 effector cells/well/25 uL. Incubate 5.5-6 hours.
5. Allow plate to cool to room temperature for 5 minutes.
6. Add 100 uL/well One-Step firefly luciferase reagent. Measure luminescence.

Figure 4A:
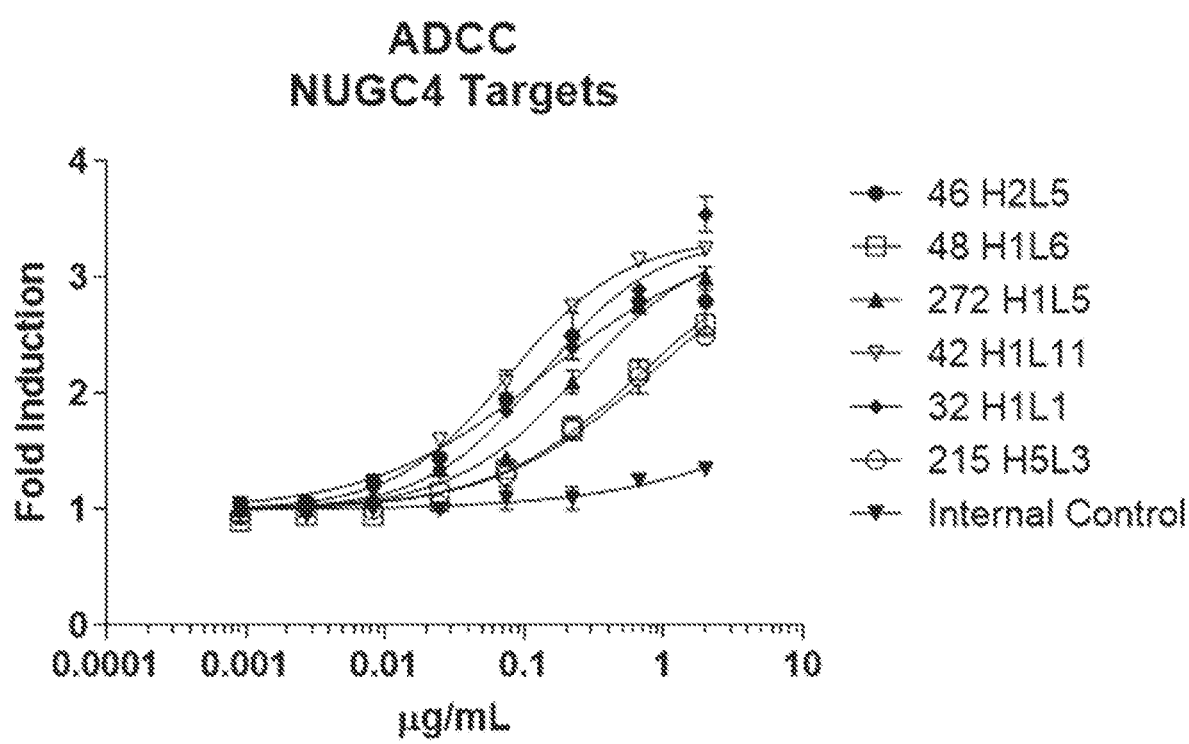
FIG. 4A: ADCC analysis of antibodies with tumor cell line NUGC4. Fold induction of cytotoxicity is shown on the Y-axis and the amount of different monoclonal antibodies tested plotted on the X-axis with the clones tested being 46H2L5 (full circle), 48H1L6 (open square), 272H1L5 (full triangle), 42H1L11 (open inverted triangle), 32H1L1 (full diamond), 215H5L3 (open circle), and control (full inverted triangle). In the experiment shown in this Figure, HEK293 cells were transfected with Human and mouse claudin18.2 and claudin18.1 for 72 hr before FACS analysis.
Figure 4B:
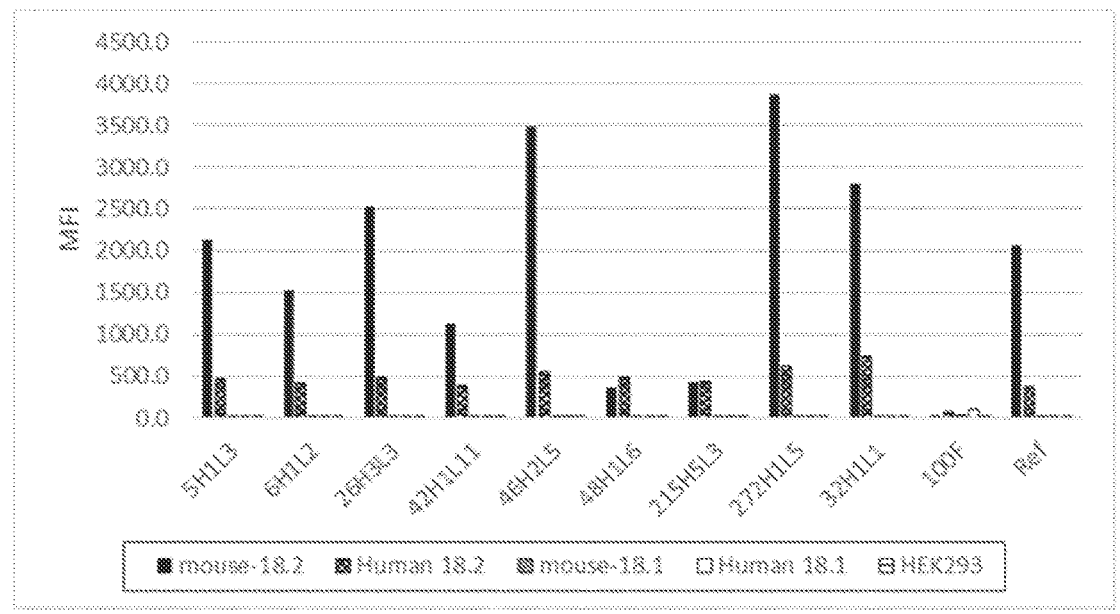
FIG. 4B shows the MFI for individual clones designated 5H1L3, 6H1L2, 26H3L3, 42H1L11, 46H2L5, 48H1L6, 215H5L3, 272H1L5, 32H1L1, and 100F are also shown for mouse −18.2, human 18.2, mouse 18.1, human 18.1, and HEK293. The quantified results are also presented in the table.

An example of the ADCC result is given in FIG. 4A, wherein ADCC analysis with tumor cell line NUGC4 had been carried out. FIG. 4B shows the MFI for individual clones designated 5H1L3, 6H1L2, 26H3L3, 42H1L11, 46H2L5, 48H1L6, 215H5L3, 272H1L5, 32H1L1, and 100F are also shown for mouse −18.2, human 18.2, mouse 18.1, human 18.1, and HEK293. The quantified results are also presented in the table presented in FIG. 4B.

Example 9. V-Region Rescue from Rabbit B-Cells and Screening of Chimeric Antibodies To rescue rabbit B-cells that were tested positive for CLDN18.2 binding, the IgG variable domain for both the heavy and light chains were captured by amplification using reverse transcriptase coupled polymerase chain reaction (RT-PCR) from mRNA isolated from positive B-cells. The VH and VL cDNAs thus obtained, were cloned and ligated onto human constant region constructs, such that the final cDNA construct encoded a chimeric rabbit human IgG.

Selected positive B-cells were lysed and mRNA prepared using the Dynabeads mRNA DIRECT Micro Kit, from Life Technologies according to the manufacturer's instructions. To recover the v-regions, mRNA generated from a single antigen positive well is used in a OneStep RT-PCR Kit (Invitrogen) reaction for both the heavy and light chains according to the manufacturer's instructions. For the reactions, gene specific primers located in the constant regions of the heavy and light chains of the rabbit IgG molecule are used to generate a single strand cDNA, followed PCR and nested PCR to amply the variable domains with specific restriction sites added to the ends of PCR products. In-house vectors containing human gamma-1 heavy chain constant region and human kappa light chain constant regions with specific restriction sites were used for sub-cloning. After addition of the restriction sites, the PCR products were subjected to the relevant Restriction enzymes digestion, gel purified and ligated into the appropriate vector.

Following sub-cloning, the ligated DNA was transformed into competent *E. coli* DH5-alpha (Invitrogen). The entire transformation pool was cultured over-night in medium containing the appropriate antibiotic resistance. The cultured bacteria were split into two parts: one part for making plasmid DNA prep (Qiagen Miniprep Kit) for use in transient HEK293 expression of chimeric antibodies, and the other part saved for plating single colonies for DNA sequencing.

To generate the chimeric antibodies, HEK293 cells were co-transfected with the DNA of both heavy and light chain from a selected well. Supernatant was harvested after three to five days of cell culture and assayed for IgG and antigen binding by ELISA. To detect the presence of IgG in the transfection supernatant, an ELISA immunoassay is done which utilizes an anti-human IgG Fc capture antibody coated to an ELISA plate, followed by the supernatants and human IgG standard. Detection of Fc-captured antibody is obtained using an anti-human IgG (H&L)-HRP reagent and TMB substrate.

The isolated DNA preps that gave positive chimeric antibody expression and antigen binding functions were processed for DNA sequencing. It should be note that the isolated DNA plasmids at this stage may or may not be homogenous for one specific V-region, as selected wells may contain one or more different B-cell clones. To break the pool into single clones, *E. coli* DH5 alpha culture pool from which the DNA was isolated previously was plated to single colonies on agar plate containing the appropriate antibiotic. Multiple colonies were picked and processed for DNA production using a rolling circle DNA amplification kit (Templiphy, GE Healthcare) following manufacturer's instructions. The DNA generated from the Templiphy reactions was sequenced and subsequently analyzed to determine the complexity of V-regions for each well. In addition to making DNA, each clone of bacteria used for the Templiphy reaction was saved for future DNA isolation.

Based on the DNA sequence analysis, plasmid DNA preps were made from the corresponding single clone *E. coli* culture containing the unique IgG heavy chain or light chain sequences. These plasmids were then used to transform HEK293 again to screen for chimeric monoclonal antibody. In case that there were multiple heavy and light chain sequences obtained from the same B-cell well (wells not clonal), every possible combination of unique heavy and light chain pairs was transfected. Supernatants were harvested after three to five days, assayed for IgG and antigen binding by ELISA. After this deconvolution step, heavy and light chain combinations which retained the desired binding activity were selected for further functional analysis and then for humanization.

Properties and Sequence Information for Top Antibody Candidates

The top 13 antibodies with unique DNA sequences were characterized with the purified chimeric proteins. The results are summarized in Table 1.

The internal reference or the reference antibody used below comprises the same heavy chain and light chain sequences as that of Zolbetuximab. The reference antibody was transiently expressed in HEK 293 cells and purified using Protein A affinity chromatography column followed by ion exchange chromatography steps.

TABLE 1

| Clone # | FACS EC50 (nM) | FACS Signal MFI (×1000) | ADCC with 293 cells expressing Claudin 18.2 (nM) | ADCC NUGC4 Cells (ng/ml) | KD (nM) (Binding Kinetics measured with ForteBio) |
|---|---|---|---|---|---|
| 6 | 0.46 | 43 | 0.014 | | 40 |
| 2 | 0.319 | 50 | 0.032 | | 123 (estimated) |
| 46 | 0.619 | 55 | 0.015 | 70 | 12 |
| 272 | 0.654 | 55 | 0.009 | 230 | 13 |
| 30 | 0.319 | 30 | 0.030 | | 30 |
| 42 | 0.417 | 35 | 0.012 | 80 | 30 |
| 5 | 1.055 | 44 | 0.044 | | 25 |
| 33 | 0.969 | 45 | 0.040 | | 16 |
| 9 | 4.22 | 18 | 0.017 | | 110 (estimated) |
| 26 | 1.08 | 40 | 0.035 | | 25 |
| 312 | | | 0.017 | | 10 |
| 31 | 1.06 | 20 | 0.044 | | 150 |
| 48 | 0.553 | 40 | 0.016 | 370 | 53 |
| Internal Reference | 1.17 | 25 | 0.014/.006 (results from two analysis) | 610 | 89/71 (results from two analysis) |

Generation of Mouse Antibodies Against CLD18.2

Example 10. Generation of Mouse Antibodies Against Human Claudin 18.2 (CLDN 18.2)

CLDN18.2-specific monoclonal antibodies (MAbs) were generated using the DNA immunization approach. Briefly, the CLDN18.2 gene insert was cloned into the modified DNA vaccine vector pJW4303. The DNA plasmid was then produced from Escherichia coli (HB101 strain) with a Mega purification kit (Qiagen, Valencia, Calif.). Twenty female 6-8 weeks old C57/B6 mice (Taconic Farms) each received multiple rounds of immunizations with CLDn18.2 encoding plasmids delivered by either Gene gun (Bio-rad) system or ID injection followed by Electroporation (BTX-Harvard Apparatus). Serum samples were taken prior to the first immunization and 2 weeks after the last immunization for the study of CLDN18.2-specific antibody responses. Mice with high specific titers were giving a final boost of HEK293 cells expressing CLDN 18.2 and euthanized 4 days later to isolate spleen aseptically. Single-cell suspension from the spleen were prepared, then fused with the SP2/0 myeloma cells by electrofusion (BTX-Harvard Apparatus). Two fusions were carried out with each with up to 10 mice. Culture supernatants were analyzed to screen hybridomas with binding to HEK 293 cells expressing CLDN18.2 but not CLDN18.1. Positive clones were expanded, single-cell cloned, and confirmed by multiple assays.

Figure 5B:
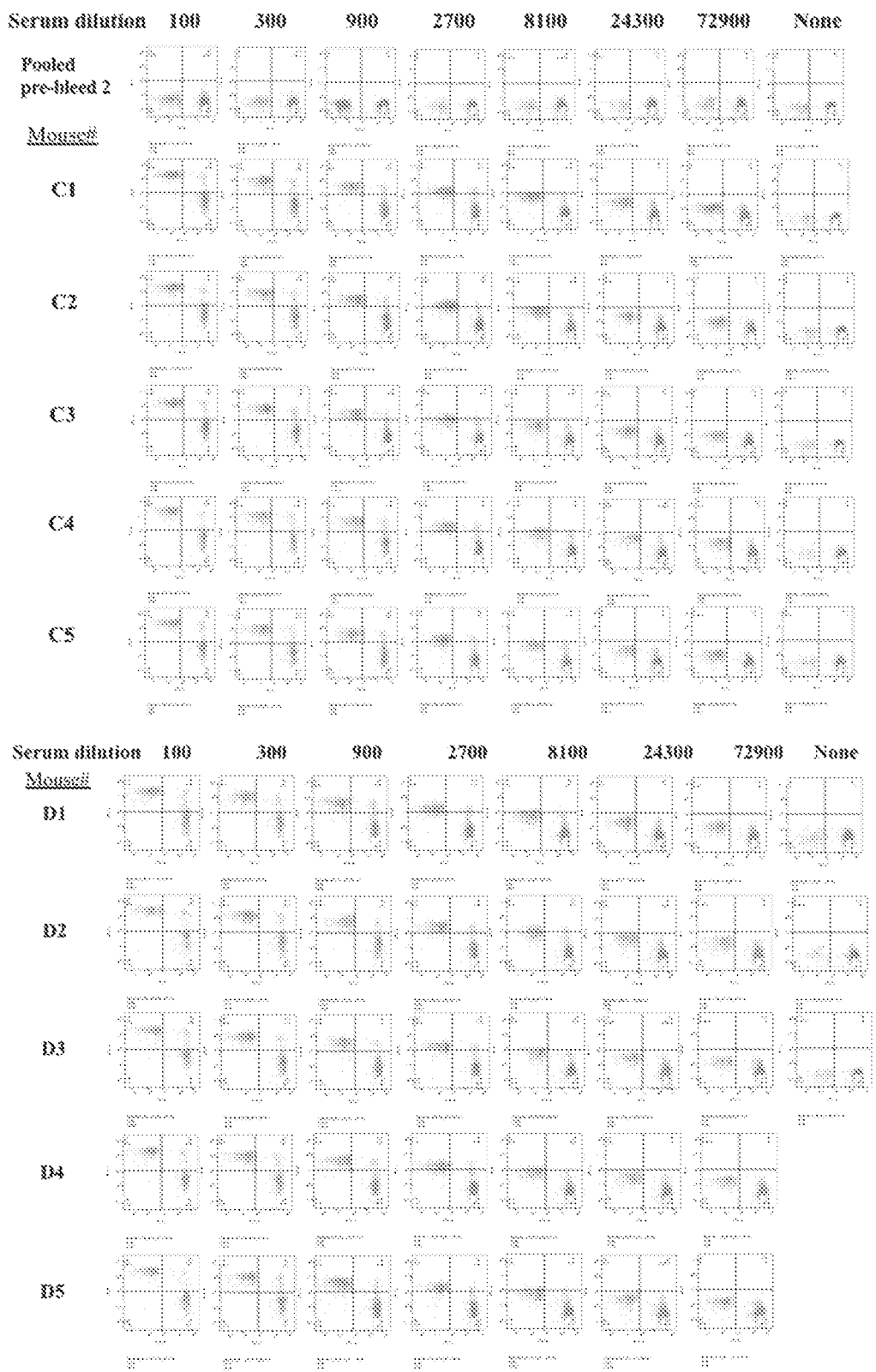

FIGS. 5A and 5B shows the results of CLDN18.2-specific antibody responses of the serum samples taken prior to the first immunization and 2 weeks after the last immunization as detected by FACS.

Figure 6:
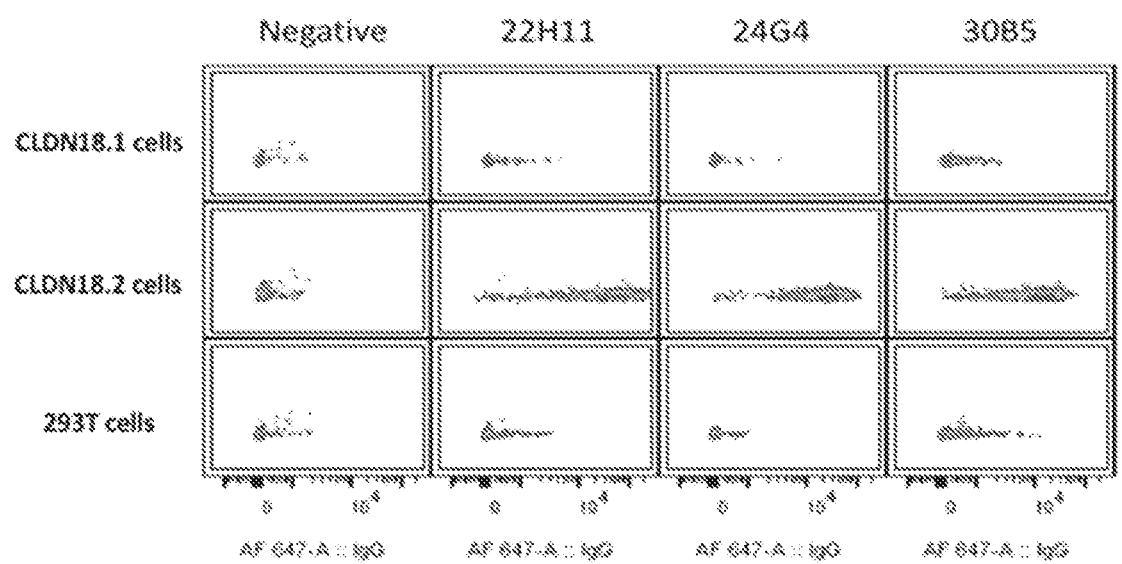
FIG. 6. FACS Screening of the First Fusion Identified Three Hybridomas Which Specifically Bound to CLDN 18.2 but Not CLDN 18.1.

FIG. 6 shows the results of the positive hybridomas from the first fusion identified by FACS analysis. A hybridoma was identified as positive when it showed binding to HEK293 cells expressing CLDN18.2 but with no or minimum binding to the HEK293 cells expressing CLDN18.1 or HEK293 cells.

Figure 7:
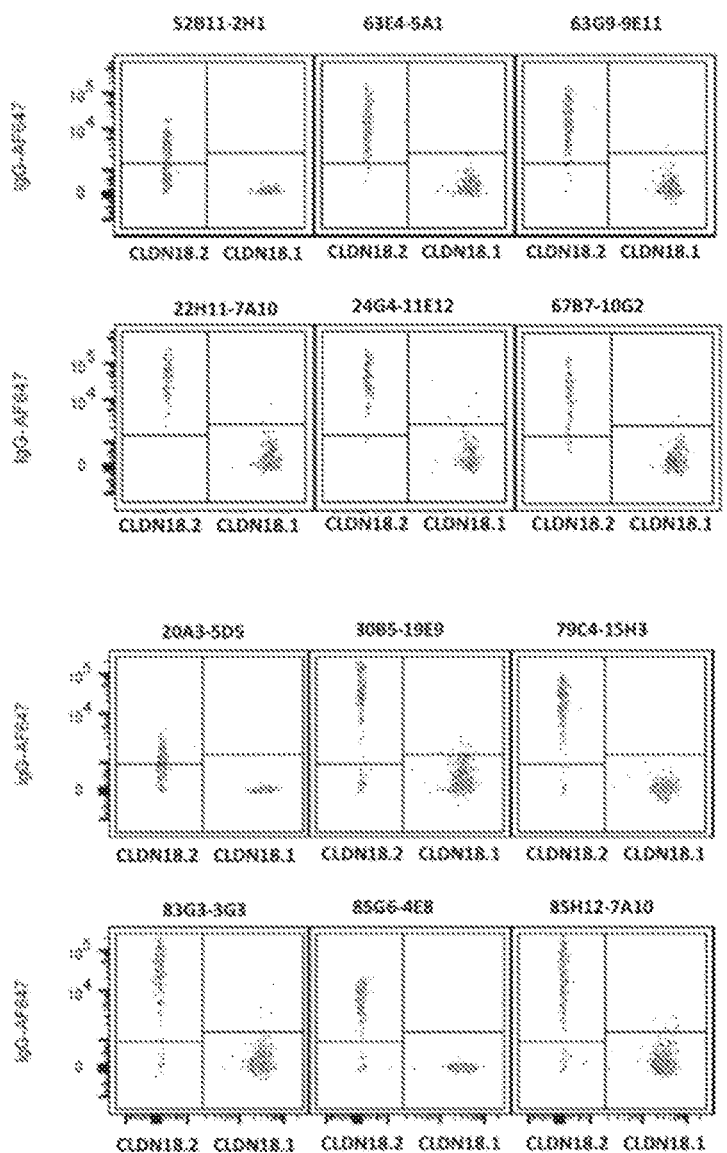
FIG. 7. FACS Analysis of Subclones of Positive Hybridomas Identified Clones Which Specifically Bound to CLDN 18.

The positive hybridomas from the two fusions were subcloned and the subclones were further screened for their selective binding to CLDN 18.2 vs CLDN 18.1. Twelve positive subclones were identified (FIG. 7). The hybridoma cells were expanded and vialed. The vials were frozen for further testing and subsequent cloning.

The hybridoma vials were thaw and cultured. And their supernants were further analyzed by FACS. FIG. 8A shows titration curves of the bindings of the supernants of the hybridomas to CLDN 18.2 expressed on HEK 293 cells, FIG. 8B shows the specificity of the bindings of the supernants to HEK 293 cells expressing CLDN 18.2 vs. 18.1, and FIG. 8C shows the FACS intensity of the binding of the supernants to CLDN 18.2 vs CLDN 18.1 expressed on the HEK 293 cells.

Example 11. Cloning of the Selected Clones

Positive subclones including 79C4, 11E12, 83G3, 30B5 and 85H12 were selected to be cloned. Antibody variable regions of the selected clones were cloned. The heavy chain variable domain sequences of the selected clones are shown in Table 34, the light chain variable domains in Table 35, and the CDR for each top candidate are provided Tables 29-33.

V-gene cloning was carried out using the procedure described below.

RNA extraction: 1×10E6 mouse hybridoma cells were collected by centrifuge at 900 g for 5 min. Total RNA was extracted by using RNeasy Mini Kit (Qiagen, Germany) following manufacture's protocol. RNA was quantified by NanoDrop 1000 (Thermo Fisher).

cDNA synthesis: iScript cDNA Synthesis Kit (Catalog 1708891, Bio-Rad) was used for cDNA synthesis. Briefly, in 20 uL reaction volume, 1 ug total RNA, 4 uL reaction buffer with random primers, 1 uL iScript reverse transcriptase and nuclease-free water (variable) were mixed. The reaction mix was incubated at 25° C. for 10 min, 46° C. for 30 min, and 95° C. for 1 min in a thermal cycler (Bio-Rad) as described in manufacture's protocol. Alternatively, SMARTer RACE 5'/3' Kit (Catalog 634858, Takara) was used to synthesis cDNA as described in manufacture's manual.

V-gene amplification: EMD Millipore Novagen Mouse Ig-Primer Set (Catalog 698313, EMD Millipore) and High Fidelity Platinum Taq DNA Polymerase (Catalog 11304011, Invitrogen) are used to amplify heavy chain and light chain variable regions. Briefly, in 50 uL reaction volume, 5 uL 10× reaction buffer, 1 uL 10 mM dNTP mix, 1 uL forward/reverse primers, 1 uL cDNA product, 0.2 uL DNA polymerase and nuclease-free water (fill to 50 uL) were mixed. The reaction mix was incubated in a thermal cycler (Bio-Rad) at 95° C. for 15 seconds, 55° C. for 15 seconds and 72° C. for 30 seconds for 30 cycles, then extended at 72° C. for another 5 min. PCR products were cloned into TOPO TA cloning vector (Catalog K457501, Invitrogen) and transformed in to E. coli Top10 competent cells as described in manufacture's manual. Single colonies were picked for sequencing by GeneWiz (South Plainfield, N.J. 07080).

To confirm the sequences of the subclones, chimeric antibodies were generated. The heavy chain and light chain variable genes were cloned into pFUSEhIG1 and pFUSE-hIGK (InvivoGen, San Diego), respectively, for full antibody expression. HEK293 cells were co-transfected with the DNA of both heavy and light chain from each of the selected subclones. The supernatants were test by FACS binding to HEK293 cells expressing CLDN18.2 vs HEK293 cells expressing CLDN 18.1. An example of the FACS analysis is shown in FIG. 9. FIG. 9A shows titration curves of the bindings of the supernatants of the clones to CLDN 18.2 expressed on HEK 293 cells. FIG. 9B shows the specificity of the bindings of the supernatants to HEK 293 cells expressing CLDN 18.2 vs. 18.1. FIG. 9C shows the FACS intensity of the binding of the supernatants to CLDN 18.2 vs CLDN 18.1 expressed on the HEK 293 cells.

In addition, function analysis with ADCC reporter assay was also carried out following the protocol described in Example 8. An example of the ADCC reporter assay result is shown in FIG. 10.

Humanization of Selected Antibodies Against CLD18.2

Example 12. Humanization of the Rabbit Antibody Clone 46

Clone 46 was selected for humanization. Humanization was carried out using the standard CDR-grafting technologies coupled with the latest research on antibody structure and up-to-date database of mature human IgG sequences. A number of human framework sequences were identified that had been used as "acceptor" frameworks for the CDR sequences of Clone 46. These acceptor sequences had all come from mature Human IgG from a human source and not from phage display or other technologies. As a result, the humanized sequences were expected to be non-immunogenic and retained the canonical structure of the CDR-loops. Key residues important for the VH/VL interface and canonical loop structure have been maintained as much as possible in the humanized variants using the CDRx platform.

Five pairs of the humanized heavy chains (SEQ ID NO: 187-191, Table 27) and light chains (SEQ ID NO: 193-197, Table 28) were generated. All the possible pairs were expressed transiently with HEK293 cells and the supernatants of the transient expression were tested for binding and ADCC activity. Based on the initial results (data not shown), pairs of HC5/LC5, HC4/LC5, HC3/LC1, HC5/LC1, HC4/LC1 had the highest binding affinities and the ADCC activities. HC4 (SEQ ID NO: 190) and HC5 (SEQ ID NO: 191) were further optimized to generate SEQ ID NO: 199-201 for optimized HC4 and 202-204 for optimized HC5. LC chains LC1 (SEQ ID NO: 193) and LC5 (SEQ ID NO: 197) were also optimized to generate SEQ ID NO: 205 for optimized LC1 and SEQ ID NO: 206 for optimized LC5. After further screening, two lead molecules ASK589-B (or B) and ASK589-C (or C) were identified as the lead molecules from the humanized rabbit antibody. Molecule B comprises the heavy chain with an amino acid sequence as shown in SEQ ID NO: 202, and the light chain with an amino acid sequence as shown in SEQ ID NO: 205. Molecule C comprises the heavy chain with an amino acid sequence as shown in SEQ ID NO: 204, and the light chain with an amino acid sequence as shown in SEQ ID NO: 205.

Example 13. Humanization of the Mouse Antibody Clones 11E12 and 83G3

Mouse hybridoma clones 11E12 and 83G3 were selected for humanization. 11E12 Fv homology model was built up by using pdb 4OZ4 as model structure and humanization design was double checked with another hereo model built up on pdb 1HIL and pdb 3TT1. 83G3 Fv homology model was built up by using pdb 2I9L as model structure and humanization design was double checked with another hereo model built up on pdb 1MCP and pdb 2I9L. During the humanization process, mouse CDRs were grafted into the human framework acceptor, residues in human framework which are different from those in mouse framework were studied. Backmutations from human residue to mouse residue were designed based on the following rule: a. If new contact (ironical interaction, hydrogen bond, hydrophobic interaction) will be created between this human residue to mouse Fv CDR residue, canonical residue, interface residue or vernier residue, this human residue needs to be back-mutated to mouse residue; b. If an old contact (ironical interaction, hydrogen bond, hydrophobic interaction) between a mouse residue and canonical residue, interface residue or vernier residue will be lost when a human residue replacing a mouse residue, this human residue needs to be back mutated to mouse residue; and c. Replacement of mouse canonical residue, interface residue or vernier residue with human residue needs to be carefully studied and usually avoided.

Schrodinger surface analysis and Schrodinger post-translational modification of each antibody and huVHv1VLv1 (data from the humanized version with the highest humanization percentage) were also carried out. In addition, all potential cell epitope, B cell epitope, MHC II epitope and antigenicity epitope predicted by Protean 3D in the framework of the highest humanized version VHv1VLv1, which contained backmutations, were called out.

The variable domain sequences of the humanized 11E12 are listed in Table 36. The variable domain sequences of the humanized 83G3 are listed in Table 37.

The humanized antibodies were transient expressed in HEK 293 cells and purified as described above. The antibodies were further tested for their functionalities and specificity toward CLDN18.2. ASK589-M1 (or M1) was selected for further characterization. Molecule M1 comprises the heavy chain variable domain with an amino acid sequence as shown in SEQ ID NO: 254, and the light chain variable domain with an amino acid sequence as shown in SEQ ID NO: 260. M5 is the mutated version of M1, which comprises the heavy chain variable domain with an amino acid sequence as shown in SEQ ID NO: 257, and the light chain variable domain with an amino acid sequence as shown in SEQ ID NO: 260.

Functionality Analysis of the Humanized Antibodies Against CLD18.2

Example 14. Binding Assay

Binding of the humanized antibodies to the targets CLDN 18.2 proteins expressed on HEK293 cells and NUGC4 cells was analyzed by FACS. The results are shown in FIG. 11. FIG. 11A shows the binding to HEK293 cells transfected with CLDN18.2. The results showed that M5 had higher binding and higher binding affinity comparing to the reference molecule. FIG. 11B shows the binding to NUGC4 cells which naturally express CLDN18.2. The results showed that M5 and B had significantly higher binding and much higher binding affinity comparing to the reference molecule.

Example 15. ADCC Reporter Assay

The humanized antibodies were tested using the ADCC Reporter assay as described in Example 11. The results are shown in FIG. 12. FIG. 12 A shows the results of ADCC Reporter Assay for the humanized antibodies M5 and B with target cells HEK 293 stably transfected with CLDN 18.2. The results indicated that M5 and B had slightly better or similar activities as that of the reference antibody on the HEK293 cells which had high levels of CLDN18.2 expressed on their surfaces. FIGS. 12B and C showed the results with gastric cancer cells NUGC4 (FIG. 12B) and DAN-G (FIG. 12C), which naturally express CLDN18.2 but at significantly lower levels comparing to HEK293 cells stably transfected with CLDN 18.2. The results showed that Molecules M5 and B had significantly higher ADCC activities than the reference antibody in killing the gastric cancer cells.

Example 16. CDC Assay

The CDC assay was carried out following using RPMI 1640+1% low-IgG fetal bovine serum as the assay medium. Titrate the test antibodies at 2× concentration in 50 uL/well assay medium. Add target cells at 20,000 cells/well in 25 uL. Incubate 15 minutes at 37° C. Add 25 uL/well 40% human complement (10% final concentration). For spontaneous cell death use targets with medium only. For maximum cell death use targets+1% Triton X-100. Incubate 1 hour at 37° C. Add 100 uL/well CellTiter-Glo (Promega cat. #G7571). Measure luminescence. The CDC activity is calculated using the following equation: Specific release=(experimental-spontaneous)/(maximum-spontaneous)*100.

FIG. 13 shows the CDC Results of the Humanized Molecules B, M1 and M5, as comparing to the reference antibody. FIG. 13A shows the results with B and M1 versus Reference against HEK293 cells expressing CLDN 18.2; FIG. 13B shows the results with M5 versus Reference against target HEK293 Cells Expressing CLDN 18.2; FIG. 13C shows the results with B and M1 versus Reference against target NUGC4 cells. All the results showed that antibodies M1, M5 and B had higher CDC activities than the reference antibody.

Specificity of the Humanized Antibodies M1, B and M5

Example 17. Binding to Other Claudin Family Members

The genes expressing a number of claudin family members were transiently transfected into the HEK 293 cells. All of the claudins except CLDN 7 and CLDN18.2 were also fused with a FLAG on the C-terminals. The binding of the antibodies M1, M5 and B as well as the reference antibody to the claudins expressed on the HEK 293 cells were tested using FACS as described above. The results showed that all the antibodies tested here selectively bound to CLDN18.2 but none of the other claudin family members shown here (FIG. 14A). The results also showed that all the claudins with FLAG were expressed as demonstrated by the binding of the FLAG antibody (FIG. 14B).

Example 18. Specificity Analysis Using Protein Chip

In order to test whether the humanized antibodies were specific for CLDN 18.2, the Membrane Proteome Array (MPA) assay was carried out for profiling the specificity of the antibodies which target human membrane protein CLDN 18.2. The MPA can be used to determine antibody target specificity, deconvolute orphan antibody targets, and characterize the target profile of biosimilar candidates. Membrane Proteome Array (MPA) assay was carried out similarly as described previously (Tucker et al PNAS May 29, 2018 115 (22) E4990-E4999). Flow cytometry was used to directly detect antibody binding to membrane proteins expressed in human HEK-293T cells. All MPA targets were designed to have native conformations and the appropriate post-translational modifications. The antibodies were tested for reactivity against the MPA library of over 5,300 human membrane proteins, including GPCRs, ion channels, and transporters. Identified targets were validated in secondary screens to confirm reactivity. The data (not shown) showed that M5 was specific binding to CLDN18.2 and did not unexpectedly bind to any of the membrane proteins in the test at a level above background.

PK Study

Example 19. Pharmacokinetics Study in Cyno Monkeys

The humanized antibodies M1, M5, B and C were tested in the Cyno PK study following the relevant government regulations using experimental animals. 10 male and 10 female animals with the body weights of 3-4 kg. The dosage was 5 mg/kg every week for a total of four doses. The study was designed to five groups as shown in the table below.

| Group | Dosage (mg/kg) | #of doses | #of animals | Sex | Testing Article | Conc. (mg/ml) | Dosing Duration (min) | Dosing flow rate (ml/kg/min) |
|---|---|---|---|---|---|---|---|---|
| A | 5 | 4 | 5 | 3M, 2F | ASKB589B_DS | 1 | 20 | 0.25 |
| B | 5 | 4 | 5 | 2M, 3F | ASKB589C_DS | 1 | 20 | 0.25 |
| C | 5 | 4 | 4 | 2M, 2F | ASK-M5_DS | 1 | 20 | 0.25 |
| D | 5 | 4 | 2 | 1M, 1F | M1_DS | 1 | 20 | 0.25 |
| E | 5 | 4 | 4 | 2M, 2F | 589R_DS | 1 | 20 | 0.25 |

Samples were taken as described in the table below.

| Sample | serum |
|---|---|
| Sample Handling | Whole blood (for PK, ~1 mL) samples were taken from the vein. The samples were labeled and put on ice. After the clotting, the samples were centrifuged at 2-8, 1200-1500 × g for 10-15 minute, |
| Sample Time Window | 2 h samples allow +5 min; 24 h~2 d samples allow +10 min; 4 d~7 d samples allow +30 min |
| # of PK samples | 300 |

PK samples were taken per schedule shown in the table below.

| | Time | Groups 1, 2, 3, 4, 5 |
|---|---|---|
| 1 | 0 min (prior to dosing) | ✓ |
| 2 | Right after dosing | ✓ |
| 3 | 2 h | ✓ |
| 4 | 24 h | ✓ |
| 5 | 2 d | ✓ |
| 6 | 4 d | ✓ |
| 7 | 7 d (prior to $2^{nd}$ dosing) | ✓ |
| 8 | 14 d (prior to $3^{rd}$ dosing) | ✓ |
| 9 | 21 d (prior to $4^{th}$ doing) | ✓ |
| 10 | Right after $4^{th}$ dosing | ✓ |
| 11 | 21 d-2 h | ✓ |
| 12 | 22 d | ✓ |
| 13 | 24 d | ✓ |
| 14 | 27 d | ✓ |
| 15 | 34 d | ✓ |

Note:
✓, indicates that the sample was taken

Figure 15:
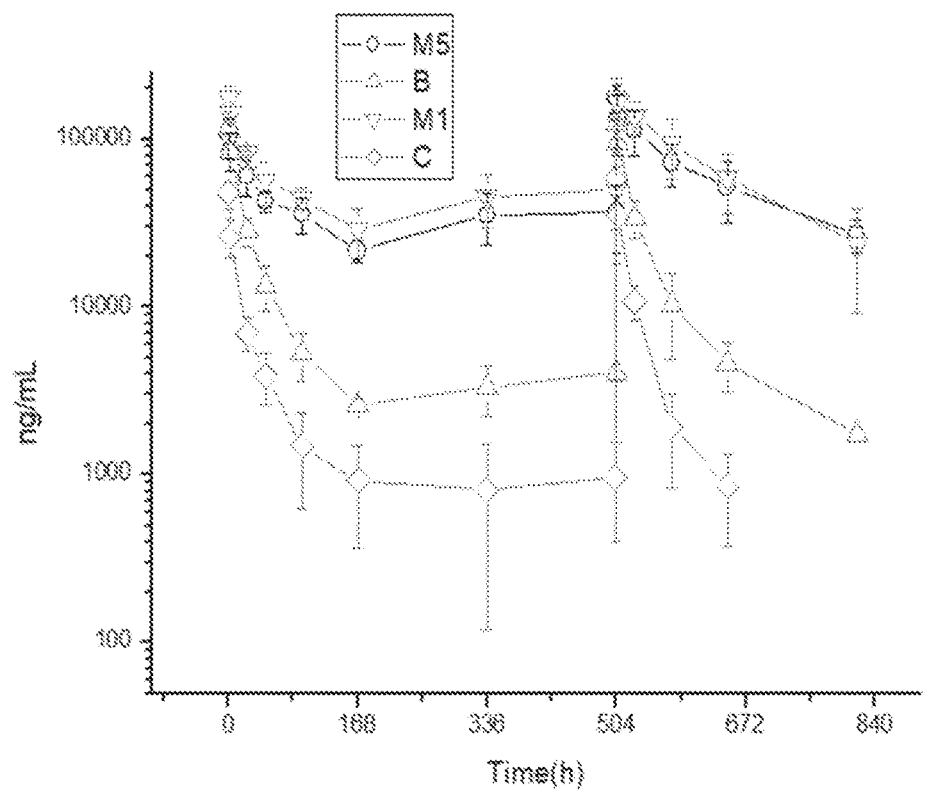
FIG. 15. Results from Cyno PK Study.

ELISA assay using the purified antigen was used to test the drug concentration in the serum. The PK data is shown in FIG. 15. The results showed that antibodies M1 and M5 had linear PK with no obvious immunogenicity at 5 mg/kg.

Animal Model Efficacy Study

Example 20. Animal Model Efficacy Study

Mice used for the experiment were Balb/C female mice 6 weeks old. Mice were allowed to recover from shipping for 1 week prior to initiation of experiment. CT26/18.2 cells were implanted subcutaneously at 1×10$^6$ cells in 100 uL PBS. After 7 days tumors averaged ~70 mm$^3$. Mice were randomized into 6 groups of 10 mice such that each group had the same mean tumor size. Treatments were initiated at day 7.

The study groups are listed below:
1. Placebo
2. Mouse Antibody Reference (10 mg/Kg)
3. Mouse antibody M5 (10 mg/Kg)
4. Mouse antibody M5 (1 mg/Kg)
5. 5-Fluorouracil (40 mg/Kg)
6. 5-Fluorouracil+M5 (3 mg/Kg)

The antibodies in the forms of mouse IgG2a were expressed and purified. They were dosed every 3 days I.P. 5-FU was dosed every 2 days I.P. for a total of 3 treatments. The tumor sizes were measured every 3 days.

Figure 16:
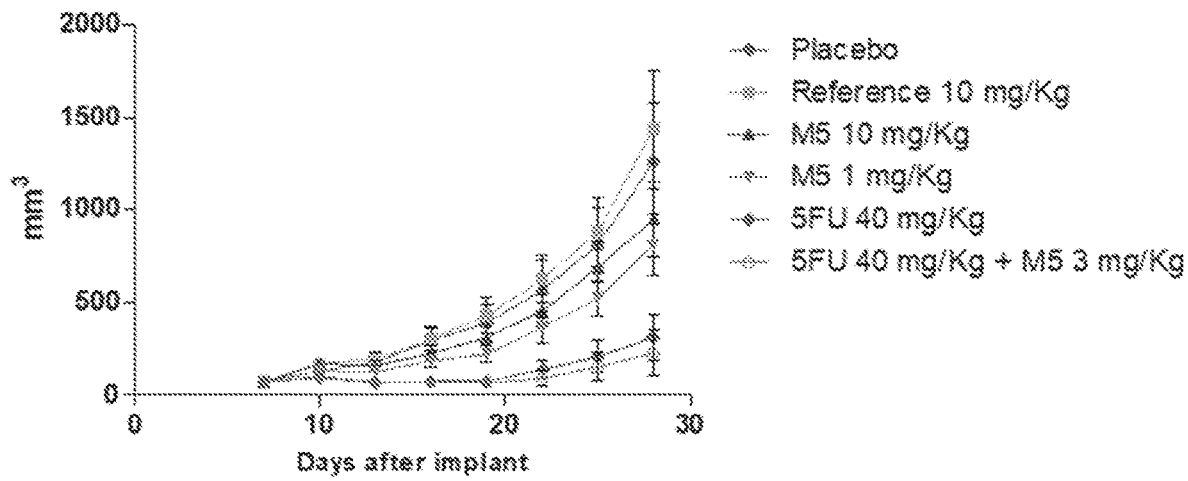
FIG. 16. Results from Animal Model Efficacy Study.

The in vivo efficacy data is shown in FIG. 16. The data showed that mouse antibody M5 was effective in suppressing tumor growth at 1 mg/kg and 10 mg/kg. The reference antibody did show any activities in this study.

TABLE 2

| SEQ ID NO: | Clone | Heavy chain variable domain Protein Sequence |
|---|---|---|
| 1 | 49E05 | CQSLEESGGGLVKPGGTLTLTCKASGIDFSSYYYMCWVRQAPGKGLEWIACIFNGDASTYYASWAHGRFTISKTSSTTVTLQMTGLTAADTATYFCARSDYSVAFAAFLYPTYFTLWGPGTLVTVSS |
| 2 | 49E12 | CQSLEESGGDLVKPGASLTLTCTASGFDLSSFVYICWVRQAPGKGLEWIGCIAINGGVTYYASWAKGRFTISKTSSTTVTLQMTSLTGADTATYFCARDDTSSNSYYNDLWGPGTLVTVSS |
| 3 | 50H08 | CQSLEESGGGLVQPGASLTLTCKASGFSFSSSYWICWVRQAPGKGLEWIACIYTTTSNIGYASWAKGRFTISKTSSTTVTLQMTSLTAADTATYFCAREDYDYYSFHPWGPGTLVTVSS |
| 4 | 52E07 | CQSLEESGGGLVQPEGSLTLTCTASGFSFSSSYWICWVRQAPGKGLEWIACVYTTTGNIGYASWAKGRFTISVPSSTTVTLQLTSLTAADTATYFCAREGSDIYAFHPWGPGTLVTVSS |
| 5 | 52G02 | QSLEESGGDLVKPGASLTLTCKASGFSFSSGYYISWIRQAPGKGLEWIACIYAGGSGTTYYATWAKGRFTVSETSSTTVTLQMTSLTAADTATYFCARDYIGTRTYYFDFWGPGTLVTVST |
| 6 | 54B08 | QEQLVESGGGLVQPEGSLTLTCTASGFSFSGNYYMWWVRQAPGKGLEWIACIHIDSGRPWYASWAKGRFTISKTSSTTVTLQMTSLTVADTATYFCARGVSSVYWRTYFNLWGPGTLVTVSS |
| 7 | 54C02 | QQQLVESGGGLVKPGGTLTLTCTVSGFYFNRGYWICWVRQAPGKGLEWIGCIDTGSGVPYYANWAKGRFTISKTSSTAVTLQMTSLTAADTATYFCARNSDSIYFNLWGPGTLVTVSS |
| 8 | 59A08 | QEQLVESGGGLVKPGGTLTLTCTASGFSFSSGFYISWVRQAPGKGPELISHIYTTSTTTWYASWAKGRFTISKTSSTTVTLQMTSLTAADTATYFCARAGYVDYGYAPYDMDLWGPGTLVTVSS |
| 9 | 59E07 | QSLEESGGGLVQPEGSLTLTCKASGFSFSYNVYMCWVRQAPGKGLEWIGCIYAVSSNTIYYANWAKGRFTISKTSSTTVTLQLPSLTAADTATYFCATRDANAGYSFNLWGPGTLVTVSS |

TABLE 2-continued

| SEQ ID NO: | Clone | Heavy chain variable domain Protein Sequence |
|---|---|---|
| 10 | 59F10 | QSLEESGGDLVQPEGSLTLTCKASGFSFSSGYYMCWVRQAPGKGLGLIACIDAGGRG DTVYASWAKGRFTISKTSSTTVTLQLNSLTAADTAIYFCARRGYSSISSNFGAFNPWGP GTLVTVSS |
| 11 | 59G03 | QELKESGGRLVTPGGSLTLTCTASGFSFNSNYYMCWVRQAPGKGLEWIACIYGGTTV NTYYATWAKGRFAISKTSSTTVTLQMTSLTAADTATYFCAREDLTAYSSYVITLWGPGT LVTVSS |
| 12 | 77B06 | QEQLEESGGDLVKPEGSLTLTCTVSGFSFNRGYWICWVRQAPGKGLEWIGCVDTGS GSSYYANWAKGRFTISKTSSTAVTLQMTSLTAADTATYFCARNSDSIYFNLWGPGTLV TVSS |
| 13 | 80D08 | CQSLEESGGALVKPGASLTLTCTASGFSFTSRDYICWVRQAPGKGLEWTGCIAIDGGV IYYATWAKGRFTISKTSSTTVTLQMTSLTAADTATYFCARDDIGSNSYYNDLWGPGTLV TVSS |
| 14 | 80G08 | QEQLEESGGGLVKPGASLTLTCTASGFSFSNNYYISWVRQAPGKGLEWIACIYTGYSW TYYASWAKGRFTISKTSSTTVTLQMTSLTVADTATYFCARADSGYSGFNLWGPGTLVT VSS |
| 15 | 81E11 | CQSLEESGGGLVQPGASLTLTCTASGFSFSSSYWICWVRQAPGKGLEWIACIYTTTNN IGYANWAKGRFTISKTSSTTVTLQMTSLTAADTATYFCAREDYDYYSFHPWGPGTLVT VSS |
| 16 | 82C08 | QQQLEESGGGLVKPGGTLTLTCTASGFTFSSYWISWVRQAPGKGLEWIAYIFTSSITFT AYASWAKGRFTVSKTSSTTVTLQLTSLTAADTATYFCARDLSSTSYYFNLWGPGTLVT VSS |
| 17 | 82F02 | QEQLVESGGGLVQPEGSLTLTCTASGFSFSGNYHMWWVRQAPGKGLEWIACIHTDS GRTWYASWAKGRFTISKTSSTTVTLQMTSLTVADTATYFCARGVSSVYWRTYFNLWG PGTLVTVSS |
| 18 | 99A09 | QEQLEESGGDLVKPEGSLTLTCTVSGFSFSNNYWICWVRQAPGKGLEWIACIYLGSS GYTYFASWARGRFTISKPSSTTVTLQMTSLTAADTATYFCARSYYTGYAGYIYPTYFN LWGPGTLVTVSS |
| 19 | SD215 | QEQLVESGGGLVKPGGTLTLTCTASGFSFSSGFYISWVRQAPGKGPELISHIYTTSTTT WYASWAKGRFTISKTSSTTVTLQMTSLTAADTATYFCARAGYVDYGYAPYDMDLWGP GTLVTVSS |
| 20 | SD232 | EQLVESGGGLVQPEGSLTLTCTASGFSFSSYYMCWVRQAPGKGLEWIGCIHTDSGRT WYASWAKGRFTISKTSSTTVTLQMTSLTVADTATYFCARGISSVYWRTYFNLWGPGTL VTVSS |
| 21 | SD272 | QQQLEESGGGLVKPGGTLTLTCTVSGFSFNAGYWICWVRQAPGKGLEWIGCIDTGSG VSYYASWAKGRFTISKTSSTAVTLQMTGLTVADTATYFCARNTDSIYFNLWGPGTLVT VSS |
| 22 | SD312 | QSLEESGGDLVQPEGSLTLTCKASGFSFSSGYYMCWVRQAPGKGLGLIACIDAGGRG DTVYASWAKGRFTISKTSSTTVTLQLNSLTAADTAIYFCARRGYSSISSNFGAFNPWGP GTLVTVSS |
| 23 | SD331 | QQQLEESGGGLVKPEGSLTLTCKASGFDFTSYYYMCWVRQAPGKGLELIAYIESSSG RIWYASWAKGRFTISKTSSTTVTLQMTSLTGADTASYFCARDISSSGYHGFKWWPG TLVTVSS |

TABLE 3

| SEQ ID NO: | Clone | Light chain variable domain Protein Sequence |
|---|---|---|
| 24 | 49E05 | DIVMTQTPVSVSEPVGGIVTIKCQASQSIGSNLAWYQQKPGQPPKLLIYLASTLASGVP SRFKGSGSGTEFTLTISDLECADAATYYCQGYYWSSSRSYGSAFGGGTEVVVV |
| 25 | 49E12 | AYDMTQTPASVSEPVGGAVTIKCQASQSIGSNLAWYQQKPGQPPKLLIYGASTLASGV SSRFKGSGSGTQFTLTISGVECADAATYYCQQGYTYSHADNAFGGGTEVVVV |
| 26 | 50H08 | AYDMTQTPSSVSAAVGGTVTIKCQASQSIGTYLAWYQQKPGQPPKRLIYKASSLPSGV SSRFKGGGSGTEFTLTISGVECADAATYYCQQAYTHTYLDNGFGGGTEVVVV |
| 27 | 52E07 | AYDMTQTPASVEVAVGGTVTIKCQASQSISSYLSWYQQKPGQPPKLLIYKASTLASGV SSRFKGSGSGTEFTLTISGVECADAATYYCQQAYTHTNLDNGFGGGTEVVVV |

TABLE 3-continued

| SEQ ID NO: | Clone | Light chain variable domain Protein Sequence |
|---|---|---|
| 28 | 52G02 | AQVLTQTPSSVSAAVGGTVTINCQASQSVYKNNYLSWYQQKPGQPPKLLIYEASKLAS GVPSRFSGSGSGTQFTLTISGVQCDDAATYYCAGEFTCISADCFAFGGGTEVVVV |
| 29 | 54B08 | DVVLTQTPSSASEPVGGTVTIKCQASQTIGSNLAWYQQKPGQPPKLLIYGASNLPSGV PSRFSGSASGTEFTLTISGVQCDDAATYYCQSAYWLDSGDNGFGGGTEVVVV |
| 30 | 54C02 | DIVMTQTPASVSEPVGGTVTIKCQASQSIGGYLSWYQQKPGQPPKLLIYKASTLASGVP SRFKGSGSGTDFTLTISDLECADAATYYCQNYAGVSIYGAVFGGGTKVVVV |
| 31 | 59A08 | ALVMTQTPSSVSAAVGGTVTIKCQASQSISGYLAWYQQKPGQPPKLLIYRASTLASGV SSRFKGSGSGTEYTLTISGVECADAATYYCQQGYSMYYIETSFGGGTKVVVV |
| 32 | 59E07 | GYDMTQTPASVSAAVGGTITIKCQASQSISNWLAWYQQKPGQPPKLLIYSASTLASGV PSRFKGSGSGTQFTLTISDMQCDDAATYYCEGGYSSGDRNVFGGGTKVVVV |
| 33 | 59F10 | AYDMTQTPASVEVAVGGTVTIKCQASQSISSYLAWYQQKPGQPPKQLIYGASTLASGV SSRFKGSGSGTQFTLTISGVECADSATYYCQQGYTSIYVDNAFGGGTKVVVV |
| 34 | 59G03 | AYDMTQTPASVSEPVGGTVTIKCQASETIYRNLAWYQQKPGQPPKLLIYAASTLASGV PSRFKGSGSGTQFTLTISDLECADAATYYCQQAYTRVNIDNAFGGGTKVVVV |
| 35 | 77B06 | DIVMTQTPVSVSEPVGGTVTIKCQASQSISSYLSWYQQKPGQPPKLLIYRASTLASGVP SRFKGSGSGTEYTLTISDLECADAAAYYCQNYAGVSLYGAVFGGGTEVVVV |
| 36 | 80D08 | AYDMTQTPASVSAAVGGTVTINCQASQNIYSNLAWYQQKPGQRPKLLIYRASTLASGV PSRFRGSGSGTQFTLTISDLECADAATYYCQQGYTYIHADNAFGGGTEVVVV |
| 37 | 80G08 | DVVMTQTPASVSEPVGGTVTIKCQASQSIDSRLAWYQQKPGQPPKLLIYGASTLASGV PSRFKGSGSGTEYTLTISGVQCADAATYYCQCSVTISTGVGGAFGGGTKVVVV |
| 38 | 81E11 | AYDMTQTPASVSAAVGGTVTIKCQASQSIGTYLAWYQQKPGQPPKRLLYKASSLASG VSSRFKGGGSGTEFSLTISGVECADAATYYCQQAYTHTYLDNGFGGGTKVVVV |
| 39 | 82C08 | AYDVTQTPASVEVAVGGTVTIKCQASETVSYRLAWYQQKPGQPPKLLIYDASTLASGV PSRFSGSGSETEFTLTISGVECADAAIYYCQQGYTRNNIDNTFGGGTKVVVV |
| 40 | 82F02 | DVVLTQTPSSASEPVGGTVTIKCQASQTIGSNLAWYHQKPGQPPKLLIYGASNLASGV PSRFSGSASGTQFTLTISGVQCDDAATYYCQSAYWLDSGDNGFGGGTKVVVV |
| 41 | 99A09 | NIVMTQTPSPVSAAVGGTVTIKCQASQSISSYLAWYQQKPGQPPKLLIYKASTLASGVS SRLKGSGSGTEFTLTISDLECADAATYYCQTYDYSSSNSYGSNAFGGGTKVVVV |
| 42 | SD215 | ALVMTQTPSSVSAAVGGTVTIKCQASQSISGYLAWYQQKPGQPPKLLIYRASTLASGV SSRFKGSGSGTEYTLTISGVECADAATYYCQQGYSMYYIETSFGGGTEVVVV |
| 43 | SD232 | DVVMTQTPSSVSEPVGGTVTIRCQASQSIGSNLAWYQQKPGQPPKLLIYGASNLASGV PSRFSGSASGTQFTLTISGVQCDDAATYYCQSAYWLDSGDNGFGGGTKVVVV |
| 44 | SD272 | DIVMTQTPASVEAAVGGTVTIKCQASQTIYSYLSWYQQKPGQPPKLLIYKASTLASGVS SRFKGSGSGTEFTLTISDLECADAAAYYCQTYAGVSIYGAAFGGGTKVVVV |
| 45 | SD312 | AYDMTQTPASVEVAVGGTVTIKCQASQSISSYLAWYQQKPGQPPKQLIYGASTLASGV SSRFKGSGSGTQFTLTISGVECADSATYYCQQGYTSIYVDNAFGGGTKVVVV |
| 46 | SD331 | AIKMTQTPASVEAAVGGTVTIKCQASQSISNYLAWYQQKPGQPPKLLIYRASTLESGVP SRFKGSGSGTDFTLTISDLECADAATYYCQQVYSITNIDNAFGGGTEVVVV |

TABLE 4

| SEQ ID NO: | Clone 49E05 | Protein Sequence |
|---|---|---|
| 47 | CDR1 VH | GIDFSSYYY |
| 48 | CDR2 VH | IFNGDAST |
| 49 | CDR3 VH | RSDYSVAFAAFLYPTYFTL |
| 50 | CDR1 VL | QSIGSN |
| 51 | CDR2 VL | LAS |
| 52 | CDR3 VL | QGYYWSSSRSYGSA |

TABLE 5

| SEQ ID NO: | Clone 49E12 | Protein Sequence |
|---|---|---|
| 53 | CDR1 VH | GFDLSSFVY |
| 54 | CDR2 VH | IAINGGV |
| 55 | CDR3 VH | ARDDTSSNSYYNDL |
| 56 | CDR1 VL | QSIGSN |
| 57 | CDR2 VL | GAS |
| 58 | CDR3 VL | QQGYTYSHADNA |

TABLE 6

| SEQ ID NO: | Clone 50H08 | Protein Sequence |
|---|---|---|
| 59 | CDR1 VH | GFSFSSSYW |
| 60 | CDR2 VH | IYTTTSN |
| 61 | CDR3 VH | AREDYDYYSFHP |
| 62 | CDR1 VL | QSIGTY |
| 63 | CDR2 VL | KAS |
| 64 | CDR3 VL | QQAYTHTYLDNG |

TABLE 7

| SEQ ID NO: | Clone 52E07 | Protein Sequence |
|---|---|---|
| 65 | CDR1 VH | GFSFSSSYW |
| 66 | CDR2 VH | VYTTTGN |
| 67 | CDR3 VH | AREGSDIYAFHP |
| 68 | CDR1 VL | QSISSY |
| 69 | CDR2 VL | KAS |
| 70 | CDR3 VL | QQAYTHTNLDNG |

TABLE 8

| SEQ ID NO: | Clone 52G02 | Protein Sequence |
|---|---|---|
| 71 | CDR1 VH | GFSFSSGYY |
| 72 | CDR2 VH | IYAGGSGTT |
| 73 | CDR3 VH | ARDYIGTRTYYFDF |
| 74 | CDR1 VL | QSVYKNNY |
| 75 | CDR2 VL | EAS |
| 76 | CDR3 VL | AGEFTCISADCFA |

TABLE 9

| SEQ ID NO: | Clone 54B08 | Protein Sequence |
|---|---|---|
| 77 | CDR1 VH | GFSFSGNYY |
| 78 | CDR2 VH | IHIDSGRP |

TABLE 9-continued

| SEQ ID NO: | Clone 54B08 | Protein Sequence |
|---|---|---|
| 79 | CDR3 VH | RGVSSVYWRTYFNL |
| 80 | CDR1 VL | QTIGSN |
| 81 | CDR2 VL | GAS |
| 82 | CDR3 VL | QSAYWLDSGDNG |

TABLE 10

| SEQ ID NO: | Clone 54C02 | Protein Sequence |
|---|---|---|
| 83 | CDR1 VH | GFYFNRGYW |
| 84 | CDR2 VH | IDTGSGV |
| 85 | CDR3 VH | ARNSDSIYFNL |
| 86 | CDR1 VL | QSIGGY |
| 87 | CDR2 VL | KAS |
| 88 | CDR3 VL | QNYAGVSIYGAV |

TABLE 11

| SEQ ID NO: | Clone 59A08 | Protein Sequence |
|---|---|---|
| 89 | CDR1 VH | GFSFSSGFY |
| 90 | CDR2 VH | IYTTSTTT |
| 91 | CDR3 VH | RAGYVDYGYAPYDMDL |
| 92 | CDR1 VL | QSISGY |
| 93 | CDR2 VL | RAS |
| 94 | CDR3 VL | QQGYSMYYIETS |

TABLE 12

| SEQ ID NO: | Clone 59E07 | Protein Sequence |
|---|---|---|
| 95 | CDR1 VH | GFSFSYNVY |
| 96 | CDR2 VH | IYAVSSNTI |
| 97 | CDR3 VH | ATRDANAGYSFNL |
| 98 | CDR1 VL | QSISNW |
| 99 | CDR2 VL | SAS |
| 100 | CDR3 VL | EGGYSSGDRNV |

TABLE 13

| SEQ ID NO: | Clone 59F10 | Protein Sequence |
|---|---|---|
| 101 | CDR1 VH | GFSFSSGYY |
| 102 | CDR2 VH | IDAGGRGDT |
| 103 | CDR3 VH | ARRGYSSISSNFGAFNP |

TABLE 13-continued

| SEQ ID NO: | Clone 59F10 | Protein Sequence |
|---|---|---|
| 104 | CDR1 VL | QSISSY |
| 105 | CDR2 VL | GAS |
| 106 | CDR3 VL | QQGYTSIYVDNA |

TABLE 14

| SEQ ID NO: | Clone 59G03 | Protein Sequence |
|---|---|---|
| 107 | CDR1 VH | GFSFNSNYY |
| 108 | CDR2 VH | IYGGTTVNT |
| 109 | CDR3 VH | AREDLTAYSSYVITL |
| 110 | CDR1 VL | ETIYRN |
| 111 | CDR2 VL | AAS |
| 112 | CDR3 VL | QQAYTRVNIDNA |

TABLE 15

| SEQ ID NO: | Clone 77B06 | Protein Sequence |
|---|---|---|
| 113 | CDR1 VH | GFSFNRGYW |
| 114 | CDR2 VH | VDTGSGS |
| 115 | CDR3 VH | ARNSDSIYFNL |
| 198 | CDR3 VH | ARNSDSIYFNI |
| 116 | CDR1 VL | QSISSY |
| 117 | CDR2 VL | RAS |
| 118 | CDR3 VL | QNYAGVSLYGAV |

TABLE 16

| SEQ ID NO: | Clone 80D08 | Protein Sequence |
|---|---|---|
| 119 | CDR1 VH | GFSFTSRDY |
| 120 | CDR2 VH | IAIDGGV |
| 121 | CDR3 VH | ARDDIGSNSYYNDL |
| 122 | CDR1 VL | QNIYSN |
| 123 | CDR2 VL | RAS |
| 124 | CDR3 VL | QQGYTYIHADNA |

TABLE 17

| SEQ ID NO: | Clone 80G08 | Protein Sequence |
|---|---|---|
| 125 | CDR1 VH | GFSFSNNYY |
| 126 | CDR2 VH | IYTGYSW |
| 127 | CDR3 VH | ARADSGYSGFNL |
| 128 | CDR1 VL | QSIDSR |

TABLE 17-continued

| SEQ ID NO: | Clone 80G08 | Protein Sequence |
|---|---|---|
| 129 | CDR2 VL | GAS |
| 130 | CDR3 VL | QCSVTISTGVGGA |

TABLE 18

| SEQ ID NO: | Clone 81E11 | Protein Sequence |
|---|---|---|
| 131 | CDR1 VH | GFSFSSSYW |
| 132 | CDR2 VH | IYTTTNN |
| 133 | CDR3 VH | AREDYDYYSFHP |
| 134 | CDR1 VL | QSIGTY |
| 135 | CDR2 VL | KAS |
| 136 | CDR3 VL | QQAYTHTYLDNG |

TABLE 19

| SEQ ID NO: | Clone 82C08 | Protein Sequence |
|---|---|---|
| 137 | CDR1 VH | GFTFSSYW |
| 138 | CDR2 VH | IFTSSITF |
| 139 | CDR3 VH | ARDLSSTSYYFNL |
| 140 | CDR1 VL | ETVSYR |
| 141 | CDR2 VL | DAS |
| 142 | CDR3 VL | QQGYTRNNIDNT |

TABLE 20

| SEQ ID NO: | Clone 82F02 | Protein Sequence |
|---|---|---|
| 143 | CDR1 VH | GFSFSGNYH |
| 144 | CDR2 VH | IHTDSGRT |
| 145 | CDR3 VH | RGVSSVYWRTYFNL |
| 146 | CDR1 VL | QTIGSN |
| 147 | CDR2 VL | GAS |
| 148 | CDR3 VL | QSAYWLDSGDNG |

TABLE 21

| SEQ ID NO: | Clone 99A09 | Protein Sequence |
|---|---|---|
| 149 | CDR1 VH | GFSFSNNYW |
| 150 | CDR2 VH | IYLGSSGYT |
| 151 | CDR3 VH | ARSYYTGYAGYIYPTYFNL |
| 152 | CDR1 VL | QSISSY |
| 153 | CDR2 VL | KAS |
| 154 | CDR3 VL | QTYDYSSSNSYGSNA |

TABLE 22

| SEQ ID NO: | Clone SD215 | Protein Sequence |
|---|---|---|
| 155 | CDR1 VH | GFSFSSGFY |
| 156 | CDR2 VH | IYTTSTTT |
| 157 | CDR3 VH | RAGYVDYGYAPYDMDL |
| 158 | CDR1 VL | QSISGY |
| 159 | CDR2 VL | RAS |
| 160 | CDR3 VL | QQGYSMYYIETS |

TABLE 23

| SEQ ID NO: | Clone SD232 | Protein Sequence |
|---|---|---|
| 161 | CDR1 VH | GFSFSSYY |
| 162 | CDR2 VH | IHTDSGR |
| 163 | CDR3 VH | ARGISSVYWRTYFNL |
| 164 | CDR1 VL | QSIGSN |
| 165 | CDR2 VL | GAS |
| 166 | CDR3 VL | QSAYWLDSGDNG |

TABLE 24

| SEQ ID NO: | Clone SD272 | Protein Sequence |
|---|---|---|
| 167 | CDR1 VH | GFSFNAGYW |
| 168 | CDR2 VH | IDTGSGVS |
| 169 | CDR3 VH | RNTDSIYFNL |

TABLE 24-continued

| SEQ ID NO: | Clone SD272 | Protein Sequence |
|---|---|---|
| 170 | CDR1 VL | QTIYSY |
| 171 | CDR2 VL | KAS |
| 172 | CDR3 VL | QTYAGVSIYGAA |

TABLE 25

| SEQ ID NO: | Clone SD312 | Protein Sequence |
|---|---|---|
| 173 | CDR1 VH | GFSFSSGYY |
| 174 | CDR2 VH | IDAGGRGDT |
| 175 | CDR3 VH | ARRGYSSISSNFGAFNP |
| 176 | CDR1 VL | QSISSY |
| 177 | CDR2 VL | GAS |
| 178 | CDR3 VL | QQGYTSIYVDNA |

TABLE 26

| SEQ ID NO: | Clone SD331 | Protein Sequence |
|---|---|---|
| 179 | CDR1 VH | GFDFTSYYY |
| 180 | CDR2 VH | IESSSGRI |
| 181 | CDR3 VH | RDISSSGYHGFKW |
| 182 | CDR1 VL | QSISNY |
| 183 | CDR2 VL | RAS |
| 184 | CDR3 VL | QQVYSITNIDNA |

TABLE 27

Amino Acid Sequences of the Humanized Variants - Heavy Chain

| SEQ ID NO: | Name | Sequence |
|---|---|---|
| 186 | HC0 | MGWTLVFLFLLSVTAGVHSQQQLVESGGGLVKPGGTLTLTCTVSGFYFNRGYWICWVR QAPGKGLEWIGCIDTGSGVPYYANWAKGRFTISKTSSTAVTLQMTSLTAADTATYFCAR NSDSIYFNLWGPGTLVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTKVDKKVE PKSCDKTHTCPPCPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVSNKALPAPIEK TISKAKGQPREPQVYTLPPSRDELTKNQVSLTCLVKGFYPSDIAVEWESNGQPENNYKT TPPVLDSDGSFFLYSKLTVDKSRWQQGNVFSCSVMHEALHNHYTQKSLSLSPGK |
| 187 | HC1 | MGWTLVFLFLLSVTAGVHSEVQLVESGGGLVKPGGSLRLSCTASGFYFNRGYWICWLR QAPGKGLEWACIDTGSGVPYYANWAKGRFTVSRDNAKNSLFLQMNSLRAEDTAVYYC ARNSDSIYFNLWGPGTLVTVSSASTKGPSVFPLAPSSKSTSGGTAALGCLVKDYFPEPV TVSWNSGALTSGVHTFPAVLQSSGLYSLSSVVTVPSSSLGTQTYICNVNHKPSNTKVDK KVEPKSCDKTHTCPPCPAPELLGGPSVFLFPPKPKDTLMISRTPEVTCVVVDVSHEDPEV KFNWYVDGVEVHNAKTKPREEQYNSTYRVVSVLTVLHQDWLNGKEYKCKVSNKALPAP IEKTISKAKGQPREPQVYTLPPSRDELTKNQVSLTCLVKGFYPSDIAVEWESNGQPENNY KTTPPVLDSDGSFFLYSKLTVDKSRWQQGNVFSCSVMHEALHNHYTQKSLSLSPGK |
| 188 | HC2 | MGWTLVFLFLLSVTAGVHSQVQLVESGGGVVQPGRSLRLPCAASGFYFNRGYWICWV RQAPGKGLEWACIDTGSGVPYYANWAKGRFTISRDTSKNTLYLQMDSLRAEDTAVYY CARNSDSIYFNLWGRGTLVTVSSASTKGPSVFPLAPSSKSTSGGTAALGCLVKDYFPEP VTVSWNSGALTSGVHTFPAVLQSSGLYSLSSVVTVPSSSLGTQTYICNVNHKPSNTKVD KKVEPKSCDKTHTCPPCPAPELLGGPSVFLFPPKPKDTLMISRTPEVTCVVVDVSHEDPE VKFNWYVDGVEVHNAKTKPREEQYNSTYRVVSVLTVLHQDWLNGKEYKCKVSNKALPA PIEKTISKAKGQPREPQVYTLPPSRDELTKNQVSLTCLVKGFYPSDIAVEWESNGQPENN YKTTPPVLDSDGSFFLYSKLTVDKSRWQQGNVFSCSVMHEALHNHYTQKSLSLSPGK |

TABLE 27-continued

Amino Acid Sequences of the Humanized Variants - Heavy Chain

| SEQ ID NO: | Name | Sequence |
|---|---|---|
| 189 | HC3 | MGWTLVFLFLLSVTAGVHSEVQLVESGGDLAQPGGSLRLSCAVSGFYFNRGYWICWVR<br>QAPGKGLEWVSCIDTGSGVPYYANWAKGRFTISRDNSKNTVYLQMTSLRAEDTALYFC<br>ARNSDSIYFNLWGQGTLVTVSSASTKGPSVFPLAPSSKSTSGGTAALGCLVKDYFPEPV<br>TVSWNSGALTSGVHTFPAVLQSSGLYSLSSVVTVPSSSLGTQTYICNVNHKPSNTKVDK<br>KVEPKSCDKTHTCPPCPAPELLGGPSVFLFPPKPKDTLMISRTPEVTCVVVDVSHEDPEV<br>KFNWYVDGVEVHNAKTKPREEQYNSTYRVVSVLTVLHQDWLNGKEYKCKVSNKALPAP<br>IEKTISKAKGQPREPQVYTLPPSRDELTKNQVSLTCLVKGFYPSDIAVEWESNGQPENNY<br>KTTPPVLDSDGSFFLYSKLTVDKSRWQQGNVFSCSVMHEALHNHYTQKSLSLSPGK |
| 190 | HC4 | MGWTLVFLFLLSVTAGVHSQVQLVESGGGLVKPGGSLRLSCAASGFYFNRGYWICWIR<br>QAPGKGLEWVSCIDTGSGVPYYANWAKGRFTISRDNAKNSLYLQMNSLRTEDTAVYFC<br>ARNSDSIYFNLWGQGTLVTVSSASTKGPSVFPLAPSSKSTSGGTAALGCLVKDYFPEPV<br>TVSWNSGALTSGVHTFPAVLQSSGLYSLSSVVTVPSSSLGTQTYICNVNHKPSNTKVDK<br>KVEPKSCDKTHTCPPCPAPELLGGPSVFLFPPKPKDTLMISRTPEVTCVVVDVSHEDPEV<br>KFNWYVDGVEVHNAKTKPREEQYNSTYRVVSVLTVLHQDWLNGKEYKCKVSNKALPAP<br>IEKTISKAKGQPREPQVYTLPPSRDELTKNQVSLTCLVKGFYPSDIAVEWESNGQPENNY<br>KTTPPVLDSDGSFFLYSKLTVDKSRWQQGNVFSCSVMHEALHNHYTQKSLSLSPGK |
| 191 | HC5 | MGWTLVFLFLLSVTAGVHSEVQLVESGGGLVKPGGSLRLSCAVSGFYFNRGYWICWVR<br>QAPGKGLEWIGCIDTGSGVPYYANWAKGRFTISRHTSKTTLTLQMNSLRAEDTASYFCA<br>RNSDSIYFNLWGPGTLVTVSSASTKGPSVFPLAPSSKSTSGGTAALGCLVKDYFPEPVT<br>VSWNSGALTSGVHTFPAVLQSSGLYSLSSVVTVPSSSLGTQTYICNVNHKPSNTKVDKK<br>VEPKSCDKTHTCPPCPAPELLGGPSVFLFPPKPKDTLMISRTPEVTCVVVDVSHEDPEVK<br>FNWYVDGVEVHNAKTKPREEQYNSTYRVVSVLTVLHQDWLNGKEYKCKVSNKALPAPI<br>EKTISKAKGQPREPQVYTLPPSRDELTKNQVSLTCLVKGFYPSDIAVEWESNGQPENNY<br>KTTPPVLDSDGSFFLYSKLTVDKSRWQQGNVFSCSVMHEALHNHYTQKSLSLSPGK |
| 199 | HC4M1 | MGWTLVFLFLLSVTAGVHSQVQLVESGGGLVKPGGSLRLSCAASGFYFNRGYWICWIR<br>QAPGKGLEWVSCIDTGSGVPYYANWAKGRFTISRDNAKNSLYLQMNSLRTEDTAVYFC<br>ARNSDSIYFNIWGQGTLVTVSSASTKGPSVFPLAPSSKSTSGGTAALGCLVKDYFPEPVT<br>VSWNSGALTSGVHTFPAVLQSSGLYSLSSVVTVPSSSLGTQTYICNVNHKPSNTKVDKK<br>VEPKSCDKTHTCPPCPAPELLGGPSVFLFPPKPKDTLMISRTPEVTCVVVDVSHEDPEVK<br>FNWYVDGVEVHNAKTKPREEQYNSTYRVVSVLTVLHQDWLNGKEYKCKVSNKALPAPI<br>EKTISKAKGQPREPQVYTLPPSRDELTKNQVSLTCLVKGFYPSDIAVEWESNGQPENNY<br>KTTPPVLDSDGSFFLYSKLTVDKSRWQQGNVFSCSVMHEALHNHYTQKSLSLSPGK |
| 200 | HC4M2 | MGWTLVFLFLLSVTAGVHSQVQLVESGGGLVKPGGSLRLSCAASGFYFNRGYWISWIR<br>QAPGKGLEWVSSIDTGSGVPYYANWAKGRFTISRDNAKNSLYLQMNSLRTEDTAVYFC<br>ARNSDSIYFNLWGQGTLVTVSSASTKGPSVFPLAPSSKSTSGGTAALGCLVKDYFPEPV<br>TVSWNSGALTSGVHTFPAVLQSSGLYSLSSVVTVPSSSLGTQTYICNVNHKPSNTKVDK<br>KVEPKSCDKTHTCPPCPAPELLGGPSVFLFPPKPKDTLMISRTPEVTCVVVDVSHEDPEV<br>KFNWYVDGVEVHNAKTKPREEQYNSTYRVVSVLTVLHQDWLNGKEYKCKVSNKALPAP<br>IEKTISKAKGQPREPQVYTLPPSRDELTKNQVSLTCLVKGFYPSDIAVEWESNGQPENNY<br>KTTPPVLDSDGSFFLYSKLTVDKSRWQQGNVFSCSVMHEALHNHYTQKSLSLSPGK |
| 201 | HC4M3 | MGWTLVFLFLLSVTAGVHSQVQLVESGGGLVKPGGSLRLSCAASGFYFNRGYWISWIR<br>QAPGKGLEWVSSIDTGSGVPYYANWAKGRFTISRDNAKNSLYLQMNSLRTEDTAVYFC<br>ARNSDSIYFNIWGQGTLVTVSSASTKGPSVFPLAPSSKSTSGGTAALGCLVKDYFPEPVT<br>VSWNSGALTSGVHTFPAVLQSSGLYSLSSVVTVPSSSLGTQTYICNVNHKPSNTKVDKK<br>VEPKSCDKTHTCPPCPAPELLGGPSVFLFPPKPKDTLMISRTPEVTCVVVDVSHEDPEVK<br>FNWYVDGVEVHNAKTKPREEQYNSTYRVVSVLTVLHQDWLNGKEYKCKVSNKALPAPI<br>EKTISKAKGQPREPQVYTLPPSRDELTKNQVSLTCLVKGFYPSDIAVEWESNGQPENNY<br>KTTPPVLDSDGSFFLYSKLTVDKSRWQQGNVFSCSVMHEALHNHYTQKSLSLSPGK |
| 202 | HC5M1 | MGWTLVFLFLLSVTAGVHSEVQLVESGGGLVKPGGSLRLSCAVSGFYFNRGYWICWVR<br>QAPGKGLEWIGCIDTGSGVPYYANWAKGRFTISRHTSKTTLTLQMNSLRAEDTASYFCA<br>RNSDSIYFNIWGPGTLVTVSSASTKGPSVFPLAPSSKSTSGGTAALGCLVKDYFPEPVTV<br>SWNSGALTSGVHTFPAVLQSSGLYSLSSVVTVPSSSLGTQTYICNVNHKPSNTKVDKKV<br>EPKSCDKTHTCPPCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALPAPIE<br>KTISKAKGQPREPQVYTLPPSRDELTKNQVSLTCLVKGFYPSDIAVEWESNGQPENNYK<br>TTPPVLDSDGSFFLYSKLTVDKSRWQQGNVFSCSVMHEALHNHYTQKSLSLSPGK |
| 203 | HC5M2 | MGWTLVFLFLLSVTAGVHSEVQLVESGGGLVKPGGSLRLSCAVSGFYFNRGYWISWVR<br>QAPGKGLEWIGSIDTGSGVPYYANWAKGRFTISRHTSKTTLTLQMNSLRAEDTASYFCA<br>RNSDSIYFNLWGPGTLVTVSSASTKGPSVFPLAPSSKSTSGGTAALGCLVKDYFPEPVT<br>VSWNSGALTSGVHTFPAVLQSSGLYSLSSVVTVPSSSLGTQTYICNVNHKPSNTKVDKK<br>VEPKSCDKTHTCPPCPAPELLGGPSVFLFPPKPKDTLMISRTPEVTCVVVDVSHEDPEVK<br>FNWYVDGVEVHNAKTKPREEQYNSTYRVVSVLTVLHQDWLNGKEYKCKVSNKALPAPI<br>EKTISKAKGQPREPQVYTLPPSRDELTKNQVSLTCLVKGFYPSDIAVEWESNGQPENNY<br>KTTPPVLDSDGSFFLYSKLTVDKSRWQQGNVFSCSVMHEALHNHYTQKSLSLSPGK |
| 204 | HC5M3 | MGWTLVFLFLLSVTAGVHSEVQLVESGGGLVKPGGSLRLSCAVSGFYFNRGYWISWVR<br>QAPGKGLEWIGSIDTGSGVPYYANWAKGRFTISRHTSKTTLTLQMNSLRAEDTASYFCA |

TABLE 27-continued

Amino Acid Sequences of the Humanized Variants - Heavy Chain

| SEQ ID NO: | Name | Sequence |
|---|---|---|
|  |  | RNSDSIYFNIWGPGTLVTVSSASTKGPSVFPLAPSSKSTSGGTAALGCLVKDYFPEPVTV<br>SWNSGALTSGVHTFPAVLQSSGLYSLSSVVTVPSSSLGTQTYICNVNHKPSNTKVDKKV<br>EPKSCDKTHTCPPCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALPAPIE<br>KTISKAKGQPREPQVYTLPPSRDELTKNQVSLTCLVKGFYPSDIAVEWESNGQPENNYK<br>TTPPVLDSDGSFFLYSKLTVDKSRWQQGNVFSCSVMHEALHNHYTQKSLSLSPGK |
| 249 | 11E12VH_Hu1 | QVQLVQSGAEVKKPGASVKVSCKAS<u>GYTFTSYVIN</u>WVRQATGQGLEWIG<u>EIHPRGGNT</u><br><u>YYSEKFRG</u>RATMTRDTSISTAYMELSSLRSEDTAVYYCAR<u>IRRGNAMDY</u>WGQGTTLTVS<br>SASTKGPSVFPLAPSSKSTSGGTAALGCLVKDYFPEPVTVSWNSGALTSGVHTFPAVLQ<br>SSGLYSLSSVVTVPSSSLGTQTYICNVNHKPSNTKVDKKVEPKSCDKTHTCPPCPAPELL<br>GGPSVFLFPPKPKDTLMISRTPEVTCVVVDVSHEDPEVKFNWYVDGVEVHNAKTKPREE<br>QYNSTYRVVSVLTVLHQDWLNGKEYKCKVSNKALPAPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK |
| 250 | 11E12VH_Hu2 | QVQLVQSGAEVKKPGASVKVSCKAS<u>GYTFTSYVIN</u>WVRQATGQGLEWIG<u>EIHPRGGNT</u><br><u>YYSEKFRG</u>RATLTRDTSISTAYMELSSLRSEDTAVYYCAR<u>IRRGNAMDY</u>WGQGTTLTVS<br>SASTKGPSVFPLAPSSKSTSGGTAALGCLVKDYFPEPVTVSWNSGALTSGVHTFPAVLQ<br>SSGLYSLSSVVTVPSSSLGTQTYICNVNHKPSNTKVDKKVEPKSCDKTHTCPPCPAPELL<br>GGPSVFLFPPKPKDTLMISRTPEVTCVVVDVSHEDPEVKFNWYVDGVEVHNAKTKPREE<br>QYNSTYRVVSVLTVLHQDWLNGKEYKCKVSNKALPAPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK |
| 251 | 11E12VH_Hu3 | QVQLVQSGAEVKKPGASVKVSCKAS<u>GYTFTSYVIN</u>WVRQATGQGLEWIG<u>EIHPRGGNT</u><br><u>YYSEKFRG</u>RATLTRDTSISTAYMELSSLRSEDTAVYYCARL<u>RRGNAMDY</u>WGQGTTLTVS<br>SASTKGPSVFPLAPSSKSTSGGTAALGCLVKDYFPEPVTVSWNSGALTSGVHTFPAVLQ<br>SSGLYSLSSVVTVPSSSLGTQTYICNVNHKPSNTKVDKKVEPKSCDKTHTCPPCPAPELL<br>GGPSVFLFPPKPKDTLMISRTPEVTCVVVDVSHEDPEVKFNWYVDGVEVHNAKTKPREE<br>QYNSTYRVVSVLTVLHQDWLNGKEYKCKVSNKALPAPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK |

TABLE 28

Amino Acid Sequences of the Humanized Variants - Light Chain

| SEQ ID NO: | Name | Sequence |
|---|---|---|
| 192 | LC0 | MVSSAQFLGLLLLCFQGTRCDIVMTQTPASVSEPVGGTVTIKCQASQSIGGYLSWYQQK<br>PGQPPKLLIYKASTLASGVPSRFKGSGSGTDFTLTISDLECADAATYYCQNYAGVSIYGA<br>VFGGGTKVVVVRTVAAPSVFIFPPSDEQLKSGTASVVCLLNNFYPREAKVQWKVDNALQ<br>SGNSQESVTEQDSKDSTYSLSSTLTLSKADYEKHKVYACEVTHQGLSSPVTKSFNRGEC |
| 193 | LC1 | MVSSAQFLGLLLLCFQGTRCDIVMTQSPSSLSASVGDRVTITCQASQSIGGYLSWYQQK<br>PGKAPKLLIYKASTLASGVPSRFSGSGSGTDFTLTISSLQPEDFATYYCQNYAGVSIYGAV<br>FGGGTKVVIKRTVAAPSVFIFPPSDEQLKSGTASVVCLLNNFYPREAKVQWKVDNALQS<br>GNSQESVTEQDSKDSTYSLSSTLTLSKADYEKHKVYACEVTHQGLSSPVTKSFNRGEC |
| 194 | LC2 | MVSSAQFLGLLLLCFQGTRCDIVLTQSPSSLSASVGDRITITCQASQSIGGYLSWYQQKP<br>GTPPKLLIYKASTLASGVPSRFSGSGSGTDFTLTISRLQPEDVATYYCQNYAGVSIYGAVF<br>GGGTKLEIKRTVAAPSVFIFPPSDEQLKSGTASVVCLLNNFYPREAKVQWKVDNALQSG<br>NSQESVTEQDSKDSTYSLSSTLTLSKADYEKHKVYACEVTHQGLSSPVTKSFNRGEC |
| 195 | LC3 | MVSSAQFLGLLLLCFQGTRCDIQMTQSPSSLSASVGDRITITCQASQSIGGYLSWYQQKP<br>GRVPKLLIYKASTLASGVPSRFSGSGSGTEFTLTISSLQAEDVATYYCQNYAGVSIYGAVF<br>GGGTKVEIKRTVAAPSVFIFPPSDEQLKSGTASVVCLLNNFYPREAKVQWKVDNALQSG<br>NSQESVTEQDSKDSTYSLSSTLTLSKADYEKHKVYACEVTHQGLSSPVTKSFNRGEC |
| 196 | LC4 | MVSSAQFLGLLLLCFQGTRCDIQMTQSPSSLSASVGDRVTISCQASQSIGGYLSWYQQK<br>PGQAPKLLIYKASTLASGVPSRFSGSGSGTDFTLTISSLQPEDVATYYCQNYAGVSIYGA<br>VFGQGTKVEIKRTVAAPSVFIFPPSDEQLKSGTASVVCLLNNFYPREAKVQWKVDNALQ<br>SGNSQESVTEQDSKDSTYSLSSTLTLSKADYEKHKVYACEVTHQGLSSPVTKSFNRGEC |
| 197 | LC5 | MVSSAQFLGLLLLCFQGTRCDIQMTQSPSSVSASVGDRVTITCQASQSIGGYLSWYQQK<br>PGQPPKLLIYKASTLASGVPSRFKGSGSGTDFTLTISSLDSEDAATYYCQNYAGVSIYGA<br>VFGGGTKVVVKRTVAAPSVFIFPPSDEQLKSGTASVVCLLNNFYPREAKVQWKVDNALQ<br>SGNSQESVTEQDSKDSTYSLSSTLTLSKADYEKHKVYACEVTHQGLSSPVTKSFNRGEC |
| 205 | LC1M1 | MVSSAQFLGLLLLCFQGTRCDIVMTQSPSSLSASVGDRVTITCQASQSIGGYISWYQQKP<br>GKAPKLLIYKASTLASGVPSRFSGSGSGTDFTLTISSLQPEDFATYYCQNYAGVSIYGAVF |

TABLE 28-continued

Amino Acid Sequences of the Humanized Variants - Light Chain

| SEQ ID NO: | Name | Sequence |
|---|---|---|
| | | GGGTKVVIKRTVAAPSVFIFPPSDEQLKSGTASVVCLLNNFYPREAKVQWKVDNALQSG NSQESVTEQDSKDSTYSLSSTLTLSKADYEKHKVYACEVTHQGLSSPVTKSFNRGEC |
| 206 | LC5M1 | MVSSAQFLGLLLLCFQGTRCDIQMTQSPSSVSASVGDRVTITCQASQSIGGYISWYQQK PGQPPKLLIYKASTLASGVPSRFKGSGSGTDFTLTISSLDSEDAATYYCQNYAGVSIYGA VFGGGTKVVVKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVTKSFNRGEC |
| 252 | 11E12_VL_Hu1 | DIVMTQSPSSLAVSLGERATINC<u>KSSQSLLNSGNQRNYLT</u>WYQQKPGQPPKLLIY<u>WAST RES</u>GVPDRFSGSGSGTDFTLTISSLQAEDVAVYYC<u>QNSYNYPYT</u>FGQGTKLEIKRTVAA PSVFIFPPSDEQLKSGTASVVCLLNNFYPREAKVQWKVDNALQSGNSQESVTEQDSKDS TYSLSSTLTLSKADYEKHKVYACEVTHQGLSSPVTKSFNRGEC |
| 253 | 11E12_VL_Hu2 | DIVMTQSPSSLPVSLGERATINC<u>KSSQSLLNSGNQRNYLT</u>WYQQKPGQPPKLLIY<u>WAST RES</u>GVPDRFSGSGSGTDFTLTISSLQAEDVAVYYC<u>QNSYNYPYT</u>FGQGTKLEIKRTVAA PSVFIFPPSDEQLKSGTASVVCLLNNFYPREAKVQWKVDNALQSGNSQESVTEQDSKDS TYSLSSTLTLSKADYEKHKVYACEVTHQGLSSPVTKSFNRGEC |

TABLE 29

CDRs of Antibodies cloned from Hybridomas - Clone 79C4

| SEQ ID NO: | Clone 79C4 | Protein Sequence |
|---|---|---|
| 207 | CDR1 VH | <u>GFTFSNYWMN</u> |
| 208 | CDR2 VH | <u>EIRLKSKNYATHYAESVKG</u> |
| 209 | CDR3 VH | <u>GHYGTNYGDY</u> |
| 210 | CDR1 VL | <u>RASQEISGYLS</u> |
| 211 | CDR2 VL | <u>AASTLDS</u> |
| 212 | CDR3 VL | <u>LQYDSSPWT</u> |

TABLE 30

CDRs of Antibodies cloned from Hybridomas - Clone 11E12

| SEQ ID NO: | Clone 11E12 | Protein Sequence |
|---|---|---|
| 213 | CDR1 VH | <u>GYTFTSYVIN</u> |
| 214 | CDR2 VH | <u>EIHPRGGNTYYSEKFRG</u> |
| 215 | CDR3 VH | <u>LRRGNAMDY</u> |
| 247 | CDR3 VH | <u>IRRGNAMDY</u> |
| 216 | CDR1 VL | <u>KSSQSLLNSGNQRNYLT</u> |
| 217 | CDR2 VL | <u>WASTRES</u> |
| 218 | CDR3 VL | <u>QNSYNYPYT</u> |

TABLE 31

CDRs of Antibodies cloned from Hybridomas - Clone 83G3

| SEQ ID NO: | Clone 83G3 | Protein Sequence |
|---|---|---|
| 219 | CDR1 VH | <u>GFTFTSYWIH</u> |
| 220 | CDR2 VH | <u>YIDPSNTYTKFNQKFKD</u> |
| 221 | CDR3 VH | <u>GRGFAY</u> |
| 222 | CDR1 VL | <u>DKSSQSLFNSGNQKHYLT</u> |
| 223 | CDR2 VL | <u>RASTRES</u> |
| 224 | CDR3 VL | <u>QNDYSFPLT</u> |

TABLE 32

CDRs of Antibodies cloned from Hybridomas - Clone 30B5

| SEQ ID NO: | Clone 30B5 | Protein Sequence |
|---|---|---|
| 225 | CDR1 VH | <u>GFTFSNYWMN</u> |
| 226 | CDR2 VH | <u>EIRLKSKNYATHYAESVKG</u> |
| 227 | CDR3 VH | <u>GHYGTNYGDY</u> |
| 228 | CDR1 VL | <u>KSSQSLFNSGNQKHYLT</u> |
| 229 | CDR2 VL | <u>RASTRES</u> |
| 230 | CDR3 VL | <u>QNDYSFPLT</u> |

TABLE 33

CDRs of Antibodies cloned from Hybridomas - Clone 85H12

| SEQ ID NO: | Clone 85H12 | Protein Sequence |
|---|---|---|
| 231 | CDR1 VH | <u>GFTFSNYWMN</u> |
| 232 | CDR2 VH | <u>EIRLKSKNYATHYAESVKG</u> |
| 233 | CDR3 VH | <u>GHYGTNYGDY</u> |
| 234 | CDR1 VL | <u>KSSQSLFNSGNQKHYLT</u> |
| 235 | CDR2 VL | <u>RASTRES</u> |
| 236 | CDR3 VL | <u>QNDYSFPLT</u> |

TABLE 34

Heavy chain variable domain Protein Sequence

| SEQ ID NO: | Clone | Heavy chain variable domain Protein Sequence |
|---|---|---|
| 237 | 79C4 | EVKLEESGGGLVQPGGSMKLSCVAS<u>GFTFSNYWMN</u>WVRQSPEKGLEWVA<u>EIRLKSKNY ATHYAESVKG</u>RFTISRDDSIGSVYLQMNNLRAEDTGIYYCAR<u>GHYGTNYGDY</u>WGQGTSV TVSS |
| 238 | 11E12 | QVQLQQSGAELARPGASVKLSCKAS<u>GYTFTSYVIN</u>WVKQTGQGLEWIG<u>EIHPRGGNTY YSEKFRG</u>RATLTADKSSSTAYMEFRSLTSEDSAVYFCAI<u>LRRGNAMDY</u>WDQGTAVTVSS |
| 239 | 83G3 | QVQLQQSGAELAKPGASVKLSCKAS<u>GFTFTSYWIH</u>WVKQRPGQGLEWIG<u>YIDPSNTYTK FNQKFKD</u>KATLTADKSSSTAYMQLNSLTFEDSAVYYCAT<u>GRGFAY</u>WGQGTLVTVSS |
| 240 | 30B5 | EVKLEESGGGLVQPGGSMKLSCVAS<u>GFTFSNYWMN</u>WVRQSPEKGLEWVA<u>EIRLKSKNY ATHYAESVKG</u>RFTISRDDSIGSVYLQMNNLRAEDTGIYYCAR<u>GHYGTNYGDY</u>WGQGTSV TVSS |
| 241 | 85H12 | EVKLEESGGGLVQPGGSMKLSCVAS<u>GFTFSNYWMN</u>WVRQSPEKGLEWVA<u>EIRLKSKNY ATHYAESVKG</u>RFTISRDDSIGSVYLQMNNLRAEDTGIYYCAR<u>GHYGTNYGDY</u>WGQGTSV TVSS |
| 248 | 11E12 mutein | QVQLQQSGAELARPGASVKLSCKAS<u>GYTFTSYVIN</u>WVKQTGQGLEWIG<u>EIHPRGGNTY YSEKFRG</u>RATLTADKSSSTAYMEFRSLTSEDSAVYFCARI<u>RRGNAMDY</u>WDQGTAVTVSS |

TABLE 35

Light chain variable domain Protein Sequence

| SEQ ID NO: | Clone | Light chain variable domain Protein Sequence |
|---|---|---|
| 242 | 79C4 | DIQTTQSPSSLSASLGERVTLTC<u>RASQEISGYLS</u>WLQQKPDGTIKRLIY<u>AASTLDS</u>GVP KRFSGSRSGSDYSLTINSLESEDFVDYYC<u>LQYDSSPWT</u>FGGGTKLEIK |
| 243 | 11E12 | DIVMTQSPSSLPVTAGEMVTMSC<u>KSSQSLLNSGNQRNYLT</u>WYQQKPGQPPKLLIY<u>WA STRES</u>GVPDRFTGSGSGTDFTLTISSVQAEDLAVYYC<u>QNSYNYPYT</u>FGGGTKLERK |
| 244 | 83G3 | DIVMTQSPSSLTVTAGEKVTVSC<u>KSSQSLFNSGNQKHYLT</u>WYQQKPGQPPKWY<u>RAS TRES</u>GVPDRFTGSGSGTDFTLTIRNVQAEDLAVYYC<u>QNDYSFPLT</u>FGAGTKLELK |
| 245 | 30B5 | DIVMTQSPSSLTVTAGEKVTVSC<u>KSSQSLFNSGNQKHYLT</u>WYQQKPGQPPKLLIY<u>RAS TRES</u>GVPDRFTGSGSGTDFTLTIRNVQAEDLAVYYC<u>QNDYSFPLT</u>FGAGTKLELK |
| 246 | 85H12 | DIVMTQSPSSLTVTAGEKVTVSC<u>KSSQSLFNSGNQKHYLT</u>WYQQKPGQPPKLLIY<u>RAS TRES</u>GVPDRFTGSGSGTDFTLTIRNVQAEDLAVYYC<u>QNDYSFPLT</u>FGAGTKLELK |

TABLE 36

11E12 Humanized Sequences

| SEQ ID NO: | Name | Humanized heavy chain and light chain variable domain Protein Sequences |
|---|---|---|
| 254 | hu11E12VHv1 | QVQLVQSGAEVKKPGASVKVSCKAS<u>GYTFTSYVIN</u>WVRQATGQGLEWIG<u>EIHPR GGNTYYSEKFRG</u>RVTLTADTSISTAYMELSSLRSEDTAVYYCAI<u>LRRGNAMDY</u>WD QGTTVTVSS |
| 255 | hu11E12VHv2 | QVQLVQSGAEVKKPGASVKVSCKAS<u>GYTFTSYVIN</u>WVKQTGQGLEWIG<u>EIHPR GGNTYYSEKFRG</u>RATLTADKSISTAYMELSSLRSEDTAVYFCAI<u>LRRGNAMDY</u>WD QGTTVTVSS |
| 256 | hu11E12VHv3 | QVQLVQSGAEVKKPGASVKLSCKAS<u>GYTFTSYVIN</u>WVKQKTGQGLEWIG<u>EIHPRG GNTYYSEKFRG</u>RATLTADKSISTAYMELSSLRSEDTAVYFCAI<u>LRRGNAMDY</u>WDQ GTTVTVSS |
| 257 | hu11E12VHv1B | QVQLVQSGAEVKKPGASVKVSCKAS<u>GYTFTSYVIN</u>WVRQATGQGLEWIG<u>EIHPR GGNTYYSEKFRG</u>RVTLTADTSISTAYMELSSLRSEDTAVYYCAR<u>LRRGNAMDY</u>W DQGTTVTVSS |

TABLE 36-continued

11E12 Humanized Sequences

| SEQ ID NO: | Name | Humanized heavy chain and light chain variable domain Protein Sequences |
|---|---|---|
| 258 | hu11E12VHv2B | QVQLVQSGAEVKKPGASVKVSCKAS<u>GYTFTSYVIN</u>WVKQKTGQGLEWIGE<u>IHPR</u><br><u>GGNTYYSEKFRG</u>RATLTADKSISTAYMELSSLRSEDTAVYFCAR<u>LRRGNAMDY</u>W<br>DQGTTVTVSS |
| 259 | hu11E12VHv3B | QVQLVQSGAEVKKPGASVKLSCKAS<u>GYTFTSYVIN</u>WVKQKTGQGLEWIGE<u>IHPRG</u><br><u>GNTYYSEKFRG</u>RATLTADKSISTAYMELSSLRSEDTAVYFCAR<u>LRRGNAMDY</u>WD<br>QGTTVTVSS |
| 260 | hu11E12VLv1 | DIVMTQSPSSLAVSLGEMATINC<u>KSSQSLLNSGNQRNYLT</u>WYQQKPGQPPKLLIY<br><u>WASTRES</u>GVPDRFSGSGSGTDFTLTISSLQAEDVAVYYC<u>QNSYNYPYT</u>FGQGTK<br>LERK |
| 261 | hu11E12VLv2 | DIVMTQSPSSLAVSAGEMVTMNC<u>KSSQSLLNSGNQRNYLT</u>WYQQKPGQPPKLLI<br>Y<u>WASTRES</u>GVPDRFSGSGSGTDFTLTISSVQAEDLAVYYC<u>QNSYNYPYT</u>FGQGT<br>KLEIK |
| 262 | hu11E12VLv3 | DIVMTQSPSSLAVSAGEMVTMNC<u>KSSQSLLNSGNQRNYLT</u>WYQQKPGQPPKLLI<br>Y<u>WASTRES</u>GVPDRFSGSGSGTDFTLTISSVQAEDLAVYYC<u>QNSYNYPYT</u>FGQGT<br>KLERK |

TABLE 37

83G3 Humanized Sequences

| SEQ ID NO: | Clone | Humanized heavy chain and light chain variable domain Protein Sequences |
|---|---|---|
| 263 | hu83G3VHv1 | QVQLVQSGAEVKKPGASVKVSCKAS<u>GFTFTSYWIH</u>WVRQRPGQGLEWIG<u>YID</u><br><u>PSNTYTKFNQKFKD</u>RVTLTADTSTSTAYMELSSLRSEDTAVYYC<u>ATGRGFAY</u>W<br>GQGTLVTVSS |
| 264 | hu83G3VHv2 | QVQLVQSGAEVKKPGASVKLSCKAS<u>GFTFTSYWIH</u>WVRQRPGQGLEWIG<u>YID</u><br><u>PSNTYTKFNQKFKD</u>RATLTADTSTSTAYMELSSLRSEDTAVYYC<u>ATGRGFAY</u>W<br>GQGTLVTVSS |
| 265 | hu83G3VHv3 | QVQLQQSGAEVKKPGASVKLSCKAS<u>GFTFTSYWIH</u>WVRQRPGQGLEWIG<u>YID</u><br><u>PSNTYTKFNQKFKD</u>RATLTADTSTSTAYMELSSLRSEDTAVYYC<u>ATGRGFAY</u>W<br>GQGTLVTVSS |
| 266 | hu83G3VLv1 | DIVMTQSPSSLAVSLGE<u>R</u>ATINC<u>KSSQSLFNSGNQKHYLT</u>WYQQKPGQPP<u>K</u>LL<br>IY<u>RASTRES</u>GVPDRFSGSGSGTDFTLTISSLQAEDVAVYYC<u>QNDYSFPLT</u>FGQ<br>GTKLEIK |
| 267 | hu83G3VLv2 | DIVMTQSPSSLAVSLGE<u>R</u>ATVNC<u>KSSQSLFNSGNQKHYLT</u>WYQQKPGQPP<u>K</u>L<br>LIY<u>RASTRES</u>GVPDRFSGSGSGTDFTLTISSLQAEDVAVYYC<u>QNDYSFPLT</u>FGQ<br>GTKLEIK |
| 268 | hu83G3VLv3 | DIVMTQSPSSLAVSLGE<u>R</u>ATVNC<u>KSSQSLFNSGNQKHYLT</u>WYQQKPGQPP<u>K</u>L<br>LIY<u>RASTRES</u>GVPDRFSGSGSGTDFTLTIRSLQAEDVAVYYC<u>QNDYSFPLT</u>FGQ<br>GTKLEIK |
| 269 | hu83G3VLv4 | DIVMTQSPSSLAVSLGE<u>R</u>ATVNC<u>KSSQSLFNSGNQKHYLT</u>WYQQKPGQPP<u>K</u>L<br>LIY<u>RASTRES</u>GVPDRFTGSGSGTDFTLTISSLQAEDVAVYYC<u>QNDYSFPLT</u>FGQ<br>GTKLEIK |

The above non-limiting examples are provided for illustrative purposes only in order to facilitate a more complete understanding of the disclosed subject matter. These examples should not be construed to limit any of the embodiments described in the present specification, including those pertaining to the antibodies, pharmaceutical compositions, or methods and uses for treating cancer, a neurodegenerative or an infectious disease.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular compound, composition, article, apparatus, methodology, protocol, and/or reagent, etc., described herein, unless expressly stated as such. In addition, those of ordinary skill in the art will recognize that certain changes, modifications, permutations, alterations, additions, subtractions and sub-combinations thereof can be made in accordance with the teachings herein without departing from the spirit of the present specification. It is therefore intended that the following appended claims and claims hereafter introduced are interpreted to include all such changes, modifications, permutations, alterations, additions, subtractions and sub-combinations as are within their true spirit and scope.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. For instance, as mass spectrometry instruments can vary slightly in determining the mass of a given analyte, the term "about" in the context of the mass of an ion or the mass/charge ratio of an ion refers to +/−0.50 atomic mass unit. At the very least, and not as an attempt to limit the application of the doctrine of equivalents to the scope of the claims, each numerical indication should at least be construed in light of the number of reported significant digits and by applying ordinary rounding techniques.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising" (and equivalent open-ended transitional phrases thereof like including, containing and having) encompasses all the expressly recited elements, limitations, steps and/or features alone or in combination with unrecited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases "consisting of" or "consisting essentially of" in lieu of or as an amended for "comprising." When used in the claims, whether as filed or added per amendment, the closed-ended transitional phrase "consisting of" excludes any element, limitation, step, or feature not expressly recited in the claims. The closed-ended transitional phrase "consisting essentially of" limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps and/or features specifically recited in the claim whereas the meaning of the closed-ended transitional phrase "consisting essentially of" is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase "comprising" (and equivalent open-ended transitional phrases thereof) includes within its meaning, as a limiting case, claimed subject matter specified by the closed-ended transitional phrases "consisting of" or "consisting essentially of." As such embodiments described herein or so claimed with the phrase "comprising" are expressly or inherently unambiguously described, enabled and supported herein for the phrases "consisting essentially of" and "consisting of."

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Lastly, the terminology used herein is for the purpose of describing particular embodiments only, and is not intended to limit the scope of the present invention, which is defined solely by the claims. Accordingly, the present invention is not limited to that precisely as shown and described.

The invention claimed is:

1. An antibody which binds to human CLDN18.2 protein, the antibody selected from the group consisting of:
   a. an antibody comprising a heavy chain variable region comprising heavy chain CDR1 containing the amino acid sequence as set forth in SEQ ID NO: 47, heavy chain CDR2 containing the amino acid sequence as set forth in SEQ ID NO: 48, and heavy chain CDR3 containing the amino acid sequence as set forth in SEQ ID NO: 49, and a light chain variable region comprising light chain CDR1 containing the amino acid sequence as set forth in SEQ ID NO: 50, light chain CDR2 containing the amino acid sequence as set forth in SEQ ID NO: 51, and light chain CDR3 containing the amino acid sequence as set forth in SEQ ID NO: 52;
   b. an antibody comprising a heavy chain variable region comprising heavy chain CDR1 containing the amino acid sequence as set forth in SEQ ID NO: 53, heavy chain CDR2 containing the amino acid sequence as set forth in SEQ ID NO: 54, and heavy chain CDR3 containing the amino acid sequence as set forth in SEQ ID NO: 55, and a light chain variable region comprising light chain CDR1 containing the amino acid sequence as set forth in SEQ ID NO: 56, light chain CDR2 containing the amino acid sequence as set forth in SEQ ID NO: 57, and light chain CDR3 containing the amino acid sequence as set forth in SEQ ID NO: 58;
   c. an antibody comprising a heavy chain variable region comprising heavy chain CDR1 containing the amino acid sequence as set forth in SEQ ID NO: 59, heavy chain CDR2 containing the amino acid sequence as set forth in SEQ ID NO: 60, and heavy chain CDR3 containing the amino acid sequence as set forth in SEQ ID NO: 61, and a light chain variable region comprising light chain CDR1 containing the amino acid sequence as set forth in SEQ ID NO: 62, light chain CDR2 containing the amino acid sequence as set forth in SEQ ID NO: 63, and light chain CDR3 containing the amino acid sequence as set forth in SEQ ID NO: 64;
   d. an antibody comprising a heavy chain variable region comprising heavy chain CDR1 containing the amino acid sequence as set forth in SEQ ID NO: 65, heavy chain CDR2 containing the amino acid sequence as set forth in SEQ ID NO: 66, and heavy chain CDR3 containing the amino acid sequence as set forth in SEQ ID NO: 67, and a light chain variable region comprising light chain CDR1 containing the amino acid sequence as set forth in SEQ ID NO: 68, light chain CDR2 containing the amino acid sequence as set forth in SEQ ID NO: 69, and light chain CDR3 containing the amino acid sequence as set forth in SEQ ID NO: 70;
   e. an antibody comprising a heavy chain variable region comprising heavy chain CDR1 containing the amino acid sequence as set forth in SEQ ID NO: 71, heavy chain CDR2 containing the amino acid sequence as set forth in SEQ ID NO: 72, and heavy chain CDR3 containing the amino acid sequence as set forth in SEQ ID NO: 73, and a light chain variable region comprising light chain CDR1 containing the amino acid sequence as set forth in SEQ ID NO: 74, light chain CDR2 containing the amino acid sequence as set forth in SEQ ID NO: 75, and light chain CDR3 containing the amino acid sequence as set forth in SEQ ID NO: 76;
   f. an antibody comprising a heavy chain variable region comprising heavy chain CDR1 containing the amino acid sequence as set forth in SEQ ID NO: 77, heavy chain CDR2 containing the amino acid sequence as set forth in SEQ ID NO: 78, and heavy chain CDR3 containing the amino acid sequence as set forth in SEQ ID NO: 79, and a light chain variable region comprising light chain CDR1 containing the amino acid sequence as set forth in SEQ ID NO: 80, light chain CDR2 containing the amino acid sequence as set forth in SEQ ID NO: 81, and light chain CDR3 containing the amino acid sequence as set forth in SEQ ID NO: 82;
   g. an antibody comprising a heavy chain variable region comprising heavy chain CDR1 containing the amino acid sequence as set forth in SEQ ID NO: 83, heavy chain CDR2 containing the amino acid sequence as set forth in SEQ ID NO: 84, and heavy chain CDR3 containing the amino acid sequence as set forth in SEQ ID NO: 85, and a light chain variable region comprising light chain CDR1 containing the amino acid sequence as set forth in SEQ ID NO: 86, light chain CDR2 containing the amino acid sequence as set forth in SEQ ID NO: 87, and light chain CDR3 containing the amino acid sequence as set forth in SEQ ID NO: 88;
   h. an antibody comprising a heavy chain variable region comprising heavy chain CDR1 containing the amino acid sequence as set forth in SEQ ID NO: 89, heavy chain CDR2 containing the amino acid sequence as set forth in SEQ ID NO: 90, and heavy chain CDR3 containing the amino acid sequence as set forth in SEQ ID NO: 91, and a light chain variable region comprising light chain CDR1 containing the amino acid sequence as set forth in SEQ ID NO: 92, light chain CDR2 containing the amino acid sequence as set forth in SEQ ID NO: 93, and light chain CDR3 containing the amino acid sequence as set forth in SEQ ID NO: 94;
   i. an antibody comprising a heavy chain variable region comprising heavy chain CDR1 containing the amino acid sequence as set forth in SEQ ID NO: 95, heavy chain CDR2 containing the amino acid sequence as set forth in SEQ ID NO: 96, and heavy chain CDR3 containing the amino acid sequence as set forth in SEQ ID NO: 97, and a light chain variable region comprising light chain CDR1 containing the amino acid sequence as set forth in SEQ ID NO: 98, light chain CDR2 containing the amino acid sequence as set forth in SEQ ID NO: 99, and light chain CDR3 containing the amino acid sequence as set forth in SEQ ID NO: 100;
   j. an antibody comprising a heavy chain variable region comprising heavy chain CDR1 containing the amino acid sequence as set forth in SEQ ID NO: 101, heavy chain CDR2 containing the amino acid sequence as set forth in SEQ ID NO: 102, and heavy chain CDR3 containing the amino acid sequence as set forth in SEQ ID NO: 103, and a light chain variable region comprising light chain CDR1 containing the amino acid sequence as set forth in SEQ ID NO: 104, light chain CDR2 containing the amino acid sequence as set forth in SEQ ID NO: 105, and light chain CDR3 containing the amino acid sequence as set forth in SEQ ID NO: 106;
   k. an antibody comprising a heavy chain variable region comprising heavy chain CDR1 containing the amino acid sequence as set forth in SEQ ID NO: 107, heavy chain CDR2 containing the amino acid sequence as set forth in SEQ ID NO: 108, and heavy chain CDR3 containing the amino acid sequence as set forth in SEQ ID NO: 109, and a light chain variable region comprising light chain CDR1 containing the amino acid sequence as set forth in SEQ ID NO: 110, light chain CDR2 containing the amino acid sequence as set forth in SEQ ID NO: 111, and light chain CDR3 containing the amino acid sequence as set forth in SEQ ID NO: 112;

l. an antibody comprising a heavy chain variable region comprising heavy chain CDR1 containing the amino acid sequence as set forth in SEQ ID NO: 113, heavy chain CDR2 containing the amino acid sequence as set forth in SEQ ID NO: 114, and heavy chain CDR3 containing the amino acid sequence as set forth in SEQ ID NO: 115 or 198, and a light chain variable region comprising light chain CDR1 containing the amino acid sequence as set forth in SEQ ID NO: 116, light chain CDR2 containing the amino acid sequence as set forth in SEQ ID NO: 117, and light chain CDR3 containing the amino acid sequence as set forth in SEQ ID NO: 118;

m. an antibody comprising a heavy chain variable region comprising heavy chain CDR1 containing the amino acid sequence as set forth in SEQ ID NO: 113, heavy chain CDR2 containing the amino acid sequence as set forth in SEQ ID NO: 114, and heavy chain CDR3 containing the amino acid sequence as set forth in SEQ ID NO: 198, and a light chain variable region comprising light chain CDR1 containing the amino acid sequence as set forth in SEQ ID NO: 116, light chain CDR2 containing the amino acid sequence as set forth in SEQ ID NO: 117, and light chain CDR3 containing the amino acid sequence as set forth in SEQ ID NO: 118;

n. an antibody comprising a heavy chain variable region comprising heavy chain CDR1 containing the amino acid sequence as set forth in SEQ ID NO: 119, heavy chain CDR2 containing the amino acid sequence as set forth in SEQ ID NO: 120, and heavy chain CDR3 containing the amino acid sequence as set forth in SEQ ID NO: 121, and a light chain variable region comprising light chain CDR1 containing the amino acid sequence as set forth in SEQ ID NO: 122, light chain CDR2 containing the amino acid sequence as set forth in SEQ ID NO: 123, and light chain CDR3 containing the amino acid sequence as set forth in SEQ ID NO: 124;

o. an antibody comprising a heavy chain variable region comprising heavy chain CDR1 containing the amino acid sequence as set forth in SEQ ID NO: 125, heavy chain CDR2 containing the amino acid sequence as set forth in SEQ ID NO: 126, and heavy chain CDR3 containing the amino acid sequence as set forth in SEQ ID NO: 127, and a light chain variable region comprising light chain CDR1 containing the amino acid sequence as set forth in SEQ ID NO: 128, light chain CDR2 containing the amino acid sequence as set forth in SEQ ID NO: 129, and light chain CDR3 containing the amino acid sequence as set forth in SEQ ID NO: 130;

p. an antibody comprising a heavy chain variable region comprising heavy chain CDR1 containing the amino acid sequence as set forth in SEQ ID NO: 131, heavy chain CDR2 containing the amino acid sequence as set forth in SEQ ID NO: 132, and heavy chain CDR3 containing the amino acid sequence as set forth in SEQ ID NO: 133, and a light chain variable region comprising light chain CDR1 containing the amino acid sequence as set forth in SEQ ID NO: 134, light chain CDR2 containing the amino acid sequence as set forth in SEQ ID NO: 135, and light chain CDR3 containing the amino acid sequence as set forth in SEQ ID NO: 136;

q. an antibody comprising a heavy chain variable region comprising heavy chain CDR1 containing the amino acid sequence as set forth in SEQ ID NO: 137, heavy chain CDR2 containing the amino acid sequence as set forth in SEQ ID NO: 138, and heavy chain CDR3 containing the amino acid sequence as set forth in SEQ ID NO: 139, and a light chain variable region comprising light chain CDR1 containing the amino acid sequence as set forth in SEQ ID NO: 140, light chain CDR2 containing the amino acid sequence as set forth in SEQ ID NO: 141, and light chain CDR3 containing the amino acid sequence as set forth in SEQ ID NO: 142;

r. an antibody comprising a heavy chain variable region comprising heavy chain CDR1 containing the amino acid sequence as set forth in SEQ ID NO: 143, heavy chain CDR2 containing the amino acid sequence as set forth in SEQ ID NO: 144, and heavy chain CDR3 containing the amino acid sequence as set forth in SEQ ID NO: 145, and a light chain variable region comprising light chain CDR1 containing the amino acid sequence as set forth in SEQ ID NO: 146, light chain CDR2 containing the amino acid sequence as set forth in SEQ ID NO: 147, and light chain CDR3 containing the amino acid sequence as set forth in SEQ ID NO: 148;

s. an antibody comprising a heavy chain variable region comprising heavy chain CDR1 containing the amino acid sequence as set forth in SEQ ID NO: 149, heavy chain CDR2 containing the amino acid sequence as set forth in SEQ ID NO: 150, and heavy chain CDR3 containing the amino acid sequence as set forth in SEQ ID NO: 151, and a light chain variable region comprising light chain CDR1 containing the amino acid sequence as set forth in SEQ ID NO: 152, light chain CDR2 containing the amino acid sequence as set forth in SEQ ID NO: 153, and light chain CDR3 containing the amino acid sequence as set forth in SEQ ID NO: 154;

t. an antibody comprising a heavy chain variable region comprising heavy chain CDR1 containing the amino acid sequence as set forth in SEQ ID NO: 155, heavy chain CDR2 containing the amino acid sequence as set forth in SEQ ID NO: 156, and heavy chain CDR3 containing the amino acid sequence as set forth in SEQ ID NO: 157, and a light chain variable region comprising light chain CDR1 containing the amino acid sequence as set forth in SEQ ID NO: 158, light chain CDR2 containing the amino acid sequence as set forth in SEQ ID NO: 159, and light chain CDR3 containing the amino acid sequence as set forth in SEQ ID NO: 160;

u. an antibody comprising a heavy chain variable region comprising heavy chain CDR1 containing the amino acid sequence as set forth in SEQ ID NO: 161, heavy chain CDR2 containing the amino acid sequence as set forth in SEQ ID NO: 162, and heavy chain CDR3 containing the amino acid sequence as set forth in SEQ ID NO: 163, and a light chain variable region comprising light chain CDR1 containing the amino acid sequence as set forth in SEQ ID NO: 164, light chain CDR2 containing the amino acid sequence as set forth in SEQ ID NO: 165, and light chain CDR3 containing the amino acid sequence as set forth in SEQ ID NO: 166;

v. an antibody comprising a heavy chain variable region comprising heavy chain CDR1 containing the amino acid sequence as set forth in SEQ ID NO: 167, heavy chain CDR2 containing the amino acid sequence as set forth in SEQ ID NO: 168, and heavy chain CDR3 containing the amino acid sequence as set forth in SEQ ID NO: 169, and a light chain variable region comprising light chain CDR1 containing the amino acid sequence as set forth in SEQ ID NO: 170, light chain CDR2 containing the amino acid sequence as set forth in SEQ ID NO: 171, and light chain CDR3 containing the amino acid sequence as set forth in SEQ ID NO: 172;

w. an antibody comprising a heavy chain variable region comprising heavy chain CDR1 containing the amino acid sequence as set forth in SEQ ID NO: 173, heavy chain CDR2 containing the amino acid sequence as set forth in SEQ ID NO: 174, and heavy chain CDR3 containing the amino acid sequence as set forth in SEQ ID NO: 175, and a light chain variable region comprising light chain CDR1 containing the amino acid sequence as set forth in SEQ ID NO: 176, light chain CDR2 containing the amino acid sequence as set forth in SEQ ID NO: 177, and light chain CDR3 containing the amino acid sequence as set forth in SEQ ID NO: 178;

x. an antibody comprising a heavy chain variable region comprising heavy chain CDR1 containing the amino acid sequence as set forth in SEQ ID NO: 179, heavy chain CDR2 containing the amino acid sequence as set forth in SEQ ID NO: 180, and heavy chain CDR3 containing the amino acid sequence as set forth in SEQ ID NO: 181, and a light chain variable region comprising light chain CDR1 containing the amino acid sequence as set forth in SEQ ID NO: 182, light chain CDR2 containing the amino acid sequence as set forth in SEQ ID NO: 183, and light chain CDR3 containing the amino acid sequence as set forth in SEQ ID NO: 184;

y. an antibody comprising a heavy chain variable region comprising heavy chain CDR1 containing the amino acid sequence as set forth in SEQ ID NO: 207, heavy chain CDR2 containing the amino acid sequence as set forth in SEQ ID NO: 208, and heavy chain CDR3 containing the amino acid sequence as set forth in SEQ ID NO: 209, and a light chain variable region comprising light chain CDR1 containing the amino acid sequence as set forth in SEQ ID NO: 210, light chain CDR2 containing the amino acid sequence as set forth in SEQ ID NO: 211, and light chain CDR3 containing the amino acid sequence as set forth in SEQ ID NO: 212;

z. an antibody comprising a heavy chain variable region comprising heavy chain CDR1 containing the amino acid sequence as set forth in SEQ ID NO: 213, heavy chain CDR2 containing the amino acid sequence as set forth in SEQ ID NO: 214, and heavy chain CDR3 containing the amino acid sequence as set forth in SEQ ID NO: 215, and a light chain variable region comprising light chain CDR1 containing the amino acid sequence as set forth in SEQ ID NO: 216, light chain CDR2 containing the amino acid sequence as set forth in SEQ ID NO: 217, and light chain CDR3 containing the amino acid sequence as set forth in SEQ ID NO: 218;

aa. an antibody comprising a heavy chain variable region comprising heavy chain CDR1 containing the amino acid sequence as set forth in SEQ ID NO: 213, heavy chain CDR2 containing the amino acid sequence as set forth in SEQ ID NO: 214, and heavy chain CDR3 containing the amino acid sequence as set forth in SEQ ID NO: 247, and a light chain variable region comprising light chain CDR1 containing the amino acid sequence as set forth in SEQ ID NO: 216, light chain CDR2 containing the amino acid sequence as set forth in SEQ ID NO: 217, and light chain CDR3 containing the amino acid sequence as set forth in SEQ ID NO: 218;

bb. an antibody comprising a heavy chain variable region comprising heavy chain CDR1 containing the amino acid sequence as set forth in SEQ ID NO: 219, heavy chain CDR2 containing the amino acid sequence as set forth in SEQ ID NO: 220, and heavy chain CDR3 containing the amino acid sequence as set forth in SEQ ID NO: 221, and a light chain variable region comprising light chain CDR1 containing the amino acid sequence as set forth in SEQ ID NO: 222, light chain CDR2 containing the amino acid sequence as set forth in SEQ ID NO: 223, and light chain CDR3 containing the amino acid sequence as set forth in SEQ ID NO: 224;

cc. an antibody comprising a heavy chain variable region comprising heavy chain CDR1 containing the amino acid sequence as set forth in SEQ ID NO: 225, heavy chain CDR2 containing the amino acid sequence as set forth in SEQ ID NO: 226, and heavy chain CDR3 containing the amino acid sequence as set forth in SEQ ID NO: 227, and a light chain variable region comprising light chain CDR1 containing the amino acid sequence as set forth in SEQ ID NO: 228, light chain CDR2 containing the amino acid sequence as set forth in SEQ ID NO: 229, and light chain CDR3 containing the amino acid sequence as set forth in SEQ ID NO: 230;

dd. an antibody comprising a heavy chain variable region comprising heavy chain CDR1 containing the amino acid sequence as set forth in SEQ ID NO: 231, heavy chain CDR2 containing the amino acid sequence as set forth in SEQ ID NO: 232, and heavy chain CDR3 containing the amino acid sequence as set forth in SEQ ID NO: 233, and a light chain variable region comprising light chain CDR1 containing the amino acid sequence as set forth in SEQ ID NO: 234, light chain CDR2 containing the amino acid sequence as set forth in SEQ ID NO: 235, and light chain CDR3 containing the amino acid sequence as set forth in SEQ ID NO: 236.

2. An antibody according to claim 1, wherein the antibody is humanized.

3. An antibody according to claim 1, which has a format selected from a single-chain Fv antibody (scFv), a Fab antibody, a Fab' antibody, and a (Fab')2 antibody.

4. An antibody according to claim 1, wherein the antibody binds to human CLDN18.2 with stronger affinity than binding to human CLDN18.1.

5. An antibody according to claim 1, wherein the antibody binds to human CLDN18.2 with at least 100 times higher affinity than binding to human CLDN18.1.

6. An antibody according to claim 1, wherein the antibody binds to human CLDN18.2 but does not bind to human CLDN18.1.

7. An antibody according to claim 2, wherein the antibody is conjugated with one or more cytotoxic agent.

8. An antibody according to claim 2, wherein the heavy chain and/or light chain of said antibody is fused with a human albumin; and wherein said albumin domain is conjugated with one or more cytotoxic agent.

9. An antibody according to claim 1, wherein the antibody further comprises one or more antagonists of IL-2 or IL-15.

10. An antibody according to claim 2, wherein the heavy chain and/or light chain of said antibody is fused with an antigen binding domain, and wherein said antigen binding domain binds human CD3.

11. An antibody according to claim 2, wherein the heavy chain and/or light chain of said antibody is fused with one or more antigen binding domains, and wherein said antigen binding domain binds human PD-L1, CD47 or signal-regulatory protein alpha (SIRPα).

12. A humanized antibody according to claim 1, which comprises a light chain with an amino acid sequence selected from SEQ ID NO: 193-197, 205, 252, and 253, and a heavy chain with an amino acid sequence selected from SEQ ID NO: 187-191, 199-204, 249, 250, and 251.

13. A humanized antibody according to claim 1, which comprises a heavy chain variable domain with an amino acid sequence selected from SEQ ID NO: 254-258, and 259, and a light chain variable domain with an amino acid sequence selected from SEQ ID NO: 260, 261 and 262.

14. A humanized antibody according to claim 1, which comprises a heavy chain variable domain with an amino acid sequence selected from consisting of SEQ ID NO: 263, 264, and 265, and a light chain variable domain with an amino acid sequence selected from the group consisting of SEQ ID NO: 266, 267, 268 and 269.

15. A pharmaceutical composition comprising an antibody according to claim 1.

16. An antibody according to claim 13, wherein the heavy chain and/or light chain of said antibody is fused with one or more IL-2 polypeptides, one or more IL-2 analogs, one or more IL-15 polypeptides, or one or more IL-15 analogs.

* * * * *